(12) United States Patent
Forrest

(10) Patent No.: US 12,337,000 B2
(45) Date of Patent: Jun. 24, 2025

(54) THERAPEUTIC MODULATORS OF THE REVERSE MODE OF ATP SYNTHASE

(71) Applicant: Michael David Forrest, Poole (GB)

(72) Inventor: Michael David Forrest, Poole (GB)

( * ) Notice: Subject to any disclaimer, the term of this patent is extended or adjusted under 35 U.S.C. 154(b) by 478 days.

(21) Appl. No.: 16/629,390

(22) PCT Filed: Jul. 13, 2018

(86) PCT No.: PCT/EP2018/069175
§ 371 (c)(1),
(2) Date: Jan. 8, 2020

(87) PCT Pub. No.: WO2019/012149
PCT Pub. Date: Jan. 17, 2019

(65) Prior Publication Data
US 2020/0306253 A1    Oct. 1, 2020

(30) Foreign Application Priority Data

| Jul. 13, 2017 | (GB) | ................................. | 1711250 |
| Sep. 28, 2017 | (GB) | ................................. | 1715756 |
| Sep. 28, 2017 | (GB) | ................................. | 1715758 |
| Oct. 1, 2017 | (GB) | ................................. | 1715938 |
| Oct. 9, 2017 | (GB) | ................................. | 1716492 |
| Jan. 4, 2018 | (GB) | ................................. | 1800092 |
| Jan. 8, 2018 | (GB) | ................................. | 1800291 |
| Jan. 15, 2018 | (GB) | ................................. | 1800581 |
| Jan. 17, 2018 | (WO) | ................. PCT/EP2018/051127 | |
| Jan. 30, 2018 | (GB) | ................................. | 1801536 |
| Apr. 19, 2018 | (GB) | ................................. | 1806421 |
| May 21, 2018 | (GB) | ................................. | 1808331 |
| Jun. 8, 2018 | (GB) | ................................. | 1809497 |
| Jun. 21, 2018 | (GB) | ................................. | 1810236 |
| Jul. 8, 2018 | (GB) | ................................. | 1811188 |

(51) Int. Cl.
*A61K 31/53*    (2006.01)
*C07D 233/61*    (2006.01)

(52) U.S. Cl.
CPC ............ *A61K 31/53* (2013.01); *C07D 233/61* (2013.01)

(58) Field of Classification Search
CPC ....... A61K 31/53; A61P 35/00; C07D 251/54; C07D 233/61
See application file for complete search history.

(56) References Cited

U.S. PATENT DOCUMENTS

| 436,494 | A | 9/1890 | Edgar | |
| 522,540 | A | 7/1894 | Walker | |
| 3,647,794 | A | 3/1972 | Regnier et al. | |
| 4,364,946 | A * | 12/1982 | Labeyrie | ................. A61K 31/53 514/245 |
| 4,492,696 | A | 1/1985 | Reginier et al. | |
| 4,514,398 | A | 4/1985 | Regnier et al. | |
| 4,514,399 | A | 4/1985 | Regnier et al. | |
| 4,593,026 | A | 6/1986 | Regnier et al. | |
| 5,225,405 | A | 7/1993 | Paramelle et al. | |
| 5,670,617 | A | 9/1997 | Frankel et al. | |
| 5,674,980 | A | 10/1997 | Frankel et al. | |
| 5,747,641 | A | 5/1998 | Frankel et al. | |
| 5,804,604 | A | 9/1998 | Frankel et al. | |
| 5,869,478 | A | 2/1999 | Ding et al. | |
| 5,907,030 | A | 5/1999 | Shen et al. | |
| 6,093,692 | A | 7/2000 | Shen et al. | |
| 6,225,445 | B1 | 5/2001 | Shen et al. | |
| 6,316,003 | B1 | 11/2001 | Frankel et al. | |
| 6,372,717 | B1 | 4/2002 | Greff | |
| 6,498,020 | B1 | 12/2002 | Walker et al. | |
| 6,620,419 | B1 | 9/2003 | Lintner | |
| 6,730,293 | B1 | 5/2004 | Rothbard et al. | |
| 6,846,836 | B2 | 1/2005 | Hamann et al. | |

(Continued)

FOREIGN PATENT DOCUMENTS

| AU | 2019208238 A1 | 2/2021 |
| CA | 3050553 A1 | 1/2021 |

(Continued)

OTHER PUBLICATIONS

Bisaha SN, Malley MF, Pudzianowski A, Monshizadegan H, Wang P, Madsen CS, Gougoutas JZ, Stein PD (2005) A switch in enantiomer preference between mitochondrial F1F0-ATPase chemotypes. Bioorganic and medicinal chemistry letters. 15(11):2749-51.

Atwal KS, Ahmad S, Ding CZ, Stein PD, Lloyd J, Hamann LG, Green DW, Ferrara FN, Wang P, Rogers WL, Doweyko LM, Miller AV, Bisaha SN, Schmidt JB, Lil, Yost KJ, Lan HJ, Madsen CS (2004) N-[1-Aryl-2-(1-imidazolo)ethyl]-guanidine derivatives as potent inhibitors of the bovine mitochondrial F1F0 ATP hydrolase. Bioorganic and medicinal chemistry letters. 14(4):1027-1030.

Foster AB (1985) Deuterium isotope effects in the metabolism of drugs and xenobiotics: implications for drug design. Advances in Drug Research. 14:1-40.

(Continued)

*Primary Examiner* — Barbara P Badio

(57) ABSTRACT

Compounds of the following formula (I) slow the ATP-hydrolysing mode of ATP synthase and are useful for treating various diseases and disorders including cancer, particularly cancers that utilise the Warburg effect.

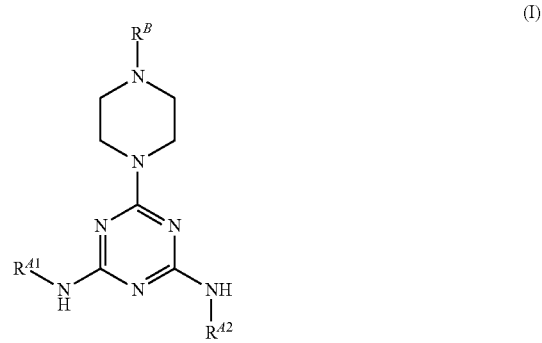

(I)

8 Claims, 45 Drawing Sheets

(56) References Cited

U.S. PATENT DOCUMENTS

| | | |
|---|---|---|
| 6,916,813 B2 | 7/2005 | Atwal et al. |
| 6,974,799 B2 | 12/2005 | Lintner |
| 6,992,169 B2 | 1/2006 | Fischer et al. |
| 7,049,286 B2 | 5/2006 | Tchelingerian |
| 7,052,704 B2 | 5/2006 | Shen et al. |
| 7,182,963 B2 | 2/2007 | Lintner |
| 7,265,092 B2 | 9/2007 | Li |
| 7,393,835 B2 | 7/2008 | Mochly-Rosen |
| 7,507,711 B2 | 3/2009 | Mochly-Rosen |
| 7,538,085 B2 | 5/2009 | Pei |
| 7,659,252 B2 | 2/2010 | Wen et al. |
| 7,671,009 B2 | 3/2010 | Ludin et al. |
| 7,833,984 B2 | 11/2010 | Mochly-Rosen |
| 7,863,417 B2 | 1/2011 | Ziegler et al. |
| 7,985,401 B2 | 7/2011 | Jiang et al. |
| 7,998,493 B2 | 8/2011 | Lintner |
| 8,080,517 B2 | 12/2011 | Bonny |
| 8,183,339 B1 | 5/2012 | Bonny |
| 8,278,413 B2 | 10/2012 | Bonny |
| 8,404,648 B2 | 3/2013 | Lintner et al. |
| 8,410,045 B2 | 4/2013 | Michel et al. |
| 8,680,022 B2 | 3/2014 | Gregory |
| 8,729,010 B2 | 5/2014 | Rothbard et al. |
| 8,791,062 B2 | 7/2014 | Hsu et al. |
| 8,865,881 B2 | 10/2014 | Balazs et al. |
| 8,946,166 B2 | 2/2015 | Garcia Sanz et al. |
| 8,974,774 B2 | 3/2015 | Dake et al. |
| 9,067,967 B2 | 6/2015 | García Antón et al. |
| 9,132,198 B2 | 9/2015 | Kelley et al. |
| 9,211,248 B2 | 12/2015 | Dake et al. |
| 9,255,124 B2 | 2/2016 | MacLean |
| 9,315,564 B2 | 4/2016 | Serraïma et al. |
| 9,351,972 B2 | 5/2016 | Dax et al. |
| 9,642,895 B2 | 5/2017 | Dai et al. |
| 9,657,288 B2 | 5/2017 | Winter et al. |
| 9,695,251 B2 | 7/2017 | Tsien et al. |
| 9,790,483 B2 | 10/2017 | Raines et al. |
| 10,053,677 B2 | 8/2018 | Greenfield |
| 10,258,695 B2 | 4/2019 | Raines et al. |
| 10,287,331 B2 | 5/2019 | Lorberboum-Galski et al. |
| 10,293,020 B2 | 5/2019 | Wilson |
| 10,385,380 B2 | 8/2019 | Whitney et al. |
| 10,428,323 B2 | 10/2019 | Raines et al. |
| 10,501,496 B2 | 12/2019 | Pei et al. |
| 10,577,303 B1 | 3/2020 | Raines et al. |
| 10,596,259 B2 | 3/2020 | Savariar et al. |
| 10,624,968 B2 | 4/2020 | Bennett et al. |
| 10,626,147 B2 | 4/2020 | Pei et al. |
| 10,660,839 B2 | 5/2020 | Peschard et al. |
| 10,668,000 B2 | 6/2020 | Peschard et al. |
| 10,729,749 B2 | 8/2020 | Greenfield et al. |
| 10,736,932 B2 | 8/2020 | Briesewitz et al. |
| 2003/0026781 A1 | 2/2003 | Anderson et al. |
| 2003/0032593 A1 | 2/2003 | Wender et al. |
| 2004/0009972 A1 | 1/2004 | Ding et al. |
| 2004/0072739 A1 | 4/2004 | Anderson et al. |
| 2004/0132667 A1 | 7/2004 | Lintner |
| 2005/0272723 A1 | 12/2005 | Glick |
| 2006/0041105 A1 | 2/2006 | Jiang et al. |
| 2007/0077259 A1 | 4/2007 | Dake et al. |
| 2008/0038203 A1 | 2/2008 | Dake et al. |
| 2008/0089950 A1 | 4/2008 | Chen et al. |
| 2008/0234183 A1 | 9/2008 | Hallbrink et al. |
| 2009/0202540 A1 | 8/2009 | Gant |
| 2009/0275099 A1 | 11/2009 | Glick |
| 2010/0093639 A1 | 4/2010 | Waugh et al. |
| 2010/0311671 A1 | 12/2010 | Johnson et al. |
| 2012/0134922 A1 | 5/2012 | Tsien et al. |
| 2013/0053433 A1 | 2/2013 | Cho et al. |
| 2013/0078295 A1 | 3/2013 | Cebrian Puche et al. |
| 2014/0140929 A1 | 5/2014 | Ahmed et al. |
| 2014/0161871 A1 | 6/2014 | Hsu et al. |
| 2014/0227174 A1 | 8/2014 | Muraski et al. |
| 2014/0234275 A1 | 8/2014 | Williams |
| 2014/0322307 A1 | 10/2014 | Ferrer Montiel et al. |
| 2015/0025221 A1 | 1/2015 | Hsu et al. |
| 2015/0359902 A1 | 12/2015 | Savariar et al. |
| 2017/0190743 A1 | 7/2017 | Pei et al. |
| 2017/0258930 A1 | 9/2017 | Muraski et al. |
| 2017/0355730 A1 | 12/2017 | Pei et al. |
| 2018/0000717 A1 | 1/2018 | Peschard et al. |
| 2018/0015137 A1 | 1/2018 | de Keizer |
| 2018/0280525 A1 | 10/2018 | Teufel et al. |
| 2019/0282654 A1 | 9/2019 | Pei et al. |
| 2019/0284239 A1 | 9/2019 | Pei |
| 2019/0284240 A1 | 9/2019 | Pei et al. |
| 2019/0358346 A1 | 11/2019 | Frost et al. |
| 2020/0032238 A1 | 1/2020 | Raines et al. |
| 2020/0138829 A1* | 5/2020 | Chen ............... A61K 31/366 |
| 2020/0247758 A1 | 8/2020 | Forrest |
| 2020/0291070 A1 | 9/2020 | Pei |
| 2020/0306253 A1 | 10/2020 | Forrest |
| 2021/0038729 A1 | 2/2021 | Zonari et al. |

FOREIGN PATENT DOCUMENTS

| | | |
|---|---|---|
| CN | 105693806 A | 6/2016 |
| JP | 06-072878 A | 3/1994 |
| SU | 320118 A3 | 2/1973 |
| WO | 8808011 A1 | 10/1988 |
| WO | 1992000091 A1 | 1/1992 |
| WO | 1992009300 A1 | 6/1992 |
| WO | 9622773 A1 | 8/1996 |
| WO | 9703657 A1 | 2/1997 |
| WO | 9712912 A1 | 4/1997 |
| WO | 0062743 A2 | 10/2000 |
| WO | 0196369 A1 | 12/2001 |
| WO | 2003050261 A2 | 6/2003 |
| WO | 2005042034 A1 | 5/2005 |
| WO | 2006073448 A2 | 7/2006 |
| WO | 2007035474 A2 | 3/2007 |
| WO | 2007108749 A1 | 9/2007 |
| WO | 2008148063 A1 | 12/2008 |
| WO | 2009036092 A2 | 3/2009 |
| WO | 2009098450 A2 | 8/2009 |
| WO | 2011008996 A2 | 1/2011 |
| WO | 2012142529 A2 | 10/2012 |
| WO | 2013086020 A1 | 6/2013 |
| WO | 2013185046 A1 | 12/2013 |
| WO | 2014123543 A2 | 8/2014 |
| WO | 2014170347 A1 | 10/2014 |
| WO | 2015179691 A2 | 11/2015 |
| WO | 2016033314 A1 | 3/2016 |
| WO | 2016067035 A1 | 5/2016 |
| WO | 2017048812 A1 | 3/2017 |
| WO | 2017191460 A1 | 11/2017 |
| WO | 2018134265 A1 | 7/2018 |
| WO | 2018232491 A1 | 12/2018 |
| WO | 2019012149 A1 | 1/2019 |
| WO | 2019148194 A2 | 8/2019 |
| WO | 2019148195 A2 | 8/2019 |
| WO | 2019149450 A1 | 8/2019 |
| WO | 2021186325 A1 | 9/2021 |

OTHER PUBLICATIONS

Vander Heiden MG, Cantley LC, Thompson CB (2009) Understanding the Warburg effect: the metabolic requirements of cell proliferation. Science. 324(5930):1029-1033.

Patani GA, Lavoie EJ (1996) Bioisosterism: a rational approach in drug design. Chemical reviews. 96(8):3147-3176.

Hong S, Pedersen PL (2008) ATP synthase and the actions of inhibitors utilized to study its roles in human health, disease, and other scientific areas. Microbiology and Molecular Biology Reviews. 72(4):590-641.

Chinese patent Examiner's examination report for Chinese patent application CN105693806A. Machine translation thereof is also submitted.

Salomon AR, Voehringer DW, Herzenberg LA, Khosla C (2000) Understanding and exploiting the mechanistic basis for selectivity of polyketide inhibitors of F0F1-ATPase. Proceedings of the National Academy of Sciences. 97(26):14766-14771.

(56) References Cited

OTHER PUBLICATIONS

"Deuterium" Encyclopedia Britannica online. Accessed Dec. 22, 2021. https://www.britannica.com/science/deuterium.
Sgarbi G, Barbato S, Costanzini A, Solaini G, Baracca A (2018) The role of the ATPase inhibitor factor 1 (IF1) in cancer cells adaptation to hypoxia and anoxia. Biochimica et Biophysica Acta (BBA)—Bioenergetics. 1859 (2):99-109.
Yin T, Lu L, Xiong Z, Wei S, Cui D (2015) ATPase inhibitory factor 1 is a prognostic marker and contributes to proliferation and invasion of human gastric cancer cells. Biomedicine & Pharmacotherapy. 70:90-6.
Johnson KM, Swenson L, Opipari JR AW, Reuter R, Zarrabi N, Fierke Ca, . . . & Glick GD (2009) Mechanistic basis for differential inhibition of the F1F0-ATPase by aurovertin. Biopolymers: Original Research on Biomolecules. 91(10):830-840.
Forrest MD (2015) Why cancer cells have a more hyperpolarised mitochondrial membrane potential and emergent prospects for therapy. bioRxiv. 025197.
Unpublished U.S. Appl. No. 16/571,759, filed Sep. 16, 2019. Inventor/Applicant: Michael David Forrest.
Unpublished U.S. Appl. No. 16/514,246, filed Jul. 17, 2019. Inventor/Applicant: Michael David Forrest.
Unpublished U.S. Appl. No. 16/679,184, filed Nov. 9, 2019. Inventor/Applicant: Michael David Forrest.
Unpublished U.S. Appl. No. 16/907,195, filed Jun. 20, 2020. Inventor/Applicant: Michael David Forrest.
Unpublished U.S. Appl. No. 17/092,271, filed Nov. 8, 2020. Inventor/Applicant: Michael David Forrest.
Unpublished U.S. Appl. No. 17/166,011, filed Feb. 3, 2021. Inventor/Applicant: Michael David Forrest.
Unpublished U.S. Appl. No. 17/316,787, filed May 11, 2021. Inventor/Applicant: Michael David Forrest.
Unpublished U.S. Appl. No. 17/383,575, filed Jul. 23, 2021. Inventor/Applicant: Michael David Forrest.
Unpublished U.S. Appl. No. 17/493,887, filed Oct. 5, 2021. Inventor/Applicant: Michael David Forrest.
Unpublished U.S. Appl. No. 16/939,094, filed Jul. 27, 2020. Inventor/Applicant: Michael David Forrest.
Unpublished U.S. Appl. No. 62/878,418, filed Jul. 25, 2019. Inventor/Applicant: Michael David Forrest.
Title: "Patents, yes; ideas, maybe". The Economist, Hong Kong. Oct. 14, 2010. Online: https://www.economist.com/business/2010/10/14/patents-yes-ideas-maybe (accessed on Oct. 14, 2021).
Title: "CNIPA clamps down on 'abnormal' application practices in fresh drive for patent quality". Author: Xiaoling Duan (of Wanhuida Intellectual Property, China). Publisher: IAM Media. With offices in London, Hong Kong, and Washington DC. Online: https://www.iam-media.com/cnipa-clamps-down-abnormal-application-practices-in-fresh-drive-patent-quality (accessed on Oct. 14, 2021).
Notice of passing examination, and acceptance of patent application, in Australia. For AU application No. 2018209175. Includes a list of prior art documents considered during Examination. Also submitted, in a separate document, are the accepted claims for AU application No. 2018209175.
Unpublished U.S. Appl. No. 17/201,570, filed Mar. 15, 2021. Inventor/Applicant: Michael David Forrest.
Unpublished U.S. Appl. No. 17/576,963, filed Jan. 16, 2022. Inventor/Applicant: Michael David Forrest.
Unpublished U.S. Appl. No. 63/302,034, filed Jan. 22, 2022. Inventor/Applicant: Michael David Forrest.
Unpublished U.S. Appl. No. 17/705,283, filed Mar. 26, 2022. Inventor/Applicant: Michael David Forrest.
Atwal KS, Wang P, Rogers WL, Sleph P, Monshizadegan H, Ferrara FN, Traeger S, Green DW, Grover GJ (2004) Small molecule mitochondrial F1F0 ATPase hydrolase inhibitors as cardioprotective agents. Identification of 4-(N-arylimidazole)-substituted benzopyran derivatives as selective hydrolase inhibitors. Journal of medicinal chemistry. 47(5):1081-1084.
Hamann LG, Ding CZ, Miller AV, Madsen CS, Wang P, Stein PD, Pudzianowski AT, Green DW, Monshizadegan H, Atwal KS (2004) Benzodiazepine-based selective inhibitors of mitochondrial F1FO ATP hydrolase. Bioorganic & medicinal chemistry letters. 14(4):1031-1034.
Grover GJ, Marone PA, Koetzner L, Seto-Young D (2008) Energetic signalling in the control of mitochondrial F1F0 ATP synthase activity in health and disease. The international journal of biochemistry & cell biology. 40(12):2698-2701.
Grover GJ, Malm J (2008) Pharmacological Profile of the Selective Mitochondrial F1F0 ATP Hydrolase Inhibitor BMS-199264 in Myocardial Ischemia. Cardiovascular therapeutics. 26(4):287-296.
Grover GJ, Atwal KS, Sleph PG, Wang FL, Monshizadegan H, Monticello T, Green DW (2004) Excessive ATP hydrolysis in ischemic myocardium by mitochondrial F1F0-ATPase: effect of selective pharmacological inhibition of mitochondrial ATPase hydrolase activity. American Journal of Physiology-Heart and Circulatory Physiology. 287(4):H1747-H1755.
Ivanes F (2013) New mechanisms of protection of cardiomyocytes from ischemia/reperfusion injury. Doctoral dissertation. Université Claude Bernard-Lyon 1, Lyon, France.
Ivanes F, Faccenda D, Gatliff J, Ahmed AA, Cocco S, Cheng CHK, Allan E, Russell C, Duchen MR, Campanella M (2014) The compound BTB06584 is an IF1-dependent selective inhibitor of the mitochondrial F1Fo-ATPase. British journal of pharmacology. 171(18):4193-4206.
Kramar R, Hohenegger M, Srour AN, Khanakah G (1984) Oligomycin toxicity in intact rats. Inflammation Research. 15(5):660-3.
Gao C, Shen Y, Jin F, Miao Y, Qiu X (2016) Cancer stem cells in small cell lung cancer cell line H446: higher dependency on oxidative phosphorylation and mitochondrial substrate-level phosphorylation than non-stem cancer cells. PloS one. 11(5):e0154576.
Cuezva JM, Krajewska M, De Heredia ML, Krajewski S, Santamaría G, Kim H, Zapata JM, Marusawa H, Chamorro M, Reed JC (2002) The bioenergetic signature of cancer. Cancer research. 62(22):6674-81.
Aldea M, Clofent J, De Arenas CN, Chamorro M, Velasco M, Berrendero JR, Navarro C, Cuezva JM (2011) Reverse phase protein microarrays quantify and validate the bioenergetic signature as biomarker in colorectal cancer. Cancer letters. 311(2):210-8.
Hjerpe E, Brage SE, Carlson J, Stolt MF, Schedvins K, Johansson H, Shoshan M, Åvall-Lundqvist E (2013) Metabolic markers GAPDH, PKM2, ATP5B and BEC-index in advanced serous ovarian cancer. BMC clinical pathology. 13(1):30.
Johnson KM, Chen X, Boitano A, Swenson L, Opipari JR AW, Glick GD (2005) Identification and validation of the mitochondrial F1F0-ATPase as the molecular target of the immunomodulatory benzodiazepine Bz-423. Chemistry & biology. 12(4):485-96.
Hanahan D, Weinberg RA (2000) The hallmarks of cancer. Cell. 100(1):57-70.
Walenta S, Wetterling M, Lehrke M, Schwickert G, Sundfør K, Rofstad EK, Mueller-Klieser W (2000) High lactate levels predict likelihood of metastases, tumor recurrence, and restricted patient survival in human cervical cancers. Cancer research. 60(4):916-21.
Paull KD, Shoemaker RH, Hodes L, Monks A, Scudiero DA, Rubinstein L, Plowman J, Boyd MR (1989) Display and analysis of patterns of differential activity of drugs against human tumor cell lines: development of mean graph and Compare algorithm. JNCI: Journal of the National Cancer Institute. 81(14):1088-92.
Holbeck SL, Collins JM, Doroshow JH (2010) Analysis of Food and Drug Administration-approved anticancer agents in the NCI60 panel of human tumor cell lines. Molecular cancer therapeutics. 9(5):1451-60.
Reinhold WC, Sunshine M, Liu H, Varma S, Kohn KW, Morris J, Doroshow J, Pommier Y (2012) CellMiner: a web-based suite of genomic and pharmacologic tools to explore transcript and drug patterns in the NCI-60 cell line set. Cancer research. 72(14):3499-511.
Gholami AM, Hahne H, Wu Z, Auer FJ, Meng C, Wilhelm M, Kuster B (2013) Global proteome analysis of the NCI-60 cell line panel. Cell reports. 4(3):609-20.
Shoemaker RH (2006) The NCI60 human tumour cell line anticancer drug screen. Nature Reviews Cancer. 6:813-23.

(56) References Cited

OTHER PUBLICATIONS

Martineau LC (2012) Simple thermodynamic model of unassisted proton shuttle uncoupling and prediction of activity from calculated speciation, lipophilicity, and molecular geometry. Journal of theoretical biology. 303:33-61.

Jacques V, Czarnik AW, Judge TM, Van Der Ploeg LH, Dewitt SH (2015) Differentiation of antiinflammatory and antitumorigenic properties of stabilized enantiomers of thalidomide analogs. Proceedings of the National Academy of Sciences. 112(12):E1471-9.

Houston MA, Augenlicht LH, Heerdt BG (2011) Stable differences in intrinsic mitochondrial membrane potential of tumor cell subpopulations reflect phenotypic heterogeneity. International journal of cell biology.

Heerdt BG, Houston MA, Augenlicht LH (2005) The intrinsic mitochondrial membrane potential of colonic carcinoma cells is linked to the probability of tumor progression. Cancer Research. 65:9861-9867.

Heerdt BG, Houston MA, Augenlicht LH (2006) Growth properties of colonic tumor cells are a function of the intrinsic mitochondrial membrane potential. Cancer Research. 66(3):1591-6.

Bonnet S, Archer SL, Allalunis-Turner J, Haromy A, Beaulieu C, Thompson R, Lee CT, Lopaschuk GD, Puttagunta L, Bonnet S, Harry G (2007) A mitochondria-K+ channel axis is suppressed in cancer and its normalization promotes apoptosis and inhibits cancer growth. Cancer cell. 11(1):37-51.

Ye XQ, Wang GH, Huang GJ, Bian XW, Qian GS, Yu SC (2011) Heterogeneity of mitochondrial membrane potential: a novel tool to isolate and identify cancer stem cells from a tumor mass? Stem Cell Reviews and Reports. 7(1):153-60.

Lee DG, Choi BK, Kim YH, Oh HS, Park SH, Bae YS, Kwon BS (2016) The repopulating cancer cells in melanoma are characterized by increased mitochondrial membrane potential. Cancer Letters. 382(2):186-94.

Boonstra J, Post JA (2004) Molecular events associated with reactive oxygen species and cell cycle progression in mammalian cells. Gene. 337:1-3.

Fantin VR, St-Pierre J, Leder P (2006) Attenuation of LDH-A expression uncovers a link between glycolysis, mitochondrial physiology, and tumor maintenance. Cancer cell. 9(6):425-434.

Christofk HR, Vander Heiden MG, Harris MH, Ramanathan A, Gerszten RE, Wei R, Fleming MD, Schreiber SL, Cantley LC (2008) The M2 splice isoform of pyruvate kinase is important for cancer metabolism and tumour growth. Nature. 452(7184):230-233.

Bonnet S, Archer SL, Allalunis-Turner J, Haromy A, Beaulieu C, Thompson R, Lee CT, Lopaschuk GD, Puttagunta L, Bonnet S, Harry G, Hashimoto K, Porter CJ, Andrade MA, Thebaud B, Michelakis ED (2007) A mitochondria-K+ channel axis is suppressed in cancer and its normalization promotes apoptosis and inhibits cancer growth. Cancer cell. 11(1):37-51.

Wadhwa R, Sugihara T, Yoshida A, Nomura H, Reddel RR, Simpson R, Maruta H, Kaul SC (2000) Selective toxicity of MKT-077 to cancer cells is mediated by its binding to the hsp70 family protein mot-2 and reactivation of p53 function. Cancer Research. 60:6818-6821.

Schulz TJ, Thierbach R, Voigt A, Drewes G, Mietzner B, Steinberg P, Pfeiffer AFH, Ristow M (2006) Induction of oxidative metabolism by mitochondrial frataxin inhibits cancer growth: Otto Warburg revisited. Journal of Biological Chemistry. 281:977-81.

Devi GS, Prasad MH, Saraswathi I, Raghu D, Rao DN, Reddy PP (2000) Free radicals antioxidant enzymes and lipid peroxidation in different types of leukemias. Clinica Chimica Acta. 293:53-62.

Szatrowski TP, Nathan CF (1991) Production of large amounts of hydrogen peroxide by human tumor cells. Cancer research. 51(3):794-798.

Lu W, Hu Y, Chen G, Chen Z, Zhang H, Wang F, Feng L, Pelicano H, Wang H, Keating MJ, Liu J (2012) Novel role of NOX in supporting aerobic glycolysis in cancer cells with mitochondrial dysfunction and as a potential target for cancer therapy. PLoS biology. 10(5):e1001326.

Block K, Gorin Y (2012) Aiding and abetting roles of NOX oxidases in cellular transformation. Nature Reviews Cancer. 12(9):627-37.

Ben-Porath I, Thomson MW, Carey VJ, Ge R, Bell GW, Regev A, Weinberg RA (2008) An embryonic stem cell-like gene expression signature in poorly differentiated aggressive human tumors. Nature genetics. 40(5):499.

Chung S, Dzeja PP, Faustino RS, Perez-Terzic C, Behfar A, Terzic A (2007) Mitochondrial oxidative metabolism is required for the cardiac differentiation of stem cells. Nature Clinical Practice Cardiovascular Medicine. 4:S60-S67.

Teslaa T, Teitell MA (2014) Pluripotent stem cell energy metabolism: an update. The EMBO journal. e201490446.

Hong Y, Stambrook PJ (2004) Restoration of an absent G1 arrest and protection from apoptosis in embryonic stem cells after ionizing radiation. Proceedings of the National Academy of Sciences (PNAS). 101(40):14443-14448.

Gordon CJ (1991) Toxic-induced hypothermia and hypometabolism: Do they increase uncertainty in the extrapolation of toxicological data from experimental animals to humans? Neuroscience & Biobehavioral Reviews. 15(1):95-8.

Zamzami N, Kroemer G (2001) The mitochondrion in apoptosis: how Pandora's box opens. Nature Reviews Molecular Cell Biology. 2:67-71.

Donadelli M, Dando I, Dalla Pozza E, Palmieri M (2015) Mitochondrial uncoupling protein 2 and pancreatic cancer: A new potential target therapy. World journal of gastroenterology. 21(11):3232.

Ayyasamy V, Owens KM, Desouki MM, Liang P, Bakin A, Thangaraj K, Buchsbaum DJ, Lobuglio AF, Singh KK (2011) Cellular Model of Warburg Effect Identifies Tumor Promoting Function of UCP2 in Breast Cancer and Its Suppression by Genipin. Plos ONE. 6(9):e24792. doi:10.1371/journal.pone.0024792.

Bindu B, Bindra A, Rath G (2017) Temperature management under general anesthesia: Compulsion or option. Journal of anaesthesiology, clinical pharmacology. 33(3):306.

Bell EF (1983) Infant incubators and radiant warmers. Early human development. 8(3-4):351-75.

Nair AB, Jacob S (2016) A simple practice guide for dose conversion between animals and human. Journal of basic and clinical pharmacy. 7(2):27.

Ward TH, Cummings J, Dean E, Greystoke A, Hou JM, Backen A, Ranson M, Dive C (2008) Biomarkers of apoptosis. British journal of cancer. 99(6):841.

Zheng J, Ramirez VD (2000) Inhibition of mitochondrial proton F0F1-ATPase/ATP synthase by polyphenolic phytochemicals. British journal of pharmacology. 130(5):1115-23.

Zhu A, Lee D, Shim H (2011) Metabolic positron emission tomography imaging in cancer detection and therapy response. In Seminars in oncology (vol. 38, No. 1, pp. 55-69). WB Saunders.

Zhang L, Martins AF, Mai Y, Zhao P, Funk AM, Clavijo Jordan MV, Zhang S, Chen W, Wu Y, Sherry AD (2017) Imaging Extracellular Lactate In Vitro and In Vivo Using CEST MRI and a Paramagnetic Shift Reagent. Chemistry—A European Journal. 23(8):1752-6.

Chen LQ, Pagel MD (2015) Evaluating pH in the Extracellular Tumor Microenvironment Using CEST MRI and Other Imaging Methods. Advances in radiology.

Anderson M, Moshnikova A, Engelman DM, Reshetnyak YK, Andreev OA (2016) Probe for the measurement of cell surface pH in vivo and ex vivo. Proceedings of the National Academy of Sciences (PNAS). 113(29):8177-8181.

Manzoor AA, Schroeder T, Dewhirst MW (2008) One-stop-shop tumor imaging: buy hypoxia, get lactate free. The Journal of clinical investigation. 118(5):1616.

Ng J, Shuryak I (2015) Minimizing second cancer risk following radiotherapy: current perspectives. Cancer management and research. 7:1.

Armstrong GT, Kawashima T, Leisenring W, Stratton K, Stovall M, Hudson MM, Sklar CA, Robison LL, Oeffinger KC (2014) Aging and risk of severe, disabling, life-threatening, and fatal events in the childhood cancer survivor study. Journal of clinical oncology. 32(12):1218.

Castro RF, Azzalis LA, Feder D, Perazzo FF, Pereira EC, Junqueira VB, Rocha KC, Machado CD, Paschoal FC, Gnann LA, Fonseca FL (2012) Safety and efficacy analysis of liposomal insulin-like growth

(56) References Cited

OTHER PUBLICATIONS factor-1 in a fluid gel formulation for hair-loss treatment in a hamster model. Clinical and Experimental Dermatology: Experimental dermatology. 37(8):909-12.

Patel A, Cholkar K, Agrahari V, Mitra AK (2013) Ocular drug delivery systems: an overview. World journal of pharmacology. 2(2):47.

Gaudana R, Ananthula HK, Parenky A, Mitra AK (2010) Ocular drug delivery. The AAPS journal. 12(3):348-60.

Wong WL, Su X, Li X, Cheung CM, Klein R, Cheng CY, Wong TY (2014) Global prevalence of age-related macular degeneration and disease burden projection for 2020 and 2040: a systematic review and meta-analysis. The Lancet Global Health. 2(2):e106-16.

Hao J, Li SK (2019) Inner ear drug delivery: Recent advances, challenges, and perspective. European Journal of Pharmaceutical Sciences. 126:82-92.

Liu H, Hao J, Li KS (2013) Current strategies for drug delivery to the inner ear. Acta Pharmaceutica Sinica B. 3(2):86-96.

Lin MT, Beal MF (2006) Mitochondrial dysfunction and oxidative stress in neurodegenerative diseases. Nature. 443(7113):787-95.

Kang YS, Jung HJ, Oh JS, Song DY (2016) Use of PEGylated Immunoliposomes to Deliver Dopamine Across the Blood-Brain Barrier in a Rat Model of Parkinson's Disease. CNS Neuroscience & Therapeutics. 22(10):817-23.

Di Gioia S, Trapani A, Mandracchia D, De Giglio E, Cometa S, Mangini V, Arnesano F, Belgiovine G, Castellani S, Pace L, Lavecchia MA (2015) Intranasal delivery of dopamine to the striatum using glycol chitosan/sulfobutylether-β-cyclodextrin based nanoparticles. European Journal of Pharmaceutics and Biopharmaceutics. 94:180-93.

Oorschot DE (1996) Total No. of neurons in the neostriatal, pallidal, subthalamic, and substantia nigral nuclei of the rat basal ganglia: a stereological study using the cavalieri and optical disector methods. Journal of Comparative Neurology. 366:580-599.

Naoi M, Maruyama W (1999) Cell death of dopamine neurons in aging and Parkinson's disease. Mechanisms of ageing and development. 111(2):175-88.

Strong R, Miller RA, Astle CM, Baur JA, De Cabo R, Fernandez E, Guo W, Javors M, Kirkland JL, Nelson JF, Sinclair DA (2012) Evaluation of resveratrol, green tea extract, curcumin, oxaloacetic acid, and medium-chain triglyceride oil on life span of genetically heterogeneous mice. Journals of Gerontology Series A: Biomedical Sciences and Medical Sciences. 68(1):6-16.

Harrison DE, Strong R, Sharp ZD, Nelson JF, Astle CM, Flurkey K, Nadon NL, Wilkinson JE, Frenkel K, Carter CS, Pahor M (2009) Rapamycin fed late in life extends lifespan in genetically heterogeneous mice. Nature. 460(7253):392.

Colman RJ, Anderson RM, Johnson SC, Kastman EK, Kosmatka KJ, Beasley TM, Allison DB, Cruzen C, Simmons HA, Kemnitz JW, Weindruch R (2009) Caloric restriction delays disease onset and mortality in rhesus monkeys. Science. 325(5937):201-4.

Ackert-Bicknell CL, Anderson LC, Sheehan S, Hill WG, Chang B, Churchill GA, Chesler EJ, Korstanje R, Peters LL (2017) Aging research using mouse models. Current protocols in mouse biology. 5(2):95-133.

Sukoff Rizzo SJ, Anderson LC, Green TL, Mcgarr T, Wells G, Winter SS (2018) Assessing Healthspan and Lifespan Measures in Aging Mice: Optimization of Testing Protocols, Replicability, and Rater Reliability. Current Protocols in Mouse Biology. 8(2):e45.

Richardson A, Fischer KE, Speakman JR, De Cabo R, Mitchell SJ, Peterson CA, Rabinovitch P, Chiao YA, Taffet G, Miller RA, Rentería RC (2015) Measures of healthspan as indices of aging in mice—a recommendation. Journals of Gerontology Series A: Biomedical Sciences and Medical Sciences. 71(4):427-30.

Vermeij WP, Hoeijmakers JH, Pothof J (2016) Genome integrity in aging: human syndromes, mouse models, and therapeutic options. Annual review of pharmacology and toxicology. 56:427-45.

Harkema L, Youssef SA, De Bruin A (2016) Pathology of mouse models of accelerated aging. Veterinary pathology. 53(2):366-89.

Hasty P, Campisi J, Hoeijmakers J, Van Steeg H, Vijg J (2003) Aging and genome maintenance: lessons from the mouse? Science. 299(5611):1355-9.

De Boer J, Hoeijmakers JH (1999) Cancer from the outside, aging from the inside: mouse models to study the consequences of defective nucleotide excision repair. Biochimie. 81(1-2):127-37.

Baker DJ, Jeganathan KB, Cameron JD, Thompson M, Juneja S, Kopecka A, Kumar R, Jenkins RB, De Groen PC, Roche P, Van Deursen JM (2004) BubR1 insufficiency causes early onset of aging-associated phenotypes and infertility in mice. Nature genetics. 36(7):744.

De Boer J, De Wit J, Van Steeg H, Berg RJ, Morreau H, Visser P, Lehmann AR, Duran M, Hoeijmakers JH, Weeda G (1998) A mouse model for the basal transcription/DNA repair syndrome trichothiodystrophy. Molecular cell. 1(7):981-90.

De Boer J, Andressoo JO, De Wit J, Huijmans J, Beems RB, Van Steeg H, Weeda G, Van Der Horst GT, Van Leeuwen W, Themmen AP, Meradji M (2002) Premature aging in mice deficient in DNA repair and transcription. Science. 296(5571):1276-9.

Andressoo JO, Mitchell JR, De Wit J, Hoogstraten D, Volker M, Toussaint W, Speksnijder E, Beems RB, Van Steeg H, Jans J, De Zeeuw CI (2006) An Xpd mouse model for the combined xeroderma pigmentosum/Cockayne syndrome exhibiting both cancer predisposition and segmental progeria. Cancer cell. 10(2):121-32.

Cheo DL, Ruven HJ, Meira LB, Hammer RE, Burns DK, Tappe NJ, Van Zeeland AA, Mullenders LH, Friedberg EC (1997) Characterization of defective nucleotide excision repair in XPC mutant mice. Mutation Research/Fundamental and Molecular Mechanisms of Mutagenesis. 374(1):1-9.

Melis JP, Wijnhoven SW, Beems RB, Roodbergen M, Van Den Berg J, Moon H, Friedberg E, Van Der Horst GT, Hoeijmakers JH, Vijg J, Van Steeg H (2008) Mouse models for xeroderma pigmentosum group A and group C show divergent cancer phenotypes. Cancer research. 68(5):1347-53.

Niedernhofer LJ, Garinis Ga, Raams A, Lalai AS, Robinson AR, Appeldoorn E, Odijk H, Oostendorp R, Ahmad A, Van Leeuwen W, Theil AF (2006) A new progeroid syndrome reveals that genotoxic stress suppresses the somatotroph axis. Nature. 444(7122):1038.

Weeda G, Donker I, De Wit J, Morreau H, Janssens R, Vissers cj, Nigg A, Van Steeg H, Bootsma D, Hoeijmakers JH (1997) Disruption of mouse ERCC1 results in a novel repair syndrome with growth failure, nuclear abnormalities and senescence. Current Biology. 7(6):427-39.

Spoor M, Nagtegaal AP, Ridwan Y, Borgesius NZ, Van Alphen B, Van Der Pluijm I, Hoeijmakers JH, Frens MA, Borst JG (2012) Accelerated loss of hearing and vision in the DNA-repair deficient Ercc1δ/-mouse. Mechanisms of ageing and development. 133(2-3):59-67.

Vogel H, Lim DS, Karsenty G, Finegold M, Hasty P (1999) Deletion of Ku86 causes early onset of senescence in mice. Proceedings of the National Academy of Sciences (PNAS). 96(19):10770-5.

Reiling E, Dollé ME, Youssef SA, Lee M, Nagarajah B, Roodbergen M, De Bruin A, Hoeijmakers JH, Vijg J, Van Steeg H, Hasty P (2014) The progeroid phenotype of Ku80 deficiency is dominant over DNA-PKCS deficiency. PloS one. 9(4):e93568.

Zhang Y, Padalecki SS, Chaudhuri AR, De Waal E, Goins BA, Grubbs B, Ikeno Y, Richardson A, Mundy GR, Herman B (2007) Caspase-2 deficiency enhances aging-related traits in mice. Mechanisms of ageing and development. 128(2):213-21.

Bergeron L, Perez GI, MacDonald G, Shi L, Sun Y, Jurisicova A, Varmuza S, Latham KE, Flaws JA, Salter JC, Hara H (1998) Defects in regulation of apoptosis in caspase-2-deficient mice. Genes & development. 12(9):1304-14.

Nadon NL, Strong R, Miller RA, Nelson J, Javors M, Sharp ZD, Peralba JM, Harrison DE (2008) Design of aging intervention studies: the NIA interventions testing program. Age. 30(4):187-99.

Miller RA, Harrison DE, Astle CM, Floyd RA, Flurkey K, Hensley KL, Javors MA, Leeuwenburgh C, Nelson JF, Ongini E, Nadon NL (2007) An aging interventions testing program: study design and interim report. Aging cell. 6(4):565-75.

Martin-Montalvo A, Mercken EM, Mitchell SJ, Palacios HH, Mote PL, Scheibye-Knudsen M, Gomes AP, Ward TM, Minor RK, Blouin

(56) References Cited

OTHER PUBLICATIONS

MJ, Schwab M (2013) Metformin improves healthspan and lifespan in mice. Nature communications. 4:2192.
Miller RA, Harrison DE, Astle CM, Baur JA, Boyd AR, De Cabo R, Fernandez E, Flurkey K, Javors MA, Nelson JF, Orihuela CJ (2011) Rapamycin, but not resveratrol or simvastatin, extends life span of genetically heterogeneous mice. The Journals of Gerontology: Series A. 66(2):191-201.
Strong R, Miller RA, Astle CM, Floyd RA, Flurkey K, Hensley KL, Javors MA, Leeuwenburgh C, Nelson JF, Ongini E, Nadon NL (2008) Nordihydroguaiaretic acid and aspirin increase lifespan of genetically heterogeneous male mice. Aging cell. 7(5):641-50.
Baur JA, Pearson KJ, Price NL, Jamieson HA, Lerin C, Kalra A, Prabhu VV, Allard JS, Lopez-Lluch G, Lewis K, Pistell PJ (2006) Resveratrol improves health and survival of mice on a high-calorie diet. Nature. 444(7117):337.
Spilman P, Podlutskaya N, Hart MJ, Debnath J, Gorostiza O, Bredesen D, Richardson A, Strong R, Galvan V (2010) Inhibition of mTOR by rapamycin abolishes cognitive deficits and reduces amyloid-β levels in a mouse model of Alzheimer's disease. PloS one. 5(4):e9979.
Morley JE, Armbrecht HJ, Farr SA, Kumar VB (2012) The senescence accelerated mouse (SAMP8) as a model for oxidative stress and Alzheimer's disease. Biochimica et Biophysica Acta (BBA)-Molecular Basis of Disease. 1822(5):650-6.
Zahr NM, Mayer D, Pfefferbaum A, Sullivan EV (2008) Low striatal glutamate levels underlie cognitive decline in the elderly: evidence from in vivo molecular spectroscopy. Cerebral Cortex. 18(10):2241-50.
Rupsingh R, Borrie M, Smith M, Wells JL, Bartha R (2011) Reduced hippocampal glutamate in Alzheimer disease. Neurobiology of aging. 32(5):802-10.
Fayed N, Modrego PJ, Rojas-Salinas G, Aguilar K (2011) Brain glutamate levels are decreased in Alzheimer's disease: a magnetic resonance spectroscopy study. American Journal of Alzheimer's Disease & Other Dementias. (6):450-6.
Yurko-Mauro K (2010) Cognitive and cardiovascular benefits of docosahexaenoic acid in aging and cognitive decline. Current Alzheimer Research. 7(3):190-6.
Syslová K, Böhmová A, Mikoška M, Kuzma M, Pelclová D, Kačer P (2014) Multimarker screening of oxidative stress in aging. Oxidative medicine and cellular longevity. 2014.
Stadtman ER, Berlett BS (1998) Reactive oxygen-mediated protein oxidation in aging and disease. Drug metabolism reviews. 30(2):225-43.
Nomura Y, Wang BX, Qi SB, Namba T, Kaneko S (1989) Biochemical changes related to aging in the senescence-accelerated mouse. Experimental gerontology. 24(1):49-55.
Kitamura Y, Zhao XH, Ohnuki T, Takei M, Nomura Y (1992) Age-related changes in transmitter glutamate and NMDA receptor/channels in the brain of senescence-accelerated mouse. Neuroscience letters. 137(2):169-72.
Nomura Y, Kitamura Y, Ohnuki T, Arima T, Yamanaka Y, Sasaki K, Oomura Y (1997) Alterations in acetylcholine, NMDA, benzodiazepine receptors and protein kinase C in the brain of the senescence-accelerated mouse: an animal model useful for studies on cognitive enhancers. Behavioural brain research. 83(1-2):51-5.
Nomura Y, Okuma Y (1999) Age-related defects in lifespan and learning ability in SAMP8 mice. Neurobiology of aging. 20(2):111-5.
Tomobe K, Nomura Y (2009) Neurochemistry, neuropathology, and heredity in SAMP8: a mouse model of senescence. Neurochemical research. 34(4):660-9.
Zhao XH, Kitamura Y, Nomura Y (1992) Age-related changes in NMDA-induced [3H] acetylcholine release from brain slices of senescene-accelerated mouse. International journal of developmental neuroscience. 10(2):121-9.
Mills KF, Yoshida S, Stein LR, Grozio A, Kubota S, Sasaki Y, Redpath P, Migaud ME, Apte RS, Uchida K, Yoshino J (2016) Long-term administration of nicotinamide mononucleotide mitigates age-associated physiological decline in mice. Cell metabolism. 24(6):795-806.
Peto MV, De La Guardia C, Winslow K, Ho A, Fortney K, Morgen E (2017) MortalityPredictors.org: a manually-curated database of published biomarkers of human all-cause mortality. Aging (Albany NY). 9(8):1916.
Cheng D, Logge W, Low JK, Garner B, Karl T (2013) Novel behavioural characteristics of the APP Swe/PS1AE9 transgenic mouse model of Alzheimer's disease. Behavioural brain research. 245:120-7.
Borgesius NZ, De Waard MC, Van Der Pluijm I, Omrani A, Zondag GC, Van Der Horst GT, Melton DW, Hoeijmakers JH, Jaarsma D, Elgersma Y (2011) Accelerated age-related cognitive decline and neurodegeneration, caused by deficient DNA repair. Journal of Neuroscience. 31(35):12543-53.
Rangaraju S, Solis GM, Thompson RC, Gomez-Amaro RL, Kurian L, Encalada SE, Niculescu III AB, Salomon Dr, Petrascheck M (2015) Suppression of transcriptional drift extends C. elegans lifespan by postponing the onset of mortality. Elife. 4:e08833.
Barger JL, Anderson RM, Newton MA, Da Silva C, Vann JA, Pugh TD, Someya S, Prolla TA, Weindruch R (2015) A conserved transcriptional signature of delayed aging and reduced disease vulnerability is partially mediated by SIRT3. PloS One. 10(4):e0120738.
Yaku K, Okabe K, Nakagawa T (2018) NAD metabolism: Implications in aging and longevity. Ageing research reviews. 47:1-17.
Ivanisevic J, Stauch KL, Petrascheck M, Benton HP, Epstein AA, Fang M, Gorantla S, Tran M, Hoang L, Kurczy ME, Boska MD (2016) Metabolic drift in the aging brain. Aging (Albany NY). 8(5):1000.
Huxley AF (1959) Ion movements during nerve activity. Annals of the New York Academy of Sciences. 81(2):221-46.
Chapman RA (1967) Dependence on temperature of the conduction velocity of the action potential of the squid giant axon. Nature. 213(5081):1143.
Maldonado CA, Wooley BD, Pancrazio JJ (2015) The excitatory effect of temperature on the Hodgkin-Huxley model. The Premier Undergraduate Neuroscience Journal.[interaktyvus].
Fitzhugh R (1966) Theoretical effect of temperature on threshold in the Hodgkin-Huxley nerve model. The Journal of general physiology. 49(5):989-1005.
Kuang S, Wang J, Zeng T, Cao A (2008) Thermal impact on spiking properties in Hodgkin-Huxley neuron with synaptic stimulus. Pramana. 70(1):183-90.
Goldin MA, Mindlin GB (2017) Temperature manipulation of neuronal dynamics in a forebrain motor control nucleus. PLoS computational biology. 13(8):e1005699.
Garedew A, Henderson SO, Moncada S (2010) Activated macrophages utilize glycolytic ATP to maintain mitochondrial membrane potential and prevent apoptotic cell death. Cell Death & Differentiation. 17(10):1540-50.
Mantovani A, Marchesi F, Malesci A, Laghi L, Allavena P (2017) Tumour-associated macrophages as treatment targets in oncology. Nature reviews Clinical oncology. 14(7):399-416.
Colotta F, Allavena P, Sica A, Garlanda C, Mantovani A (2009) Cancer-related inflammation, the seventh hallmark of cancer: links to genetic instability. Carcinogenesis. 30(7):1073-81.
Honeycutt JB, Wahl A, Baker C, Spagnuolo Ra, Foster J, Zakharova O, Wietgrefe S, Caro-Vegas C, Madden V, Sharpe G, Haase AT (2016) Macrophages sustain HIV replication in vivo independently of T cells. The Journal of clinical investigation. 126(4):1353.
Arainga M, Edagwa B, Mosley RL, Poluektova LY, Gorantla S, Gendelman HE (2017) A mature macrophage is a principal HIV-1 cellular reservoir in humanized mice after treatment with long acting antiretroviral therapy. Retrovirology. 14(1):17.
Appelberg KS, Wallet MA, Taylor JP, Cash MN, Sleasman JW, Goodenow MM (2017) HIV-1 Infection Primes Macrophages through STAT Signaling to Promote Enhanced Inflammation and Viral Replication. AIDS Research and Human Retroviruses. 33(7):690-702.
Burdo TH, Lentz MR, Autissier P, Krishnan A, Halpern E, Letendre S, Rosenberg ES, Ellis RJ, Williams KC (2011) Soluble CD163 made by monocyte/macrophages is a novel marker of HIV activity

(56) References Cited

OTHER PUBLICATIONS in early and chronic infection prior to and after anti-retroviral therapy. Journal of Infectious Diseases. 204(1):154-63.
Blond D, Raoul H, Le Grand R, Dormont D (2000) Nitric oxide synthesis enhances human immunodeficiency virus replication in primary human macrophages. Journal of virology. 74(19):8904-12.
Blond D, Cheret A, Raoul H, Le Grand R, Caufour P, Theodoro F, Dormont D (1998) Nitric oxide synthesis during acute SIVmac251 infection of macaques. Research in virology. 149(2):75-86.
Rostasy K, Monti L, Yiannoutsos C, Kneissl M, Bell J, Kemper TL, Hedreen JC, Navia BA (1999) Human immunodeficiency virus infection, inducible nitric oxide synthase expression, and microglial activation: pathogenetic relationship to the acquired immunodeficiency syndrome dementia complex. Annals of neurology. 46(2):207-16.
Torre D, Ferrario G (1996) Immunological aspects of nitric oxide in HIV-1 infection. Medical hypotheses. 47(5):405-7.
Lamers SL, Salemi M, Galligan Dc, De Oliveira T, Fogel GB, Granier SC, Zhao L, Brown JN, Morris A, Masliah E, McGrath MS (2009) Extensive HIV-1 intra-host recombination is common in tissues with abnormal histopathology. PloS one. 4(3):e5065.
Rock RB, Gekker G, Hu S, Sheng WS, Cheeran M, Lokensgard JR, Peterson PK (2004) Role of microglia in central nervous system infections. Clinical microbiology reviews. 17(4):942-64.
Carballo M, Conde M, Tejedo J, Gualberto A, Jimenez J, Monteseirín J, Santa María C, Bedoya FJ, Hunt III SW, Pintado E, Baldwin AS (2002) Macrophage inducible nitric oxide synthase gene expression is blocked by a benzothiophene derivative with anti-HIV properties. Molecular genetics and metabolism. 75(4):360-8.
Zhang X, Goncalves R, Mosser DM (2008) The isolation and characterization of murine macrophages. Current protocols in immunology. 83(1):14-1.
Samaniego R, Palacios BS, Domíguez-Soto Á, Vidal C, Salas A, Matsuyama T, Sánchez-Torres C, Torre I, Miranda-Carús ME, Sánchez-Mateos P, Puig-Kröger A (2014) Macrophage uptake and accumulation of folates are polarization-dependent in vitro and in vivo and are regulated by activin A. Journal of leukocyte biology. 95(5):797-808.
Bukrinsky MI, Nottet HS, Schmidtmayerova H, Dubrovsky L, Flanagan CR, Mullins ME, Lipton S, Gendelman HE (1995) Regulation of nitric oxide synthase activity in human immunodeficiency virus type 1 (HIV-1)-infected monocytes: implications for HIV associated neurological disease. Journal of Experimental Medicine. 181(2):735-45.
Jin X, McGrath MS, Xu H (2015) Inhibition of HIV expression and integration in macrophages by methylglyoxal-bis-guanylhydrazone. Journal of virology. 89(22):11176-11189.
Yamasaki K, Chuang VT, Maruyama T, Otagiri M (2013) Albumin-drug interaction and its clinical implication. Biochimica et Biophysica Acta (BBA)-General Subjects. 1830(12):5435-43.
Karimi M, Sahandi Zangabad P, Ghasemi A, Amiri M, Bahrami M, Malekzad H, Ghahramanzadeh ASL H, Mahdieh Z, Bozorgomid M, Ghasemi A, Rahmani Taji Boyuk MR (2016) Temperature-responsive smart nanocarriers for delivery of therapeutic agents: applications and recent advances. ACS applied materials & interfaces. 8(33):21107-33.
Ta T, Porter TM (2013) Thermosensitive liposomes for localized delivery and triggered release of chemotherapy. Journal of controlled release. 169(1-2):112-25.
Zangabad PS, Mirkiani S, Shahsavari S, Masoudi B, Masroor M, Hamed H, Jafari Z, Taghipour YD, Hashemi H, Karimi M, Hamblin MR (2017) Stimulus-responsive liposomes as smart nanoplatforms for drug delivery applications. Nanotechnology reviews. 7(1):95-122.
Kneidl B, Peller M, Winter G, Lindner LH, Hossann M (2014) Thermosensitive liposomal drug delivery systems: state of the art review. International journal of nanomedicine. 9:4387.
Sun T, Zhang YS, Pang B, Hyun DC, Yang M, Xia Y (2014) Engineered nanoparticles for drug delivery in cancer therapy. Angewandte Chemie International Edition. 53(46):12320-64.

Zhang L, Wei MJ, Zhao CY, Qi HM (2008) Determination of the inhibitory potential of 6 fluoroquinolones on CYP1A2 and CYP2C9 in human liver microsomes. Acta Pharmacologica Sinica. 29(12):1507-14.
O'Ferrall RM (2010) A pictorial representation of zero-point energy and tunnelling contributions to primary hydrogen isotope effects. Journal of Physical Organic Chemistry. 23(7):572-579.
Slaughter LM, Wolczanski PT, Klinckman TR, Cundari TR (2000) Inter- and intramolecular experimental and calculated equilibrium isotope effects for (silox)2(tBu3SIND) TIR + RH (silox=tBu3SiO): Inferred kinetic isotope effects for RH/D addition to transient (silox)2TiNSitBu3. Journal of the American Chemical Society. 122(33):7953-7975.
Elison C, Rapoport H, Laursen R, Elliott HW (1961) Effect of deuteration of N—CH3 group on potency and enzymatic N-demethylation of morphine. Science. 134(3485):1078-9.
Slebocka-Tilk H, Motallebi S, Nagorski RW, Turner P, Brown RS, McDonald R (1995) Electrophilic Bromination of 7-Norbornylidene-7'-Norbornane. The Observation of an Unusually Large Inverse Deuterium Kinetic Isotope Effect. Journal of the American Chemical Society. 117(34):8769-8776.
Parker VD, Reitstoen B (1997) Radical cation-nucleophile combination reactions. The effect of structure of nitrogen-centered nucleophiles on reaction rates. Acta Chemica Scandinavica. 51(10):1035-1040.
Hayflick L (1965) The limited in vitro lifetime of human diploid cell strains. Experimental cell research. 37(3):614-36.
Owen SC, Doak AK, Wassam P, Shoichet MS, Shoichet BK (2012) Colloidal aggregation affects the efficacy of anticancer drugs in cell culture. ACS chemical biology. 7(8):1429-35.
Owen SC, Doak AK, Ganesh AN, Nedyalkova L, McLaughlin CK, Shoichet BK, Shoichet MS (2014) Colloidal drug formulations can explain "bell-shaped" concentration-response curves. ACS chemical biology. 9(3):777-84.
Dolfi SC, Chan LL, Qiu J, Tedeschi PM, Bertino JR, Hirshfield KM, Oltvai ZN, Vazquez A (2013) The metabolic demands of cancer cells are coupled to their size and protein synthesis rates. Cancer & metabolism. 1(1):20.
Cabanac A, Briese E (1992) Handling elevates the colonic temperature of mice. Physiology & behavior. 51(1):95-8.
Michel C, Cabanac M (1999) Opposite effects of gentle handling on body temperature and body weight in rats. Physiology & behavior. 67(4):617-22.
McCullough L, Arora S (2004) Diagnosis and treatment of hypothermia. American family physician. 70(12):2325-32.
Freund G (1973) Hypothermia after acute ethanol and benzyl alcohol administration. Life sciences. 13(4):345-9.
Myers RD (1981) Alcohol's effect on body temperature: hypothermia, hyperthermia or poikilothermia? Brain research bulletin. 7(2):209-20.
Kalant H, Le AD (1983) Effects of ethanol on thermoregulation. Pharmacology & therapeutics. 23(3):313-64.
Malcolm RD, Alkana RL (1983) Temperature dependence of ethanol lethality in mice. Journal of Pharmacy and Pharmacology. 35(5):306-11.
Briese E, Hernandez L (1996) Ethanol anapyrexia in rats. Pharmacology Biochemistry and Behavior. 54(2):399-402.
Lomax P, Bajorek JG, Bajorek TA, Chaffee RR (1981) Thermoregulatory mechanisms and ethanol hypothermia. European journal of pharmacology. 71(4):483-7.
Gad SC, Spainhour CB, Shoemake C, Pallman DR, Stricker-Krongrad A, Downing PA, Seals RE, Eagle LA, Polhamus K, Daly J (2016) Tolerable levels of nonclinical vehicles and formulations used in studies by multiple routes in multiple species with notes on methods to improve utility. International journal of toxicology 2:95-178.
Gad SC, Cassidy CD, Aubert N, Spainhour B, Robbe H (2006) Nonclinical vehicle use in studies by multiple routes in multiple species. International journal of toxicology. 25(6):499-521.
Gordon CJ, Puckett ET, Repasky ES, Johnstone AF (2017) A Device that Allows Rodents to Behaviorally Thermoregulate when Housed in Vivariums. Journal of the American Association for Laboratory Animal Science. 56(2):173-6.

(56) References Cited

OTHER PUBLICATIONS

Boily P (2009) Role of voluntary motor activity on menthol-induced hyperthermia in mice. Journal of Thermal Biology. 34(8):420-5.

Gaskill BN, Rohr SA, Pajor EA, Lucas JR, Garner JP (2009) Some like it hot: mouse temperature preferences in laboratory housing. Applied Animal Behaviour Science. 116(2):279-85.

Marschner JA, Schäfer H, Holderied A, Anders HJ (2016) Optimizing mouse surgery with online rectal temperature monitoring and preoperative heat supply. Effects on post-ischemic acute kidney injury. PLoS One. 11(2):e0149489.

Lindstedt SL, Calder III WA (1981) Body size, physiological time, and longevity of homeothermic animals. The Quarterly Review of Biology. 56(1):1-6.

Rouslin WI (1987) The mitochondrial adenosine 5'-triphosphatase in slow and fast heart rate hearts. American Journal of Physiology-Heart and Circulatory Physiology. 252(3):H622-7.

Tacutu R, Thornton D, Johnson E, Budovsky A, Barardo D, Craig T, Diana E, Lehmann G, Toren D, Wang J, Fraifeld VE, De Magalhaes JP (2018) Human Ageing Genomic Resources: new and updated databases. Nucleic Acids Research 46(D1):D1083-D1090.

Wilson DJ (2019) The harmonic mean p-value for combining dependent tests. Proceedings of the National Academy of Sciences. 116(4):1195-1200.

Rouslin W (1988) Factors affecting the loss of mitochondrial function during zero-flow ischemia (autolysis) in slow and fast heart-rate hearts. Journal of molecular and cellular cardiology. 20(11):999-1007.

Rouslin W, Broge CW (1989) Regulation of mitochondrial matrix pH and adenosine 5'-triphosphatase activity during ischemia in slow heart-rate hearts. Role of Pi/H+ symport. Journal of Biological Chemistry. 264(26):15224-9.

Rouslin W, Broge CW (1990) Regulation of the mitochondrial adenosine 5'-triphosphatase in situ during ischemia and in vitro in intact and sonicated mitochondria from slow and fast heart-rate hearts. Archives of biochemistry and biophysics. 280(1):103-11.

Rouslin WI, Broge CW, Grupp IL (1990) ATP depletion and mitochondrial functional loss during ischemia in slow and fast heart-rate hearts. American Journal of Physiology-Heart and Circulatory Physiology. 259(6):H1759-66.

Rouslin W, Broge CW (1992) Why the Mitochondrial ATPase Inhibitor IF1 Fails to Inhibit the Mitochondrial ATPase in Situ in Fast Heart-Rate Mammalian and Avian Hearts. Annals of the New York Academy of Sciences. 671(1):505-6.

Rouslin W, Broge CW (1993) Mechanisms of ATP conservation during ischemia in slow and fast heart rate hearts. American Journal of Physiology-Cell Physiology. 264(1):C209-16.

Rouslin W, Frank GD, Broge CW (1995) Content and binding characteristics of the mitochondrial ATPase inhibitor, IF1 in the tissues of several slow and fast heart-rate homeothermic species and in two poikilotherms. Journal of bioenergetics and biomembranes. 27(1):117-25.

Rouslin W, Broge CW, Guerrieri F, Capozza G (1995) ATPase activity, IF1 content, and proton conductivity of ESMP from control and ischemic slow and fast heart-rate hearts. Journal of bioenergetics and biomembranes. 27(4):459-66.

Rouslin W, Broge CW (1996) IF1 function in situ in uncoupler-challenged ischemic rabbit, rat, and pigeon hearts. Journal of Biological Chemistry. 271(39):23638-41.

Ballard A, Ahmad HO, Narduolo S, Rosa L, Chand N, Cosgrove DA, Varkonyi P, Asaad N, Tomasi S, Buurma NJ, Leach AG (2018) Quantitative Prediction of Rate Constants for Aqueous Racemization To Avoid Pointless Stereoselective Syntheses. Angewandte Chemie. 130(4):994-7.

Chatterjee B, Krishnakumar V, Gunanathan C (2016) Selective a-Deuteration of Amines and Amino Acids Using D2O. Organic letters. 18(22):5892-5.

Michelotti A, Rodrigues F, Roche M (2017) Development and Scale-Up of Stereoretentive a-Deuteration of Amines. Organic Process Research & Development. 21(11):1741-4.

Neubert L, Michalik D, Bahn S, Imm S, Neumann H, Atzrodt J, Derdau V, Holla W, Beller M (2012) Ruthenium-catalyzed selective a,β-deuteration of bioactive amines. Journal of the American Chemical Society. 134(29):12239-44.

Taglang C, Martínez-Prieto LM, Del Rosal I, Maron L, Poteau R, Philippot K, Chaudret B, Perato S, Sam Lone A, Puente C, Dugave C (2015) Enantiospecific C—H Activation Using Ruthenium Nanocatalysts. Angewandte Chemie International Edition. 54(36):10474-7.

Pieters G, Taglang C, Bonnefille E, Gutmann T, Puente C, Berthet JC, Dugave C, Chaudret B, Rousseau B (2014) Regioselective and stereospecific deuteration of bioactive aza compounds by the use of ruthenium nanoparticles. Angewandte Chemie International Edition. 53(1):230-4.

Bhatia S, Spahlinger G, Boukhumseen N, Boll Q, Li Z, Jackson JE (2016) Stereoretentive H/D Exchange via an Electroactivated Heterogeneous Catalyst at sp3 C-H Sites Bearing Amines or Alcohols. European Journal of Organic Chemistry. 24:4230-5.

Chatterjee B, Gunanathan C (2015) Ruthenium Catalyzed Selective a- and a, β-Deuteration of Alcohols Using D2O. Organic letters. 17(19):4794-7.

Khaskin E, Milstein D (2013) Simple and Efficient Catalytic Reaction for the Selective Deuteration of Alcohols. ACS Catalysis. 3(3):448-52.

Bai W, Lee KH, Tse SK, Chan KW, Lin Z, Jia G (2015) Ruthenium-catalyzed deuteration of alcohols with deuterium oxide. Organometallics. 34(15):3686-98.

Breno KL, Tyler DR (2001) C-H Bond Activation in Aqueous Solution: A Linear Free Energy Relationship Investigation of the Rate-Limiting Step in the H/D Exchange of Alcohols Catalyzed by a Molybdocene. Organometallics. 20(18):3864-8.

Balzarek C, Weakley TJ, Tyler DR (2000) C-H Bond Activation in Aqueous Solution: Kinetics and Mechanism of H/D Exchange in Alcohols Catalyzed by Molybdocenes. Journal of the American Chemical Society. 122(39):9427-34.

Balzarek C, Tyler DR (1999) Intra-and Intermolecular H/D Exchange in Aqueous Solution Catalyzed by Molybdocenes. Angewandte Chemie International Edition. 38(16):2406-8.

Maegawa T, Fujiwara Y, Inagaki Y, Monguchi Y, Sajiki H (2008) A convenient and effective method for the regioselective deuteration of alcohols. Advanced Synthesis & Catalysis. 350(14-15):2215-8.

Bossi G, Putignano E, Rigo P, Baratta W (2011) Pincer Ru and Os complexes as efficient catalysts for racemization and deuteration of alcohols. Dalton Transactions. 40(35):8986-95.

Zhang L, Nguyen DH, Raffa G, Desset S, Paul S, Dumeignil F, Gauvin RM (2016) Efficient deuterium labelling of alcohols in deuterated water catalyzed by ruthenium pincer complexes. Catalysis Communications. 84:67-70.

Palmer WN, Chirik PJ (2017) Cobalt-Catalyzed Stereoretentive Hydrogen Isotope Exchange of C (sp3)—H Bonds. ACS Catalysis. 7(9):5674-8.

Sajiki H, Aoki F, Esaki H, Maegawa T, Hirota K (2004) Efficient C-H/C-D Exchange Reaction on the Alkyl Side Chain of Aromatic Compounds Using Heterogeneous Pd/C in D2O. Organic letters. 6(9):1485-7.

Esaki H, Aoki F, Umemura M, Kato M, Maegawa T, Monguchi Y, Sajiki H (2007) Efficient H/D Exchange Reactions of Alkyl-Substituted Benzene Derivatives by Means of the Pd/C—H2—D2O System. Chemistry—A European Journal. 13(14):4052-63.

Hale LV, Szymczak NK (2016) Stereoretentive deuteration of a-chiral amines with D2O. Journal of the American Chemical Society. 138(41):13489-92.

Derdau V, Atzrodt J (2006) CH/CD exchange reactions of aromatic compounds in D2O with NaBD4-activated catalysts. Synlett. (12):1918-22.

Derdau V, Atzrodt J, Zimmermann J, Kroll C, Brückner F (2009) Hydrogen-Deuterium Exchange Reactions of Aromatic Compounds and Heterocycles by NaBD4-Activated Rhodium, Platinum and Palladium Catalysts. Chemistry—A European Journal. 15(40):10397-404.

(56) References Cited

OTHER PUBLICATIONS

Ito N, Watahiki T, Maesawa T, Maegawa T, Sajiki H (2008) HD exchange reaction taking advantage of the synergistic effect of heterogeneous palladium and platinum mixed catalyst. Synthesis. 09:1467-78.
Kar S, Goeppert A, Sen R, Kothandaraman J, Prakash GS (2018) Regioselective deuteration of alcohols in D20 catalysed by homogeneous manganese and iron pincer complexes. Green Chemistry. 20(12):2706-2710.
Klucznikt, Mikulak-Klucznik B, McCormack MP, Lima H, Szymkuć S, Bhowmick M, Molga K, Zhou Y, Rickershauser L, Gajewska EP, Toutchkine A, Dittwald P, Startek MP, Kirkovits GJ, Roszak R, Adamski A, Sieredzińska B, Mrksich M, Trice SLI, Grzybowski BA (2018) Efficient syntheses of diverse, medicinally relevant targets planned by computer and executed in the laboratory. Chem. 4(3):522-32.
Segler MH, Preuss M, Waller MP (2017) Learning to Plan Chemical Syntheses. arXiv preprint. arXiv:1708.04202.
Loh YY, Nagao K, Hoover AJ, Hesk D, Rivera NR, Colletti SL, Davies IW, MacMillan DW (2017) Photoredox-catalyzed deuteration and tritiation of pharmaceutical compounds. Science. 358(6367):1182-1187.
Yu RP, Hesk D, Rivera N, Pelczer I, Chirik PJ (2016) Iron-catalysed tritiation of pharmaceuticals. Nature. 529(7585):195.
Zhan M, Zhang T, Huang H, Xie Y, Chen Y (2014) A simple method for α-position deuterated carbonyl compounds with pyrrolidine as catalyst. Journal of Labelled Compounds and Radiopharmaceuticals. 57(8):533-9.
Fodor-Csorba K, Galli G, Holly S, Gács-Baitz E (2002) Microwave-assisted deuterium exchange reactions for the preparation of reactive intermediates. Tetrahedron letters. 43(21):3789-92.
Bloom S, Pitts CR, Woltornist R, Griswold A, Holl MG, Lectka T (2013) Iron (II)-catalyzed benzylic fluorination. Organic letters. 15(7):1722-4.
Bloom S, Sharber SA, Holl MG, Knippel JL, Lectka T (2013) Metal-Catalyzed Benzylic Fluorination as a Synthetic Equivalent to 1, 4-Conjugate Addition of Fluoride. The Journal of organic chemistry. 78(21):11082-6.
Xia JB, Zhu C, Chen C (2013) Visible light-promoted metal-free C—H activation: diarylketone-catalyzed selective benzylic mono- and difluorination. Journal of the American Chemical Society. 135(46):17494-500.
Cantillo D, De Frutos O, Rincon JA, Mateos C, Kappe CO (2014) A continuous-flow protocol for light-induced benzylic fluorinations. The Journal of organic chemistry. 79(17):8486-90.
Liu W, Groves JT (2013) Manganese-Catalyzed Oxidative Benzylic C—H Fluorination by Fluoride Ions. Angewandte Chemie. 125(23):6140-3.
Nodwell MB, Bagai A, Halperin SD, Martin RE, Knust H, Britton R (2015) Direct photocatalytic fluorination of benzylic C—H bonds with N-fluorobenzenesulfonimide. Chemical Communications. 51(59):11783-6.
Ma JJ, Yi WB, Lu GP, Cai C (2015) Transition-metal-free C—H oxidative activation: persulfate-promoted selective benzylic mono- and difluorination. Organic & biomolecular chemistry. 13(10):2890-4.
Champagne PA, Desroches J, Hamel JD, Vandamme M, Paquin JF (2015) Monofluorination of organic compounds: 10 years of innovation. Chemical reviews. 115(17):9073-174.
Sasmal S, Rana S, Lahiri GK, Maiti D (2018) Manganese-salen catalyzed oxidative benzylic chlorination. Journal of Chemical Sciences. 130(7):88.
Combe SH, Hosseini A, Parra A, Schreiner PR (2017) Mild Aliphatic and Benzylic Hydrocarbon C—H Bond Chlorination Using Trichloroisocyanuric Acid. The Journal of organic chemistry. 82(5):2407-13.
Ayonon A, Nalbandian C, Guillemard L, Gustafson J (2017) Benzylic bromination catalyzed by triphenylphosphine selenide via Lewis basic activation. Tetrahedron Letters. 58(30):2940-3.
Shibatomi K, Zhang Y, Yamamoto H (2008) Lewis acid catalyzed benzylic bromination. Chemistry—An Asian Journal. 3(8-9):1581-4.
Cantillo D, De Frutos O, Rincon JA, Mateos C, Kappe CO (2013) A scalable procedure for light-induced benzylic brominations in continuous flow. The Journal of organic chemistry. 79(1):223-9.
Combe SH, Hosseini A, Song L, Hausmann H, Schreiner PR (2017) Catalytic Halogen Bond Activation in the Benzylic C—H Bond Iodination with Iodohydantoins. Organic letters. 19(22):6156-9.
Laduron F, Tamborowski V, Moens L, Horváth A, De Smaele D, Leurs S (2005) Efficient and scalable method for the selective alkylation and acylation of secondary amines in the presence of primary amines. Organic process research & development. 9(1):102-4.
Takeda R, Abe H, Shibata N, Moriwaki H, Izawa K, Soloshonok VA (2017) Asymmetric synthesis of α-deuterated α-amino acids. Organic & biomolecular chemistry. 15(33):6978-83.
O'Reilly E, Balducci D, Paradisi F (2010) A stereoselective synthesis of a-deuterium-labelled (S)-α-amino acids. Amino acids. 39(3):849-58.
Johns RB, Whelan DJ (1966) Synthesis of a-deuterated amino acids. Australian Journal of Chemistry. 19(11):2143-7.
Mosin O, Ignatov I, Skladnev D, Shvets V (2015) The Biosynthesis of Deuterium Labeled Amino Acids Using a Strain of Facultative Methylotrophic Bacterium Brevibacterium Methylicum 5662 With RuMP Cycle of Carbon Assimilation. European Journal of Molecular Biotechnology. (1):37-52.
Blomquist AT, Cedergren RJ, Hiscock BF, Tripp SL, Harpp DN (1966) Synthesis of highly deuterated amino acids. Proceedings of the National Academy of Sciences (PNAS). 55(3):453-6.
Thanassi JW (1971) General procedure for the preparation of deuterated and tritiated amino acids by incorporation of solvent isotope during synthesis. The Journal of organic chemistry. 36(20):3019-21.
Rigoulet M, Ouhabi R, Leverve X, Putod-Paramelle F, Guérin B (1989) Almitrine, a new kind of energy-transduction inhibitor acting on mitochondrial ATP synthase. Biochimica et Biophysica Acta (BBA)-Bioenergetics. 975(3):325-9.
Rigoulet M, Fraisse L, Ouhabi R, Guérin B, Fontaine E, Leverve X (1990) Flux-dependent increase in the stoichiometry of charge translocation by mitochondrial ATPase/ATP synthase induced by almitrine. Biochimica et Biophysica Acta (BBA)-Bioenergetics. 1018(1):91-7.
Leverve XM, Fontaine E, Putod-Paramelle F, Rigoulet M (1994) Decrease in cytosolic ATP/ADP ratio and activation of pyruvate kinase after in vitro addition of almitrine in hepatocytes isolated from fasted rats. The FEBS Journal. 224(3):967-74.
Rigoulet M (1990) Control processes in oxidative phosphorylation: kinetic constraints and stoichiometry. Biochimica et Biophysica Acta (BBA)-Bioenergetics. 1018(2-3):185-9.
European Medicines Agency (May 23, 2013) Assessment report for almitrine-containing medicinal products for oral use. http://www.ema.europa.eu/docs/en_GB/document_library/Referrals_document/Almitrine/Recommendation_provided_by_Pharmacovigilance_Risk_Assessment_Committee/WC500144134.pdf (accessed on Dec. 7, 2017).
Stavchansky S, Doluisio JT, Macleod CM, Szalkowski MB, Bachand RT, Heilman R, Sebree TB, Geary RS (1989) Single oral dose proportionality pharmacokinetics of almitrine bismesylate in humans. Biopharmaceutics & drug disposition. 10(3):229-37.
Stavchansky S, Doluisio JT, MacLeod CM, Sebree TB, Heilman R, Bachand Jr RT, Szalkowski MB, Geary RS (1989) Relative bioavailability of almitrine bismesylate in humans. Biopharmaceutics & drug disposition. 10(3):239-46.
Stavchansky S, Doluisio JT, MacLeod CM, Szalkowski MB, Bachand Jr RT, Heilman R, Sebree TB, Geary RS (1989) One year administration of almitrine bismesylate (Vectarion) to chronic obstructive pulmonary disease patients: pharmacokinetic analysis. Biopharmaceutics & drug disposition. 10(3):247-55.
Bury T, Jeannot JP, Ansquer JC, Radermecker M (1989) Dose-response and pharmacokinetic study with almitrine bismesylate after single oral administrations in COPD patients. European Respiratory Journal. 2(1):49-55.

(56) References Cited

OTHER PUBLICATIONS

European Medicines Agency (May 29, 2013) Oral almitrine to be withdrawn by EU Member States. http://www.ema.europa.eu/docs/en_GB/document_library/Referrals_document/Almitrine/Position_provided_by_CMDh/WC500143802.pdf (accessed on Jun. 20, 2018).
Gordon BH (1995) The pharmacokinetics and metabolism of almitrine bismesylate. Doctoral dissertation, College of Medicine, Biological Sciences and Psychology, University of Leicester, United Kingdom.
Yang X, Yu Y, Xu J, Shu H, Liu H, Wu Y, . . . & Shang Y (2020) Clinical course and outcomes of critically ill patients with SARS-CoV-2 pneumonia in Wuhan, China: a single-centered, retrospective, observational study. The Lancet Respiratory Medicine. 8(5):475-481.
Esnault P, Hraiech S, Bordes J, Forel Jm, Adda M, Rambaud R, . . . & Guervilly C (2019) Evaluation of Almitrine Infusion During Veno-Venous Extracorporeal Membrane Oxygenation for Severe Acute Respiratory Distress Syndrome in Adults. Anesthesia & Analgesia. 129(2):e48-e51.
Cotton JF (2014) The latest pharmacologic ventilator. Anesthesiology: The Journal of the American Society of Anesthesiologists. 121(3):442-4.
Golder FJ, Hewitt MM, McLeod JF (2013) Respiratory stimulant drugs in the post-operative setting. Respiratory physiology & neurobiology. 189(2):395-402.
Howard P (1989) Hypoxia, almitrine, and peripheral neuropathy. Thorax. 44(4):247.
Winkelmann BR, Kullmer TH, Kneissl DG, Trenk D, Kronenberger H (1994) Low-dose almitrine bismesylate in the treatment of hypoxemia due to chronic obstructive pulmonary disease. Chest. 105(5):1383-91.
Weitzenblum E, Schrijen F, Apprill M, Prefaut C, Yernault JC (1991) One year treatment with almitrine improves hypoxaemia but does not increase pulmonary artery pressure in COPD patients. European Respiratory Journal. 4(10):1215-22.
Górecka D, Sliwinski P, Palasiewicz G, Pachocki R, Zielinski J (2003) Effects of almitrine bismesylate on arterial blood gases in patients with chronic obstructive pulmonary disease and moderate hypoxaemia: a multicentre, randomised, double-blind, placebo-controlled study. Respiration. 70(3):275-83.
Kayacan O, Beder S, Deda G, Karnak D (2001) Neurophysiological changes in COPD patients with chronic respiratory insufficiency. Acta neurologica belgica. 101(3):160-5.
Allen MB, Prowse KE (1989) Peripheral nerve function in patients with chronic bronchitis receiving almitrine or placebo. Thorax. 44(4):292-7.
Jarratt JA, Morgan CN, Twomey JA, Abraham R, Sheaff PC, Pilling JB, Payan J, Mitchell JD, Tang O, Arnaud F (1992) Neuropathy in chronic obstructive pulmonary disease: a multicentre electrophysiological and clinical study. European Respiratory Journal. 5(5):517-24.
Appenzeller O, Parks RD, MacGee J (1968) Peripheral neuropathy in chronic disease of the respiratory tract. The American journal of medicine. 44(6):873-80.
Faden A, Mendoza E, Flynn F (1981) Subclinical neuropathy associated with chronic obstructive pulmonary disease: possible pathophysiologic role of smoking. Archives of neurology. 38(10):639-42.
Moore N, Lerebours G, Senant J, Ozenne G, David PH, Nouvet G (1985) Peripheral neuropathy in chronic obstructive lung disease. The Lancet. 326(8467):1311.
Nowak D, Brüch M, Arnaud F, Fabel H, Kiessling D, Nolte D, Overlack A, Rolke M, Ulmer WT, Worth H, Wywiol A (1990) Peripheral neuropathies in patients with chronic obstructive pulmonary disease: a multicenter prevalence study. Lung. 168(1):43-51.
Malik RA, Masson EA, Sharma AK, Lye RH, Ah-See AK, Compton AM, Tomlinson DR, Hanley SP, Boulton AJ (1990) Hypoxic neuropathy: relevance to human diabetic neuropathy. Diabetologia. 33(5):311-8.
Hendriksen PH, Oey PL, Wieneke GH, Van Huffelen AC, Gispen WH (1992) Hypoxic neuropathy versus diabetic neuropathy An electrophysiological study in rats. Journal of the neurological sciences. 110(1):99-106.
Bulut Çelik S, Can H, Sözmen MK, Şengezer T, Kaplan YC, Utlu G, Şener A, Aybek Yılmaz A, Aygün O (2017) Evaluation of the neuropathic pain in the smokers. Ağrı—The Journal of The Turkish Society of Algology. 29(3):122-6.
Pohjanpää AK, Rimpelä AH, Rimpelä M, Karvonen JS (1997) Is the strong positive correlation between smoking and use of alcohol consistent over time? A study of Finnish adolescents from 1977 to 1993. Health Education Research. 12(1):25-36.
Rogliani P, Lucà G, Lauro D (2015) Chronic obstructive pulmonary disease and diabetes. COPD research and practice. 1(1):3.
Das M (2017) Treating chemotherapy-induced peripheral neuropathy. The Lancet Oncology. 18(4):e202.
Shah A, Hoffman EM, Mauermann ML, Loprinzi CL, Windebank AJ, Klein CJ, Staff NP (2018) Incidence and disease burden of chemotherapy-induced peripheral neuropathy in a population-based cohort. Journal of Neurology, Neurosurgery & Psychiatry. 89(6):636-641.
Miaskowski C, Mastick J, Paul SM, Abrams G, Cheung S, Sabes JH, Kober KM, Schumacher M, Conley YP, Topp K, Smoot B (2018) Impact of chemotherapy-induced neurotoxicities on adult cancer survivors' symptom burden and quality of life. Journal of Cancer Survivorship. 12(2):234-45.
Seretny M, Currie GL, Sena ES, Ramnarine S, Grant R, MacLeod MR, . . . & Fallon M (2014) Incidence, prevalence, and predictors of chemotherapy-induced peripheral neuropathy: a systematic review and meta-analysis. Pain. 155(12):2461-2470, Abstract only.
Savage L (2007) Chemotherapy-Induced Pain Puzzles Scientists. Journal of the National Cancer Institute. 99(14):1070-1071.
Wallington M, Saxon EB, Bomb M, Smittenaar R, Wickenden M, McPhail S, Rashbass J, Chao D, Dewar J, Talbot D, Peake M (2016) 30-day mortality after systemic anticancer treatment for breast and lung cancer in England: a population-based, observational study. The Lancet Oncology. 17(9):1203-16.
Smith EM, Pang H, Cirrincione C, Fleishman S, Paskett ED, Ahles T, Bressler LR, Fadul CE, Knox C, Le-Lindqwister N, Gilman PB (2013) Effect of duloxetine on pain, function, and quality of life among patients with chemotherapy-induced painful peripheral neuropathy: a randomized clinical trial. Jama. 309(13):1359-67.
B'Chir A, Mebazaa A, Losser MR, Romieu M, Payen D (1998) Intravenous almitrine bismesylate reversibly induces lactic acidosis and hepatic dysfunction in patients with acute lung injury. Anesthesiology: The Journal of the American Society of Anesthesiologists. 89(4):823-30.
Chan SC, Liu CL, Lo CM, Lam BK, Lee EW, Wong Y, Fan ST (2006) Estimating liver weight of adults by body weight and gender. World journal of gastroenterology. 12(14):2217.
Michard F, Wolff MA, Herman B, Wysocki M (2001) Right ventricular response to high-dose almitrine infusion in patients with severe hypoxemia related to acute respiratory distress syndrome. Critical care medicine. 29(1):32-36.
Yamanaka Y, Shimada T, Mochizuki R, Suzuki Y, Takenouchi K, Takeda T, Uno H, Izawa Y, Fujiwara K (1997) Neuronal and muscular inclusions in rats with hindlimb dysfunction after treating with difluorobenzhydrylpiperadine. Toxicologic pathology. 25(2):150-7.
Yamanaka Y, Sakamoto E, Sakuma Y, Uno H, Koyama T, Izawa Y, Fujiwara K (1995) Lipidosis of the dorsal root ganglia in rats treated with an almitrine metabolite. Archives of toxicology. 69(6):391.
Polavarapu S, Mani AM, Gundala NK, Hari AD, Bathina S, Das UN (2014) Effect of polyunsaturated fatty acids and their metabolites on bleomycin-induced cytotoxic action on human neuroblastoma cells in vitro. PloS one. 9(12):e114766.
Dilly SJ, Clark AJ, Marsh A, Mitchell DA, Cain R, Fishwick CW, Taylor PC (2017) A chemical genomics approach to drug reprofiling in oncology: Antipsychotic drug risperidone as a potential adenocarcinoma treatment. Cancer letters. 393:16-21.
Barker HE, Paget JT, Khan AA, Harrington KJ (2015) The tumour microenvironment after radiotherapy: mechanisms of resistance and recurrence. Nature reviews Cancer. 15(7):409.

(56) References Cited

OTHER PUBLICATIONS

Zhou Y, Hileman EO, Plunkett W, Keating MJ, Huang P (2003) Free radical stress in chronic lymphocytic leukemia cells and its role in cellular sensitivity to ROS-generating anticancer agents. Blood. 101(10):4098-104.

Wondrak GT (2009) Redox-directed cancer therapeutics: molecular mechanisms and opportunities. Antioxidants & redox signaling. 11(12):3013-69.

Berndtsson M, Hägg M, Panaretakis T, Havelka AM, Shoshan MC, Linder S (2007) Acute apoptosis by cisplatin requires induction of reactive oxygen species but is not associated with damage to nuclear DNA. International journal of cancer. 120(1):175-80.

Sullivan R, Pare GC, Frederiksen LJ, Semenza GL, Graham CH (2008) Hypoxia-induced resistance to anticancer drugs is associated with decreased senescence and requires hypoxia-inducible factor-1 activity. Molecular cancer therapeutics. 7(7):1961-73.

Doktorova H, Hrabeta J, Khalil MA, Eckschlager T (2015) Hypoxia-induced chemoresistance in cancer cells: The role of not only HIF-1. Biomedical Papers of the Medical Faculty of Palacky University in Olomouc. 159(2).

Payen D, Muret J, Beloucif S, Gatecel C, Kermarrec N, Guinard N, Mateo J (1998) Inhaled nitric oxide, almitrine infusion, or their coadministration as a treatment of severe hypoxemic focal lung lesions. Anesthesiology: The Journal of the American Society of Anesthesiologists. 89(5):1157-65.

Saadjian AY, Philip-Joel FF, Barret A, Levy S, Arnaud AG (1994) Effect of almitrine bismesylate on pulmonary vasoreactivity to hypoxia in chronic obstructive pulmonary disease. European Respiratory Journal. 7(5):862-8.

Prost JF, Desche P, Jardin F, Margairaz A (1991) Comparison of the effects of intravenous almitrine and positive end-expiratory pressure on pulmonary gas exchange in adult respiratory distress syndrome. European Respiratory Journal. 4(6):683-7.

Gallart L, Lu QI, Puybasset L, Umamaheswara Rao GS, Coriat P, Rouby JJ, No Almitrine Study Group (1998) Intravenous almitrine combined with inhaled nitric oxide for acute respiratory distress syndrome. American journal of respiratory and critical care medicine. 158(6):1770-7.

Silva-Costa-Gomes T, Gallart L, Valles J, Trillo L, Minguella J, Puig MM (2005) Low-vs high-dose almitrine combined with nitric oxide to prevent hypoxia during open-chest one-lung ventilation. British journal of anaesthesia. 95(3):410-6.

Amundson SA, Do KT, Vinikoor LC, Lee RA, Koch-Paiz CA, Ahn J, Reimers M, Chen Y, Scudiero DA, Weinstein JN, Trent JM (2008) Integrating global gene expression and radiation survival parameters across the 60 cell lines of the National Cancer Institute Anticancer Drug Screen. Cancer research. 68(2):415-24.

Mix KA, Lomax JE, Raines RT (2017) Cytosolic delivery of proteins by bioreversible esterification. Journal of the American Chemical Society. 139(41):14396-14398.

Ressler VT, Mix KA, Raines RT (2019) Esterification delivers a functional enzyme into a human cell. ACS chemical biology. 14(4):599-602.

Zorzi A, Middendorp SJ, Wilbs J, Deyle K, Heinis C (2017) Acylated heptapeptide binds albumin with high affinity and application as tag furnishes long-acting peptides. Nature communications. 8(1):1-9.

Ekrami HM, Kennedy AR, Shen WC (1995) Water-soluble fatty acid derivatives as acylating agents for reversible lipidization of polypeptides. FEBS letters. 371(3):283-286.

Gordon-Smith DJ, Carbajo RJ, Yang JC, Videler H, Runswick MJ, Walker JE, Neuhaus D (2001) Solution structure of a C-terminal coiled- coil domain from bovine IF1: The inhibitor protein of F1 ATPase. Journal of molecular biology. 308(2):325-339.

Cabezon E, Butler PJG, Runswick MJ, Walker JE (2000) Modulation of the oligomerization state of the bovine F1-ATPase inhibitor protein, IF1, by pH. Journal of Biological Chemistry. 275(33):25460-25464.

Bason JV, Runswick MJ, Fearnley IM, Walker JE (2011) Binding of the inhibitor protein IF1 to bovine F1-ATPase. Journal of molecular biology. 406(3):443-453.

Yampolsky LY, Stoltzfus A (2005) The exchangeability of amino acids in proteins. Genetics. 170(4):1459-1472.

Wender PA, Mitchell DJ, Pattabiraman K, Pelkey ET, Steinman L, Rothbard JB (2000) The design, synthesis, and evaluation of molecules that enable or enhance cellular uptake: peptoid molecular transporters. Proceedings of the National Academy of Sciences. 97(24):13003-13008.

Vázquez J, Sun C, Du J, Fuentes L, Sumners C, Raizada MK (2003) Transduction of a functional domain of the AT1 receptor in neurons by HIV-Tat PTD. Hypertension. 41(3):751-756.

Tünnemann G, Martin RM, Haupt S, Patsch C, Edenhofer F, Cardoso MC (2006) Cargo-dependent mode of uptake and bioavailability of TAT-containing proteins and peptides in living cells. The FASEB journal. 20(11):1775-1784.

Rothbard JB, Garlington S, Lin Q, Kirschberg T, Kreider E, McGrane PL, . . . & Khavari PA (2000) Conjugation of arginine oligomers to cyclosporin A facilitates topical delivery and inhibition of inflammation. Nature medicine. 6(11):1253-1257.

Vivès E, Schmidt J, Pèlegrin A (2008) Cell-penetrating and cell-targeting peptides in drug delivery. Biochimica et Biophysica Acta (BBA)—Reviews on Cancer. 1786(2):126-138.

Begley R, Liron T, Baryza J, Mochly-Rosen D (2004) Biodistribution of intracellularly acting peptides conjugated reversibly to Tat. Biochemical and biophysical research communications. 318(4):949-954.

Miyaji Y, Walter S, Chen L, Kurihara A, Ishizuka T, Saito M, . . . Okazaki O (2011) Distribution of KAI-9803, a novel 8-protein kinase C inhibitor, after intravenous administration to rats. Drug metabolism and disposition. 39(10):1946-1953.

Flynn CR, Cheung-Flynn J, Smoke CC, Lowry D, Roberson R, Sheller MR, Brophy CM (2010) Internalization and intracellular trafficking of a PTD-conjugated anti-fibrotic peptide, AZX100, in human dermal keloid fibroblasts. Journal of pharmaceutical sciences. 99(7):3100-3121.

Brewer SJ, Sassenfeld HM (1985) The purification of recombinant proteins using C-terminal polyarginine fusions. Trends in Biotechnology. 3(5):119-122.

Holm T, Räägel H, Andaloussi SE, Hein M, Mäe M, Pooga M, Langel Ü (2011) Retro-inversion of certain cell-penetrating peptides causes severe cellular toxicity. Biochimica et Biophysica Acta (BBA)—Biomembranes. 1808(6):1544-1551.

Chen L, Wright LR, Chen CH, Oliver SF, Wender PA, Mochly-Rosen D (2001) Molecular transporters for peptides: delivery of a cardioprotective EPKC agonist peptide into cells and intact ischemic heart using a transport system, R7. Chemistry & biology. 8(12):1123-1129.

Mitchell DJ, Steinman L, Kim DT, Fathman CG, Rothbard JB (2000) Polyarginine enters cells more efficiently than other polycationic homopolymers. The Journal of Peptide Research. 56(5):318-325.

Nasrollahi SA, Taghibiglou C, Azizi E, Farboud ES (2012) Cell-penetrating peptides as a novel transdermal drug delivery system. Chemical biology & drug design. 80(5):639-646.

Jiang T, Olson ES, Nguyen QT, Roy M, Jennings PA, Tsien RY (2004) Tumor imaging by means of proteolytic activation of cell-penetrating peptides. Proceedings of the National Academy of Sciences. 101(51):17867-17872.

Savariar EN, Felsen CN, Nashi N, Jiang T, Ellies LG, Steinbach P, . . . Nguyen QT (2013) Real-time in vivo molecular detection of primary tumors and metastases with ratiometric activatable cell-penetrating peptides. Cancer research. 73(2):855-864.

Unkart JT, Chen SL, Wapnir IL, González JE, Harootunian A, Wallace AM (2017) Intraoperative tumor detection using a ratiometric activatable fluorescent peptide: a first-in-human phase 1 study. Annals of surgical oncology. 24(11):3167-3173.

Futaki S, Ohashi W, Suzuki T, Niwa M, Tanaka S, Ueda K, . . . & Sugiura Y (2001) Stearylated arginine-rich peptides: a new class of transfection systems. Bioconjugate chemistry. 12(6):1005-1011.

Katayama S, Hirose H, Takayama K, Nakase I, Futaki S (2011) Acylation of octaarginine: Implication to the use of intracellular delivery vectors. Journal of controlled release. 149(1):29-35.

(56) References Cited

OTHER PUBLICATIONS

Taylor BN, Mehta RR, Yamada T, Lekmine F, Christov K, Chakrabarty AM, . . . Gupta TK D (2009) Noncationic peptides obtained from azurin preferentially enter cancer cells. Cancer research. 69(2):537-546.
Kang YC, Son M, Kang S, Im S, Piao Y, Lim KS, . . . Pak YK (2018) Cell-penetrating artificial mitochondria-targeting peptide-conjugated metallothionein 1A alleviates mitochondrial damage in Parkinson's disease models. Experimental & molecular medicine. 50(8):1-13.
Appiah Kubi G, Qian Z, Amiar S, Sahni A, Stahelin RV, Pei D (2018) Non-Peptidic Cell-Penetrating Motifs for Mitochondrion-Specific Cargo Delivery. Angewandte Chemie. 130(52):17429-17434.
Rath S, Sharma R, Gupta R, Ast T, Chan C, Durham TJ, . . . & Mootha VK (2021) MitoCarta3. 0: an updated mitochondrial proteome now with sub-organelle localization and pathway annotations. Nucleic acids research. 49(D1):D1541-D1547.
Armenteros JJA, Salvatore M, Emanuelsson O, Winther O, Von Heijne G, Elofsson A, Nielsen H (2019) Detecting sequence signals in targeting peptides using deep learning. Life science alliance:2(5).
Fukasawa Y, Tsuji J, Fu SC, Tomii K, Horton P, Imai K (2015) MitoFates: Improved Prediction of Mitochondrial Targeting Sequences and Their Cleavage Sites. Molecular & Cellular Proteomics. 14(4):1113-1126.
Formentini L, Pereira MP, Sánchez-Cenizo L, Santacatterina F, Lucas JJ, Navarro C, Martínez-Serrano A, Cuezva JM (2014) In vivo inhibition of the mitochondrial H+-ATP synthase in neurons promotes metabolic preconditioning. The EMBO journal. 33(7):762-78.
Mayford M, Bach ME, Huang YY, Wang L, Hawkins RD, Kandel ER (1996) Control of memory formation through regulated expression of a CaMKII transgene. Science. 274(5293):1678-83.
Wang P, Powell SR (2010) Decreased sensitivity associated with an altered formulation of a commercially available kit for detection of protein carbonyls. Free Radical Biology and Medicine. 49(2):119-21.
Sohal RS, Orr WC (2012) The redox stress hypothesis of aging. Free Radical Biology and Medicine. 52(3):539-55.
Santacatterina F, Sánchez-Cenizo L, Formentini L, Mobasher MA, Casas E, Rueda CB, Martínez-Reyes I, De Arenas CN, García-Bermúdez J, Zapata JM, Sánchez-Aragó M (2016) Down-regulation of oxidative phosphorylation in the liver by expression of the ATPase inhibitory factor 1 induces a tumor-promoter metabolic state. Oncotarget. 7(1):490.
Formentini L, Santacatterina F, De Arenas CN, Stamatakis K, López-Martínez D, Logan A, Fresno M, Smits R, Murphy MP, Cuezva JM (2017) Mitochondrial ROS production protects the intestine from inflammation through functional M2 macrophage polarization. Cell reports. 19(6):1202-13.
García-Bermúdez J, Sánchez-Aragó M, Soldevilla B, Del Arco A, Nuevo-Tapioles C, Cuezva JM (2015) PKA phosphorylates the ATPase inhibitory factor 1 and inactivates its capacity to bind and inhibit the mitochondrial H+-ATP synthase. Cell reports. 12(12):2143-55.
Green DW, Grover GJ (2000) The IF1 inhibitor protein of the mitochondrial F1F0-ATPase. Biochimica et Biophysica Acta (BBA)—Bioenergetics. 1458(2-3):343-55.
Van Raaij MJ, Orriss GL, Montgomery MG, Runswick MJ, Fearnley IM, Skehel JM, Walker JE (1996) The ATPase inhibitor protein from bovine heart mitochondria: the minimal inhibitory sequence. Biochemistry. 35(49):15618-25.
Schnizer R, Van Heeke G, Amaturo D, Schuster SM (1996) Histidine-49 is necessary for the pH-dependent transition between active and inactive states of the bovine F1-ATPase inhibitor protein. Biochimica et Biophysica Acta (BBA)—Protein Structure and Molecular Enzymology. 1292(2):241-8.
Ando C, Ichikawa N (2008) Glutamic acid in the inhibitory site of mitochondrial ATPase inhibitor, IF1, participates in pH sensing in both mammals and yeast. Journal of biochemistry. 144(4):547-53.

Gledhill JR, Montgomery MG, Leslie AG, Walker JE (2007) How the regulatory protein, IF1, inhibits F1-ATPase from bovine mitochondria. Proceedings of the National Academy of Sciences. 104(40):15671-6.
Stout JS, Partridge BE, Dibbern DA, Schuster SM (1993) Peptide analogs of the beef heart mitochondrial F1-ATPase inhibitor protein. Biochemistry. 32(29):7496-502.
Papa S, Zanotti F, Cocco T, Perrucci C, Candita C, Minuto M (1996) Identification of functional domains and critical residues in the adenosinetriphosphatase inhibitor protein of mitochondrial F0F1 ATP synthase. European journal of biochemistry. 240(2):461-7.
Zanotti F, Raho G, Vuolo R, Gaballo A, Papa F, Papa S (2000) Functional domains of the ATPase inhibitor protein from bovine heart mitochondria. FEBS letters. 482(1-2):163-6.
Zanotti F, Raho G, Gaballo A, Papa S (2004) Inhibitory and anchoring domains in the ATPase inhibitor protein IF1 of bovine heart mitochondrial ATP synthase. Journal of bioenergetics and biomembranes. 36(5):447-57.
De Chiara C, Nicastro G, Spisni A, Zanotti F, Cocco T, Papa S (2002) Activity and NMR structure of synthetic peptides of the bovine ATPase inhibitor protein, IF1. Peptides. 23(12):2127-41.
Yu C, Li Y, Holmes A, Szafranski K, Faulkes CG, Coen CW, Buffenstein R, Platzer M, De Magalhães JP, Church GM (2011) RNA sequencing reveals differential expression of mitochondrial and oxidation reduction genes in the long-lived naked mole-rat when compared to mice. PloS one. 6(11):e26729.
Gautam A, Singh H, Tyagi A, Chaudhary K, Kumar R, Kapoor P, Raghava GP (2012) CPPsite: a curated database of cell penetrating peptides. Database.
Horton KL, Stewart KM, Fonseca SB, Guo Q, Kelley SO (2008) Mitochondria-penetrating peptides. Chemistry & biology. 15(4):375-82.
Jean SR, Ahmed M, Lei EK, Wisnovsky SP, Kelley SO (2016) Peptide-mediated delivery of chemical probes and therapeutics to mitochondria. Accounts of chemical research. 49(9):1893-902.
Appiah Kubi G, Qian Z, Amiar S, Sahni A, Stahelin RV, Pei D (2018) Non-Peptidic Cell-Penetrating Motifs for Mitochondrion-Specific Cargo Delivery. Angewandte Chemie. 130(52):17429-34.
Zielonka J, Joseph J, Sikora A, Hardy M, Ouari O, Vasquez-Vivar J, Cheng G, Lopez M, Kalyanaraman B (2017) Mitochondria-targeted triphenylphosphonium-based compounds: syntheses, mechanisms of action, and therapeutic and diagnostic applications. Chemical reviews. 117(15):10043-120.
Pathak RK, Marrache S, Harn DA, Dhar S (2014) Mito-DCA: a mitochondria targeted molecular scaffold for efficacious delivery of metabolic modulator dichloroacetate. ACS chemical biology. 9(5):1178-87.
Naso MF, Tomkowicz B, Perry WL, Strohl WR (2017) Adeno-associated virus (AAV) as a vector for gene therapy. BioDrugs. 31(4):317-34.
Whittemore K, Derevyanko A, Martinez P, Serrano R, Pumarola M, Bosch F, Blasco MA (2019) Telomerase gene therapy ameliorates the effects of neurodegeneration associated to short telomeres in mice. Aging (Albany NY). 11(10):3280.
Qian Z, Liu T, Liu YY, Briesewitz R, Barrios AM, Jhiang SM, Pei D (2012) Efficient delivery of cyclic peptides into mammalian cells with short sequence motifs. ACS chemical biology. 8(2):423-31.
Qian Z, Martyna A, Hard RL, Wang J, Appiah-Kubi G, Coss C, Phelps MA, Rossman JS, Pei D (2016) Discovery and mechanism of highly efficient cyclic cell-penetrating peptides. Biochemistry. 55(18):2601-12.
Lian W, Jiang B, Qian Z, Pei D (2014) Cell-permeable bicyclic peptide inhibitors against intracellular proteins. Journal of the American Chemical Society. 136(28):9830-3.
Qian Z, Rhodes CA, McCroskey LC, Wen J, Appiah-Kubi G, Wang DJ, Guttridge DC, Peid (2017) Enhancing the cell permeability and metabolic stability of peptidyl drugs by reversible bicyclization. Angewandte Chemie International Edition. 56(6):1525-9.
Heinis C, Rutherford T, Freund S, Winter G (2009) Phage-encoded combinatorial chemical libraries based on bicyclic peptides. Nature chemical biology. 5(7):502.
Baeriswyl V, Rapley H, Pollaro L, Stace C, Teufel D, Walker E, Chen S, Winter G, Tite J, Heinis C (2012) Bicyclic peptides with

(56) References Cited

OTHER PUBLICATIONS optimized ring size inhibit human plasma kallikrein and its orthologues while sparing paralogous proteases. ChemMedChem. 7(7):1173-6.

Angelini A, Cendron L, Chen S, Touati J, Winter G, Zanotti G, Heinis C (2012) Bicyclic peptide inhibitor reveals large contact interface with a protease target. ACS chemical biology. 7(5):817-21.

Teufel DP, Bennett G, Harrison H, Van Rietschoten K, Pavan S, Stace C, Le Floch F, Van Bergen T, Vermassen E, Barbeaux P, Hu TT (2018) Stable and long-lasting, novel bicyclic peptide plasma kallikrein inhibitors for the treatment of diabetic macular edema. Journal of medicinal chemistry. 61(7):2823-36.

Eder M, Pavan S, Bauder-Wüst U, Van Rietschoten K, Baranski AC, Harrison H, Campbell S, Stace CL, Walker EH, Chen L, Bennett G (2019) Bicyclic peptides as a new modality for imaging and targeting of proteins overexpressed by tumors. Cancer research. 79(4):841-52.

Rhodes CA, Pei D (2017) Bicyclic Peptides as Next-Generation Therapeutics. Chemistry—A European Journal. 23(52):12690-703.

Lee YW, Luther DC, Kretzmann JA, Burden A, Jeon T, Zhai S, Rotello VM (2019) Protein delivery into the cell cytosol using non-viral nanocarriers. Theranostics. 9(11):3280-3292.

Chatin B, Mével M, Devallière J, Dallet L, Haudebourg T, Peuziat P, Colombani T, Berchel M, Lambert O, Edelman A, Pitard B (2015) Liposome-based formulation for intracellular delivery of functional proteins. Molecular Therapy-Nucleic Acids. 4:e244.

Shi B, Keough E, Matter A, Leander K, Young S, Carlini E, Sachs AB, Tao W, Abrams M, Howell B, Sepp-Lorenzino L (2011) Biodistribution of small interfering RNA at the organ and cellular levels after lipid nanoparticle-mediated delivery. Journal of Histochemistry & Cytochemistry. 59(8):727-740.

Reist M, Carrupt PA, Francotte E, Testa B (1998) Chiral inversion and hydrolysis of thalidomide: mechanisms and catalysis by bases and serum albumin, and chiral stability of teratogenic metabolites. Chemical research in toxicology. 11(12):1521-1528.

Cundy KC, Crooks PA (1983) Unexpected pehnomenon in the high-performance liquid chromatographic anlaysis of racemic 14C-labelled nicotine: Separation of enantiomers in a totally achiral system. Journal of Chromatography A. 281:17-33.

Pepper C, Smith HJ, Barrell KJ, Nicholls PJ, Hewlins MJ (1994) Racemisation of drug enantiomers by benzylic proton abstraction at physiological pH. Chirality. 6(5):400-404.

Fulmer GR, Miller AJ, Sherden NH, Gottlieb HE, Nudelman A, Stoltz BM, Bercaw JE, Goldberg KI (2010) NMR chemical shifts of trace impurities: common laboratory solvents, organics, and gases in deuterated solvents relevant to the organometallic chemist. Organometallics. 29(9):2176-9.

Tillack K, Aboutalebi H, Kramer ER (2015) An efficient and versatile system for visualization and genetic modification of dopaminergic neurons in transgenic mice. PloS one. 10(8):e0136203.

Pickrell AM, Pinto M, Hida A, Moraes CT (2011) Striatal dysfunctions associated with mitochondrial DNA damage in dopaminergic neurons in a mouse model of Parkinson's disease. Journal of Neuroscience. 31(48):17649-58.

Chen L, Xie Z, Turkson S, Zhuang X (2015) A53T human α-synuclein overexpression in transgenic mice induces pervasive mitochondria macroautophagy defects preceding dopamine neuron degeneration. Journal of Neuroscience. 35(3):890-905.

Schönig K, Freundlieb S, Gossen M (2013) Tet-Transgenic Rodents: a comprehensive, up-to date database. Transgenic research. 22(2):251-4.

Premsrirut PK, Dow LE, Kim SY, Camiolo M, Malone CD, Miething C, Scuoppo C, Zuber J, Dickins RA, Kogan SC, Shroyer KR (2011) A rapid and scalable system for studying gene function in mice using conditional RNA interference. Cell. 145(1):145-58.

Zinn E, Pacouret S, Khaychuk V, Turunen HT, Carvalho LS, Andres-Mateos E, Shah S, Shelke R, Maurer AC, Plovie E, Xiao R (2015) In silico reconstruction of the viral evolutionary lineage yields a potent gene therapy vector. Cell reports. 12(6):1056-68.

Ginn SL, Amaya AK, Alexander IE, Edelstein M, Abedi MR (2018) Gene therapy clinical trials worldwide to 2017: An update. The journal of gene medicine. 20(5):e3015.

Coune PG, Schneider BL, Aebischer P (2012) Parkinson's disease: gene therapies. Cold Spring Harbor perspectives in medicine. 2(4):a009431.

Axelsen TM, Woldbye DP (2018) Gene therapy for Parkinson's disease, an update. Journal of Parkinson's disease. 8(2):195-215.

Palfis, Gurruchaga JM, Ralph GS, Lepetit H, Lavisse S, Buttery PC, Watts C, Miskin J, Kelleher M, Deeley S, Iwamuro H (2014) Long-term safety and tolerability of ProSavin, a lentiviral vector-based gene therapy for Parkinson's disease: a dose escalation, open-label, phase 1/2 trial. The Lancet. 383(9923):1138-46.

Lewitt PA, Rezai AR, Leehey MA, Ojemann SG, Flaherty AW, Eskandar EN, Kostyk SK, Thomas K, Sarkar A, Siddiqui MS, Tatter SB (2011) AAV2-GAD gene therapy for advanced Parkinson's disease: a double-blind, sham-surgery controlled, randomised trial. The Lancet Neurology. 10(4):309-19.

Schriner SE, Linford NJ, Martin GM, Treuting P, Ogburn CE, Emond M, Coskun PE, Ladiges W, Wolf N, Van Remmen H, Wallace DC (2005) Extension of murine life span by overexpression of catalase targeted to mitochondria. Science. 308(5730):1909-11.

Mitsui A, Hamuro J, Nakamura H, Kondo N, Hirabayashi Y, Ishizaki-Koizumi S, Hirakawa T, Inoue T, Yodoi J (2002) Overexpression of human thioredoxin in transgenic mice controls oxidative stress and life span. Antioxidants and Redox Signaling. 4(4):693-696.

Meanwell NA (2011) Synopsis of some recent tactical application of bioisosteres in drug design. Journal of medicinal chemistry. 54(8):2529-2591.

Dhainaut A, Regnier G, Atassi G, Pierre A, Leonce S, Kraus-Berthier L, Prost JF (1992) New triazine derivatives as potent modulators of multidrug resistance. Journal of medicinal chemistry. 35(13):2481-96.

\* cited by examiner

FIGURE 9

Anti-cancer activity scales with $EC_{50}$ $F_1F_0$ ATP hydrolase

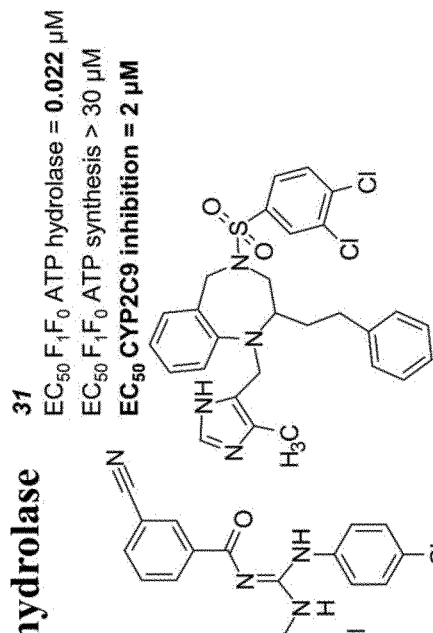

BTB06584
Inhibits $F_1F_0$ ATP hydrolase ≥ 100 μM
No inhibition of $F_1F_0$ ATP synthesis @ 100 μM

BMS-199264 HCl
$EC_{50}$ $F_1F_0$ ATP hydrolase = 0.48 μM
$EC_{50}$ $F_1F_0$ ATP synthesis = 18 μM

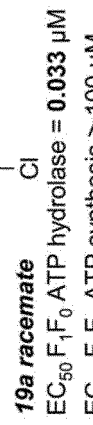

19a racemate
$EC_{50}$ $F_1F_0$ ATP hydrolase = 0.033 μM
$EC_{50}$ $F_1F_0$ ATP synthesis > 100 μM

6b, S stereoisomer
$EC_{50}$ $F_1F_0$ ATP hydrolase = 0.018 μM
$EC_{50}$ $F_1F_0$ ATP synthesis > 100 μM

6a, R stereoisomer
$EC_{50}$ $F_1F_0$ ATP hydrolase >100 μM
$EC_{50}$ $F_1F_0$ ATP synthesis > 100 μM

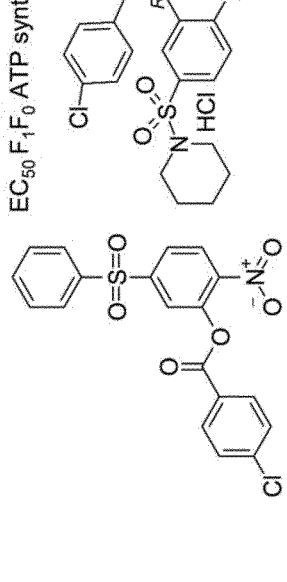

31
$EC_{50}$ $F_1F_0$ ATP hydrolase = 0.022 μM
$EC_{50}$ $F_1F_0$ ATP synthesis > 30 μM
$EC_{50}$ CYP2C9 inhibition = 2 μM

| MEAN % CANCER GROWTH INHIBITION OF NCI-60 CANCER CELL LINES | | | | |
|---|---|---|---|---|
|  | BTB06584 | BMS-199264 HCl | 6b | 6a | 31 |
| 10 μM | -3% | α 23% | 66% | 57% | 15% |
| 100 μM | 39% | β 148% | 75% | 71% | Untested |

α *Negative % = cancer growth promotion (rather than growth inhibition)*
β *% > 100 = less cancer cells at experiment end than start; if = 200% = all cancer cells dead*

Because of racemization during NCI testing: 6b≈6a≈19a
31 consumed by CYP2C9, so its anti-cancer activity is less than its $EC_{50}$ $F_1F_0$ ATP hydrolase value would predict FIGURE 12B
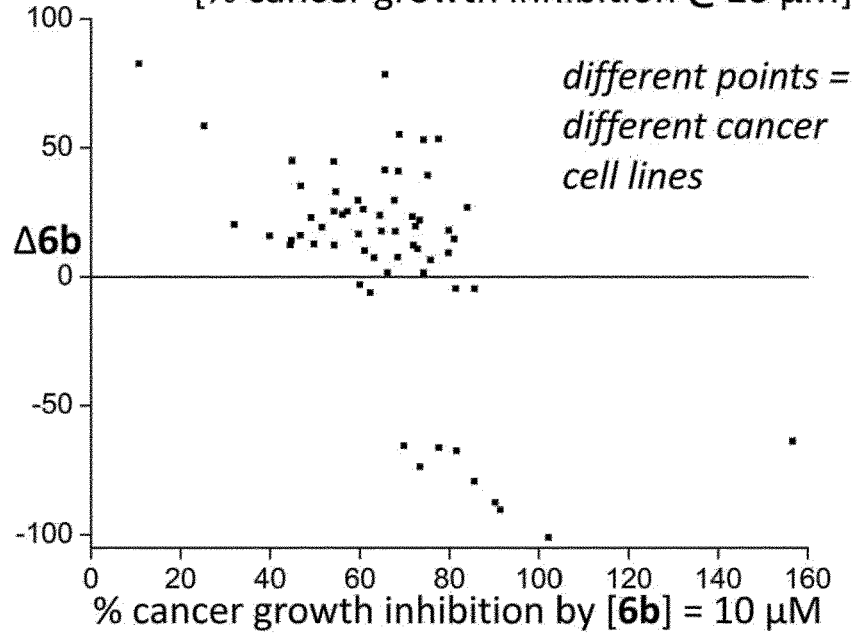
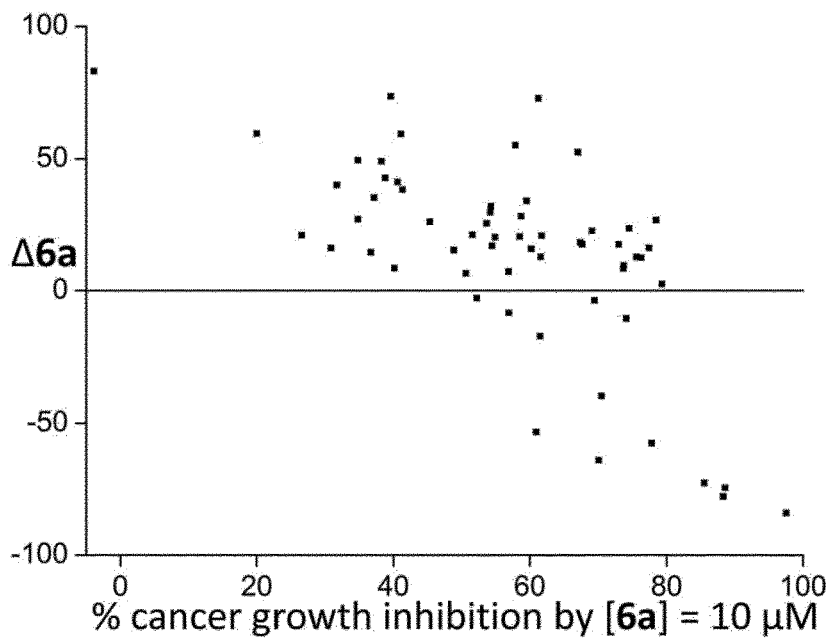
*{if % cancer growth inhibition > 100*
*= less cancer cells at experiment end than start;*
*if = 200% = all cancer cells dead}*
CONCLUSION: 6a and 6b can exert <u>LESS</u> anti-cancer activity at 100 μM than 10 μM
Pearson R (Δ6a, Δ6b) = 0.94 {p < 0.00001, Significant}

FIGURE 13A

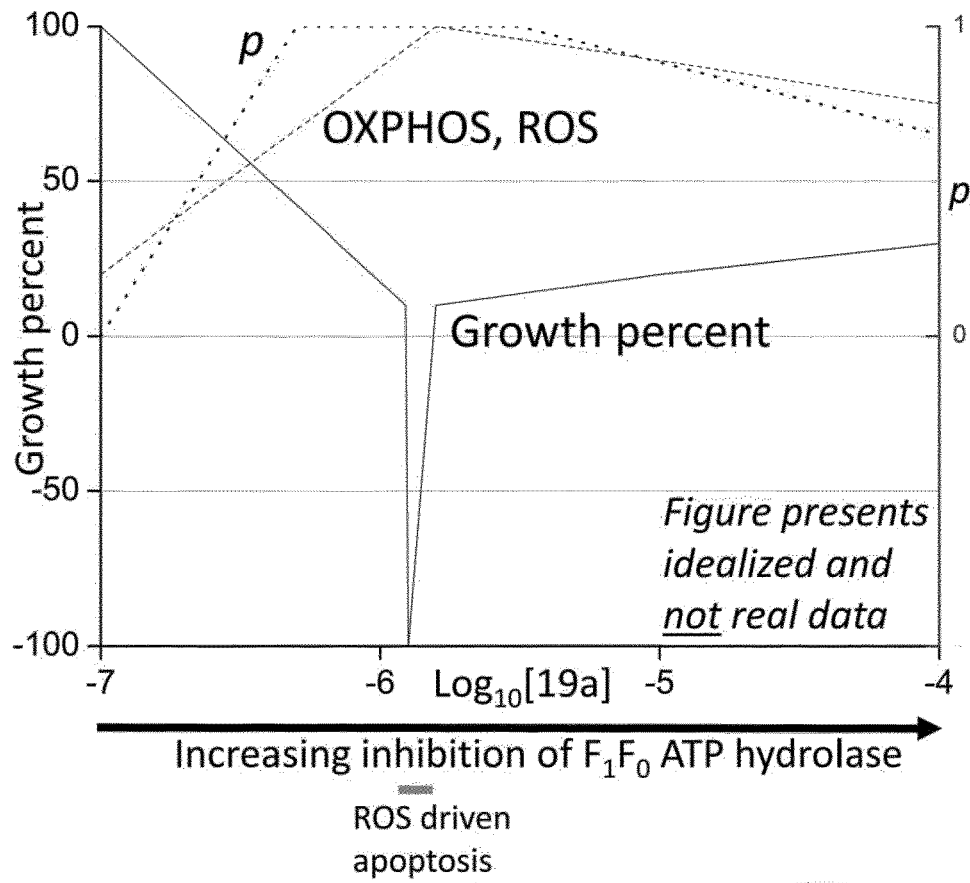

Increasing inhibition of $F_1F_0$ ATP hydrolase

ROS driven apoptosis

| INCREASING | DECREASING |
|---|---|
| ROS driven cell cycle checkpoint blockade + ROS damages information fidelity and reduces number of possible cell divisions | ROS driven cell cycle checkpoint blockade + ROS damages information fidelity and reduces number of possible cell divisions |

Number of cell divisions possible, $N$ = Hayflick limit/$p$
Hayflick limit = 40 to 60, $p$ is between 0 and 1,
when $p=0$, $N=\infty$ ("limitless replicative potential", a Hallmark of cancer),
when $p=1$, $N=$ Hayflick limit Different cancer cell lines present the 3 phases with different concentration ranges
Apoptosis isn't often seen in data because its range is narrow and typically falls inbetween tested concentrations Cancers use ES cell phenotype and commit apoptosis at lower [ROS] than normal cells Different cancer cell lines present the 2 phases with different concentration ranges

FIGURE 16

Enantiomeric excess (ee) stability: HIGH
Recorded by chiral SFC-MS

6a sample

| | Post-synthesis | |
| --- | --- | --- |
| | 6a | 6b |
| Retention time (minutes) | 2.35 | 0 |
| Area (%) | 100 | 0 |

6b sample

| | Post-synthesis | | After 2.5 months stored as powder | | After 72 hours in water@RT | | After 48 hours in phosphate solution@37°C | | After 5 days in phosphate solution@37°C | |
| --- | --- | --- | --- | --- | --- | --- | --- | --- | --- | --- |
| | 6a | 6b | 6a | 6b | 6a | 6b | 6a | 6b | 6a | 6b |
| Retention time (minutes) | 2.34 | 2.69 | 1.68 | 1.91 | 1.67 | 1.88 | 1.83 | 2.12 | 1.89 | 2.14 |
| Area (%) | 1.21 | 98.79 | 0.66 | 99.34 | 0.59 | 99.41 | 1.29 | 98.71 | 0.34 | 99.66 |

Retention times can vary because of different chiral-SFC columns (of different lengths) used
Phosphate buffer solution, 1 M, sourced from Sigma-Aldrich (product code: P3619), its recorded pH at the 37°C temperature used = 7.41
RT=room temperature, 6b in water assay: water was in contact with air (and so $CO_2$), thence water pH ~5.6

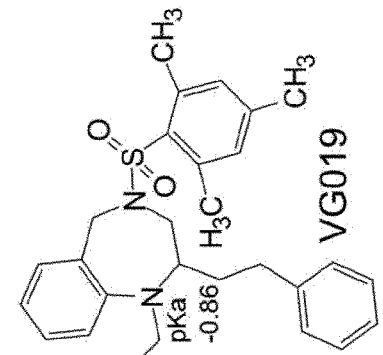
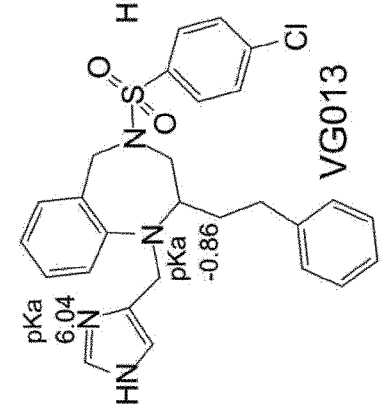
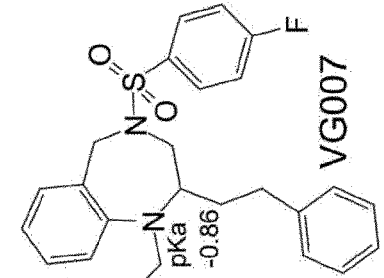
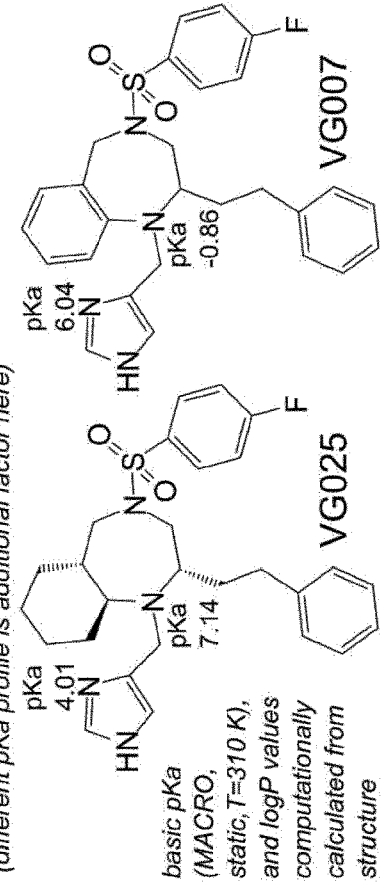
FIGURE 17A

FIGURE 17B

| | Higher logP (*if* increasing above ~3.2) reduces uncoupling | | | | BENCHMARK DRUGS |
|---|---|---|---|---|---|
| | VG025<br>logP = 4.68<br>*Most uncoupling* [ω] | VG007<br>logP = 5.04<br>*Less uncoupling* | VG013<br>logP = 5.50<br>*Even less uncoupling* | VG019<br>logP = 6.43<br>*Least uncoupling* | |
| ΔO$_2$ consumption<br>(without respiratory chain inhibitor) | -1.19% (10 μM)<br>+75% (100 μM) | +25% (100 μM) | +3.32% (10 μM)<br>+20% (100 μM) | -0.34% (100 μM) | Oligomycin (3 μM) -40%<br>FCCP (500 nM) +50% |
| Δψ$_{IM}$<br>(without respiratory chain inhibitor) | -7.3% (10 μM)<br>-47.5% (100 μM) | 0% (100 μM) | 0% (100 μM) | 0% (100 μM) | Oligomycin (3 μM) 0% [μ]<br>FCCP (500 nM) -50% |
| Δψ$_{IM}$<br>(with respiratory chain inhibitor) | -46% (10 μM)<br>-64% (100 μM) | -42.61% (100 μM) | -30.15% (10 μM)<br>-40.79% (100 μM) | -29.74% (100 μM) | Oligomycin (3 μM) -49.1%<br>FCCP (500 nM) -52.5% |

Uncoupling = increased O$_2$ consumption
Δψ$_{IM}$ -% = depolarization
+% = hyperpolarization ω, different pKa profile is additional factor here
μ, oligomycin should hyperpolarize the membrane slightly: presumably the assay used isn't sensitive enough to detect small hyperpolarizations

THERAPEUTIC MODULATORS OF THE REVERSE MODE OF ATP SYNTHASE

RELATED APPLICATIONS

This application claims the priority benefit of GB application numbers GB1711250.9 (filed 13 Jul. 2017), GB1715756.1 (filed 28 Sep. 2017), GB1715758.7 (filed 28 Sep. 2017), GB1715938.5 (filed 1 Oct. 2017), GB1716492.2 (filed 9 Oct. 2017), GB1800092.7 (filed 4 Jan. 2018), GB1800291.5 (filed 8 Jan. 2018), GB1800581.9 (filed 15 Jan. 2018), GB1801536.2 (filed 30 Jan. 2018), GB1806421.2 (filed 19 Apr. 2018), GB1808331.1 (filed 21 May 2018), GB1809497.9 (filed 8 Jun. 2018), GB1810236.8 (filed 21 Jun. 2018), GB1811188.0 (filed 8 Jul. 2018), and PCT application number PCT/EP2018/051127 (filed 17 Jan. 2017), which claims priority benefit of some aforementioned applications and also further GB application numbers GB1700772.5 (filed 17 Jan. 2017), GB1706046.8 (filed 14 Apr. 2017), GB1707945.0 (filed 17 May 2017), and GB1710198.1 (filed 27 Jun. 2017). The entire teachings of these applications are incorporated herein by reference.

FIELD OF THE INVENTION

This invention discloses compounds that preferentially slow the ATP-hydrolysing mode of ATP synthase, pharmaceutical compositions of these compounds, and methods of use for treating subjects known to have various diseases or disorders including cancer (e.g. diagnosed with), subjects suspected of having various diseases or disorders including cancer or subjects at risk of developing various diseases or disorders including cancer. In a particular embodiment, the subject is a human.

BACKGROUND OF THE INVENTION

ATP Synthase

ATP synthase (also known as $F_1F_0$ ATP synthase, $F_0F_1$ ATP synthase, $F_1F_0$-ATPase, $F_0F_1$-ATPase, $F_1F_0$ ATP hydrolase) is located at the inner mitochondrial membrane (IM). It can use the proton motive force (pmf) to generate ATP from ADP and Pi [1-3]. ATP synthase is reversible and—depending on its substrate/product concentrations, the pmf and the voltage across inner mitochondrial membrane $\{\Psi_{IM}\}$—it can work "forwards" (passaging protons, making ATP) or "backwards" (pumping protons, consuming ATP): its "forward" and "reverse" modes respectively, which may also be termed $F_1F_0$ ATP synthesis and $F_1F_0$ ATP hydrolysis respectively.

Inhibitors of ATP Synthase

There are drug inhibitors of ATP synthase, reviewed in [4] (herein incorporated in its entirety). Some inhibitors disproportionally/selectively inhibit the reverse mode, as compared to the forward mode, of ATP synthase [4-13]. Macrolides are a class of polyketide. So macrolide $F_1F_0$ ATP synthase inhibitors are polyketide $F_1F_0$ ATP synthase inhibitors, and these terms are used interchangeably herein. Polyketide $F_1F_0$ ATP synthase inhibitors (e.g. oligomycin) inhibit the forward mode, more than the reverse mode, of ATP synthase [11]. Oligomycin is well known in the art as an inhibitor of $F_1F_0$ ATP synthase, and thence oxidative phosphorylation and aerobic respiration [3]. Human life relies upon aerobic respiration. Indeed, the importance of breathing ($O_2$ in, $CO_2$ out) is widely appreciated. Thence the danger of oligomycin is easily apparent.

$IF_1$ is an endogenous protein, encoded by the ATPIF1 gene, which selectively blocks the reverse mode of ATP synthase [4]. Its activity is pH sensitive and low, but non-zero, at normal matrix pH, and significant upon matrix acidification, caused by collapse of the proton motive force across the mitochondrial inner membrane.

Prior Art Teaches that Compounds of this Disclosure are Anti-Cancer Therapeutics Polyketide $F_1F_0$ ATP synthase inhibitors (e.g. oligomycin) are poisonous to cancer [14] and normal [15] cells. Indeed, intraperitoneal injection of just 1 mg/kg oligomycin kills healthy rats (n=10) within 48 hours; LD33=0.5 mg/kg [15]. Normal cells typically need to use $F_1F_0$ ATP synthase in its forward mode and so blocking this mode is typically lethal. Thus, polyketide $F_1F_0$ ATP synthase inhibitors are not suitable as anti-cancer therapeutics: indeed, cytovaricin, ossamycin and peliomycin don't work in xenograft mouse models of cancer (data in [16], oligomycin untested) because a therapeutic window is absent because, to repeat, polyketide $F_1F_0$ ATP synthase inhibitors are highly poisonous to normal cells, whilst not even being poisonous to all cancer cells: e.g. ineffective against glycolytic cancers exhibiting the Warburg effect [14]. [17] used oligomycin in a xenograft cancer mouse model but only by applying oligomycin to the cancer cells before they were inoculated into mice, and washing the excess oligomycin off before inoculation into the mice (by culture for 2 days in drug free medium). They did the study like this (atypical, as clear to someone of the art) because oligomycin toxicity is not discriminate for cancer in a mammal. Obviously this experiment has no clinical parallel or utility. The synthesis/structure of some molecules of this disclosure has been disclosed in prior disclosures [P1, P2, P3], wherein these structures are speculated to be anti-cancer medicines merely by analogy to the anti-cancer activity of polyketide $F_1F_0$ ATP synthase inhibitors in [14]. Indeed, to mirror and use the restriction of [14], these disclosures restrict their suggestion to "cancers having tumor cells that do not exhibit the Warburg effect" (in claims of [P3], [P1] doesn't claim for any cancer, [P2] cancer claim rejected by USPTO in correspondence on Apr. 11, 2006). [P1, P2, P3] state in the Utility section of their Description, "inhibitors of mitochondrial $F_1F_0$-ATPase selectively kill metabolically active tumor cells that do not exhibit the Warburg effect i.e., cells that do not maintain a high level of anaerobic carbon metabolism even in the presence of oxygen". So, teaching that their compounds will not exert anti-cancer activity against cancers that exhibit the Warburg effect i.e. they restrict their suggestion to cancers using oxidative phosphorylation (OXPHOS) and ATP synthase, in its forward mode, to generate ATP. But what undermines this (postulated) approach is that this aerobic profile is what normal cells typically use also, especially on aggregate across an organism: well known to those of the art (evidence: importance of breathing to mammalian life). By this analogy to polyketide $F_1F_0$ ATP synthase inhibitors, these disclosures speculate these molecules are safe anti-cancer therapeutics. When in fact, by this analogy, they actually teach the opposite. This is clear when [14] isn't considered in isolation, as it shouldn't be, but alongside the rest of the literature e.g. [15], [16] and the knowledge of someone of the art (well known that normal cells need to use $F_1F_0$ ATP synthase in its forward mode, to generate ATP, and that oligomycin blocks this, and is potently dangerous). So, these prior disclosures [P1, P2, P3] teach someone of the art, that these compounds are, by their chosen analogy to polyketide $F_1F_0$ ATP synthase inhibitors, not suitable for anti-cancer therapy. It isn't sufficient to kill cancer to be an anti-cancer therapeutic. This killing must be selective, leaving normal cells alive. Metabolic poisons such as cyanide or oligomycin do not fit this criterion. By distinction, the present invention discloses selective killing of cancer cells, at compound concentrations harmless to normal cells. This couldn't have been anticipated from the prior art. Furthermore, this selective anti-cancer activity is pronounced for cancers that do exhibit the Warburg effect.

Distinctly, the present disclosure discloses experimental data. Its inventive step is to show that its compounds are safe anti-cancer therapeutics, exactly because of their distinction from polyketide $F_1F_0$ ATP synthase inhibitors. There is a broad therapeutic margin for the compounds of this disclosure as a virtue of the distinctive (from oligomycin) way they work, leveraging differences between normal and cancer cells, discovered and disclosed as part of this invention. Indeed, the compounds of this disclosure can kill highly glycolytic cancers exhibiting the Warburg effect. These cancers tend to be the most dangerous, with the worst prognosis (numerous studies find this: representatives: [18-20]).

[P1, P2, P3] do not provide any experimental evidence of any anti-cancer activity, and teach towards treating ischemia. They teach away from the present invention by suggesting, by an analogy in the unpredictable arts, that their compounds exert anti-cancer activity, like oligomycin, by inhibition of $F_1F_0$ ATP synthesis, wherein oligomycin itself is unsuitable as an anti-cancer drug. [P1, P2, P3] contains millions of compounds. The person of the art would select a subset of these for anti-cancer testing. Teaching of [P1, P2, P3] teaches the person of the art to select compounds that maximally inhibit $F_1F_0$ ATP synthesis in the submitochondrial assay they describe. Such compounds would very potently kill cancer in vitro, like oligomycin in [14], and so be excitingly entered into subsequent animal studies, wherein a lack of therapeutic margin would become evident (like polyketide $F_1F_0$ inhibitors in [16]) and no useful cancer drugs would be found, concluding the experimentation. Indeed, none found in subsequent ~16 years, despite long standing need. Whereas, by the present invention, compounds are selected from [P1, P2, P3] for anti-cancer activity by the inverse. By selection of compounds that minimally inhibit $F_1F_0$ ATP synthesis (as compared to their inhibition of $F_1F_0$ ATP hydrolysis). Indeed, by experimental evidence herein, the anti-cancer activity of such compounds is evidential. Thus, enabling the person of the art to arrive at working cancer drugs, and having the rationale to arrive at further working cancer drugs e.g. found by a method(s) disclosed herein. These drugs can cause body temperature drop, and can have a very atypical dose-anticancer response profile, which are critical teachings, with compensatory and associated methods, of this invention. These teachings are enabling for rodent trials, and more especially mouse trials (small body, more susceptible to body temperature drop), which is a step that one of the art would use to assess compounds of this invention.

Compounds of the present invention don't just exert anti-cancer activity. They can also affect normal cells, making their metabolism more efficient, which can cause weight gain/reduce weight loss/maintain body weight, all of which combats cachexia. For example, cancer driven cachexia, which is the leading cause of death in cancer patients. By contrast, polyketide $F_1F_0$ ATP synthase inhibitors are toxic to normal cells, denying them energy, rather than enabling them more energy, by efficiency gain, as molecules of this invention can do.

In short, [P1, P2, P3] teach that $F_1F_0$ ATP synthesis inhibitors only kill oxidative cancers not using Warburg metabolism, this invention experimentally shows that $F_1F_0$ ATP hydrolysis inhibitors do kill cancers using Warburg metabolism. The former teaching doesn't arrive at therapeutic cancer drugs, the latter does.

[P4] teaches away from the present invention. Its exemplary compound, Bz-423, inhibits the forward and reverse modes of ATP synthase equally or, in other data it discloses, the forward ($EC_{50}$=5.5 µM) more than the reverse ($EC_{50}$=8.9 µM) mode of ATP synthase. [P4] provides arguments and evidence that Bz-423 slows cellular proliferation, and causes apoptosis, by inhibiting $F_1F_0$ ATP synthesis and not by inhibiting $F_1F_0$ ATP hydrolysis. It extrapolates this feature of Bz-423 to other compounds it discloses (a point the (same) applicant of [P5] stresses often in examination correspondence with the USPTO). For example, in the title of Example 41 in [P4], it is written "Benzodione derivatives inhibit ATP hydrolysis, does not affect cell synthesis properties, and does not affect cell viability", and [P4] goes on to affirm this statement with experimental data, which teaches away from the present invention, wherein compound T5 is "capable of inhibiting ATP hydrolysis, not inhibiting cell synthesis, not affecting cell viability". In [P4], T5 experimental data is included to contrast with that of Bz-423, to show the lack of utility of a specific ATP hydrolysis inhibitor such as T5, as compared to the utility of the exemplary compound, Bz-423, which inhibits ATP synthesis. In this data [P4], Bz-423 inhibits $F_1F_0$ ATP synthesis and hydrolysis and cellular viability, T5 only inhibits $F_1F_0$ ATP hydrolysis and not cellular viability, =Bz-423 is the exemplary compound and $F_1F_0$ ATP synthesis inhibition, not $F_1F_0$ ATP hydrolysis inhibition, is experimentally highlighted as the responsible, exemplary mechanism. Bz-423 hyperpolarises $\Psi_{IM}$ and decreases $O_2$ consumption [21] whilst compounds of the present invention do not, as presented in experimental data of the present disclosure. Example 52 in [P4] states "For ATP synthesis (the relevant enzymatic reaction of the mitochondrial $F_1F_0$-ATPase in vivo)". Thence indirectly stating that $F_1F_0$ ATP hydrolysis is irrelevant in vivo, which the present invention discloses, with supporting experimental data, is a falsehood. This is a new fundamental biological discovery, which will surprise those of the art. [P4] teaches the use of inhibitors of the forward mode of ATP synthase, which is not teaching that arrives at the present invention; indeed, it teaches away from the present invention.

Well known to those of the art, biorxiv is a repository for documents that haven't been peer reviewed. In 2015, in a document on biorxiv, the author of this present disclosure suggested the use of $F_1F_0$ ATP hydrolysis inhibitors as anti-cancer therapeutics [22]. This document was subsequently submitted to peer reviewed journals (elife, BMC Cancer) and was found unworthy of dissemination, let alone pursuit, by those of the art. It demonstrably wasn't considered credible by those of the art. In 2017, a paper was published by others, in a peer-reviewed journal [23], with experimental data showing that inhibiting $F_1F_0$ ATP hydrolysis assists (!), rather than harms, cancer. With this conclusion reached and emphasised by its authors. This paper is one of many experimental reports, published in leading peer reviewed journals, reaching the same conclusion, which directly opposes and teaches away from this author's suggestion in a document database well known for unreviewed/unscrutinised manuscripts. Indeed, no journal publication years after a biorxiv submission would be noted very negatively by one of the art.

When selecting a path to pursue from the prior art, in the unpredictable arts, one of the art will always weigh experimental data more heavily than suggestion. Especially wherein experimental data postdates and falsifies/discredits suggestion. Experimental data in the prior art teaches away from the present invention. Indeed, it directly opposes it. Whereas the present invention is of $F_1F_0$ ATP hydrolysis inhibition conveying anti-cancer therapy, experimental data in [23] shows that $F_1F_0$ ATP hydrolysis inhibition assists cancer (!), thence increasing its danger. "The ATP synthase complex does not hydrolyze ATP in either $IF_1$-expressing or $IF_1$-silenced osteosarcoma cells" [23]. "Even severe hypoxia could not activate the hydrolysis of ATP by the $F_1F_0$-ATPase complex" [23]. "ATP synthase does not hydrolyze ATP in cancer cells" [23]. Moreover, "in cancer cells $IF_1$ overexpression fully prevents ATP synthase hydrolytic activity" and "$IF_1$ is present at higher levels in cancer cells than in untransformed cells" (also observable in gene expression databases, also reported by many other investigators in many other journal papers, $IF_1$ overexpression in cancer is a prognostic marker of poor patient outcome, $IF_1$ knockdown suppresses tumour growth in mice [24]) and "$IF_1$ overexpression promotes cancer cells survival" [23].

Some Guidance

All publications, patents and patent applications mentioned or cited in this disclosure are herein incorporated, in entirety, by reference. This disclosure uses $IC_{50}$ and $EC_{50}$ interchangeably, for a process being inhibited or reduced. Chemical structures were drawn using the chemical drawing feature in [25], and if a drawing feature is unknown to the reader they are referred to its documentation, or to explore the software themselves: all clear to those of the art. Hydrogen on structures is typically not shown, present implicitly, but it is shown for some presented structures "On Hetero and Terminal" [25] groups. Herein, the symbol D is used for deuterium ($^2H$). For compound synthesis schemes herein, starting materials are commercially available or can be readily prepared by one of ordinary skill in the art using known methods or derived by procedures analogous to those described in the literature. Examples and preparations herein describe the manner and process of making and using the invention. It should be understood that there will be other embodiments which fall within the spirit and scope of the invention

SUMMARY OF THE INVENTION

A first aspect of the invention is a compound, or a composition containing at least one compound, of the following formula:

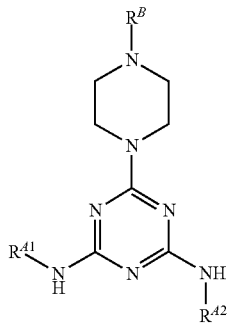

or a pharmaceutically-acceptable salt, solvate, hydrate or prodrug thereof, for use in a method of treating, ameliorating, preventing or combating cancer, or for use in a method of treating a disease or disorder selected from (i) cancer that metabolizes much of its glucose and/or glutamine to lactate, for example a cancer exhibiting the Warburg effect and/or a cancer that can be discriminated from surrounding tissue by PET imaging (e.g. $^{18}$F-FDG PET); (ii) cachexia or cancer driven cachexia; wherein:

$R^{A1}$ and $R^{A2}$ are each independently selected from the groups

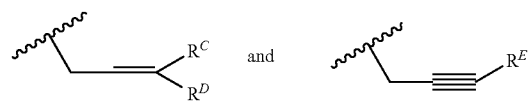

wherein $R^C$ and $R^D$ are each independently selected from hydrogen, deuterium, halogen and alkyl, and wherein $R^E$ is hydrogen, deuterium, or alkyl;

$R^B$ is selected from $R^{B1}$, hydrogen and deuterium;

wherein $R^{B1}$ is selected from phenyl, benzyl, pyridyl, pyrimidyl and pyrazinyl optionally substituted with one or more substituents $R^{B2}$;

wherein each $R^{B2}$ is independently selected from halogen, alkyl, alkoxy, nitro, amino, methoxy and polyhalogen alkyl;

or $R^B$ is a phenylalkyl of the formula:

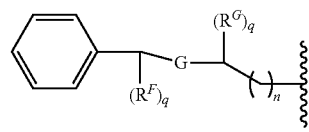

wherein $R^F$ and $R^G$ are hydrogen or alkyl, G is a carbon-carbon double bond or a carbon-carbon single bond, n is 0 or 1 and q is 0 or 1 provided that where q is 0, G is a carbon-carbon double bond and where q is 1, G is a carbon-carbon single bond, or $R^B$ is a diphenylalkyl of the formula

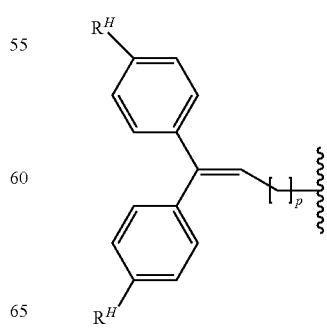

wherein $R^H$ is hydrogen or halogen, and p is 0, 1 or 2;
or $R^B$ is the group

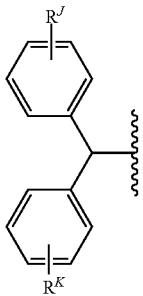

wherein $R^J$ and $R^K$ each independently represent 1-5 optional substituents on each ring, and wherein each $R^J$ and each $R^K$, when present, is independently selected from halogen, alkyl, alkoxy, nitro, amino, methoxy and polyhalogen alkyl.

In some embodiments, $R^B$ is the group:

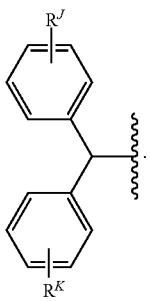

In some embodiments, $R^B$ is the group:

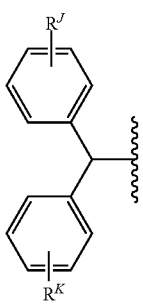

wherein $R^J$ and $R^K$ each independently represent 1 or 2 substituents on each ring, and wherein each $R^J$ and each $R^K$ is independently selected from halogen, alkyl, alkoxy, nitro, amino and polyhalogen alkyl.

In some embodiments, $R^J$ and $R^K$ each independently represent 1 or 2 substituents on each ring, and wherein each $R^J$ and each $R^K$ is independently selected from halogen.

In some embodiments, $R^J$ and $R^K$ each independently represent 1 substituent on each ring, and wherein $R^J$ and $R^K$ are independently selected from halogen.

In some embodiments, $R^B$ is the group:

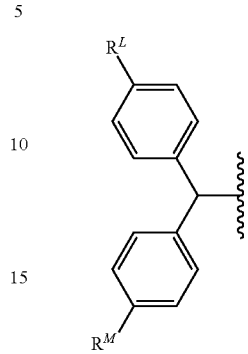

wherein $R^L$ and $R^M$ are each independently selected from halogen, alkyl, alkoxy, nitro, amino and polyhalogen alkyl.

In some embodiments, $R^L$ and $R^M$ are each independently selected from halogen.

In some embodiments, $R^L$ and $R^M$ are the same.

In some embodiments, $R^L$ and $R^M$ are each F.

In some embodiments, $R^{A1}$ and $R^{A2}$ are each independently selected from the group

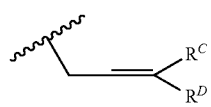

wherein $R^C$ and $R^D$ are each independently selected from hydrogen, deuterium, halogen and alkyl.

In some embodiments, $R^{A1}$ and $R^{A2}$ are the same.

In some embodiments, $R^C$ is hydrogen. In some embodiments, $R^D$ is hydrogen. In some embodiments, $R^C$ and $R^D$ are the same. In some embodiments, $R^C$ and $R^D$ are both hydrogen.

In some embodiments, the compound is:

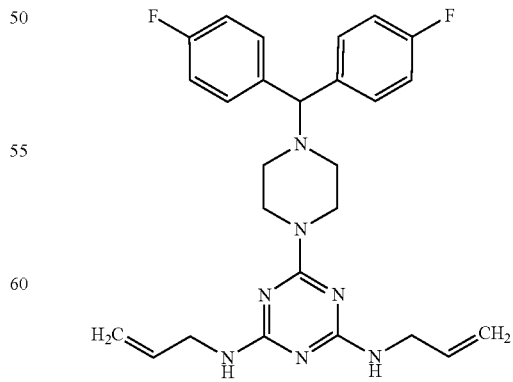

or a pharmaceutically-acceptable salt, solvate, hydrate or prodrug thereof.

In some embodiments, the compound is an isotopologue(s) of:

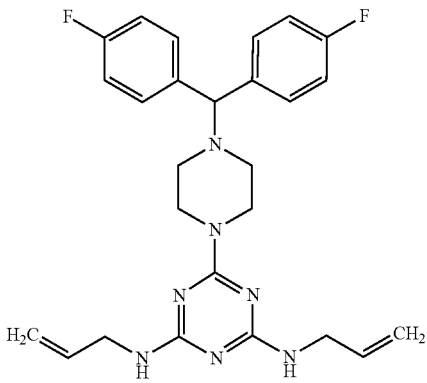 [SMILES: C=CCNc1nc(NCC=C)nc(N2CCN(C(c3ccc(F)cc3)c3ccc(F)cc3)CC2)n1]

or a pharmaceutically-acceptable salt, solvate, hydrate or prodrug thereof.

Almitrine dimesylate has been used clinically for millions of patient months to treat chronic obstructive pulmonary disease (COPD). However, after being used for decades, it is now only used sporadically. This is because postmarketing surveillance has revealed it doesn't actually treat COPD, thence there is no reward to outweigh its side-effects risk, especially since better/working COPD treatments have emerged. This invention repurposes almitrine for anti-cancer treatment. New experimental data herein shows that almitrine dimesylate exerts strong anti-cancer activity, greater than carboplatin in standardised NCI-60 testing at the National Cancer Institute (NCI, USA). Carboplatin is one of the most used chemotherapies today and is on the World Health Organisation (WHO) list of essential medicines. The potential side-effects of almitrine are mild compared to present chemotherapies, and tend to only occur with chronic use, yielding the opportunity for a therapeutic window of treatment, which will treat/ameliorate/prevent/combat cancer in a subject.

The compounds described herein, including for example almitrine dimesylate, exert anti-cancer activity because they reduce $F_1F_0$ ATP hydrolysis in cancer cells. This elucidated mechanism is the core of this invention. Herein is the discovery of a cancer-specific drug target: the reverse mode of ATP synthase. Indeed, new experimental data, disclosed herein, demonstrates that molecules which specifically inhibit $F_1F_0$ ATP hydrolysis can exert specific anti-cancer activity, at concentrations that do not harm normal cells. Any anti-cancer drug that targets/inhibits $F_1F_0$ ATP hydrolysis is componentry to this invention. This disclosure discloses numerous anti-cancer drug working examples, many of which are also new compositions of matter, and discloses rationale and methods to find further working examples, which are, in turn, componentry to this invention and encompassed by this disclosure.

Almitrine dimesylate is 6-[4-[bis(4-fluorophenyl)methyl]piperazin-1-yl]-2-N,4-N-bis(prop-2-enyl)-1,3,5-triazine-2,4-diamine methanesulfonic acid, the dimethanesulfonate salt of almitrine. Almitrine has the following structure:

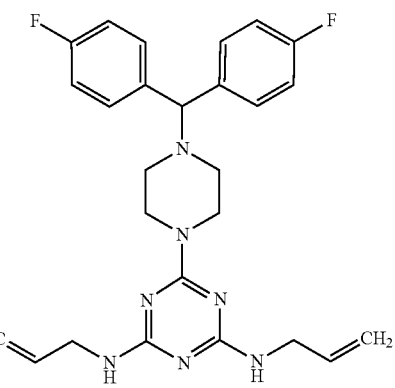

Also described herein for prevention or treatment of cancer in a subject, particularly with cancer exhibiting the Warburg effect, is to use a pharmaceutical composition with an effective amount of one or compounds of the following formula,

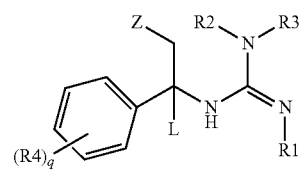

or a pharmaceutically-acceptable salt, solvate, hydrate or prodrug thereof, wherein:

L is alkyl, or substituted alkyl, or deuterated alkyl, or aminoalkyl, or thioalkyl, or alkoxy, or halogen, or haloalkyl, or haloalkoxy, or any atom or isotope permitted by valence (including any accompanying hydrogens by valence e.g. (non-limiting) OH, $NH_2$, SH, $SiH_3$, $PH_2$ etc.);

$R_1$ is hydrogen, cyano, —$SO_2R_8$, —(=O)$R_9$, heteroaryl or thiazolyl;

$R_2$ is (i) independently hydrogen, alkyl, benzyl, or substituted alkyl, or (ii) taken together with $R^3$ forms a heterocyclo;

$R_3$ is (i) independently alkyl, substituted alkyl, alkylthio, aminoalkyl, carbamyl, $B_B$-aryl, $B_B$-heterocyclo, $B_B$-heteroaryl, or $B_B$-cycloalkyl, or (ii) phenyl optionally substituted with $C_{1-4}$alkyl, halogen, trifluoromethyl, $OCF_3$, cyano, nitro, amino, hydroxy, or methoxy, or (iii) independently selected from $C_{1-4}$alkyl, alkylthio, aminoalkyl, —$B_B$-aryl, —$B_B$-heterocyclo, $B_B$-cycloalkyl, and —$B_B$-heteroaryl, optionally having one to three substituents selected from $R_{3a}$; and/or having fused thereto a five or six membered carbocyclic ring, or (iv) taken together with $R_2$ forms a heterocyclo optionally substituted with alkyl or substituted alkyl;

$B_B$ is a bond, $C_{1-4}$alkylene, $C_{2-4}$alkenylene, substituted $C_{1-4}$alkylene, substituted $C_{2-4}$alkenylene, substituted $C_{1-4}$alkylene-C(=O)NH—, —C(=O)NH—, —$C_{1-4}$alkylene-C(=O)NH—, —C(=O)$NR_{19}$—, —$C_{1-4}$alkylene-C(=O)$NR_{19}$—, or substituted $C_{1-4}$alkylene-C(=O)$NR_{19}$—, —$(CHR_{14})_m$—$(CR_{15}R_{16})_n$— or —$(CHR_{14})_p$—C(=O)NH—;

$R_{3a}$ at each occurrence is selected independently from alkyl, substituted alkyl, halogen, haloalkoxy, cyano, nitro, keto, trifluoromethyl, —$NR_{17}R_{18}$, —$SR_{17}$, —OR$_{17}$, SO$_2$R$_{17a}$, —SO$_2$NR$_{17}$R$_{18}$, —NR$_{17}$C(=O)R$_{18}$, —CO$_2$R$_{17}$, —C(=O)R$_{17}$, cycloalkyl, aryl, heterocylo, and heteroaryl, wherein when R$_{3a}$ is cycloalkyl, aryl, heterocyclo or heteroaryl, said cycloalkyl, aryl, heterocylo and heteroaryl in turn is optionally substituted with alkyl or substituted alkyl;

Z is a heteroaryl, for example an optionally-substituted bicyclic heteroaryl; or Z is triazolyl optionally substituted with one to two R$_7$ substituents or imidazolyl optionally substituted with one to two R$_7$ substituents and/or having fused thereto a benzene ring in turn optionally substituted with one to two R$_7$ substituents; and R$_7$ is alkyl, carbamyl, or substituted alkyl;

R$_4$ at each occurrence is selected independently of each other R$_4$ from the group consisting of halogen, trifluoromethyl, OCF$_3$, alkyl, substituted alkyl, haloalkyl, nitro, cyano, haloalkoxy, OR$_{25}$, SR$_{25}$, NR$_{25}$R$_{26}$, NR$_{25}$SO$_2$R$_{27}$, SO$_2$R$_{27}$, SO$_2$NR$_{25}$R$_{26}$, CO$_2$R$_{26}$, C(=O)R$_{26}$, C(=O)NR$_{25}$R$_{26}$, OC(=O)R$_{25}$, —OC(=O)NR$_{25}$R$_{26}$, NR$_{25}$C(=O)R$_{26}$, NR$_{25}$CO$_2$R$_{26}$, aryl, heteroaryl, heterocyclo and cycloalkyl;

R$_8$ is C$_{1-4}$alkyl or phenyl optionally substituted with alkyl, halogen, haloalkoxy, cyano, nitro, or trifluoromethyl;

R$_9$ is —NR$_{10}$R$_{11}$, alkyl, substituted alkyl, alkoxy, alkylthio, cycloalkyl, aryl, heteroaryl, heterocyclo, or —CO$_2$R$_{12}$, alkyl or phenyl optionally substituted with one to four of halogen, cyano, trifluoromethyl, nitro, hydroxy, C$_{1-4}$alkoxy, haloalkoxy, C$_{1-6}$alkyl, CO$_2$alkyl, SO$_2$alkyl, SO$_2$NH$_2$, amino, NH(C$_{1-4}$alkyl), N(C$_{1-4}$alkyl)$_2$, NHC(=O)alky, C(=O)alkyl, and/or C$_{1-4}$alkyl optionally substituted with one to three of trifluoromethyl, hydroxy, cyano, phenyl, pyridinyl; and/or a five or six membered heteroaryl or heterocylo in turn optionally substituted with keto or having a benzene ring fused thereto or a) C$_{1-4}$alkyl optionally substituted with one to two of:
  i) SR$_{13}$, OR$_{13}$, NR$_{13a}$R$_{13b}$, halogen, trifluoromethyl, CO$_2$R$_{13a}$, and C(=O)NR$_{13a}$R$_{13b}$;
  ii) cycloalkyl optionally substituted with one to two of C(=O)H, C$_{1-4}$acyl, alkenyl, carbamyl, and/or phenyl in turn optionally substituted with halogen;
  iii) phenyl or napthyl optionally substituted with one to two of halogen, nitro, amino, alkyl, hydroxy, C$_{1-4}$alkoxy, or having fused thereto a five or six membered heterocyclo;
  iv) pyridinyl, thiophenyl, furanyl, tetrahydrofuranyl, or azepinyl, optionally substituted with alkyl or having fused thereto a five to six membered carbocyclic ring optionally substituted with keto or C$_{1-4}$alkoxy;

b) 3 to 6 membered cycloalkyl optionally having up to four substitutents selected from alkyl, halogen, cyano, alkenyl, acyl, alkylthio, carbamyl, phenyl in turn optionally substituted with halogen; or having an aryl fused thereto;

c) phenyl optionally substituted with one to four of halogen, cyano, trifluoromethyl, nitro, hydroxy, C$_{1-4}$alkoxy, haloalkoxy, C$_{1-4}$alkyl, CO$_2$alkyl, SO$_2$alkyl, SO$_2$NH$_2$, amino NH(C$_{1-4}$alkyl), N(C$_{1-4}$alkyl)$_2$, NHC(=O)alkyl, C(=O)alkyl, and/or C$_{1-4}$alkyl optionally substituted with one to three of trifluoromethyl, hydroxy, cyano, phenyl, pyridinyl; and/or a five or six membered heteroaryl or heterocyle in turn optionally substituted with keto or having a benzene ring fused thereto;

d) pyridinyl, thiazolyl, furanyl, thiophenyl, and pyrrolyl optionally substituted with one to two of halogen, alkyl, and phenyl in turn optionally substituted with halogen or trifluoromethyl;

R$_{10}$ and R$^{11}$ are (i) independently selected from hydrogen, alkyl, substituted alkyl, alkoxy, heterocyclo, cycloalkyl, aryl, heteroaryl or C$_{1-4}$alkyl optionally substituted with one to two of —CO$_2$alkyl, —C(=O)NH(aryl), NH(aryl), cycloalkyl, phenyloxy, phenyl in turn optionally substituted with C$_{1-4}$alkyl, hydroxy, C$_{1-4}$alkoxy, halogen, amino, nitro, tetrahydrofuranyl, and/or five or six membered heterocyclo, or having a five or six membered heterocyclo fused thereto; pyrrolidinyl optionally substituted with keto; napthyl, anthracenyl, pyridinyl, thiophenyl, furanyl, imidazolyl, benzimidazolyl, or indolyl in turn optionally substituted with C$_{1-4}$alkyl or C$_{1-4}$alkoxy; or (ii) taken together form a heteroaryl or heterocyclo selected from pyrrolidinyl, piperazinyl, piperidinyl, morpholinyl, tetrahydropyridinyl, and imidazolidinyl, wherein said heterocyclo formed by R$_{10}$ and R$_{11}$ is optionally substituted with one to two of keto, CO$_2$H, C$_{1-4}$alkoxy, CO$_2$alkyl, C$_{1-4}$carbamyl, benzyl; phenyl in turn optionally substituted with alkyl, halogen, or C$_{1-4}$ alkoxy; tetrahydropyridinyl in turn optionally substituted with keto and/or phenyl; alkyl optionally substituted with amino or NHR$_{21}$ wherein R$_{21}$ is alkyl or phenyl optionally substituted with alkyl; and/or has a benzene ring fused thereto in turn optionally substituted with one to two of alkyl, C$_{1-4}$alkoxy, CO$_2$alkyl, and/or C$_{1-4}$carbamyl;

R$_{12}$ and R$_{19}$ are hydrogen or alkyl;
R$_{13}$ is hydrogen or alkyl;
R$_{13a}$ and R$_{13b}$ are selected from hydrogen, alkyl, and aryl;
R$_{14}$, R$_{15}$ and R$_{16}$ at each occurrence are independently selected from hydrogen, alkyl, hydroxy, hydroxyC$_{1-4}$alkyl, C$_{1-4}$alkoxy, and phenyl, and/or one of R$_{15}$ and one of R$_{16}$ join together to form a 3 to 6 membered cycloalkyl;

R$_{17}$ and R$_{18}$ are independently selected from hydrogen, alkyl, substituted alkyl, aryl, phenyl, or benzyl wherein the phenyl or benzyl is optionally substituted with alkyl, hydroxy, or hydroxyalkyl;

R$_{17a}$ is alkyl or substituted alkyl;
R$_{25}$ and R$_{26}$ are independently selected from hydrogen, alkyl, or substituted alkyl, or taken together form a heterocyclo or heteroaryl ring;
R$_{27}$ is alkyl or substituted alkyl;
q is 0, 1, 2, or 3;
m and n are 0, 1 or 2; and
p is 0, 1, 2, or 3.

In some embodiments, there is an enantiomeric excess of the enantiomer:

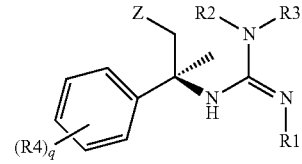

Herein, the terms "S-stereoisomer" and "S-enantiomer" refer to the arrangement of groups around the chiral centre shown in the structure above, regardless of the specific identities of the variables such as Z, L and R$_4$ within the structure. This chiral configuration is termed S by IUPAC designation if Z is nitrogen and L is deuterium for example. But, herein, where S is written next to this configuration it is not intended to limit what atoms can be Z or L according to IUPAC stereoisomer naming rules. For example, herein, Z can be carbon (or nitrogen or other atoms as specified herein) even when an S is written next to this chiral carbon. However, when R group type aliases, such as Z and L, are not used and all atoms are uniquely specified around a chiral carbon then IUPAC stereoisomer naming is adhered to.

In some embodiments, the S-enantiomer of the compound is in enantiomeric excess. In some embodiments, the enantiomeric excess of S-enantiomer exceeds 70%.

In some embodiments, L is hydrogen or deuterium.

In some embodiments, L is alkyl, or deuterium, or substituted alkyl, or deuterated alkyl, or aminoalkyl, or thioalkyl, or alkoxy, or halogen, or haloalkyl, or haloalkoxy, or any atom or isotope permitted by valence except hydrogen at natural abundance;

In some embodiments, the compound is a compound according to the formula

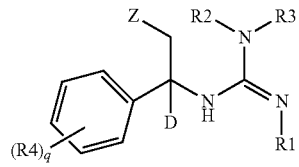

or pharmaceutically-acceptable salts, solvates, hydrates and prodrugs thereof, wherein D is deuterium (enrichment, for example, exceeding 40% deuterium incorporation at shown position, and optionally at other positions also).

In some embodiments, the compound is a compound according to the formula

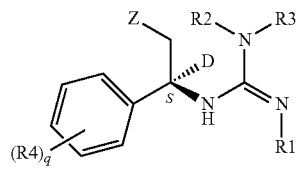

or pharmaceutically-acceptable salts, solvates, hydrates and prodrugs thereof, wherein D is deuterium (enrichment, for example, exceeding 40% deuterium incorporation at shown position, and optionally at other positions also);

S symbolises the S stereoisomer, for example, in enantiomeric excess (ee) exceeding 70%.

In some embodiments, the compound is

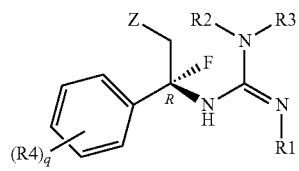

or a pharmaceutically-acceptable salt, solvate, hydrate or prodrug thereof. In some embodiments, the enantiomeric excess (ee) of the R stereoisomer exceeds 70%.

In some embodiments, the compound is

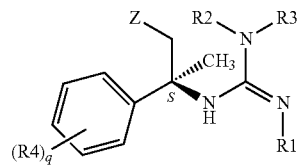

or a pharmaceutically-acceptable salt, solvate, hydrate or prodrug thereof. In some embodiments the enantiomeric excess (ee) of the S stereoisomer exceeds 70%.

In some embodiments, the compound is

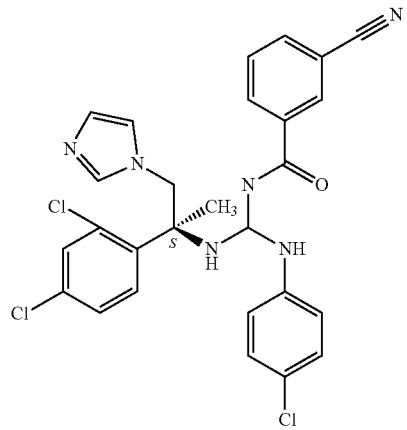

or a pharmaceutically-acceptable salt, solvate, hydrate or prodrug thereof. In some embodiments the enantiomeric excess (ee) of the S stereoisomer exceeds 70%.

In some embodiments, the compound is

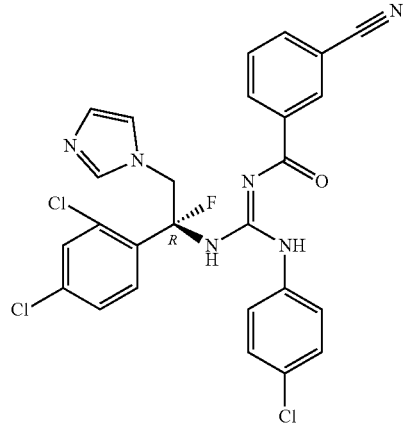

or a pharmaceutically-acceptable salt, solvate, hydrate or prodrug thereof. In some embodiments the enantiomeric excess (ee) of the R stereoisomer exceeds 70%.

FIGS. 1, 2, 3, 4, 5, 6, 7, 8 show anti-cancer activity of carboplatin (10 µM), BTB06584 (10 µM), BTB06584 (100 µM), BMS-199264 (10 µM), BMS-199264 (100 µM), compound 31 (10 µM), almitrine dimesylate (10 µM), compounds 6a and 6b (at 10 and 100 µM), respectively in the NCI one-dose assay. FIG. 9 consolidates data from prior figures to show that anti-cancer activity scales with inhibition of $F_1F_0$ ATP hydrolysis. FIG. 10 shows anti-cancer activity of BMS-199264, and FIG. 11 shows anti-cancer activity of 6a and 6b, in the NCI five-dose assay. FIG. 12 recasts data from FIGS. 8 & 11. FIG. 13 interprets data from FIGS. 8, 11, and 12. FIG. 14 interprets data from FIG. 10. FIG. 15 presents in vivo mouse data for compounds 6a and 6b. FIG. 16 presents experimental data on the racemization rate of 6b. FIG. 17 discloses that invention compounds can reduce $F_1F_0$ ATP synthesis by uncoupling the proton motive force, with supporting experimental data.

Compounds of this invention, which reduce $F_1F_0$ ATP hydrolysis, can also be used to treat/ameliorate/prevent/combat other diseases, disorders and conditions. Compounds of this invention attack cancer characteristics shared with embryonic stem cells, which aren't found in the adult human body, but are in the blastocyst ~5 days after fertilization. Thus compounds of this invention have utility for preventing unwanted pregnancy, with a later time window than presently available options. Reducing $F_1F_0$ ATP hydrolysis reduces a futile cycle of ATP synthesis and hydrolysis, used by the body for heat generation (supporting mouse data herein). If exogenous heat replaces this reduced endogenous heat (higher room temperature, wearing more clothes, geographical relocation to the tropics etc.), this reduces energy (food) consumption and treats/ameliorates/prevents/combats cachexia, cancer driven cachexia and weight loss, wherein cachexia is the biggest cause of death in cancer patients. Reducing this ATP synthesis/hydrolysis cycle means the oxidative phosphorylation rate is slower, less ROS are produced and the body accumulates less ROS damage per unit time i.e. aging slows. Therefore, $F_1F_0$ ATP hydrolysis inhibitors of this invention extend lifespan and healthspan, can treat/ameliorate/prevent/combat accelerated aging diseases, progeroid syndromes and the diseases of aging (e.g. Alzheimer's disease, dementia, Parkinson's disease, cancer etc.). It is noteworthy that compounds of this invention both treat and prevent cancer, whereas many present cancer treatments (e.g. radiotherapy) increase subsequent cancer risk. Activated macrophages are distinct from resting macrophages, and other normal adult cells, because the nitric oxide they produce to kill pathogens switches off their use of oxidative phosphorylation and they rely on $F_1F_0$ ATP hydrolysis to maintain $\Psi_{IM}$. Compounds of this invention inhibit $F_1F_0$ ATP hydrolysis and so depolarise $\Psi_{IM}$ in activated (not resting) macrophages, which triggers their apoptosis. Compounds of this invention treat/ameliorate/prevent/combat macrophage associated diseases or disorders (e.g. Macrophage Activation Syndrome, HIV hides safely in activated macrophages during anti-retroviral therapy {ART} and from here repopulates HIV virus in blood plasma when ART is interrupted or discontinued, virus neuroinvasion via macrophages, thence HIV-associated neurocognitive disorders, Tumour Associated Macrophages (TAMs) are a large component of tumour mass, are an integral drive to cancer pathology, correlate with poor patient prognosis). $F_1F_0$ ATP hydrolysis inhibitors, by increasing metabolic/bioenergetic efficiency (less heat produced), can cause energy/weight gain in a subject, which has therapeutic, aesthetic, physical/mental performance applications, and commercial applications in livestock and farming. Compounds of this invention reduce $F_1F_0$ ATP hydrolysis and can reduce body temperature to a value controlled by intersection of compound dosage and ambient temperature (even at maximum effect, compound can't make body fall below, only to, ambient temperature; body temperature controlled by controlling ambient temperature), which can treat/ameliorate/prevent/combat a disease or disorder that causes a higher than normal body temperature (e.g. fever, infection, sepsis, malignant hyperthermia, neuroleptic malignant syndrome etc.) and a disease or disorder combated (or surgery or medical treatment helped) by hypothermia (e.g. neuroprotection/cardioprotection/tissue protection after a stroke or ischemia, deep hypothermic circulatory arrest for surgery etc.).

An aspect of the invention is a pharmaceutical composition comprising at least one compound as described herein and a pharmaceutically-acceptable carrier or diluent.

An aspect of the invention is a compound or composition as described herein for use in a method of treatment of the human or animal body by therapy.

An aspect of the invention is a compound or composition as described herein for use in a method of treating, ameliorating, preventing or combating a disease or disorder selected from (i) cancer that metabolizes much of its glucose and/or glutamine to lactate, for example a cancer exhibiting the Warburg effect and/or a cancer that can be discriminated from surrounding tissue by PET imaging (e.g. $^{18}$F-FDG PET);

(ii) cachexia, cancer driven cachexia or weight loss;

(iii) disease or disorder that causes a higher than normal body temperature such as high environmental temperature, ingesting an uncoupler (e.g. 2,4-dinitrophenol), infection, sepsis, stroke, fever, pyrexia, hyperpyrexia, hyperthermia, malignant hyperthermia, neuroleptic malignant syndrome, serotonin syndrome, thyroid storm, heatstroke, thermoregulatory disorder(s), Kawasaki syndrome, drug or drug withdrawal induced hyperthermia, idiosyncratic drug reaction, fever of unknown or uncertain origin, reaction to incompatible blood product(s), metabolic disorder(s), cancer, injury;

(iv) Tumour Associated Macrophages (TAMs) or any macrophage associated disease or disorder such as Macrophage Activation Syndrome (MAS), HIV, AIDS, HIV-associated neurocognitive disorders (HAND), HIV associated cancers, AIDS-defining cancers, non-AIDS defining cancers;

(v) virus neuroinvasion via macrophages, as used for example by HIV and SARS coronavirus;

(vi) neurocognitive or neurodegenerative diseases/disorders, for example those caused by a virus;

(vii) acute or chronic or systemic inflammation or any inflammatory disease/disorder/syndrome or any auto-inflammatory disease/disorder/syndrome or any autoimmune disease/disorder/syndrome;

(viii) low or less than desired metabolic/bioenergetic efficiency in a subject, or low or less than desired physical or mental performance, or low or less than desired body weight;

(ix) disease or disorder treatable by conferring hypothermia in a subject for some medical or other purpose which can include slowing a chemical reaction(s) rate in a subject for therapeutic benefit, preventing/minimizing brain and/or tissue damage, deep hypothermic circulatory arrest for surgery, hypothermia for a surgical purpose, hypothermia for cardiac and/or cardiovascular surgery and/or brain surgery (neurosurgery), Emergency Preservation and Resuscitation (EPR), preserving detached body parts such as limbs and/or organs (for example during organ storage and/or transplant), protective hypothermia, targeted temperature management, therapeutic hypothermia, hypothermia therapy for neonatal encephalopathy, birth asphyxia, haemorrhage, hypovolemia, decompression sickness, burn injury(s) including skin burn, inflammation, allergic reaction, anaphylaxis, tissue/organ rejection, hypoxia, hypoxemia, anoxemia, anoxia, anemia, hypervolemia, altitude sickness, obstructed airway, asthma attack, hypoxia in a body/tissue/organ, hypoglycemia, reperfusion injury (ischemia-reperfusion injury), upon release of a ligature or tourniquet, uraemia, crush syndrome, compartment syndrome, traumatic brain and/or spinal cord injury, major trauma, infection, bacterial and/or viral infection(s) (e.g. meningitis), sepsis, septic shock, ischemic brain/heart/kidney injury, neuroprotection and/or cardioprotection and/or tissue protection during/after a stroke and/or ischemia and/or cardiac arrest and/or resuscitation and/or a period(s) of poor blood flow anywhere in a subject;
(x) poisoning by a toxic amount of a compound(s) in a subject e.g. carbon monoxide/methanol/heavy metal/pesticide poisoning, snake/spider/bee/insect/lizard venom, metabolic poison(s), bacterial toxin(s), endotoxemia or drug/substance overdose e.g. heroin, ethanol, prescription medication(s) or over the counter medication(s);
(xi) accelerated aging disease or progeroid syndrome including Werner syndrome, Bloom syndrome, Rothmund-Thomson syndrome, Cockayne syndrome, xeroderma pigmentosum, trichothiodystrophy, combined xeroderma pigmentosum-Cockayne syndrome, restrictive dermopathy, Wiedemann-Rautenstrauch syndrome, Hutchinson-Gilford progeria syndrome (progeria);
(xii) disease or disorder of ageing (incidence increases with increased age/senescence) and/or a disease/disorder associated with elevated reactive oxygen species including degenerative diseases, neurodegenerative diseases, amyotrophic lateral sclerosis (ALS), Parkinson's disease, Alzheimer's disease, Huntington's disease, spinocerebellar ataxias, Friedreich's ataxia, dementia, Batten disease, polyglutamine diseases, osteoporosis, atherosclerosis, cardiovascular disease, myocardial infarction, cerebrovascular disease, stroke, heart failure, chronic obstructive pulmonary disease (COPD), hypertension, arthritis, cataracts, type 2 diabetes, andropause, sarcopenia, age-related macular degeneration (AMD), hearing loss, movement disability, cancer;
(xiii) aging, wherein these compounds slow ageing, extend lifespan and healthspan; or
(xiv) skin aging.

Another aspect is a method of treating, ameliorating, preventing or combating any such disease or disorder by administering to a subject in need thereof a therapeutically effective amount of a compound or composition as described herein.

Another aspect is the use of a compound or composition as described herein for the manufacture of a medicament for the treatment, amelioration, prevention or combating of any such disease or disorder.

In some embodiments, the subject is further administered with one or more compounds or compositions approved for human use, optionally for anti-cancer use, by the United States Food and Drug Administration (FDA) and/or European Medicines Agency (EMA), optionally in the same pharmaceutical composition.

In some embodiments, the mg/kg dose administered to the subject is comparable with or larger than the mg/kg dose which would be administered to a subject of smaller bodily size, and optionally the mg/kg dosage administered to adult humans is comparable or greater than the No Observed Adverse Effects Level (NOAEL) mg/kg dosage in mice housed at 22° C.

BRIEF DESCRIPTION OF THE DRAWINGS

FIG. 9 consolidates data from prior figures to show that anti-cancer activity scales with inhibition of $F_1F_0$ ATP hydrolysis.

FIG. 11A to FIG. 11I show anti-cancer activity of 6a and 6b compounds in the NCI five-dose assay, showing activity against cancer cell lines of the breast, prostate, kidney, ovary, skin, Central Nervous System (CNS), colon, lung, blood, respectively.

FIG. 12A and FIG. 12B recasts data from FIG. 8B, FIG. 8C, FIG. 8E and FIG. 8F.

FIG. 13A and FIG. 13B interprets data from figures FIG. 8A to FIG. 8H, FIG. 11A to FIG. 11I, and FIG. 12A to FIG. 12C.

FIG. 16 presents experimental data on the racemization rate of 6b.

FIG. 17A and FIG. 17B discloses that some compounds of this disclosure can reduce $F_1F_0$ ATP synthesis by uncoupling the proton motive force, with supporting experimental data.

DETAILED DESCRIPTION OF THE INVENTION

Figure 1:
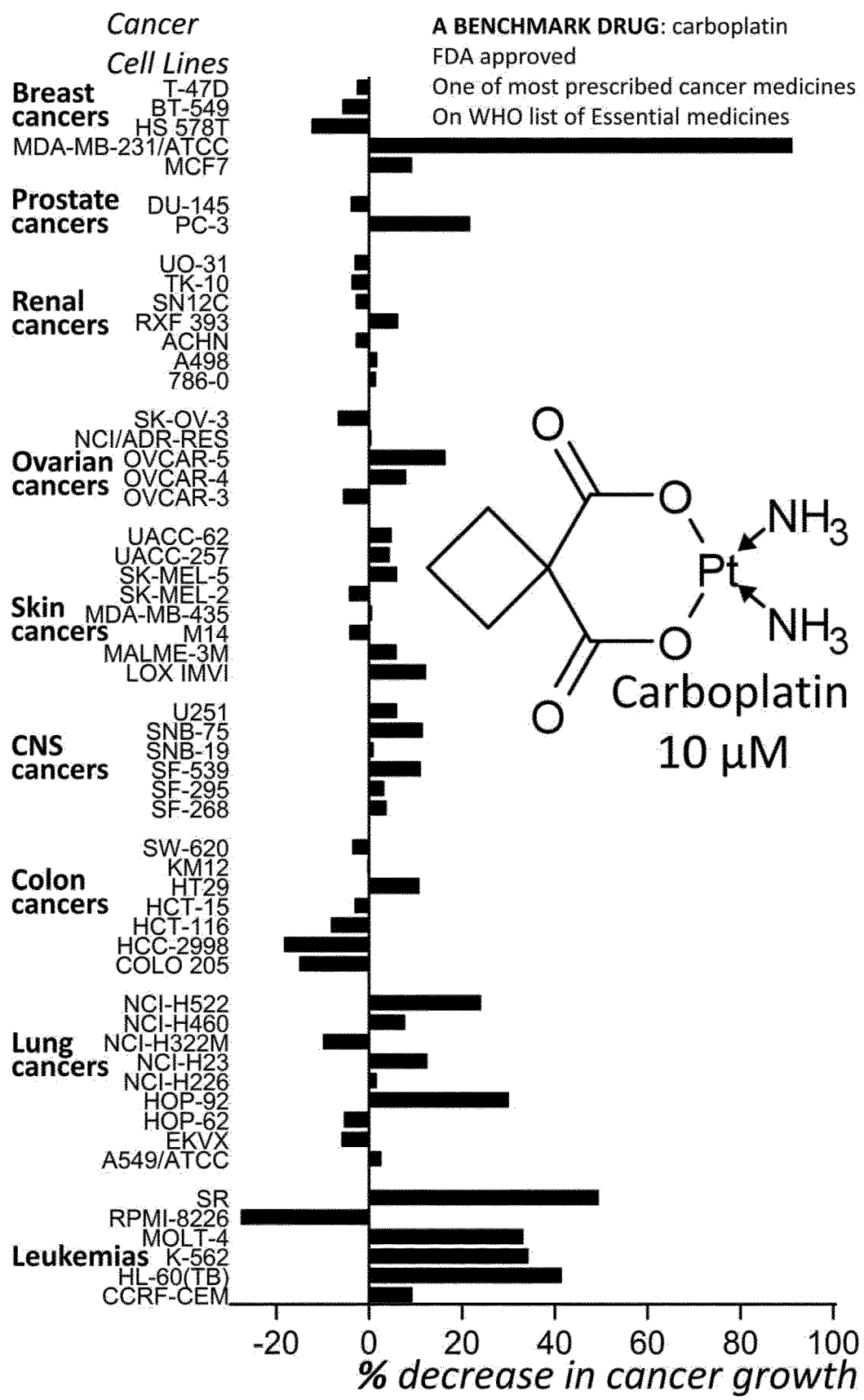
FIG. 1 shows anti-cancer activity of carboplatin in the NCI one-dose assay (10 µM).

As used herein with reference to the utilities described, the terms "treating" or "treatment" encompass both responsive and prophylaxis measures designed to inhibit or delay the onset of the disease or disorder, or to alleviate, ameliorate, lessen, reduce, modulate or cure the disease or disorder and/or one or more of its symptoms. The terms "subject" and "patient" refer to organisms to be treated by the compounds/methods of the present invention and can refer to a human or animal.

The invention of this disclosure hinges on the discovery, disclosed herein, that some cancers rely on $F_1F_0$ ATP hydrolysis, even under normoxia (indeed under hyperoxia: ~21% $O_2$), during some or all of their cell cycle. Evidence herein: compounds of this disclosure, which specifically inhibit $F_1F_0$ ATP hydrolysis, slow cancer proliferation at concentrations that they do not harm normal cells.

In some of the most dangerous cancers, refractory to present [chemo/radio] therapies, during some or all of their cell cycle, reactive oxygen species (ROS) decrease [NADPH], because NADPH is consumed in ROS mitigation processes, and this then pulls through increased pentose phosphate pathway (PPP) and glycolytic flux. But such a pivotal increase in glycolytic/PPP flux can only occur because of $F_1F_0$ ATP hydrolysis, a distinctive feature to these cancers, which stops ATP produced by glycolysis from accumulating and slowing glycolysis by negative feedback inhibition of key glycolytic enzymes. This increased PPP flux maintains [NADPH] and ROS mitigation. In this way, these cancers can maintain a very high ROS mitigation capability, maintain very low intracellular [ROS], and tend to be the most resistant to conventional [chemo/radio] therapies, which work, or often don't work (!), by increasing [ROS]. Compounds of this disclosure undermine this process/resistance. By inhibiting $F_1F_0$ ATP hydrolysis, they increase the anti-cancer efficacy of any chemical or treatment that increases reactive oxygen species (ROS) in cancer cells. An embodiment of this disclosure is any such co-treatment(s). Indeed, a compound(s) of this disclosure increases the success rate of standard of care [chemo/radio] therapies and permits their use at lower dosing, which reduces their horrendous side-effects. This disclosure encompasses a compound(s) of this invention in co-therapy with chemotherapy, or radiotherapy or any US Food and Drug Administration (FDA) and/or European Medicines Agency (EMA) approved drug(s) or treatment, for example, a drug/treatment approved for cancer therapy. Chemotherapies are well known to those of the art, including, but not limited to, cisplatin, carboplatin, taxol, oxaliplatin etc.

In other embodiments, a compound(s) of this disclosure is used as cancer therapy alone. Indeed, this is a much more cancer-targeted therapeutic approach. The most dangerous cancers use this distinctive metabolism, with ATP synthase distinctively in reverse, consuming glycolytic ATP, to yield high glycolytic rate, thence abundant glycolytic intermediates for biosynthesis and, crucially, to keep [ROS] low (as prior disclosed), which is necessary to cancer immortality ("limitless replicative potential", a Hallmark of cancer [26]) and thence danger. This distinction is targeted, by compound(s) of this disclosure, without significant damage to normal cells. Normal adult cells normally use a different metabolism, with ATP synthase more in forward mode, and a higher ATP yield from glucose, but at the cost of higher [ROS] and mortality.

This reliance of normal cells upon the forward mode of ATP synthase makes them exquisitely susceptible to oligomycin. The compounds of this disclosure are useful for anti-cancer treatment, unlike oligomycin, because of their distinction from oligomycin, which couldn't have been foreseen without the inventive steps of this disclosure. In normal cells that are actively respiring (known as state 3 respiration [3]), inhibitors of the forward mode of ATP synthase (e.g. oligomycin) cause a state 3 to state 4 transition, hyperpolarize decrease $O_2$ consumption and reduce [ATP] (so called "modulators" of the forward mode of ATP synthase, e.g. Bz-423, can also cause one or more of these effects) whilst a specific inhibitor of the reverse mode of ATP synthase does not exert these effects at a working concentration ([12-13], herein incorporated in their entirety). However, at this working concentration, after inhibition of the respiratory chain (e.g. blocked by rotenone, or some other respiratory chain inhibitor, or by a reduced $O_2$ concentration), a specific inhibitor of the reverse mode of ATP synthase will depolarise $\Psi_{IM}$. This feature distinguishes a molecule that inhibits the reverse mode of ATP synthase significantly more than it inhibits/modifies the forward mode of ATP synthase, and/or inhibits/modifies ATP synthesis. Such a molecule, put into use as an anti-cancer therapeutic, is an embodiment of this invention. A further embodiment is the process/method of seeking new anti-cancer molecules by assaying whether a candidate molecule can depolarise $\Psi_{IM}$, when $\Psi_{IM}$ is maintained by $F_1F_0$ ATP hydrolysis (e.g. when OXPHOS is blocked by a respiratory chain inhibitor or insufficient $O_2$), but that can't hyperpolarize $\Psi_{IM}$ and/or decrease $O_2$ consumption, when $\Psi_{IM}$ is maintained by proton pumping by complexes of the respiratory chain. If a candidate molecule meets these requirements, it is an anti-cancer therapeutic, as determined by the invention of this disclosure.

Some cancers intrinsically rely upon ATP synthase in reverse, as revealed by experimental data of this disclosure, and further cancers can have this reliance imposed upon them, to maintain $\Psi_{IM}$ in the hypoxia of a solid tumour, which also makes them susceptible to drugs of this disclosure. Significant lactate release is correlated with the most dangerous cancers and poor patient outcomes (numerous studies find this: example: [27]). High lactate release indicates high glycolytic rate, which $F_1F_0$ ATP hydrolysis enables, and which drugs of this disclosure attack. This invention confronts the most deadly cancers by discovering/disclosing a cancer-specific weakness, and the means to selectively attack it.

All the following molecules are—in use as anti-cancer therapeutics—embodiments of this invention: (1) Molecules that inhibit the reverse, and not the forward, mode of ATP synthase, (2) Molecules that inhibit the reverse more than forward mode of ATP synthase, (3) Molecules that inhibit the reverse mode of ATP synthase, and not its forward mode, but that shuttle protons across the mitochondrial inner membrane, dissipating the pmf as heat (uncoupling [3]), which reduces $F_1F_0$ ATP synthesis, and in a further embodiment: uncoupling molecules that reduce $F_1F_0$ ATP hydrolysis more than $F_1F_0$ ATP synthesis, (4) Molecules that inhibit ATP hydrolysis more than ATP synthesis at the mitochondrial inner membrane, (5) Molecules that have a lower $IC_{50}$ or $EC_{50}$ for $F_1F_0$ ATP hydrolysis than $F_1F_0$ ATP synthesis. This invention discloses the process/method of using one or more molecular species, each with one or more of the characteristics in the aforementioned numbered points, as an anti-cancer medicine or treatment. Some examples are presented in this disclosure. Any cancer therapy or treatment or drug that leverages, relies upon, utilises or targets that cancers employ ATP synthase in its reverse mode is an embodiment of this disclosure.

Mechanistic Distinction from Polyketide $F_1F_0$ ATP Synthase Inhibitors

The compounds of this invention act by a distinctly different mechanism, upon cancer cells, than oligomycin. Drugs that act against the same molecular target have a similar pattern of activity against the different cancer cell lines of the NCI-60 assay i.e. the smaller, and the larger, of their GI50 values are against the same cell lines (GI50 is compound concentration that causes 50% growth inhibition of a cell line relative to no-drug control). The degree of (dis)similarity can be measured using the COMPARE algorithm [28-29], which employs a Pearson correlation coefficient. For example, [30] found that the COMPARE algorithm can successfully group different FDA-approved anti-cancer drugs by their method of action using their NCI-60 GI50 data. Oligomycin A (NSC: 717694 [16]) inhibits $F_1F_0$ ATP synthase [4, 14] and so do other polyketides: cytovaricin (NSC: 349622 [16]), ossamycin (NSC: 76627 [16]) and peliomycin (NSC: 76455 [16]); indeed, their NCI-60 pattern responses (GI50 values) correlate with that of oligomycin A: 0.896, 0.809 and 0.865 respectively (COMPARE algorithm output, all significant at $p<0.05$). However, the NCI-60 pattern response (GI50 values) of BMS-199264 is uncorrelated to that of oligomycin A (0.009). As is that of compounds 6b (0.198, not significant at $p<0.05$) and 6a, which are separated stereoisomers of racemate 19a that both epimerize towards being the 19a racemate during NCI testing, and that have very correlated anti-cancer activity (0.754, $p<0.00001$). This mechanistic distinction from oligomycin is vital because polyketide $F_1F_0$ ATP synthase inhibitors are poisonous to normal cells [15], which means they fail in cancer xenograft mouse experiments [16] and are without clinical utility.

Figure 5:
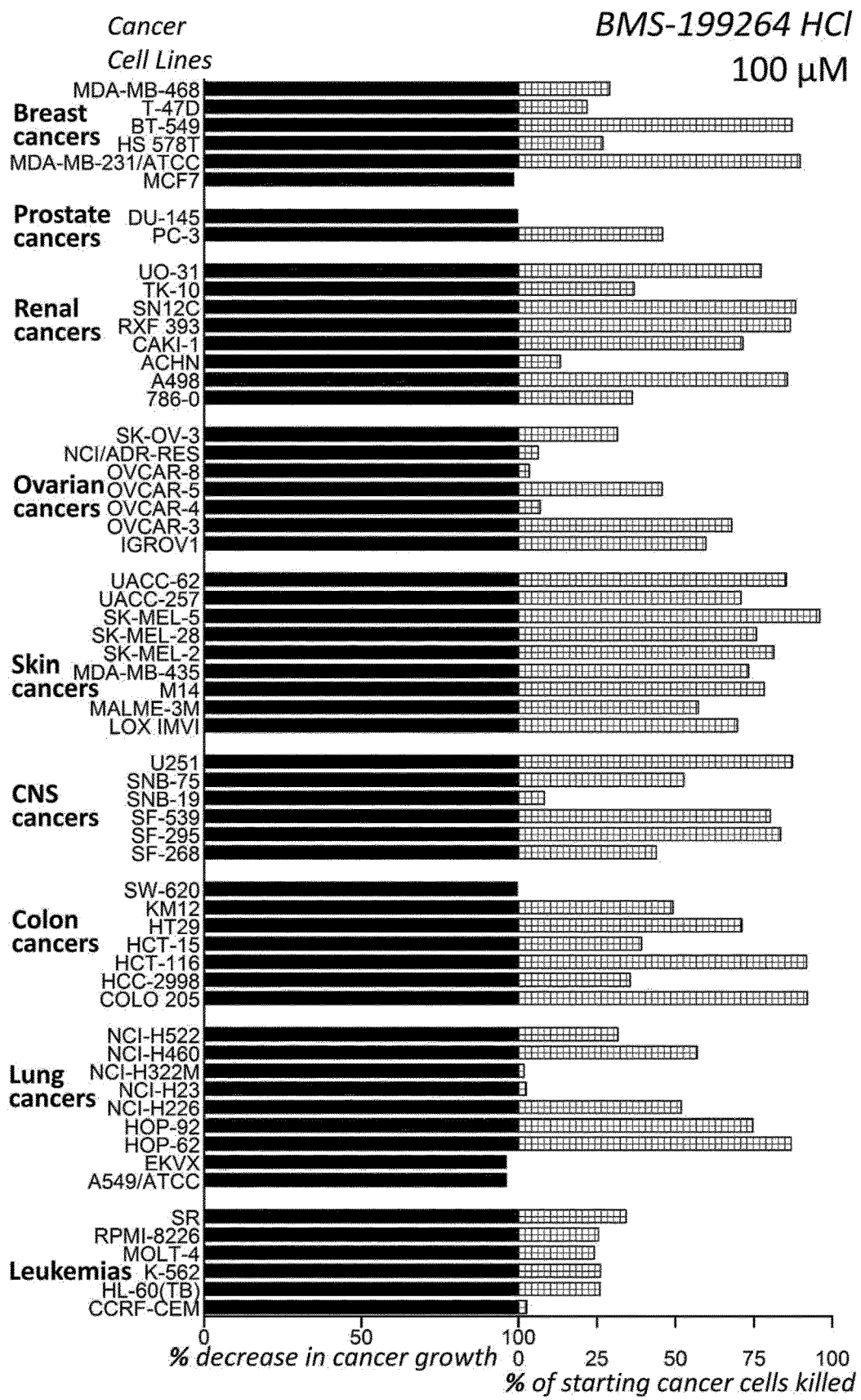
FIG. 5 shows anti-cancer activity of BMS-199264 in the NCI one-dose assay (100 µM).

Higher HIF-1α (and lower pyruvate kinase {liver isoenzyme}, lower aspartate aminotransferase 2 {mitochondrial} and lower ATP synthase) gene expressions are reported to be a marker of the Warburg effect [14] and correlate (at $p<0.05$) with insensitivity to the polyketide $F_1F_0$ ATP synthase inhibitor, cytovaricin (Table 1 of [14]). By contrast, using the same cell lines and gene expression data set used to make Table 1 of [14], BMS-199264 sensitivity ($GI_{50}$) does not correlate (at $p<0.05$) with any of these gene expressions. Nor does compound 6b (at $p<0.05$). And actually higher HIF-1α expression, a marker of the Warburg effect, correlates (0.714, but statistically insignificant at $p<0.05$) with higher sensitivity to BMS-199264 and to 6b (0.332, but statistically insignificant at $p<0.05$). FIG. 5 of [14] presents apoptolidin resistant NCI-60 cell lines, resistant because they utilise the Warburg effect [14], but the majority of these cell lines are more sensitive to BMS-19264 than the average, with a lower GI50 value than the average GI50 value (3.9 μM) for BMS-199264.

The lower the bioenergetic cellular index (BEC) of a cancer cell [18], the more it demonstrates the Warburg effect and the more it relies on glycolytic rather than oxidative metabolism. BEC is, by one measure [19], the ratio amount of the β subunit of F1 ATPase ((β-F1-ATPase; gene: ATPSB) to that of Glyceraldehyde 3-phosphate dehydrogenase (GAPDH). I calculated BEC for the same cell lines analysed for Table 1 of [14], using the mRNA transcript amounts of ATPSB and GAPDH in each cell line, data sourced from [31-32], and then calculating the ([ATPSB]/[GAPDH] transcript ratio) for each of these cancer cell lines. Using transcript data rather than protein data is a limitation, but [33] report that a protein's cellular amount is generally well correlated (0.76) to its mRNA transcript amount, at least for cells in the NCI-60 assay, for the protein subset they studied. And furthermore, [14] relied on transcript data, so best comparison with [14] is made using such data. Polyketide $F_1F_0$ ATP synthase inhibitors don't work well against cancer cells exhibiting the Warburg effect [14] and, indeed, for the cell lines analysed (same ones used as for Table 1 in [14]) there is a significant (at $p<0.05$) negative Pearson correlation between $\log_{10}(GI50)$ and BEC for oligomycin A (−0.9411). So, this correlation shows that the more a cancer uses Warburg metabolism, the less its danger is mitigated by oligomycin A. This significantly reduces the utility of oligomycin A as a cancer medicine because a low BEC score (indicating Warburg metabolism) is characteristic to some of the most dangerous cancers, with the worst patient outcomes [18-20]. By contrast, there is no significant (at $p<0.05$) Pearson correlation for BMS-199264 and BEC (+0.3639). Or 6b and BEC (0.0298). This means that, distinctly from the polyketide $F_1F_0$ ATP synthase inhibitors, their anti-cancer action is not restricted to those, often less dangerous, cancers that don't utilise Warburg metabolism.

Molecules of this disclosure undermine cancer by inhibiting the reverse mode of ATP synthase. It is true that polyketide $F_1F_0$ ATP synthase inhibitors also inhibit this mode, but distinctly, in addition, they also inhibit the forward mode of ATP synthase, indeed more potently [11], and whilst they can exert anti-cancer activity, because this forward mode is vital to many cancers, it is also vital to many normal cells. This makes polyketide $F_1F_0$ ATP synthase inhibitors unsuitable as clinical molecules. Molecules of this disclosure are therapeutic because of their distinction from, not their similarity to, polyketide $F_1F_0$ ATP synthase inhibitors.

Figure 2:
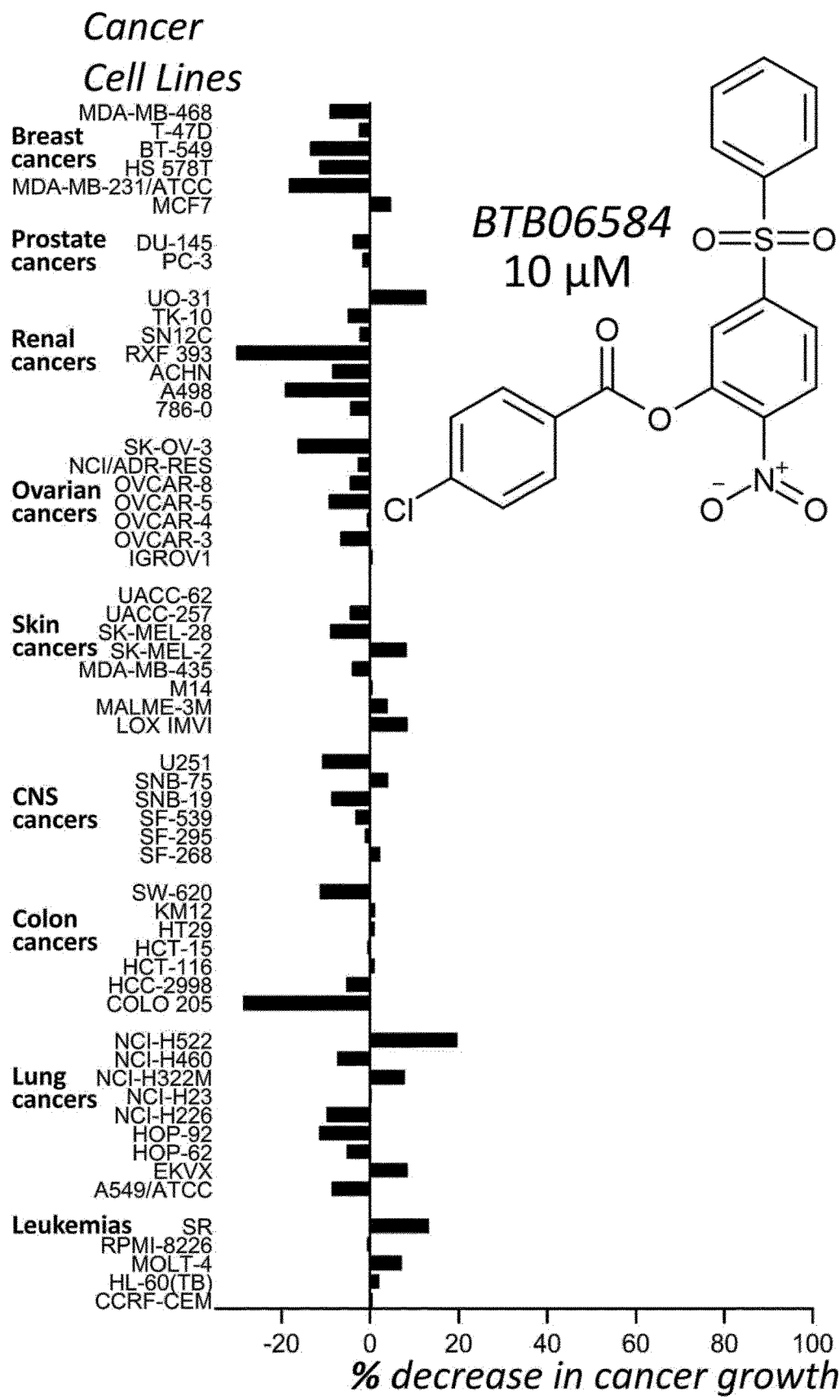
FIG. 2 shows anti-cancer activity of BTB06584 in the NCI one-dose assay (10 µM).
Figure 3:
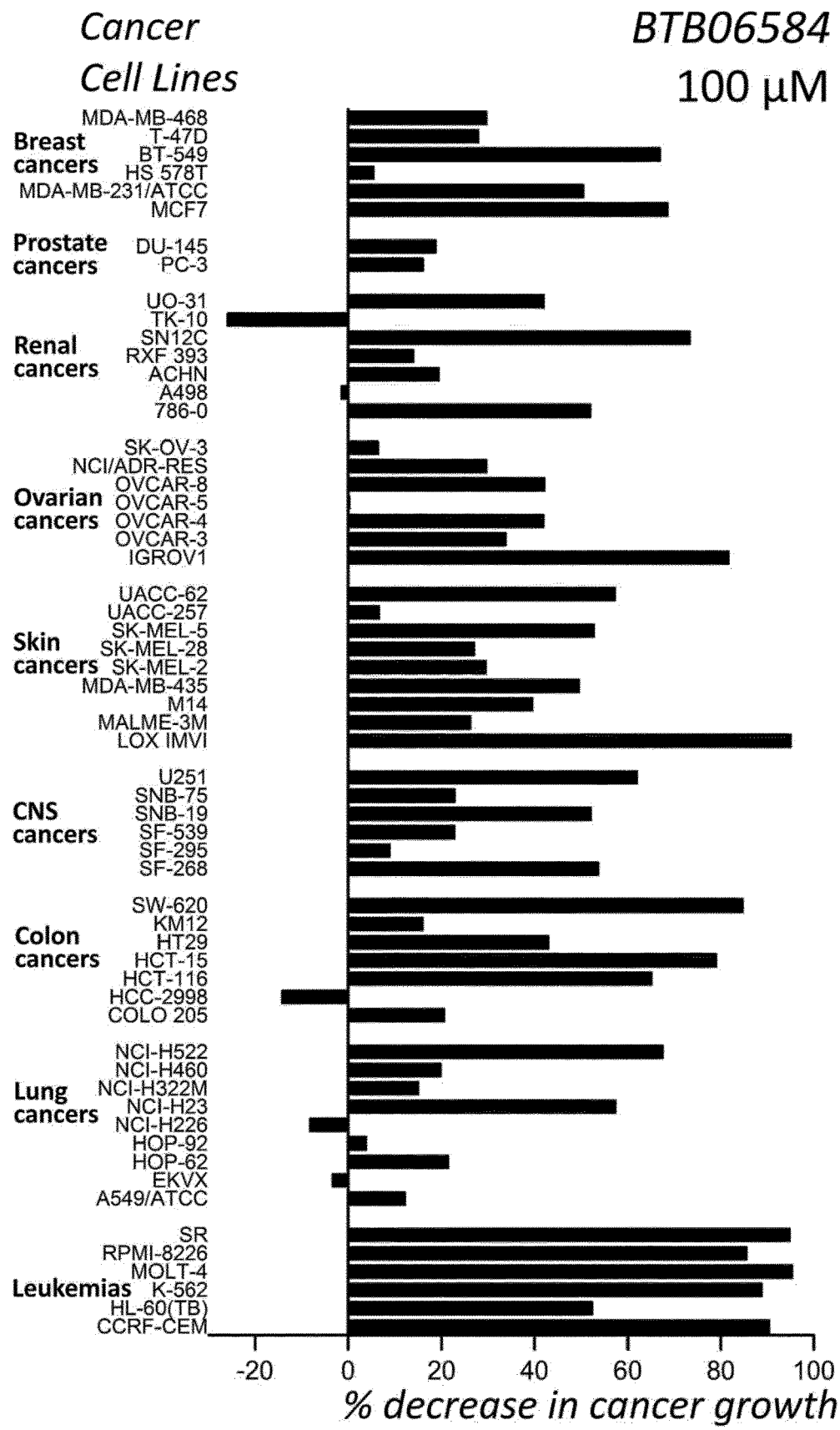
FIG. 3 shows anti-cancer activity of BTB06584 in the NCI one-dose assay (100 µM).
Figure 4:
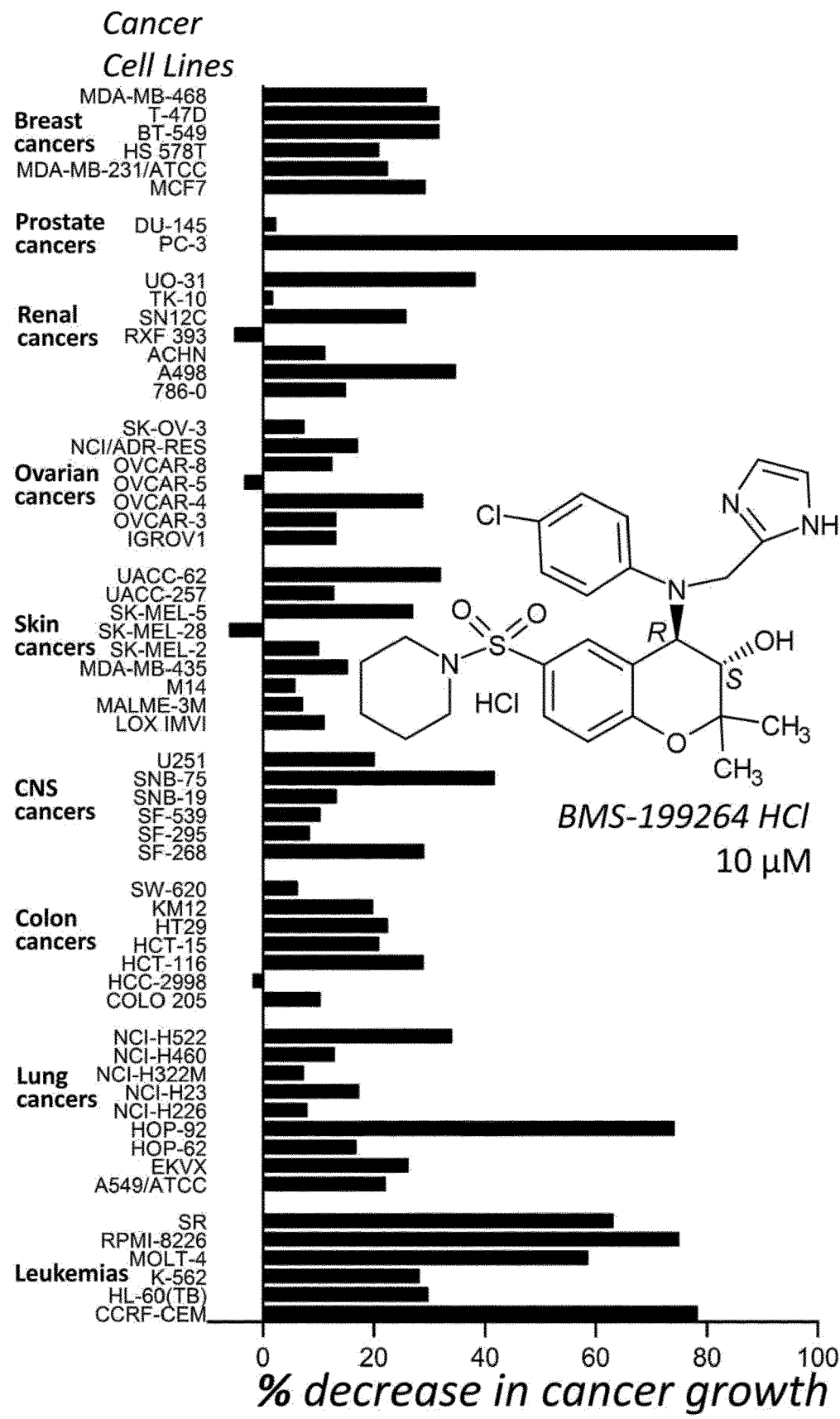
FIG. 4 shows anti-cancer activity of BMS-199264 in the NCI one-dose assay (10 µM).

[14] sum up with "Many cancer cells maintain a high level of anaerobic carbon metabolism even in the presence of oxygen, a phenomenon that is historically known as the Warburg effect. From our results, we conclude that macrolide inhibitors of the mitochondrial $F_0F_1$-ATP synthase selectively kill metabolically active tumor cells that do not exhibit the Warburg effect". So, [14] find that these macrolides only kill cancers reliant upon OXPHOS, so using $F_1F_0$-ATP synthase in its forward mode to generate ATP (which unfortunately is also the metabolic profile of many key types of normal cell) and thus macrolide inhibition of the forward mode of $F_1F_0$-ATP synthase is key to this (unspecific) anti-cancer activity. By contrast, the molecules of this disclosure exert anti-cancer activity by inhibition of the reverse mode of ATP synthase. BMS-199264 [4, 7, 9, 10, 11], BTB06584 [13], 31 [8] and the stereoisomer 6b (and its racemate, 19a) [5, 6] have been described previously, as molecules that can inhibit this mode, and this invention discloses their utility as anti-cancer therapeutics, with supporting experimental data, thence identifying new cancer drugs and, more fundamentally/importantly, a new cancer specific drug target: $F_1F_0$-ATP hydrolysis (FIG. 9). The opposite stereoisomer to 6b, 6a, also exerts anti-cancer activity (FIG. 8) because both 6a and 6b racemize towards being the racemate, 19a, during NCI testing. BTB06584 (100 μM) exerts anti-cancer activity (FIG. 3), despite not inhibiting $F_1F_0$-ATP synthesis, as a function of inhibiting $F_1F_0$-ATP hydrolysis (at >100 μM), and critically it isn't harmful to normal cells (mouse cortical neurons) at this concentration [13]. Its anti-cancer potency (none at 10 μM, observed at 100 μM; FIGS. 2 and 3 respectively) matches its inhibitory potency for $F_1F_0$-ATP hydrolysis (none at 10 μM, requires >100 μM [13]). BMS-199264 (10 μM) exerts anti-cancer activity (FIG. 4). It doesn't harm normal cells (ex vivo rat heart) at this concentration [11]. In NCI five-dose testing [34-35], the mean $GI_{50}$ for BMS-199264 is 3.9 μM (FIG. 10), which is lower/better than 62% of the 102 FDA approved cancer drugs in [30], their mean $GI_{50}$ values sourced from Table 1 of [30]: all are directly comparable because they too are sourced from the NCI-60 five-dose assay. Furthermore, in NCI five-dose testing, the mean $GI_{50}$ for 6a and 6b is 0.666 µM and 0.446 µM respectively (FIG. 11), which, in the 6b case, is lower/better than 77% of 102 FDA approved cancer drugs in [30], including cisplatin (mean $GI_{50}$=1.4 µM), which is one of the most used, if not the most used, chemotherapies of today, but typically with terrible side-effects. At 10 µM, 6b exerts greater anti-cancer activity than BMS-199264 (FIG. 9), despite it having less effect on $F_1F_0$-ATP synthesis, because it inhibits the reverse mode of ATP synthase more potently than BMS-199264. Again, a vindication that the molecules of this disclosure exert anti-cancer activity by inhibiting the reverse mode of ATP synthase, which distinguishes them from the macrolides and, distinctly, makes them usable therapeutically. Indeed, molecules of this disclosure don't appreciably inhibit the forward mode of ATP synthase, in sharp distinction to the macrolides. The compounds that contain a protonable nitrogen atom in their imidazole reduce $F_1F_0$-ATP synthesis in SMPs because they shuttle protons across the mitochondrial inner membrane, dissipating the proton motive force (uncoupling). FIG. 17 presents structure-activity data for such uncoupling in whole cells, using compounds that are also componentry to this invention as anti-cancer drugs. BMS-199264 (log P=3.79, calculated [25]) uncouples more than 6b (log P=5.97, calculated [25]) because its log P is closer to the log P=3.2 (calculated) optimum for uncoupling [36].

19a is a racemate, wherein the S stereoisomer, and not the R stereoisomer, potently inhibits $F_1F_0$-ATP hydrolysis [5-6]. I tried to test the anti-cancer activity of the separated stereoisomers. They were successfully separated by superfluid chromatography (SFC). But subsequently underwent racemization during the NCI-60 tests. One stereoisomer sample conveyed slightly better anti-cancer activity than the other, revealing more area under the curve for S stereoisomer exposure, and possibly a slight enduing enantiomeric excess (ee) of S stereoisomer. Both samples ultimately contained a significant proportion of S stereoisomer and both had strong anti-cancer activity (FIG. 8). The Pearson correlation coefficient (R=0.8 at 10 µM; R=0.9437 at 100 µM) for their patterns of anti-cancer activity is significant (at p<0.00001). Racemization of the S stereoisomer is slowed by replacing the hydrogen atom on its chiral carbon with a deuterium atom (enrichment) and this is a new composition of matter, which is componentry to this invention, as is the method/process of using it for anti-cancer therapy. With this modification, the enantiomeric excess (ee) of the eutomer endures for longer and so per-unit anti-cancer activity is better, for longer. Analogy by the macrolide inhibitors of [14], which [P1, P2, P3] teaches, would suggest that the S and R stereoisomers have equal anti-cancer activity, and that this would be weak, because they are both comparably weak reducers of $F_1F_0$-ATP synthesis ($EC_{50}$>100 µM in SMP assays). By contrast, by the invention of this disclosure, the S stereoisomer specifically is revealed to be a potent anti-cancer therapeutic.

Stereoisomerism

For some molecules of this disclosure, one of its stereoisomers has much lower $IC_{50}$ than the other for inhibiting $F_1F_0$ ATP hydrolysis, and so, by the invention of this disclosure, this is the preferred stereoisomer for anti-cancer use. Indeed, a form with high enantiomeric excess (ee) for this preferred stereoisomer is the preferred embodiment for anti-cancer therapy, e.g. ee=>70%, ee=>95%, >99% more preferred, =100% most preferred. However, ee can be eroded by racemization. This invention discloses an improvement. Embodied by this disclosure are permutations of each of its chiral molecules, wherein the hydrogen attached to each chiral carbon is replaced with a deuterium, wherein the natural abundance of deuterium (0.015%) at this position is enhanced (non-limiting example: >3000 times greater than the natural abundance of deuterium, i.e. a >40% incorporation of deuterium). The deuterium Kinetic Isotope Effect (KIE) [37] slows racemization.

PREFERRED EMBODIMENTS

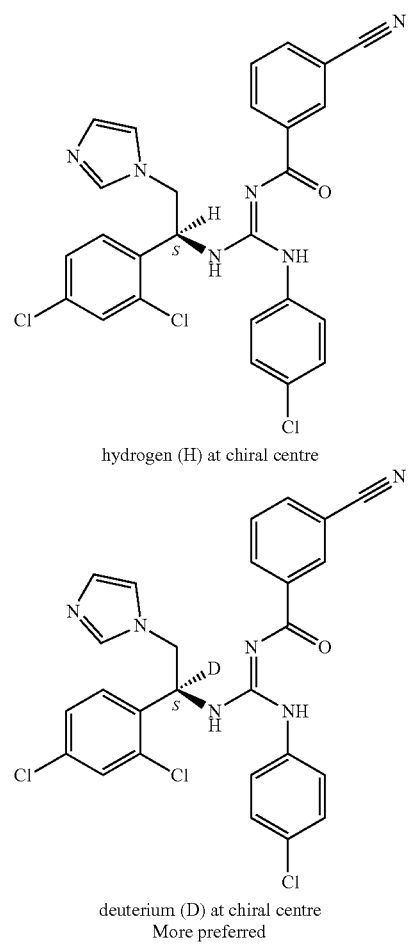

hydrogen (H) at chiral centre deuterium (D) at chiral centre
More preferred

The structure on the left has a low $EC_{50}$ against $F_1F_0$ ATP hydrolysis (0.018 µM), its [$EC_{50}$ $F_1F_0$ ATP synthesis/$EC_{50}$ $F_1F_0$ ATP hydrolysis] ratio >5,556. In rats, this drug (administered in polyethyleneglycol:water:ethanol, 1:1:1) is orally bio available (47%) with good pharmacokinetics (intravenously applied drug half-life in blood=2.1 hours, $C_{max}$=21 µM, volume of distribution=2.37 l/kg). The deuterated analogue on the right, wherein the hydrogen atom on the chiral carbon is replaced with deuterium, conferring greater stereoisomeric stability because of the kinetic isotope effect (KIE, [37]) is more preferred. The greater the % deuterium enrichment at the chiral carbon (carbon atom number 21) and the greater the enantiomeric excess, the more preferred the embodiment. In other preferred embodiments other atoms or isotopes are in place of hydrogen on the chiral carbon, blocking its racemization, ensuring enduring stereoisomeric excess. For example, fluorine. Or carbon (methyl).

The most valuable innovation of this invention is not a presented structure but a discovered, disclosed principle: the best anti-cancer compound of this invention is a molecule that inhibits $F_1F_0$ ATP hydrolysis as potently and specifically as possible, whilst it inhibits, by direct binding, the forward mode of the ATP synthase molecule as little as possible: most preferably not at all.

Destroying Cancer's Immortality, Lengthening Lives

Unlike normal adult cells, cancer cells are immortal e.g. Hela cancer cells have replicated >>billions of times in laboratories across the world after their originator, the person they killed, Henrietta Lacks, is sadly long since dead. FIG. 13 interprets (particularly) experimental data of FIGS. 8, 11, 12; interpretation expanded upon here. The core: Removing cancer's immortality, rendering it mortal, removes its danger without hurting normal cells, which are mortal anyhow. A hyperpolarised $\Psi_{IM}$ correlates with the most dangerous cancers [38-43]. I argue because this feature/mode is a function of cancer proliferation and thus, the more aggressive/dangerous the cancer, the more time they spend in this operating mode, and thus the more chance it is detected at scale by $\Psi_{IM}$ imaging. In these cancer cells, $\Psi_{IM}$=around −200 rather than the −140 mV in normal adult cells. ROS cause transient growth arrest to permanent growth arrest, to apoptosis or to necrosis, dependent on the level of ROS [44]. Constitutively activating oxidative phosphorylation (OXPHOS) in cancer cells halts their proliferation [45-46] or pushes them into apoptosis [45-49], via its inherent ROS production [47]. In cancers, a higher glycolytic rate drives greater $F_1F_0$ ATP hydrolysis, greater pmf and a hyperpolarised $\Psi_{IM}$ (~−200 mV). This reduces the "sink" drive for electrons to enter the respiratory chain (especially when there is high lactate dehydrogenase expression (out)competing for NADH) and so decreases OXPHOS rate, which decreases ROS production, whilst simultaneous aforementioned features of $F_1F_0$ ATP hydrolysis increase [NADPH] and ROS mitigation. Thus, cancers have decreased ROS production and increased ROS mitigation. The outcome is that cancers have lower [ROS] than normal cells, which is integral to their enduring information fidelity, which permits their "limitless replicative potential" (immortality), which confers their danger. ROS sensing fluorescent probes report higher [ROS] in cancer than normal cells [50], and those of the art typically think cancers do have higher [ROS], but these probes are cationic and accumulate at greater concentrations in cancer cells because of their more hyperpolarised $\Psi_{IM}$ (Nernst; Δ60 mV hyperpolarisation accumulates di-positive probe, like nitroblue tetrazolium, 100 times more). Other ROS sensing cancer studies report extracellular [ROS] [51] and some cancers overexpress NOX enzymes [52-53] at their plasma membrane, which generates greater extracellular [ROS], which reduces intracellular $O_2$ and [ROS]. High mutation rate inextricably equals higher mutation rate, ultimately too much information lost, thence limited (not limitless) proliferative capability and mortality. Cancers have high mutational load in legacy to a higher mutation rate that excavated their lower [ROS], lower mutation rate, corrupted embryonic stem cell (ES) like phenotype from the genome, and as a legacy of cancer cells that exited this state by DNA mutation/repair, accrued mutation at higher rate, and mutated back into this state given its genomic proximity. In most cases by a different mutation route than they exited (many DNA mutation routes to a low [ROS] destination). Cancer is an anti-mutator phenotype, preceded and punctuated by mutator epochs, whilst normal adult bodies are in a runaway damage/mutation loop, ageing and ultimately dying.

Raise the [ROS] in cancer to that of a normal adult cell and cancer danger attenuates. Indeed, raise [ROS] less than this: cancers have many embryonic stem (ES) cell characteristics [54-57], such as limitless replicative potential and hyperpolarised $\Psi_{IM}$, and ES cells respond to ROS damage more by apoptosis than repair [57]. In cancer cells, interventional inhibition of $F_1F_0$ ATP hydrolysis causes $\Psi_{IM}$ depolarisation, more OXPHOS, greater [ROS], which slows cancer cell proliferation, and at greater $F_1F_0$ ATP hydrolysis inhibition, even more OXPHOS, [ROS], and the cancer cell dies by apoptosis or necrosis. However, once switched into significant OXPHOS, further $F_1F_0$ ATP hydrolysis inhibition reduces OXPHOS rate, because less ATP needs to be synthesised because less ATP is hydrolysed by $F_1F_0$ ATP hydrolysis, which reduces [ROS] and anti-cancer action. So, higher doses of an $F1F_0$ ATP hydrolysis inhibitor can have less anti-cancer activity, seen in experimental data disclosed herein (FIGS. 8, 11, 12). Normal cells use OXPHOS and they benefit from this slowing of OXPHOS, less [ROS], with slower ageing and increased lifespan. Thus, $F_1F_0$ ATP hydrolysis inhibitors of this disclosure hurt cancer whilst simultaneously assisting normal cells. They will extend lifespan in subjects with or without cancer, especially useful for a subject(s) with an accelerated aging disease(s) or progeroid syndrome. They will extend healthspan by delaying, and reducing the incidence of, the diseases of ageing (any disease/pathology whose incidence increases with age and/or in which elevated ROS is a contributory factor: numerous such diseases/pathologies known to those of the art) e.g. {non-limiting} Alzheimer's disease, dementia, Parkinson's disease etc.). But with a caveat. This disclosure discloses a new fundamental biological discovery, supported by disclosed in vivo experimental data (FIG. 15): $F_1F_0$ ATP hydrolysis is not a bug but a feature, necessary for heat production and homeothermy. Thus, inhibiting $F_1F_0$ ATP hydrolysis in a subject reduces the subject's endogenous heat production, which requires substitution with exogenous heat e.g. higher ambient temperature for the subject e.g. by appropriate geographical (re)location. However, whilst this issue is very serious for smaller animals such as mice (~20 g), it is much less so for rats (~150 g), and even less for humans (~62 kg). In a simulation reported in [58], a 30% reduction in metabolic rate in man (70 kg, 170 cm, in 20° C. ambient temperature), maintained for 4 hours, only decreases core body temperature by 0.18° C. By contrast, experimental data in [58] shows that 30% reduction in metabolic rate significantly decreases core body temperature in mice, and less in rats. The flip side of this is that because much more of a small animal's metabolism comprises futile cycling of ATP synthesis and hydrolysis, to generate heat, an $F_1F_0$ ATP hydrolysis inhibitor can decrease their OXPHOS rate by a greater percentage, which will increase their lifespan by a greater percentage, than for a larger animal. Indeed, $F_1F_0$ ATP hydrolysis inhibitors of this invention will, if ambient temperature is conducive, increase the lifespan of small animals immensely and an embodiment of this invention is to enter a compound(s) of this invention into a competition to extend a rodent's lifespan, wherein there is a financial prize or other benefit e.g. the Mprize.

$F_1F_0$ ATP hydrolysis inhibitors of this invention confer greater life extension in an animal than for normal cells in culture because in culture the decrease in electron flow along the respiratory chain decreases ROS production but it also decreases $O_2$ consumption and this raises $pO_2$, which increases ROS production, whereas in an animal, their breathing slows to keep tissue $pO_2$ constant. An invention embodiment is to use an $F_1F_0$ ATP hydrolysis inhibitor of this invention in co-therapy with a respiratory stimulant (non-limiting e.g. doxapram) to elevate blood and tissue $pO_2$ to more strongly treat/ameliorate/prevent/combat cancer in a subject. Indeed, relevantly, a compound of this invention-almitrine-increases blood $pO_2$ in humans.

Eukaryotes must maintain a hyperpolarised $\Psi_{IM}$ or they will undergo apoptosis [59]. In cancers that cannot use OXPHOS because of deficiency(s) in their respiratory chain, or because of hypoxic/anoxic environment (tumours are often hypoxic), $F_1F_0$ ATP hydrolysis is the only means they can maintain $\Psi_{IM}$, which an $F_1F_0$ ATP hydrolysis inhibitor undermines and the subsequent $\Psi_{IM}$ depolarisation triggers cancer apoptosis.

Treating Cachexia

Cancers can utilise aerobic glycolysis (Warburg effect) at one or more stages of their cell cycle. ATP yield from one glucose molecule is 2 ATP by aerobic glycolysis and ~30 ATP by oxidative phosphorylation [1-3]. The former produces 2 molecules of lactate for each glucose consumed, which can be converted, at the cost of 6 ATP, to glucose by the Cori cycle in the liver [1]. Thence, in this case, the overall ATP yield of aerobic glycolysis is ~4. Assuming equal energy use, and assuming the cancer is always rather than disproportionally using aerobic glycolysis, 1 g of cancer uses ~34 times more (potential) energy than 1 g of normal tissue. However, this is likely an underestimate because cancers typically have higher energy use: cancer uses $F_1F_0$ ATP hydrolysis, with protons returning to the mitochondrial matrix by UCP2 (overexpressed in many cancers [60-61]), to burn glycolytic ATP. This releases glycolytic enzymes from ATP feedback inhibition and permits high glycolytic and PPP rate, producing glycolytic intermediates for biosynthesis and elevated [NADPH] for increased ROS mitigation, thence low [ROS], releasing significant lactate. Elevated blood [lactate] correlates with cancer danger [27]. So, if food intake does not increase upon cancer developing, a growing cancer can deny energy to normal tissues, which atrophies them, which means even more energy is available to the cancer, which grows further and a positive feedback loop (cachexia) ensues which is the leading cause of death in cancer patients. By this invention, $F_1F_0$ ATP hydrolysis inhibitor(s) switch cancers out of aerobic glycolysis, into OXPHOS, with its associated ROS, ageing, mortality, and break this positive feedback loop, treating/ameliorating/preventing/combating cancer associated cachexia in a subject(s). $F_1F_0$ ATP hydrolysis inhibitor(s) also assist cachexia sufferers by making normal cells more efficient, thence requiring less glucose, and can treat/ameliorate/prevent/combat non-cancer driven cachexia in a subject(s) too.

Embodied by this invention is a therapeutically effective amount of a compound(s) that reduces $F_1F_0$ ATP hydrolysis, for example a compound(s) of Formula (I-VI), administered in co-therapy with a therapeutically effective amount of a compound(s) that inhibits UCP2, optionally incorporated in same or different pharmaceutical composition(s), to treat/ameliorate/prevent/combat cancer and/or cachexia in a subject. Genipin and cisplatin are non-limiting examples of compounds that inhibit UCP2, cisplatin acts on additional targets also.

Body Temperature

Administered to a subject, $F_1F_0$-ATP hydrolysis inhibitor(s) conserves ATP, so less ATP needs to be synthesized, therefore respiration rate slows, thence metabolic heat production declines and body temperature can fall towards ambient temperature (if ambient <body temperature). Experimental evidence is disclosed in FIG. 15. So, when the ambient temperature isn't arduous (not requiring significant energy consuming physiological/behavioural adaptations to maintain body temperature) and dietary intake stays constant, weight gain/maintenance can occur, which can assist cachexia, for example cancer driven cachexia. This is clinically valuable because cachexia is the leading cause of death in cancer patients. If the ambient temperature is sufficiently close to the required body temperature, then the aforementioned decrease in heat generation is safe, because the body temperature can't fall below the ambient temperature. So, for example, if the ambient temperature is 37° C., inhibiting $F_1F_0$-ATP hydrolysis could make body temperature fall to this ambient temperature, but not below it, and this is safe because ~37° C. body temperature is safe. Inhibiting $F_1F_0$-ATP hydrolysis will reduce, but not abolish, metabolic heat production. So, body metabolism will still contribute to heating the body, just less so, which will shift the thermoneutral and thermal comfort zones (terms well known to those of the art [62], temperatures vary by species, as is well known to those of the art) to higher temperature(s). If the subject is located at a higher temperature to account for this shift, for example at their updated, higher thermoneutral temperature, or make behavioural adaptations (e.g. wearing more clothes), then this shift is harmless. An embodiment of this invention is setting the dosage of a compound(s) that inhibits $F_1F_0$ ATP hydrolysis with consideration of the ambient temperature, wherein higher dosages are permissible at higher ambient temperatures. The preferred ambient temperature for a dosage permits the subject to be thermoneutral, and/or thermal comfortable, without the metabolic heat (respiration) fraction driven by the $F_1F_0$ ATP hydrolysis that is lost because of this dosage. This temperature management issue is more important for smaller than larger animals, because surface area scales to mass by a fractional power (e.g. refer Kleiber's law) and so larger animals retain their generated heat better, and so a given percentage drop in (per unit mass) metabolism will cause a smaller drop in body temperature in a bigger animal. The aforementioned weight gain can be of great clinical/health/nutritional value, or aesthetic value (by non-limiting example: bodybuilders), or commercial value when applied to livestock/farm animals or any animal with a commercial value e.g. racing animals, such as horses. This invention encompasses the method/process of using compounds of this disclosure for these applications, or any others wherein weight, nutritional or energetic gain is wanted in an animal or human. An embodiment of this invention is a method in which a subject takes or is administered an effective amount of a compound(s) of this invention, for example a compound of Formula (I), (II), (III), (IV) or (V) or another compound that selectively inhibits $F_1F_0$ ATP hydrolysis, or a pharmaceutically-acceptable salt, solvate, hydrate or prodrug thereof, to treat/ameliorate/prevent/combat cachexia, cancer-associated/driven cachexia, weight loss or a disease or disorder or environmental temperature that causes a higher than normal body temperature (many known to those of the art, only a subset listed here to illustrate and not restrict the invention) which can include, but isn't limited to, ingesting an uncoupler (e.g. 2,4-dinitrophenol), infection, sepsis, stroke, fever, pyrexia, hyperpyrexia, hyperthermia, malignant hyperthermia, neuroleptic malignant syndrome, serotonin syndrome, thyroid storm, heatstroke, surgery related, infection (non-limiting e.g. roseola, measles, enteroviral infections, parasitic, viral, fungal, Chlamydial, Rickettsial, bacterial, mycobacterial, systemic bacterial, intravascular, HIV associated, nosocomial), pyrogenic infection, thermoregulatory disorder(s), connective tissue disease(s), Kawasaki syndrome, drug overdose, drug induced hyperthermia, alcohol/drug withdrawal, idiosyncratic drug reaction, fever of known (non-limiting e.g. infectious disease(s), inflammation, immunological disease(s), non-infectious inflammatory disease(s) {non-limiting eg. systemic rheumatic and autoimmune diseases, vasculitis, granulomatous diseases, autoinflammatory syndromes}, tissue destruction, reaction to incompatible blood product(s), metabolic disorder(s), inherited metabolic disorder(s), cancer, neoplasm, endogenous or exogenous pyrogen(s), injury, head injury) or unknown or uncertain origin, or to cause greater metabolic/bioenergetic efficiency in the subject, enhancing their physical or mental performance or causing body weight gain, or to confer hypothermia in a subject for some medical or other purpose which can include, but isn't limited to, slowing a chemical reaction(s) rate in a subject for therapeutic benefit, preventing/minimizing brain and/or tissue damage, deep hypothermic circulatory arrest for surgery, hypothermia for a surgical purpose, hypothermia for cardiac and/or cardiovascular surgery and/or brain surgery (neurosurgery), Emergency Preservation and Resuscitation (EPR), preserving detached body parts such as limbs and/or organs (for example during organ storage and/or transplant), protective hypothermia, targeted temperature management, therapeutic hypothermia, hypothermia therapy for neonatal encephalopathy, birth asphyxia, hypoxic-ischemic encephalopathy (HIE), haemorrhage, hypovolemia, decompression sickness, burn injury(s) including skin burn, inflammation, allergic reaction, anaphylaxis, tissue/organ rejection, hypoxia, hypoxemia, anoxemia, anoxia, anemia, hypervolemia, altitude sickness, obstructed airway, asthma attack, hypoxia in a body/tissue/organ, hypoglycemia, reperfusion injury (ischemia-reperfusion injury), upon release of a ligature or tourniquet, uraemia, crush syndrome, compartment syndrome, traumatic brain and/or spinal cord injury, major trauma, infection, bacterial and/or viral infection(s) (non-limiting e.g. meningitis), sepsis, septic shock, ischemic brain/heart/kidney injury, neuroprotection and/or cardioprotection and/or tissue protection during/after a stroke and/or ischemia and/or cardiac arrest and/or resuscitation and/or a period(s) of poor blood flow anywhere in a subject, or to confer hypothermia to treat/ameliorate/prevent/combat a poisoning by a toxic amount of a compound(s) in a subject (non-limiting e.g. carbon monoxide/methanol/heavy metal/pesticide poisoning, snake/spider/bee/insect/lizard venom, metabolic poison, bacterial toxin(s), endotoxemia, eukaryote produced toxin(s) e.g. (non-limiting) brevetoxin, drug/substance overdose e.g. (non-limiting) heroin, ethanol, a prescription medication(s), an over the counter medication such as paracetamol etc.; hypothermia is protective to toxic insult), or to confer one or more of sedation, anaesthesia, hypoactivity, hibernation, torpor, suspended animation, life extension in a subject. In an embodiment, the amplitude of hypothermia is controlled by setting the ambient temperature, wherein an effective amount of administered $F_1F_0$ ATP hydrolysis inhibitor reduces subject body temperature to the ambient temperature, and so hypothermic amplitude is controlled by controlling ambient temperature. Another embodiment is that the body temperature that the body falls to, upon administration of an effective amount of $F_1F_0$ ATP hydrolysis inhibitor, is controlled by controlling feature(s) of electromagnetic radiation upon the subject, for example emergent from a radiation heater(s), optionally controlled by servocontrol, with the set point set at the desired hypothermic body temperature, used as a body heating system alone or in combination with other body warming devices and methods (many possibilities known to those of the art), which are optionally controlled by servocontrol, optionally integrated into the same control loop, optionally used by themselves alone or in combination for this body heating purpose, to "catch" and offset the hypothermic drive, of an effective amount of $F_1F_0$ ATP hydrolysis inhibitor(s) in the body, at some desired hypothermic body temperature.

Many cancers cause fever in a subject. By the invention of this disclosure, $F_1F_0$ ATP hydrolysis inhibitors exert anti-cancer activity and can reduce body temperature if [ambient <body temperature]. Thence an embodiment of this invention is a method in which a subject takes or is administered an effective amount of a compound(s) of this invention, for example a compound of Formula (I), (II), (III), (IV) or (V) or another compound that selectively inhibits $F_1F_0$ ATP hydrolysis, or a pharmaceutically-acceptable salt, solvate, hydrate or prodrug thereof, to treat/ameliorate/prevent/combat cancer and cancer associated fever, especially (but without restriction) one or more of the following cancers, which are well known by those of the art to drive fever in many cases: non Hodgkin lymphoma (NHL), Hodgkin lymphoma, acute leukaemia, kidney cancer (renal cell cancer), liver cancer (hepatocellular carcinoma), bone cancer, adrenal gland tumours such as phaeochromocytomas, tumours in the hypothalamus, solid tumours.

Compounds of this invention, which inhibit $F_1F_0$ ATP hydrolysis, have utility for making animals and/or humans feel more comfortable in hot weather, climates and geographies. For example, being taken by or administered to people, especially the elderly, during hot summers.

This temperature aspect to compounds of this disclosure isn't relevant to the NCI-60 tests. Because in these studies, the ambient temperature is controlled at 37° C. [35], which is optimal for cells, and so if these drugs make cellular temperature fall to ambient temperature, this is not detrimental. It can be an issue for laboratory animal studies though. Laboratory mice, for example, are typically kept at room temperature (e.g. 20 to 23° C.) which renders them very reliant upon additional metabolic/physiological/behavioural heat production because their thermoneutral zone is much higher, at 30 to 32° C. (can vary depending on strain, size, age, gender etc. [62]). An administered compound(s) of this disclosure, which inhibits $F_1F_0$ ATP hydrolysis, can add to the cold stress that laboratory mice endure when kept at typical room temperature. An embodiment of this invention is the process/method of keeping laboratory animals at, or close to, their thermoneutral zone when performing animal studies with a compound(s) of this disclosure. For example, keeping mice at 30 to 32° C. And in a further embodiment, at even higher temperature to compensate for the amount that an administered compound(s) of this disclosure, by inhibiting $F_1F_0$ ATP hydrolysis, shifts the animal's thermoneutral zone to a zone of higher temperature. The amount shifted will depend on the administered dosage, so in a further embodiment, the ambient temperature is set according to the dosage used. Wherein, for a compound of this disclosure, a higher ambient temperature, within safe limits, can make a greater compound dosage safer.

An embodiment of this invention is a method in which a subject takes or is administered an effective amount of a compound(s) of this invention, for example a compound of Formula (I), (II), (III), (IV) or (V) or another compound that selectively inhibits $F_1F_0$ ATP hydrolysis, or a pharmaceutically-acceptable salt, solvate, hydrate or prodrug thereof, to treat/ameliorate/prevent/combat a medical disease/disorder, wherein the subject is monitored, for example by a healthcare/research professional/worker (doctor, oncologist, nurse, vet, pharmacist, laboratory technician, scientist) or machine/artificial intelligence substitute, for any adverse signs/symptoms/non-normality after compound administration (in an embodiment for 5 minutes, in a further embodiment for 10 minutes, and in a further embodiment for longer) and in a particular embodiment for signs of reduction in body temperature (methods well known to those of the art, in a particular embodiment the subject's body temperature is monitored) and/or the dosage administered is set, and/or modified (e.g. increased in graduations), by information from this subject wellness/normality/temperature monitoring and/or the subject is located at an ambient temperature (e.g. in a temperature controlled room/enclosure/confine/ climate and/or their body temperature is modified/regulated/ interdicted by heating effect of electromagnetic radiation e.g. infrared) that maintains their body temperature within safe limits whilst they have an effective amount of compound in their system. An embodiment of this invention is the process/method of considering the ambient temperature in the decision of whether to take or administer a compound(s) of this disclosure, and at what dosage. In an embodiment, a period of medical observation, by a clinical or healthcare professional (e.g. pharmacist), occurs after the subject takes or is administered a compound(s) of this disclosure for the first time, and in a further embodiment when the compound dosage is increased or decreased. In a further embodiment, during this period of medical observation, the subject stays in a location that has medical facilities and/or expertise to treat/combat hypothermia (well known to those of the art), in non-limiting example embodiments this is a hospital or clinic or pharmacy or workplace of healthcare professionals. In an embodiment, during this period of medical observation, the patient stays in a temperature controlled room or area, or at a location where one is available nearby, and if the patient displays signs or symptoms of hypothermia, feels uncomfortable, or their body temperature falls, they can be located in a higher ambient temperature. In an embodiment, while the subject takes or is administered a compound(s) of this invention, or in a monitoring period after it, they stay in a room/confinement/ location at a safe ambient temperature for having a compound(s) of this disclosure (non-limiting examples: wherein the ambient temperature is close to the desired body temperature, ~37° C., or exceeding it within safe limits) and are monitored by observation, and in a further embodiment their body temperature is monitored (methods well known to those of the art), as the controlled room/confinement/location temperature is reduced to a different temperature, in a further embodiment to, at or near, the ambient climatic temperature of that geography at that time, or colder. In a further embodiment, this process/method is iterated until the greatest dosage is found at which the subject has a safe body temperature at, or near, the ambient climatic temperature of that geography at that time or at the ambient temperature(s) at which the subject will spend their time at over their course of compound administration, or that their ambient temperature might fall to at some time over their course of compound administration, wherein the course of compound administration is the period during which the subject has an effective amount of compound in their body.

Many clinical oncology centres have equipment for body heating, for administrating hyperthermia, for anti-cancer treatment. And other clinical specialties have body heating equipment for heat therapy. An invention embodiment is to administer an effective amount of an $F_1F_0$ ATP hydrolysis inhibitor(s) to a subject, who is heated by such body heating equipment/apparatus, or other body heating equipment/apparatus. An embodiment of this invention is a method in which a subject takes or is administered an effective amount of a compound(s) of this invention, for example a compound of Formula (I), (II), (III), (IV) or (V) or another compound that selectively inhibits $F_1F_0$ ATP hydrolysis, or a pharmaceutically-acceptable salt, solvate, hydrate or prodrug thereof, to treat/ameliorate/prevent/combat a medical disease/disorder, wherein the subject is warmed by a device(s), for example a medical device(s) (numerous examples known to those of the art e.g. refer [63-64]), to maintain their body temperature within a safe range, optionally locating in an incubator and/or in/under a radiant heater, optionally a scale up of that often used for (especially premature and/or low birth weight) babies (such scale ups, e.g. adult radiant warmer(s), are commercially available, used for example when patients undergo general anaesthesia, which can reduce metabolic rate by 20-30% [63]; teaching of [64] incorporated herein by reference, as applied to adult or infant), and the subject's body temperature is maintained by heating the air to a desired temperature and/or by controlled electromagnetic radiation (e.g. infrared, preferably IR-A, from 0.78 to 1.4 μm), and/or by servo-controlling the body temperature at a desired set-point, most preferably at a body temperature conducive to keeping the subject alive e.g. at or near 37° C. and/or at a thermoneutral temperature for the subject (in a further embodiment the desired set-point is set at a lower temperature than a normal body temperature, to induce hypothermia in the subject for a medical purpose). Servocontrol in this context, as well known to those of the art, refers to an electronic feedback system which maintains a constant temperature at the site of a thermistor (or other) probe (for non-limiting example, on the skin over the abdomen) by regulating the heat output of an incubator and/or radiant warmer and/or other body heating device. Componentry to this invention is a servocontrol variant(s) whereby body temperature is recorded by infra-red (and/or other electromagnetic) emission from the body and/or body temperature is increased by infra-red (and/or other electromagnetic) emission towards the body, optionally where temperature detection and heating occurs at different wavelengths, optionally for use for heating a subject with an effective amount of a compound(s) that inhibits $F_1F_0$ ATP hydrolysis in their body, optionally a compound(s) of Formula (I-V). An embodiment of this invention is a method in which a subject is administered an effective amount of a compound(s) or pharmaceutical composition(s) that inhibits $F_1F_0$ ATP hydrolysis, by intravenous injection, wherein the volume injected is heated to be at or close to normal body temperature and/or wherein any method(s), including equipment, used to treat/ameliorate/prevent/combat anaesthetic associated hypothermia (methods are well known to those of the art) is used for a subject administered with a compound(s) that inhibits $F_1F_0$ ATP hydrolysis, optionally a compound(s) of Formula (I), (II), (III), (IV) or (V). An embodiment of this invention is a method in which a subject takes or is administered an effective amount of a compound(s) of this invention, for example a compound of Formula (I), (II), (III), (IV) or (V) or another compound that selectively inhibits $F_1F_0$ ATP hydrolysis, or a pharmaceutically-acceptable salt, solvate, hydrate or prodrug thereof, to treat/ameliorate/prevent/combat a medical disease/disorder, wherein the subject wears one or more clothes, optionally a hat, to maintain body temperature within safe/comfortable limits as the $F_1F_0$ ATP hydrolysis inhibitor(s) reduces metabolic heat production. An embodiment of this invention is a method in which a compound(s) of this invention, for example a compound of Formula (I), (II), (III), (IV) or (V) or another compound that selectively inhibits $F_1F_0$ ATP hydrolysis, or a pharmaceutically-acceptable salt, solvate, hydrate or prodrug thereof, is distributed, sold and/or administered with a verbal and/or written communication, optionally in a paper insert/leaflet in a packet(s) containing the compound(s) (optionally called "instructions for use", and/or "prescribing information" and/or "patient information leaflet"), that this compound(s) can reduce body temperature and, in a further embodiment, communicating that should the subject that has taken or been administered one or more of these compounds feel cold, and/or has a reduction in body temperature, they should do one or more of: wear more clothes, wear warmer clothes, locate in a hotter environment, tell a doctor or pharmacist, go to a hospital. Each of these aforementioned communications is a separate invention embodiment and combinations of these are further embodiments. In a yet further embodiment, communicating that this is a more serious problem in children, optionally communicating that this is because children have a larger surface area to volume ratio than adults, optionally communicating that this problem is especially acute with babies and optionally communicating that this compound(s) should not be administered to babies (in a further embodiment, unless the baby is in a controlled temperature environment such as an infant incubator or radiant warmer). In another embodiment, a method in which a compound(s) of this invention, for example a compound of Formula (I), (II), (III), (IV) or (V) or another compound that selectively inhibits $F_1F_0$ ATP hydrolysis, or a pharmaceutically-acceptable salt, solvate, hydrate or prodrug thereof, is distributed, sold and/or administered with a verbal and/or written communication, optionally in a paper insert/leaflet in a packet(s) containing the compound(s) (optionally called "instructions for use", and/or "prescribing information" and/or "patient information leaflet"), that alcohol shouldn't be consumed in large amounts, and in another embodiment not at all, if the subject is taking or being administered such a compound(s). Optionally communicating because alcohol can corrupt thermoregulation, which can potentially, negatively interact with the thermoregulatory effect(s) of the administered compound(s). Optionally communicating the same caveat/warning/communication in reference to other drug(s) that can disrupt thermoregulation, many of which are known to those of the art (non-limiting examples: phenothiazines {like chlorpromazine etc.}, thioxanthenes etc.), in place of or in addition to the communication relating to alcohol.

Body Heat Balance Equation (1$^{st}$ Law of Thermodynamics)

$$S=M-W-E-C-K-R;$$

S=storage of heat in body (=0=heat balance, i.e. no change in body temperature, positive=increased body temperature, negative=decreased body temperature);
M=metabolic heat production (always positive in living organisms);
W=work (positive=useful work accomplished, negative=mechanical work absorbed by body);
E=evaporative heat transfer (positive=transfer to environment);
C=convective heat transfer (positive=transfer to environment);
K=conductive heat transfer (positive=transfer to environment);
R=radiant heat exchange (positive=transfer to environment);

This concept is well known ([65], herein incorporated in entirety) and numerous strategies to keep S=0, as M decreases when an $F_1F_0$ ATP hydrolysis inhibitor is administered to the subject, will be apparent to those of the art. For (non-limiting) example, if M decreases, use an infra-red lamp to make R negative and substantial enough to offset the decrease in M (thence keep S=0), or increase the air temperature to make C negative and substantially negative to offset the decrease in M (thence keep S=0), or wear clothes to make positive values of one or more of E, C, K, R less positive to offset the decrease in M (thence keep S=0).

Translating Dosage Between Species

Larger species have lower mass specific basal metabolic rate, because this parameter scales to animal mass by a negative fractional power (e.g. refer Kleiber's law). Thence larger species metabolise drugs slower and so require, and can withstand, a lower mg/kg drug dosage, and this is factored into converting a drug dosage in one species (e.g. mouse) into one of different size (e.g. human), as is well known to those of the art (e.g. refer [66] and the FDA guidelines it refers to). However, by the invention of this disclosure, toxicity of selective $F_1F_0$ ATP hydrolysis inhibitors scales to animal mass by a negative fractional power and is less in larger animals than predicted by conventional allometric scaling methods used in the art. Because larger animals have a smaller surface area to mass ratio (animal mass is proportional to animal radius$^3$, animal surface area is proportional to animal radius$^2$, thence bigger animals have smaller surface area to mass ratio), they retain metabolically generated heat better and thence a given percentage drop in metabolic rate doesn't cause as big a percentage drop in body temperature i.e. they aren't as negatively affected by a drop in metabolic heat production, which $F_1F_0$ ATP hydrolysis inhibitors cause, which is the defining limit upon their maximally tolerated dosage (MTD), in smaller animals at least, if ambient temperature is significantly below optimal body temperature e.g. when ambient temperature=~22° C.

Mass specific metabolic rate (MR) [62] is, assuming core body temperature stays constant (heat production=heat loss), and that ambient temperature is below the lower critical temperature, which is the lower bound of ambient temperature that an animal is thermoneutral:

$$MR=C(Tb-Ta);$$

Tb=body temperature;
Ta=ambient temperature;
C=whole body thermal conductance=heat transfer rate (by all heat transfer mechanisms) from body core to environment for temperature difference of 1° C.;
I=insulation=1/C;
$MR=21.66*M^{-0.25}$;
$C=4.23*M^{-0.426}$;
where M=body weight (g);
MR and C decrease with increasing M; MR decrease increases drug toxicity; C decrease decreases drug toxicity (for an $F_1F_0$ ATP hydrolysis inhibitor), let us define a danger quotient for an $F_1F_0$ ATP hydrolysis inhibitor: its danger is proportional to C and inversely proportional to MR: danger=C/MR=$(4.23*M^{-0.426})/(21.66*M^{-0.25})$. Using M=20 g for a mouse, and M=62 kg for a human, danger quotient for mouse (=0.12) and human (=0.03). So, assuming same ambient temperature for both species, which is below the thermoneutral temperature zone of both species, the mg/kg MTD will be ~4 times more in humans than in mice, and even greater than this for a human wearing clothes (decreases C). This is far removed from what one of the art would expect: expecting mg/kg MTD in humans to be less than in mice: for example, calculating $(21.66*20^{-0.25})/(21.66*62000^{-0.25})=20^{-0.25}/62000^{-0.25}=~7.5$ times less, or using the more conservative exponent of [66] (and possibly less appropriate, at least for chemotherapeutics: refer FDA guidance cited in [66]) they would calculate $20^{-0.33}/62000^{-0.33}=14.2$ times less. Any given mg/kg dose in humans will be metabolised $(20^{-0.25})/(62000^{-0.25})=\sim 7.5$ times slower and so because we have ascertained that the maximum permissible mg/kg dose in humans is ~4 times more than in mice: then the potential anti-cancer activity of an $F_1F_0$ ATP hydrolysis inhibitor is $4*7.5=\sim 30$ times higher in a human than a mouse, at typical room temperature. So, elucidated by the invention of this disclosure, small animal studies at room temperature (~22° C.) will dramatically underestimate the anti-cancer activity possible at room temperature in humans, and severely curtail the therapeutic benefit if conventional allometric scaling is used to set the human dose from mice studies. This invention supplies a new method to better translate the dosage of an $F_1F_0$ ATP hydrolysis inhibitor between species. However, more conventional allometric scaling methods can be used [66] if the smaller species studies are conducted at an ambient temperature close to optimal homeothermic body temperature, Ta≈Tb, and especially if humans will live at this same temperature. Thus, the temperature at which the smaller species study is conducted, and the temperature that the human subjects will reside at, determines the allometric scaling method applied, to find the equivalent human dose, which would not have been apparent to someone of the art without this disclosure. Furthermore, a method as disclosed herein can be used to modulate $F_1F_0$ ATP hydrolysis inhibitor dosage between individuals of a single species, e.g. humans, of different sizes.

The equations and parameters used in this section illustrate the principles of the invention and are not restrictive. For example, other allometric exponents are contemplated and componentry to this invention. A method of this invention is to compare the MTD (or some other safety metric e.g. NOAEL, $LD_{50}$, $LD_{33}$ etc.) of an $F_1F_0$ ATP hydrolysis inhibitor(s) between animal individuals and/or species of different size (e.g. mice, rats, guinea pigs, rabbits, dogs, primates etc.) to calculate more precisely what the particular allometric scaling relation is, and optionally investigate how this scaling changes with ambient temperature. And then use this relation(s) to calculate/triangulate/estimate a safe starting dose in humans, from prior animal studies. Optionally factoring in what the ambient temperature(s) will be for the humans administered the $F_1F_0$ ATP hydrolysis inhibitor(s).

Anti-Cancer Dosage

Methods to gauge the anti-cancer activity of a treatment(s) in a subject(s), and/or to gauge the change in anti-cancer activity associated with a change (e.g. dosage change) in treatment(s), are well known to those of the art. They are routinely utilised in pre-clinical studies and clinical practice.

The following methods are very atypical from present dosage methods in the art of chemotherapy, wherein dosage is typically, simply just the maximum dosage that the patient can tolerate. The method of decreasing the administered dose of a compound(s) that inhibits $F_1F_0$ ATP hydrolysis, for (non-limiting) example a compound of Formula (I), in order for it to exert greater anti-cancer activity in a subject is an embodiment of this invention.

The anti-cancer activity of a compound(s) of Formula (I) can increase or decrease in proportion to an increase in compound dosage, wherein there is an optimal anti-cancer dosage which is not, as one of the art would expect, at the maximally tolerated dose. Decreasing or increasing (!) the dose away from this optimal dosage decreases anti-cancer activity. Herein is a method to find this optimal dosage in a subject, which is componentry to this invention, as are other methods to find the optimal dosage for a compound(s) of Formula (I), which leverage/utilise the extremely atypical dose vs. anti-cancer activity profile, disclosed herein (FIGS. 8, 11, 12).

If increased dose=increased anti-cancer activity, increase dose further. If increased dose=decreased anti-cancer activity, decrease dose by more than it was increased previously. Make the next increase in dose smaller than prior. Repeat. As this loop is repeated, and the increment increase in dose gets smaller, the person of the art knows that they are increasingly converging upon the optimal dosage. They can choose to exit the loop at any dosage they wish, knowing that the size of the dosage increase increment on loop exit is an indicator of how close they are to the optimal dosage. The smaller the dosage increase increment at loop exit, the closer that the dosage is to the optimum. The person of the art may choose to do the mirror image of the aforementioned loop and choose decreased, instead of increased, dose increments. There are permutations to these schemes as will be clear to someone of the art, now that this logic has been set out, which are componentry to this invention. To help illustrate (not restrict) the invention the following R [67] programming code is disclosed, wherein the "optimal" parameter symbolises the optimal anti-cancer dosage, and the loop iterates until the administered drug dosage, "dose", equals the optimal. Someone of the art can adjust this code, for example changing parameters and/or mathematical symbols, to explore and understand the invention further. Of course, in reality, the optimal anti-cancer dosage is unknown and is not user specified, as in the code, but the code illustrates a method to find the optimal anti-cancer dosage for a compound of Formula (I), a method componentry to this invention. All parameters are merely illustrative.

```
# R programming code
dose = 1                    # first dose to be tried
reset = dose
dt = 600                    # step size that dose will be adjusted
res = dt/100000000
# res = an accuracy parameter, larger denominator means more iterations and more accuracy
x = 0
optimum = 60
# optimal anti-cancer dose, unknown in real case, following the logic herein finds it
n = 10
# n = an accuracy parameter, MUST be >1, larger means more iterations and more accuracy
m = n
count = 0                   # how many iterations are taken to converge
while (dt > res)
{
```

```
dose = dose + dt
if (dose<optimum) {
# Increased dose = Increased anti-cancer activity, so Increase dose further
dose = dose+dt
x=x+1
}
if (dose>optimum) {                     # Increased dose = Decreased anti-cancer activity, so Decrease dose
if (dose<0){
dose=reset
dt = dt/n
}
dose = dose-(dt+(dt/n))
x=x-1
}
if (x==0){dt=dt/m}
# if dose is changed in one direction (increase or decrease) and then subsequently changed in
# opposite direction, decrease step size
if (abs(x)==2){x=0}
count = count + 1
# if (abs(dose-optimum)<1){break}        # not used, but here for interest
}
```

In place of, or after, the aforementioned, or other, method has converged the administered dose to be close to optimum, the dosage can be set randomly, optionally restricted within a range, by some formal/informal random number generator. It need not be perfectly random and can just be the arbitrary choice of a person(s). This formalised/informal random walk is used to find a compound(s) dosage, of Formula (I), with greater anti-cancer activity. It is distinct from conventional methods in its use of dosage reduction (not merely increase) to seek greater anti-cancer activity.

The most optimal dosage, or dosage range, for a compound of Formula (I) is that which causes cancer cell death. This is a narrow dosage range (FIG. 13). Flanked at lower and higher doses by dosages that exert less anti-cancer activity. An embodiment of this invention is changing the administered dosage of a compound of Formula (I) in a subject until a dosage(s) causes cancer cell death, optionally by apoptosis. Detected, for non-limiting example, by cancer regression rather than merely slowing of cancer growth and/or by apoptosis markers, well known to those of the art (e.g. refer [68]), for example, in the blood.

Using a dosage selection method disclosed herein to find a good anti-cancer dosage for a compound of Formula (I), optionally in a xenograft/syngeneic rodent(s), optionally housing the rodent(s) at an ambient temperature ≥26° C. (in further embodiments: ≥28, ≥30, ≥32, ≥34, ≥36° C.), is componentry to this invention. As is any housing/rearing of a rodent(s) at an ambient temperature ≥26° C. (in further embodiments: ≥28, ≥30, ≥32, ≥34, ≥36° C.) whilst administered with a compound(s) of Formula (I), optionally to select the starting dosage(s) for human clinical trial(s).

Uncoupling Cancer

The meaning and characteristics of an uncoupler are well known to those of the art e.g. refer [36]. An uncoupler is a molecule that can bind a proton(s) in the mitochondrial intermembrane space (IMS), move across the mitochondrial inner membrane, and release the proton(s) in the mitochondrial matrix, which dissipates the proton motive force (pmf), and that can then return to the IMS, and repeat this sequence iteratively. 2,4 dinitrophenol is an example of an uncoupler. Many other uncouplers are known to those of the art. An invention embodiment is to administrate a therapeutically effective amount of a compound(s) that inhibits $F_1F_0$ ATP hydrolysis (e.g. a compound(s) of Formula (I), (II), (III), (IV) or (V)), with a therapeutically effective amount of the same or a different compound(s) that uncouples the proton motive force, for use in a method of treatment of the human or animal body by therapy, wherein optionally the $F_1F_0$ ATP hydrolysis inhibitor(s) and uncoupler(s) are in a single pharmaceutical composition and/or are packaged, and/or distributed, and/or sold together, optionally for the treatment/amelioration/prevention/combat of cancer in a subject(s). As aforementioned, the dosage range that an $F_1F_0$ ATP hydrolysis inhibitor of Formula (I) kills cancer cells is extremely narrow. This range is broadened by co-administration of an uncoupler(s), which increases OXPHOS rate and [ROS], and reduces the concentration of $F_1F_0$ ATP hydrolysis inhibitor required. Optionally, an $F_1F_0$ ATP hydrolysis inhibitor(s) is administered with an aforementioned method(s) to (fractionally) optimise its dosage, before the administration of the uncoupler, which then decreases the dosage of uncoupler required. An $F_1F_0$ ATP hydrolysis inhibitor(s) decreases metabolic inefficiency and body temperature, an uncoupler(s) increases metabolic inefficiency and body temperature: co-administration, especially optimised co-administration, optionally wherein an optimised amount of each is in a single pharmaceutical composition, can reduce the change in body temperature that each would cause alone; and there is synergy in anti-cancer activity yielded. Componentry to this invention are compounds that inhibit $F_1F_0$ ATP hydrolysis and that uncouple the proton motive force (pmf) e.g. (non-limiting) BMS-199264. An embodiment of this invention is to administrate, or for the subject to self-administer, a therapeutically effective amount of a compound(s) that inhibits $F_1F_0$ ATP hydrolysis and that uncouples the proton motive force, for use in a method of treatment of the human or animal body by therapy, optionally for the treatment/amelioration/prevention/combat of cancer in a subject(s).

In cancers that cannot use OXPHOS because of deficiency(s) in their respiratory chain, or because of hypoxic environment (tumours are often hypoxic), which thence singly rely upon $F_1F_0$ ATP hydrolysis to maintain $\Psi_{IM}$, an uncoupler(s) will erode their $\Psi_{IM}$ and an $F_1F_0$ ATP hydrolysis inhibitor(s) will block their only means to counter this, their $\Psi_{IM}$ will collapse, triggering their apoptosis. Given the severity of this vulnerability, and the potentiating effect of the two drugs, low drug doses apply. Meanwhile, normal cells will maintain $\Psi_{IM}$ by greater OXPHOS rate.

Also componentry to this invention is the use of a therapeutic amount of uncoupler(s) to treat/ameliorate/prevent/combat cancer in a subject. If $\Psi_{IM}$ depolarises, apoptosis ensues [59]. Aerobic respiration, favoured by normal adult cells, hyperpolarises $\Psi_{IM}$ as it produces ATP. Aerobic glycolysis, favoured by many cancers some or all of the time, consumes ATP to hyperpolarise $\Psi_{IM}$. Under the challenge of an uncoupler compound(s), the former is more sustainable than the latter, even more so because of the difference in ATP yields (~30 vs. 2 ATP per glucose), and thence there is a therapeutic margin. In response, some cancers will be able to switch out of aerobic glycolysis, and into aerobic respiration, but its oxidative phosphorylation (OXPHOS) component will increase ROS, bring ageing, mortality and mitigated danger, especially because the uncoupler(s) will drive higher OXPHOS rate. Unlike other chemotherapeutics, uncouplers only interact with protons, not DNA encoded proteins, and so their therapy cannot be resisted by DNA mutation rendered changes in protein structure, which is the basis to present day cancer drug resistance, which kills.

Uncoupling is Virtuous

The imidazole containing compounds of this disclosure inhibit $F_1F_0$ ATP hydrolysis and uncouple (shuttle protons across the mitochondrial inner membrane (IM), eroding the proton motive force, pmf). The former can exert a specific anti-cancer activity, because it undermines the means some cancers maintain $\Psi_{IM}$ in normoxia (experimentally shown by data of this disclosure) or in hypoxic tumours, and the compound's uncoupling can also exert specific anti-cancer activity, explained now. The imidazole containing compounds of this disclosure bind ATP synthase at or near the IF, binding site. In normal cells they bind ATP synthase at this site and are sequestered from uncoupling, and the ATP they "save" by binding and inhibiting $F_1F_0$ ATP hydrolysis can (over)compensate for the ATP "lost" to their uncoupling. But some cancers have very high IF, expression (numerous studies show this, e.g. refer [23]). And for some cancers, this is to inhibit $F_1F_0$ ATP hydrolysis, to make their OXPHOS more efficient, which allows them to maintain [ATP] at low [02], and thence survive using OXPHOS in hypoxia (their heat generation is less but their temperature is maintained by heat conduction from surrounding tissues). This high IF, expression blocks the binding of these compounds to their binding site on ATP synthase, so the compounds aren't sequestered from uncoupling, and this uncoupling increases the $O_2$ requirement of this cancer which can't be met in the hypoxic microenvironment of its tumour, thence the cancer's intracellular [ATP] can't be maintained and its proliferation is slowed and/or it dies. So, herein, this invention discloses that the uncoupling aspect to the imidazole containing compounds of this disclosure can deliver additional, specific, anti-cancer activity, for example, against those cancers that don't rely upon $F_1F_0$ ATP hydrolysis. This invention discloses the process/method of using a compound(s) that can inhibit $F_1F_0$ ATP hydrolysis, and that can shuttle protons across the IM to dissipate the pmf (uncouple), as an anti-cancer therapeutic. Wherein the compound inhibits $F_1F_0$ ATP hydrolysis by direct interaction with ATP synthase, and reduces $F_1F_0$ ATP synthesis (primarily) by uncoupling. So, a compound needn't necessarily have a much lower $EC_{50}$ for $F_1F_0$ ATP hydrolysis than $F_1F_0$ ATP synthesis, in an SMP assay, to be componentry to this invention as an anti-cancer therapeutic. Indeed, even compounds with a lower $EC_{50}$ for $F_1F_0$ ATP synthesis than $F_1F_0$ ATP hydrolysis in an SMP assay can be componentry to this invention, as anti-cancer therapeutics, provided they do inhibit $F_1F_0$ ATP hydrolysis and provided their inhibition of $F_1F_0$ ATP synthesis is (primarily) because of uncoupling rather than inhibiting the forward mode of ATP synthase. Oligomycin, for example, does not fit these requisites. So, this invention discloses the method of using compounds that inhibit $F_1F_0$ ATP hydrolase, that don't inhibit $F_1F_0$ ATP synthase, and that uncouple the proton motive force, as anti-cancer therapeutics.

Deuterated Compounds of the Invention

Deuterium (D or $^2H$) is a stable, non-radioactive isotope of hydrogen and has an atomic weight of 2.0144. Hydrogen naturally occurs as a mixture of the isotopes $^1H$ (hydrogen or protium), D ($^2H$ or deuterium), and T ($^3H$ or tritium). Herein, all percentages for the amount of deuterium present are mole percentages. The natural abundance of deuterium is 0.015%. Thence one of the art recognizes that in all chemical structures containing an H atom(s), this H atom(s) actually represents a mixture of H and D in the compound, with about 0.015% being D. Therefore compounds that have a higher level of deuterium incorporation, i.e. compounds enriched to have a greater D incorporation than natural abundance (>0.015%), should be considered unnatural and so distinct from their non-enriched counterparts. A compound is said to be "deuterium enriched" if it has a quantity of deuterium that is greater than in naturally occurring compounds, or synthetic compounds prepared from substrates having the naturally occurring distribution of isotopes. At a lab scale amount (milligram or greater) it can be difficult to achieve 100% deuteration at any one site of a compound. Herein, when 100% deuteration is recited or a deuterium atom is specifically shown in a structure, it is assumed that a small percentage of hydrogen may still be present. Deuterium-enrichment can be achieved either by exchanging compound protons with deuterium or by synthesizing the compound with deuterium enriched starting materials, which are commercially available or can be readily prepared by someone of the art using known methods.

Embodiments of this invention include compounds of Formula (I), (II), (III), (IV), (V) and (VI) with one or more of their hydrogen atoms replaced by deuterium, at a greater frequency than the natural abundance of deuterium (0.015%). For non-limiting example: >3000 times greater than the natural abundance of deuterium (i.e. a >40% incorporation of deuterium at a hydrogen replacement position). Additional examples of the abundance of deuterium at a position in, or positions of, a compound embodiment of this invention include 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 to about 100%. In certain embodiments, the abundance of deuterium at a position in, or positions of, a compound embodiment of this invention is at least 40%. In certain other embodiments, the abundance of deuterium at a position in, or positions of, a compound embodiment of this invention is at least 60%. In further embodiments, the abundance of deuterium is at least 75%. In yet other embodiments, the abundance of deuterium is at least 90%. It is to be understood that the deuterium-enriched compounds described herein can be combined with a pharmaceutically acceptable carrier to form a pharmaceutical composition.

In the Description and Claims of this disclosure, when a position on a compound structure is designated deuterium (D), or said to have deuterium, or said to be enriched for deuterium, it is because the abundance of deuterium at that position is not at the natural value (0.015%) but greater. Typically, in excess of 40%. The phrase 'enrichment at the chiral centre' herein, for example for a compound of Formula (I), means that the molar amount of deuterium at the chiral centre, as a percentage of the total amount of all hydrogen isotopes at the chiral centre, is greater than 0.015%, especially greater than 1%, preferably greater than 40%, more preferably greater than 45%, and in ascending order of preference, ≥52.5% deuterium enrichment at the chiral centre, ≥60% deuterium enrichment at the chiral centre, ≥67.5% deuterium enrichment at the chiral centre, ≥75% deuterium enrichment at the chiral centre, ≥82.5% deuterium enrichment at the chiral centre, ≥90% deuterium enrichment at the chiral centre, ≥95% deuterium enrichment at the chiral centre, ≥97% deuterium enrichment at the chiral centre, ≥99% deuterium enrichment at the chiral centre, ≥99.5% deuterium enrichment at the chiral centre, 100% deuterium enrichment at the chiral centre. Greater % deuterium enrichment is preferred.

Further possible isotopic variants of the structures of this invention are further embodiments of this invention. An invention embodiment is a compound that inhibits the reverse mode, more than the forward mode, of ATP synthase, which has deuterium in place of hydrogen (at a greater frequency than 0.015% e.g. >40%) at one or more places upon its structure, and/or any other isotopic substitution/enrichment (at a greater than natural frequency e.g. $^{13}C$ and/or $^{15}N$ enriched; $^{13}C$ enrichment {abundance >[natural abundance=1.109%]} at the chiral carbon of compounds of Formula I is especially preferred, especially when, if applicable, its attached hydrogen is enriched for $^2H$ {abundance >[natural abundance=0.015%]; preferred is when $^{13}C$ enrichment at the chiral carbon >40%, optionally $^2H$ enrichment at the chiral carbon >40% also}).

Molecule synthesis routes described in [5, 6, 7, 8, P1, P2, P3, P4, P5, P6] (including references cited therein, where appropriate, and in their supplementary materials, all herein incorporated in their entirety)—for synthesizing molecules that inhibit F1F0 ATP hydrolysis more than $F_1F_0$ ATP synthesis—are componentry to this disclosure, as synthesis routes for synthesising anti-cancer molecules. In other embodiments of this invention, any given molecule synthesis route described in [5, 6, 7, 8, P1, P2, P3, P4, P5, P6, P7, P8] is used with starting reagents, compounds, solvents and/or intermediates that have deuterium in place of hydrogen at some position(s). Such compounds are commercially available (e.g. refer C/D/N Isotopes Inc., Pointe-Claire, or CK Isotopes Ltd., Desford, UK, or Cambridge Isotope Laboratories, Tewksbury, MA). Or they can be created in house by invoking standard synthetic protocols known in the art for introducing isotopic atoms to a chemical structure. For (non-limiting, illustrative) example, a compound can be deprotonated by LiHMDS in tetrahydrofuran (THF) at −78 to −40° C. for 20 minutes, followed by quenching with deuterium oxide ($D_2O$, "heavy water"), to obtain a deuterated compound [37]. During these steps, a group upon which hydrogen is still desired over deuterium can be Boc protected and this Boc group removed subsequently using trifluoroacetic acid (TFA) treatment at room temperature. At the end, the level of deuterium can be checked by $^1H$ NMR. The initial deprotonation step isn't absolutely necessary as H/D exchange will occur when a molecule is quenched with $D_2O$, and this reaction can be catalysed, by acid, base or metal based catalysts such as platinum. If, after $D_2O$ quenching, the level of compound deuteration is insufficient (observed using $^1H$ NMR) then the compound is quenched with $D_2O$, or some other deuterium containing solvent, for a longer period of time. Compounds of this disclosure can be synthesised in $D_2O$, during one or more chemical steps, or a starting compound, intermediate or final molecule of this disclosure can be incubated in $D_2O$ to produce a deuterated version(s). So, deuterium-enriched compounds of this invention can be prepared by substituting a deuterium-enriched reagent or solvent for a non-isotopically labeled reagent or solvent in the synthetic schemes reported in [5, 6, 7, 8, P1, P2, P3, P4, P5, P6, P7, P8].

Non-limiting example embodiments of the invention are deuterated enumerations of Markush Formulas (I), (II), (III), (IV), (V) and (VI). These isotopologues are componentry to the present invention as new compositions of matter, and in non-limiting embodiments are used singly or in combination, optionally in co-therapy with an FDA and/or EMA approved medicine(s) and/or treatment(s), for example a licensed cancer treatment, as anti-cancer therapeutics.

Methods to Find Further Compounds Component to this Invention

A method to find compounds of this invention, for example to find compounds that slow the proliferation of and/or kill cancer cells, is by screening/seeking compounds that preferentially inhibit the reverse mode of ATP synthase. For example, by separately assaying (in space and/or time) the compounds's effect upon ATP synthesis and ATP hydrolysis by ATP synthase (in its entirety or, less preferably, a component part of it). Then comparing these assay results. The greater the inhibition of reverse vs. forward mode, the more preferred this compound is for a use of this invention, optionally anti-cancer use. A further method is by screening/seeking compounds that inhibit ATP hydrolysis more than synthesis in submitochondrial particles (SMPs). ATP hydrolysis can be assayed by (non-limiting example) a spectroscopic assay for NADH fluorescence that incubates the SMPs with pyruvate kinase and lactate dehydrogenase enzymes (assay well-known to those of the art). ATP synthesis can be assayed by (non-limiting example) a spectroscopic assay for NADPH fluorescence that incubates the SMPs with hexokinase and glucose-6-phosphate dehydrogenase enzymes (assay well-known to those of the art). These assays are reported in in any one of [5, 7, 8, 11, 12, 13, 70], and/or as referenced therein, all of which are herein incorporated in their entirety. In these SMP assays, the criteria for a candidate anti-cancer compound is a low $EC_{50}$ against ATP hydrolysis (thence anti-cancer activity) and a higher $EC_{50}$ against ATP synthesis (thence safe for normal cells).

Cancer Types Particularly Targeted by this Invention

Leukemia cancer cell line examples in FIG. 8 show that Compound 6b can inhibit cancer proliferation strongly at 10 μM and then nearly not at all at 100 μM. As disclosed earlier, lower [6b] switches cancer cells into greater OXPHOS use/rate, exerting anti-cancer activity, but higher [6b] decreases OXPHOS rate, exerting less anti-cancer activity. Extrapolating this data, even greater [6b] may assist cancer and increase its proliferation rate. And if a cancer has appropriate adaptations and is using OXPHOS greatly in the first place, without 6b administration, then 6b administration may only ever help and never hinder that cancer. Compound 6b, and other $F_1F_0$ ATP hydrolysis inhibiting compounds of this invention, are best administered to cancers showing signs of glycolytic rather than oxidative metabolism. For example, those that show up, at least before treatment by this invention, in positron emission tomography (PET) imaging using fluorine-18 ($^{18}F$) fluorodeoxyglucose (FDG), $^{18}F$-FDG PET [71].

Particularly vulnerable to compounds of this invention: cancers that exhibit the Warburg effect (i.e. that produce ATP primarily by glycolysis, rather than oxidative phosphorylation, even in abundant $O_2$), highly glycolytic cancers (which metabolize glucose and/or glutamine to lactate rather than metabolizing one or both fully with the use of oxidative phosphorylation) and cancers that reside in hypoxia, which forces them to produce ATP primarily by glycolysis. As explained in a preceding section, the imidazole containing molecules of this disclosure, with their uncoupling capability, can also attack cancers that reside in hypoxia, which use high $IF_1$ expression to enable oxidative phosphorylation at low $[O_2]$. Many cancers reside in hypoxia as tumours are often hypoxic.

So, if a cancer is highly glycolytic, either because of the Warburg effect (inherent glycolytic metabolism, regardless of $[O_2]$) or because of residing in hypoxia (imposed glycolytic metabolism, because of low $[O_2]$), or uses oxidative metabolism but resides in hypoxia (survival enabled by high $IF_1$ expression), it will be treated/ameliorated/prevented/combated by a compound of this invention. How to identify such cancers?

Cancers exhibiting the Warburg effect, or that have an imposed (by low $[O_2]$) glycolytic metabolism, are those that show up in positron emission tomography (PET) imaging using $^{18}$F-FDG PET, optionally integrated with computed tomography (CT) [71]. FDG is a glucose analogue and glycolytic cancers take up more FDG than their surrounding tissue because glycolysis is an inefficient metabolism of glucose (yielding only ~2 ATP per glucose compared to ~30 ATP per glucose yielded by aerobic respiration [1-2]) and so they must uptake more glucose to obtain even the equivalent energy yield to nearby normal cells, which are using oxidative metabolism, as most normal cells do. So, if a cancer presents in this FDG-PET diagnostic (higher glucose uptake than surround), it is susceptible to a compound of this invention. Highly glycolytic cancers also release much lactate. So, if a patient has a high blood lactate level, noticeably above the normal non-pathological range, as clear to someone of the art, then their cancer is susceptible to a compound of this invention. Higher lactate levels in and around the cancer or tumour (than surrounding tissue) can also be detected using imaging technologies, for example $^{1}$H Magnetic Resonance Spectroscopy ($^{1}$H-MRS) or chemical exchange saturation transfer magnetic resonance imaging (CEST MRI) [72], or other imaging modalities and methods of the art. So, if a cancer presents (higher [lactate] than surround) in a lactate imaging diagnostic it is susceptible to a compound of this invention. Cancer release of lactic acid acidifies its extracellular space and this acidification can be detected by imaging modalities, well known to those of the art e.g. [73-74], and if a cancer can be discriminated from its surrounding tissue by this method then it is susceptible to a compound of this invention. An oxygen-sensitive chemical probe can be used to obtain 3D maps of tissue $pO_2$ [75], and if a cancer is shown to reside in notable hypoxia then it is susceptible to a compound of this disclosure, because it is either glycolytic or likely using high $IF_1$ expression to enable oxidative metabolism, both of which make it susceptible to a compound of this invention. Imaging technologies can be integrated to improve signal to noise e.g. [75] integrate $pO_2$ and lactate imaging. Such integration can give added information: for example, a cancer producing much lactate in a high $pO_2$ environment is exhibiting the Warburg effect because it is heavily utilising glycolytic metabolism in abundant $O_2$. Cancer gene expression markers and indicators of the Warburg effect, well known to those of the art e.g. [18-20], specify that a cancer is susceptible to a compound of this invention, wherein the cancer's genetic material can be retrieved by biopsy, surgery, cancer cells or parts circulating in the bloodstream or some other method of the art.

If a cancer uses oxidative phosphorylation (OXPHOS) rather than glycolytic metabolism, and it does not already improve its OXPHOS efficiency by high $IF_1$ gene expression (which many cancers do e.g. refer [23]) then a compound of this invention, by preferentially inhibiting $F_1F_0$ ATP hydrolysis, will confer this efficiency gain and actually assist, rather than harm, this cancer. How to identify these cancers? A cancer's $IF_1$ gene expression, and particularly its gene expression ratio of $IF_1$ to a core ATP synthase sub-unit (e.g. ATP6), is informative. More so if compared to the corresponding gene expressions in a normal cell of its host tissue, so detecting difference from normal. If a cancer uses oxidative, rather than glycolytic, metabolism and does not have an appreciably higher $IF_1$ (or $IF_1$/ATP6 ratio) gene expression than its corresponding normal tissue then it isn't prudent to use a compound of this invention for cancer therapy. More simply, it is best to use a compound(s) of this invention against highly glycolytic cancers and some (non-limiting) imaging methods have been described herein to identify these.

This invention discloses a method of using a compound(s) that preferentially inhibits the ATP-hydrolysing mode of ATP synthase, for example a compound(s) of Formula (I), (II), (III), (IV) or (V), or a pharmaceutically-acceptable salt, solvate, hydrate or prodrug thereof, to treat/ameliorate/prevent/combat a cancer that preferentially uses glycolytic rather than oxidative metabolism, for example a cancer exhibiting the Warburg effect, and discloses methods to identify these cancers. Identification methods specified are to illustrate the invention and not to limit its scope: this invention encompasses all methods to identify glycolytic cancers, in order to identify cancers most amenable to treatment by a compound(s) of this invention.

So, innovatively and usefully, compounds of this disclosure are selected for anti-cancer therapy by metabolic feature of the cancer, which belie how the cancer survives and proliferates, and its weaknesses, weaknesses that compounds of this disclosure attack, rather than the typical, often too arbitrary, often unhelpful, allocation by tissue type, which is the present standard in the art. A diversity of cancers, from different tissues, will be susceptible to compounds of this invention, especially the most dangerous: glycolytic cancers, with high lactate efflux, often have the worst prognosis [18-20, 27]. Experimental data of this disclosure shows that compounds of this invention are effective against many cancers.

Compounds of the present invention treat tumour growth, treat metastasis, treat metastatic cancer, treat non-metastatic cancer, treat tumour implantation, are useful as an adjunct to chemo-/radio-therapy, treat cancers including, but not limited to, Chondrosarcoma, Ewing's sarcoma, Malignant fibrous histiocytoma of bone/osteosarcoma, Osteosarcoma, Rhabdomyo sarcoma, Heart cancer, brain cancer, Astrocytoma, Brainstem glioma, Pilocytic astrocytoma, ependymoma, primitive neuroectodermal tumor, Cerebellar astrocytoma, Cerebral astrocytoma, malignant glioma, Medulloblastoma, Neuroblastoma, Oligodendroglioma, Pineal astrocytoma, Pituitary adenoma, Visual pathway and hypothalamic glioma, Breast cancer, Invasive lobular carcinoma, Tubular carcinoma, Invasive cribriform carcinoma, Medullary carcinoma, Male breast cancer, Phyllodes tumor, Inflammatory Breast Cancer, Adrenocortical carcinoma, Islet cell carcinoma, Multiple endocrine neoplasia syndrome, Parathyroid cancer, Pheochromocytoma, Thyroid cancer, Merkel cell carcinoma, intraocular melanoma, retinoblastoma, Anal cancer, Appendix cancer, cholangiocarcinoma, Carcinoid tumor, Colon cancer, Extrahepatic bile duct cancer, Gallbladder cancer, Gastric (stomach) cancer, Gastrointestinal carcinoid tumor, Gastrointestinal stromal tumor (GIST), Hepatocellular cancer, Pancreatic cancer, Rectal cancer, Bladder cancer, Cervical cancer, Endometrial cancer, Extragonadal germ cell tumor, Ovarian cancer, Ovarian epithelial cancer (surface epithelial-stromal tumor), Ovarian germ cell tumor, Penile cancer, Renal cell carcinoma, Renal pelvis and ureter, transitional cell cancer, Prostate cancer, Testicular cancer, Gestational trophoblastic tumor, Ureter and renal pelvis, transitional cell cancer, Urethral cancer, Uterine sarcoma, Vaginal cancer, Vulvar cancer, Wilms tumor, Esophageal cancer, Head and neck cancer, Nasopharyngeal carcinoma, Oral cancer, Oropharyngeal cancer, Paranasal sinus and nasal cavity cancer, Pharyngeal cancer, Salivary gland cancer, Hypopharyngeal cancer, Acute biphenotypic leukemia, Acute eosinophilic leukemia, Acute lymphoblastic leukemia, Acute myeloid leukemia, Acute myeloid dendritic cell leukemia, AIDS-related lymphoma, Anaplastic large cell lymphoma, Angioimmunoblastic T-cell lymphoma, B-cell prolymphocytic leukemia, Burkitt's lymphoma, Chronic lymphocytic leukemia, Chronic myelogenous leukemia, Cutaneous T-cell lymphoma, Diffuse large B-cell lymphoma, Follicular lymphoma, Hairy cell leukemia, Hepatosplenic T-cell lymphoma, Hodgkin's lymphoma, Hairy cell leukemia, Intravascular large B-cell lymphoma, Large granular lymphocytic leukemia, Lymphoplasmacytic lymphoma, Lymphomatoid granulomatosis, Mantle cell lymphoma, Marginal zone B-cell lymphoma, Mast cell leukemia, Mediastinal large B cell lymphoma, Multiple myeloma/plasma cell neoplasm, Myelodysplastic syndromes, Mucosa-associated lymphoid tissue lymphoma, Mycosis fungoides, Nodal marginal zone B cell lymphoma, Non-Hodgkin lymphoma, Precursor B lymphoblastic leukemia, Primary central nervous system lymphoma, Primary cutaneous follicular lymphoma, Primary cutaneous immunocytoma, Primary effusion lymphoma, Plasmablastic lymphoma, Sézary syndrome, Splenic marginal zone lymphoma, T-cell prolymphocytic leukemia, Basal-cell carcinoma, Melanoma, Skin cancer (non-melanoma), Bronchial adenomas/carcinoids, Small cell lung cancer, Mesothelioma, Non-small cell lung cancer, Pleuropulmonary blastoma, Laryngeal cancer, Thymoma and thymic carcinoma, AIDS-related cancers, Kaposi sarcoma, Epithelioid hemangioendothelioma (EHE), Desmoplastic small round cell tumor, Liposarcoma. The compounds of the present invention treat cancers including, but not limited to, those that originate in the Testis, Cerebral cortex, Skin, Fallopian tube, Parathyroid gland, Small intestine, large intestine, Kidney, Skeletal muscle, Duodenun, Spleen, Epididymis, Bone marrow, Lymph node, Adrenal gland, Esophagus, Thyroid gland, Heart muscle, Tonsil, Lung, Prostate, Rectum, Anus, Adipose tissue, Colon, Stomach, Cervix, Gallbladder, Seminal vesicle, Breast, Ovary, Endometrium, Smooth muscle, Salivary gland, Pancreas, Urinary bladder, blood, brain, gum, head, liver, nasopharynx, neck, tongue, uterus.

Cancer Imaging

An $F_1F_0$ ATP hydrolysis inhibitor compound(s) of this invention, for example a compound(s) of Formula (I), (II), (III), (IV) or (V), has greater binding affinity for ATP synthase operating in reverse than forwards. Thence such a compound(s) disproportionally accumulates in cancer cells because, as disclosed herein, cancers disproportionally utilise ATP synthase in reverse, as compared to normal cells. Thus, when the compound(s) is labelled, for example by $^{11}C$ or some other radionuclide incorporation, it can be used for cancer imaging, for example by positron emission tomography (PET). Example embodiments are one or more of $^{11}C$, $^{18}F$, $^{13}N$, $^{15}O$, $^{124}I$ incorporated into a compound of this invention at a greater than natural abundance, most preferably incorporated at their corresponding position(s) in the compound(s) e.g. $^{11}C$ in place of $^{12}C$, $^{13}N$ in place of $^{14}N$, $^{124}I$ at halogen designated position(s) etc. All radionuclide substitutions of corresponding atoms in Formula (I-V) are contemplated and componentry to the present invention, as is their use for anti-cancer imaging and/or therapy. Alternative embodiments include iodine incorporated at a position(s) designated halogen in one or more compounds of Formula (I-V), and this compound(s) is then used for iodinated x-ray contrast imaging of cancer. Alternatively $^{123}I$ is incorporated at halogen position(s) of one or more compounds of Formula (I-V), and this compound(s) is used to image cancer using single photon emission computed tomography (SPECT). If a cancer shows up (above background tissue) in one or more of these imaging modalities, it is a good signal that this cancer will be responsive to a compound of this invention for anti-cancer therapy.

Given this asymmetric accumulation of compounds of Formula (I-V) into cancer cells, radionuclides incorporated into one or more of these compound(s) can disproportionally damage cancer, and thence be used for radiotherapy. To illustrate, tritium at greater than natural abundance at one or more places on a compound(s) of this invention, wherein this compound(s) is used for anti-cancer therapy. Alternatively, or in addition, $^{125}I$ and/or $^{131}I$ incorporated, optionally at a position(s) designated halogen in Formula (I-V). Optionally, radionuclide imaging is performed prior to radionuclide therapy (radiotherapy) with compounds of this invention.

A boronated compound(s) of this invention, for example a compound(s) of Formula (I), (II), (III), (IV) or (V), substituted at one or more positions with $^{10}B$, for use in neutron capture therapy, optionally for an anti-cancer use, is componentry to the present invention, as is a method wherein $^{157}Gd$ is used in place of $^{10}B$.

Aging

An invention embodiment is a method in which a subject takes or is administered an effective amount of a compound(s) of this invention, for example a compound of Formula (I), (II), (III), (IV) or (V) or another compound that selectively inhibits $F_1F_0$ ATP hydrolysis, or a pharmaceutically-acceptable salt, solvate, hydrate or prodrug thereof, to treat/ameliorate/prevent/combat an accelerated aging disease or progeroid syndrome including, but not limited to, Werner syndrome, Bloom syndrome, Rothmund-Thomson syndrome, Cockayne syndrome, xeroderma pigmentosum, trichothiodystrophy, combined xeroderma pigmentosum-Cockayne syndrome, restrictive dermopathy, Wiedemann-Rautenstrauch syndrome, Hutchinson-Gilford progeria syndrome (progeria) and/or to treat/ameliorate/prevent/combat an aging associated disease or disease/disorder of aging (incidence increases with increased age/senescence) and/or a disease/disorder associated with reactive oxygen species (ROS, e.g. elevated [ROS]) including, but not limited to, degenerative diseases, neurodegenerative diseases, amyotrophic lateral sclerosis (ALS), Parkinson's disease, Alzheimer's disease, Huntington's disease, spinocerebellar ataxias, Friedreich's ataxia, dementia, hereditary spastic paraplegia, Batten disease, polyglutamine diseases, osteoporosis, atherosclerosis, cardiovascular disease, myocardial infarction, cerebrovascular disease, stroke, heart failure, chronic obstructive pulmonary disease (COPD), hypertension, arthritis, cataracts, type 2 diabetes, andropause, sarcopenia, age-related macular degeneration (AMD), hearing loss, movement disability, cancer etc. Not only does an $F_1F_0$ ATP hydrolysis inhibitor compound of this invention treat/ameliorate/combat cancer in a subject, it also prevents cancer in a subject, which is distinct from many other cancer treatments (e.g. radiotherapy) which are a drive to further cancer, and so compounds of this invention are especially preferred for cancer treatment in children, who have enough lifespan left for secondary cancers, as a result of radiotherapy for example [76], to be a very severe concern.

Anti-Aging Skin Cream $F_1F_0$ ATP hydrolysis inhibitor compounds of this invention slow aging but can reduce body temperature. An invention embodiment is to target an $F_1F_0$ ATP hydrolysis inhibitor compound(s) to a part/area of the body where slower aging is desired, optionally for aesthetic/cosmetic or medical/therapeutic desire or need. This body part or area will have slower aging and lesser heat production, but heat transfer from surrounding body areas will maintain the temperature of this body part/area at an acceptable value. So, the temperature issue is mitigated and slower aging endures in that body part/area. An invention embodiment is a method in which a subject takes or is administered an effective amount of a compound(s) of this invention, for example a compound of Formula (I), (II), (III), (IV) or (V) or another compound that selectively inhibits $F_1F_0$ ATP hydrolysis, or a pharmaceutically-acceptable salt, solvate, hydrate or prodrug thereof, to treat/ameliorate/prevent/combat skin aging, optionally administered to the skin, optionally by skin and/or subcutaneous injection, optionally as a skin cream, optionally to the face. In another embodiment, administered to the scalp and/or hair, optionally in a hair treatment, optionally in a shampoo, to treat/ameliorate/prevent/combat hair follicle and hair aging/loss/greying. All means of applying a compound(s) of this invention to the skin, and/or scalp and/or hair are contemplated by, and componentry to, this invention.

Brain Aging

Neurodegenerative diseases have an ageing component to their etiology [77] as their onset is a function of age (oxidative stress [77]). Indeed, all these diseases (prototypical examples include Parkinson's disease, dementia, Alzheimer's disease, amyotrophic lateral sclerosis {ALS}, Huntington's disease, Friedreich's ataxia, hereditary spastic paraplegia) can be thought of as the brain ageing faster and dying before the rest of the body (adult brain mass decreases with age [78]). In our rapidly greying societies these diseases are a demographic time bomb. Indeed, beyond immeasurable personal suffering, they stand to decimate whole economies (healthcare spending becomes unsustainable percentage of GDP, already ~30% in the USA). For example, nearly half of Americans, over 85, have dementia, which in time is an age that an increasing proportion of the population will surpass, it has no cure and can be completely debilitating, which strains families and communities [78]. Thus, any treatment that can slow brain ageing, to make brain function last as long as the rest of the body, will greatly assist in matching "healthspan" to lifespan, which is arguably the Holy Grail in modern medicine.

An invention embodiment is a method in which a subject takes or is administered an effective amount of a compound(s) of this invention, for example a compound of Formula (I), (II), (III), (IV) or (V) or another compound that selectively inhibits $F_1F_0$ ATP hydrolysis, or a pharmaceutically-acceptable salt, solvate, hydrate or prodrug thereof, to treat/ameliorate/prevent/combat brain aging and neurodegenerative disease(s). Optionally wherein the compound(s) is disproportionally delivered to the brain or central nervous system (CNS), or to specific brain/CNS area(s) or cell type(s), by administration route, strategy or targeting. Illustratively, not restrictively, brain targeting had been shown with exogenous dopamine [79-80]. Preferred brain structures/cells/neurons to target are those whose failure drives a neurodegenerative disease e.g. dopamine neurons in the pars compacta (in the substantia nigra). There are few of them, only 7,200 in rat [81], and in humans their number decline by aging at 5-10% per decade [82], which is a predisposing drive to Parkinson's disease (PD). An invention embodiment is a method in which a subject takes or is administered an effective amount of a compound(s) of this invention, for example a compound of Formula (I), (II), (III), (IV) or (V) or another compound that selectively inhibits $F_1F_0$ ATP hydrolysis, or a pharmaceutically-acceptable salt, solvate, hydrate or prodrug thereof, to treat/ameliorate/prevent/combat Parkinson's disease, optionally wherein the compound(s) is disproportionally administered to dopamine neurons in the substantia nigra. If a compound of this invention decreases their heat generation, heat transfer from neighbouring brain and/or body regions will substitute this heat.

Surgery

An embodiment of this invention is a method in which a subject takes or is administered and/or has a plasma blood level of an effective amount of a compound(s) of this invention, for example a compound of Formula (I), (II), (III), (IV), (V) or (VI) or another compound that selectively reduces $F_1F_0$ ATP hydrolysis, or a pharmaceutically-acceptable salt, solvate, hydrate or prodrug thereof, and the subject is administered an analgesic(s) and/or an anti-nausea medication(s) and/or an anxiolytic and/or antidepressant and/or a local and/or a general anaesthetic (examples well known to those of the art), and/or optionally another drug commonly used in surgery, such as an anti-anxiety/sedative drug used before general anaesthesia or after surgery (examples are well known to those of the art), optionally to treat/ameliorate/prevent/combat cancer, optionally wherein the subject undergoes surgery to remove a tumour(s).

Emergency Contraceptives

Adult bodies don't contain embryonic stem (ES) cells. ES cells are in the inner cell mass of the blastocyst, which forms ~5 days post-fertilization, and exist temporarily because they soon differentiate into other cell types, without ES cell characteristics. So, a compound(s) that specifically kills ES cells will have utility as an emergency contraceptive, taken after unprotected sex for example, with a later window of effectiveness than present emergency contraceptives. Furthermore, it will have utility as a contraceptive, which can be administered instead of, or in combination with, another contraceptive(s) such as the combined oral contraceptive pill, wherein this term and the range of compositions it can refer to are well known to those of the art.

Cancer cell metabolism is similar to that of ES cells. Both can proliferate rapidly, forever (without limit, immortal). They share gene expression fingerprints [54]. ES cells also have a hyperpolarised $\Psi_{IM}$ [55], employ aerobic glycolysis some or all of the time [56] and tend to respond to ROS damage by apoptosis rather than repair [57].

$F_1F_0$ ATP hydrolysis inhibitors have anti-cancer activity, as disclosed by this invention, and, also by this invention, anti-ES cell activity. An embodiment of this invention is a compound(s) that inhibits $F_1F_0$ ATP hydrolysis, for example a compound(s) of Formula I-V, administered or self-administered to a subject, for use in preventing/ending their pregnancy/conception, optionally co-administered (optionally in a pharmaceutical composition) with another compound(s) or combination of compounds with this use, many of which are known to those of the art e.g. progestin, antiprogestin, estrogen etc. This use could be after unprotected sex for example. In another embodiment, this use is restricted to the time during which ES cells exist in embryogenesis, which is early.

An embodiment of this invention is an $F_1F_0$ ATP hydrolysis inhibitor(s) in use as an anti-cancer medicine, or some other therapeutic use in a subject, wherein the compound(s) is distributed, sold and/or administered with a verbal and/or written warning, optionally in a paper insert in a packet containing the compound(s), that it should not be administered to a woman in the early days and/or weeks of pregnancy and/or in a woman trying to get pregnant.

Compounds of this Invention are Anti-Inflammatories

An embodiment of this invention is a method of using a therapeutically effective amount of at least one compound of this disclosure, which inhibits $F_1F_0$ ATP hydrolysis, as an immunosuppressant and/or anti-inflammatory therapeutic. This therapeutic opportunity exists because if $\Psi_{IM}$ collapses in a cell, apoptosis ensues [59], and activated macrophages, unlike resting macrophages, singly use and thence completely rely upon ATP synthase in its reverse mode, hydrolysing ATP, to maintain $\Psi_{IM}$ [83]. This is because activated macrophages produce nitric oxide (NO), which switches down/off their OXPHOS (NO increases the Km of Complex IV for $O_2$). Compounds of the present invention inhibit $F_1F_0$ ATP hydrolysis and selectively collapse $\Psi_{IM}$ in activated macrophages, selectively killing them (optionally administered in co-therapy with an uncoupler(s), to erode $\Psi_{IM}$ as the $F_1F_0$ ATP hydrolysis inhibitor(s) blocks the only means activated macrophages can counter this erosion; thence $\Psi_{IM}$ collapses at lower dose of $F_1F_0$ ATP hydrolysis inhibitor). Thus a therapeutically effective amount of at least one compound of this invention, an $F_1F_0$ ATP hydrolysis inhibitor, for example a compound of Formula (I), (II), (III), (IV) or (V) or a pharmaceutically-acceptable salt, solvate, hydrate or prodrug thereof (optionally in co-therapy with an uncoupler(s), optionally administered in the same pharmaceutical composition and/or administered/packaged/sold together, optionally the same compound is both an $F_1F_0$ ATP hydrolysis and uncoupler e.g. BMS-199264), attenuate the activated macrophage component to inflammation, and its pathologies, and treats/ameliorates/prevents/combats any disease or disorder associated with the undesirable activation or activity of macrophages, and/or any other NO producing cells of the innate immune system (e.g. monocyte-derived inflammatory dendritic cells), and/or immune or inflammation diseases/disorders/pathologies including, but not limited to, acute inflammation, chronic inflammation, systemic inflammation, inflammation because of infection or foreign bodies or injury or chemical or toxin or drug or stress or frostbite or burn or ionising radiation, inflammatory diseases/disorders/syndromes, Macrophage Activation Syndrome (MAS), autoinflammatory diseases/disorders/syndromes, age-related chronic inflammatory diseases ("inflammaging"), autoimmune diseases/disorders/syndromes, diseases/disorders of the innate immune system, sore throat, sore throat associated with cold or flu or fever, high-intensity exercise associated inflammation, ulcerative colitis, inflammatory bowel disease (IBD), irritable bowel syndrome (IBS), rheumatoid arthritis, osteoarthritis, psoriatic arthritis, atopic dermatitis, allergic airway inflammation, asthma, inflammation associated depression, exercise-induced acute inflammation, atherosclerosis, allergy, hay fever, anaphylaxis, inflammatory myopathies, drug-induced inflammation, systemic inflammatory response syndrome, sepsis-related multiple organ dysfunction/multiple organ failure, microbial infection, acute brain/lung/hepatic/renal injuries, acne vulgaris, celiac disease, celiac sprue, chronic prostatitis, colitis, diverticulitis, glomerulonephritis, hidradenitis suppurativa, hypersensitivities, interstitial cystitis, Mast Cell Activation Syndrome, mastocytosis, otitis, pelvic inflammatory disease (PID), reperfusion injury, rheumatic fever, rhinitis, sarcoidosis, transplant rejection, parasitosis, eosinophilia, type III hypersensitivity, ischaemia, chronic peptic ulcer, tuberculosis, Crohn's disease, hepatitis, chronic active hepatitis, immune hepatitis, ankylosing spondylitis, diverticulitis, fibromyalgia, systemic lupus erythematous (SLE), Alzheimer's disease, Parkinson's disease, neurodegenerative disease, cardiovascular disease, chronic obstructive pulmonary disease, bronchitis, acute bronchitis, appendicitis, acute appendicitis, bursitis, colitis, cystitis, dermatitis, encephalitis, gingivitis, meningitis, infective meningitis, myelitis, nephritis, neuritis, periodontitis, chronic periodontitis, phlebitis, prostatitis, RSD/CRPS, rhinitis, sinusitis, chronic sinusitis, tendonitis, testiculitis, tonsillitis, urethritis, vasculitis, respiratory bronchiolitis-associated interstitial lung disease and desquamative interstitial pneumonia, interstitial lung disease, Löfgren syndrome, Heerfordt syndrome, monocytosis, liver fibrosis, steatohepatitis, nonalcoholic steatohepatitis, silicosis, histiocytoses, Langerhans' cell histiocytosis, haemophagocytic lymphohistiocytosis, pulmonary langerhans cell histiocytosis, obesity, type II diabetes, gout, pseudogout, organ transplant rejection, epidermal hyperplasia, chronic fatigue syndrome, graft versus host disease (GVHD), lymphadenopathy.

In clinical utility, the anti-inflammatory activity of compounds of this invention juxtaposes well with their aforementioned ability to reduce body temperature.

The anti-inflammatory action by compounds of this invention has an anti-cancer action. Because it reduces the number of Tumour Associated Macrophages (TAMs) [84]. These can constitute a large component of tumour mass and their presence is often associated with poor patient prognosis because they can drive cancer pathology. Indeed, inflammation is now considered one of the hallmarks of cancer [85]. The anti-inflammatory action, and thence anti-cancer action, of these compounds synergises with their direct anti-cancer activities disclosed herein.

Macrophages can be subverted by pathogens, which hide inside them in safety from the immune system. Non-limiting examples of such pathogens are HIV (causes HIV/AIDS; HIV virus can lay latent in macrophages during antiretroviral therapy, wherein HIV virus becomes undetectable in blood, and then repopulate the virus in blood when antiretroviral therapy is interrupted or discontinued; HIV can replicate in macrophages [86-87]), *Mycobacterium tuberculosis* (causes tuberculosis), *Leishmania parasite* (causes Leishmaniasis), Chikungunya virus (causes Chikungunya), *Legionella pneumophila* (causes Legionnaires' disease), adenovirus (causes pink eye), *T. whipplei* (causes Whipple's Disease) and *Brucella* spp. (causes brucellosis). So, by exerting anti-macrophage activity, compounds of this disclosure can treat/ameliorate/prevent/combat such disorders and diseases. Because the compounds of this invention are selective for activated macrophages, an option is to activate macrophages before the compound administration, by administering to the patient an effective amount of a compound, protein, antibody or some other entity, e.g. pathogen, attenuated pathogen or pathogen component that activates macrophages. Some examples (non-limiting) of factors that can activate macrophages are cytokines such as interferon-gamma (IFN-gamma) and/or tumour necrosis factor (TNF), and/or IL-4, and/or IL-13, and/or IL-10, and/or IL-2, and/or IL-12, and/or IL-6, and/or IL-18 and/or chemokines (CCL3, CCL4, CCL5) and/or a bacterial endotoxin such as lipopolysaccharide (LPS), or a commercially available agent for macrophage activation in biological research (e.g. CAS 61512-20-7) or an antibody targeting a receptor on the macrophage cell surface or on the surface of a different cell type, which then activates a macrophage by mechanism. Macrophage activating antibodies are well known to those of the art.

An embodiment of this invention is the use of an effective amount of at least one compound of this invention, which inhibits $F_1F_0$ ATP hydrolysis, to treat/ameliorate/prevent/combat HIV infection, optionally with an effective amount of a compound, protein, antibody, pathogen or pathogen component that activates macrophages (isn't absolutely necessary because HIV activates macrophages [88-89], which drives the chronic inflammation pathology component to HIV infection) optionally in co-therapy with, or after, anti-retroviral therapy (ART) or combination anti-retroviral therapy (cART). Even after prolonged cART, which drives plasma HIV down to undetectable levels, HIV-1 DNA and RNA is detectable in macrophages: they are an HIV reservoir that remains extant, even during cART, and that the virus can spread from during any interruption or termination of cART [87]: thence the vital importance of the methods and compounds herein. Furthermore, these compounds treat/ameliorate/prevent/combat HIV-associated chronic inflammation.

Macrophages mediate HIV virus neuroinvasion (and neuroinvasion by other viruses also e.g. SARS coronavirus) and compounds of this invention oppose this and treat/ameliorate/prevent/combat HIV-associated neurocognitive disorders (HAND) (and neurocognitive and neurodegenerative diseases/disorders caused by other viruses also e.g. SARS coronavirus). The anti-HIV and anti-cancer activity of the compounds of this invention synergise to treat/ameliorate/prevent/combat HIV associated cancers: AIDS-defining cancers (Kaposi sarcoma, aggressive B-cell non-Hodgkin lymphoma, cervical cancer) and non-AIDS defining cancers. This disclosure encompasses a compound(s) of this invention in co-therapy with any Food and Drug Administration (FDA) and/or European Medicines Agency (EMA) approved drug(s) or treatment for HIV or AIDS. Examples include, but aren't limited to, abacavir, didanosine, emtricitabine, lamivudine, stavudine, tenofovir, disoproxil fumarate (tenofovir DF, TDF), zidovudine (azidothymidine, AZT, ZDV), atazanavir, darunavir, fosamprenavir, indinavir, nelfinavir, ritonavir, saquinavir, tipranavir, enfuvirtide, maraviroc, dolutegravir, elvitegravir, raltegravir, cobicistat.

Non-limiting examples of autoinflammatory diseases/disorders/syndromes that the compounds of this invention treat/ameliorate/prevent/combat include, but aren't limited to, recurrent fever syndromes, which can be hereditary or acquired, characterized by recurrent fever associated with rash, serositis, lymphadenopathy and musculoskeletal involvement. Examples include familial mediterranean fever (FMF), TNF receptor-associated periodic syndrome (TRAPS), Hyperimmunoglobulinemia D with recurrent fever syndrome (HIDS), cryopyrin associated periodic syndrome (CAPS), Blau syndrome, Majeed syndrome, deficiency of interleukin-1 receptor antagonist (DIRA), mevalonate kinase deficiency, pyogenic-arthritis-pyoderma gangrenosum and acne syndrome (PAPA), periodic fever aphthous stomatitis pharyngitis adenitis (PFAPA) syndrome, Behcet's disease, Still's disease, Crohn's disease, Schnitzler's syndrome, Sweet's syndrome, NLRP12-associated autoinflammatory disorders, deficiency of interleukin-1 receptor antagonist (DIRA), pyoderma gangrenosum, cystic acne, aseptic arthritis, periodic Fever Associated with mevalonate kinase deficiency (hyperimmunoglobulin D Syndrome), Pyogenic Arthritis Pyoderma Gangrenosum Acne (PAPA) syndrome, Periodic Fever Aphthous Stomatitis, Pharyngitis and Adenopathy (PFAPA) syndrome, Adult-Onset Still's Disease (AOSD), Systemic Juvenile Idiopathic Arthritis (sJIA), Chronic Recurrent Multifocal Osteomyelitis (CRMO), Synovitis Acne Pustulosis Hyperostosis Osteitis (SAPHO) syndrome, Cryopyrin associated Periodic Syndrome (CAPS), Familial cold auto inflammatory syndrome (FCAS), Muckle-Wells syndrome (MWS), Familial cold urticarial, Neonatal onset multisystemic inflammatory disorder (NOMID), hereditary Periodic Fever Syndromes, Periodic Fever Syndromes, systemic autoinflammatory diseases.

Non-limiting examples of autoimmune diseases/disorders/syndromes that the compounds of this invention treat/ameliorate/prevent/combat include, but aren't limited to, Addison's disease, Agammaglobulinemia, Alopecia areata, Amyloidosis, Ankylosing spondylitis, Anti-GBM/Anti-TBM nephritis, Antiphospholipid syndrome, autoimmune angioedema, autoimmune dysautonomia, autoimmune encephalomyelitis, autoimmune hepatitis, autoimmune inner ear disease (AIED), autoimmune myocarditis, autoimmune pancreatitis, autoimmune retinopathy, autoimmune urticaria, axonal & neuronal neuropathy (AMAN), Baló disease, Behcet's disease, benign mucosal pemphigoid, Bullous pemphigoid, Castleman disease (CD), Celiac disease, Chagas disease, chronic inflammatory demyelinating polyneuropathy (CIDP), chronic recurrent multifocal osteomyelitis (CRMO), Churg-Strauss, Cicatricial pemphigoid, Cogan's syndrome, cold agglutinin disease, congenital heart block, coxsackie myocarditis, CREST syndrome, Berger's disease, dermatitis herpetiformis, dermatomyositis, Devic's disease (neuromyelitis optica), discoid lupus, Dressler's syndrome, endometriosis, eosinophilic esophagitis (EoE), eosinophilic fasciitis, erythema nodosum, essential mixed cryoglobulinemia, Evans syndrome, fibromyalgia, fibrosing alveolitis, giant cell arteritis (temporal arteritis), giant cell myocarditis, glomerulonephritis, Goodpasture's syndrome, granulomatosis with polyangiitis, Graves' disease, Guillain-Barre syndrome, Hashimoto's thyroiditis, hemolytic anemia, immune hemolytic anemia, Henoch-Schonlein purpura (HSP), Herpes gestationis or pemphigoid gestationis (PG), hypogammalglobulinemia, IgA Nephropathy, IgG4-related sclerosing disease, Immune thrombocytopenic purpura (ITP), Inclusion body myositis (IBM), Interstitial cystitis (IC), juvenile arthritis, juvenile diabetes (Type 1 diabetes), juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multiple sclerosis, Myasthenia gravis, Myositis, Narcolepsy, Neuromyelitis optica, Neutropenia, Ocular cicatricial pemphigoid, Optic neuritis, Palindromic rheumatism (PR) PANDAS, Paraneoplastic cerebellar degeneration (PCD), Paroxysmal nocturnal hemoglobinuria (PNH), Parry Romberg syndrome, Pars planitis (peripheral uveitis), Parsonnage-Turner syndrome, Pemphigus, peripheral neuropathy, perivenous encephalomyelitis, Pernicious anemia (PA), POEMS syndrome, Polyarteritis nodosa, Polyglandular syndromes type I, II, III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Type 1 diabetes, Ulcerative colitis (UC), Undifferentiated connective tissue disease (UCTD), Uveitis, Vasculitis, Vitiligo, Wegener's granulomatosis (or Granulomatosis with Polyangiitis (GPA)), idiopathic thrombocytopenia purpura, splenomegaly.

Slow Release Formulations

An invention embodiment is to administer to a subject a therapeutic amount of at least one compound of this invention, for example a compound of Formula (I), (II), (III), (IV) or (V), in a formulation/dosage selected from modified release, extended release, long acting release, sustained release, prolonged release, controlled release, slow release or similar, as clear to someone of the art, for use in a method of treatment of the human or animal body by therapy. Such a formulation exposes the subject body to the compound(s) over a longer period of time than if the compound was applied alone. This is useful because it delivers good area under the curve for the compound, which for example exerts anti-cancer activity in the subject, without an abrupt large body temperature drop. Any body temperature drop is less in amplitude, more in duration, which is safer. Methods to make such formulations for a compound are well known to those of the art. To illustrate with some non-limiting examples: compound is administered in an excipient/tablet/pill which takes time to dissolve/degrade/disintegrate because it is, for example, poorly soluble. Furthermore, enteric coating, acrylics (e.g. chitin), liposomes, drug-polymer conjugate(s), microencapsulation (coating an active pharmaceutical ingredient around an inert core and layering it with insoluble substances to form a microsphere), dissolution systems (rate release is dependent on dissolution of an excipient; 2 categories: reservoir, matrix), diffusion systems (rate release is dependent on rate that drug dissolves through a barrier, usually a type of polymer; 2 categories: reservoir, matrix), osmotic systems, ion exchange resins, matrix systems (sub-categories: hydrophobic matrices, lipid matrices, hydrophilic matrices, biodegradable matrices, mineral matrices), stimuli induced release (e.g. temperature, ultrasonic, electronic etc.) and other encapsulation technologies known to those of the art.

An invention embodiment is using a dosage regime of $F_1F_0$ ATP hydrolysis inhibitor that doesn't cause a significant temperature drop in a human. Optionally spreading the daily therapeutic dose over multiple pills per day so that any body temperature drop is lowered in amplitude, lengthened in duration, which is safer.

Albumin as Slow Release Assist

Compound 31 of this invention is a 1,4-benzodiazepine, which is a compound class known to bind albumin in blood extensively. For example, 99% of diazepam is protein bound in the blood, wherein the overwhelming majority of this protein is albumin. Albumin can bind many things non-specifically but it has high affinity binding sites with higher affinity binding to certain substances [90], for example, 1,4-benzodiazepines. Indeed, albumin has two specific high affinity binding sites, one of which is called the "benzodiazepine site", also called Site II, the diazepam site or the indole-BDZ site, which can bind a range of benzodiazepines, and so possibly Compound 31 also. Compound 31 binding albumin in blood will buffer, slow and prolong Compound 31 exposure to the tissues, which will buffer, reduce the amplitude, slow and prolong Compound 31 effect on body temperature. In the anti-cancer data of this disclosure, Compound 31 (FIG. 6) outperformed the FDA approved, widely used, chemotherapeutic carboplatin (FIG. 1). However, it underperformed by comparison to its $EC_{50}$ $F_1F_0$ ATP hydrolysis (FIG. 9) and its sequestration by binding albumin in the 5% fetal bovine serum (FBS) added to RPMI 1640 medium used in NCI-60 testing [35] might be contributory to this underperformance (in addition to Compound 31 interaction with CYP2C9, as cited in FIG. 9 and legend). Reducing FBS amount to 2% and assaying if Compound 31 exerts greater anti-cancer activity vs. no drug control (also with FBS reduced to 2%) would reveal this. N.B. carboplatin does not bind albumin with any great affinity, indeed, its protein (i.e. mainly albumin) binding in blood is very low.

Temperature Controlled Release

An invention embodiment is a temperature-sensitive pharmaceutical composition/vehicle that only releases a compound of this invention, for example a compound of Formula (I), (II), (III), (IV), (V) or other $F_1F_0$ ATP hydrolysis inhibitor(s), when the body is at normal body temperature or higher. The latter is reached if the subject has a fever for example. Many cancers cause fever. Such a temperature-sensitive delivery composition/vehicle, releasing drug(s) at normal body temperature (37° C.) for example, can effect a safety feedback loop because as $F_1F_0$ ATP hydrolysis inhibitor is released, body temperature falls, thence less drug is released, body temperature can thence recover, further compound is released, and this loop iterates, implementing extended release and minimising the perturbation to body temperature from optimal. For non-limiting example, a $F_1F_0$ ATP hydrolysis inhibitor(s) is loaded into a structure incorporating biocompatible thermo-sensitive polymer which shrinks at a temperature exceeding its phase/volume transition temperature, releasing the compound. This volumetric change is reversible. Should the temperature subsequently fall below the phase/volume transition temperature the structure expands and compound release doesn't occur [91]. In some embodiments the phase/volume transition temperature is tuned to be at normal body temperature, in other embodiments, at a pathologically elevated body temperature(s). Biocompatible thermosensitive polymers can be used to prepare temperature-responsive hydrogels/nanogels and thence nanoparticles, optionally with polysaccharides to modulate the drug encapsulation and release efficiency, which have a phase transition temperature, above which they release the "cargo" compound(s). Transition temperature can be readily tuned by the copolymerization conditions and by varying the content of repeating units in the copolymer. Non-limiting options for making temperature sensitive vehicles for compounds of this invention include thermosensitive hydrogels/nanogels, temperature sensitive liposomes [92-94] (these have been used in clinical trials e.g. ThermoDox), thermosensitive micelles, polymeric micelles, core shell structures, core-shell microgel particles, thermoresponsive composite films, smart three dimensionally ordered porous materials, thermosensitive microcontainers, nanoscale drug delivery vehicles.

Also contemplated and componentry to this invention is a compound(s) of this invention administered/released by a pharmaceutical composition/vehicle triggered by temperature in parallel with one or more other stimuli e.g. pH, and/or a pharmaceutical composition/vehicle that disproportionally delivers a compound(s) of this invention to cancer as compared to normal tissue(s) in a subject (numerous strategies available to those of the art e.g. refer [95]). For example, by the pharmaceutical composition/vehicle release being triggered by one or more cancer associated stimuli e.g. acidic pH, or one or more externally applied stimuli to the cancer/tumour e.g. heat.

DESCRIPTION OF THE DRAWINGS

For purposes of clarity, not every component is labelled in every figure, nor is every component of each embodiment of the invention shown where illustration is not necessary to allow those of ordinary skill in the art to understand the invention.

FIGS. 2, 3, 4, 5, 6, 7, 8, 9, 10, 11, 12: Experimental evidence: molecules that specifically inhibit the reverse mode of ATP synthase: specifically exert anti-cancer activity: representative, non-limiting examples.

FIGS. 1, 2, 3, 4, 5, 6, 7, 8 show results from the NCI-60 one-dose in vitro assay [34-35] at the Developmental Therapeutics Program (DTP), at the National Cancer Institute (NCI, Bethesda, MD, USA). Its protocol is well known to those of the art, and it tests the effect, if any, of a test compound on the growth/survivability of a cancer cell line as compared to the no compound control. When this protocol was first developed, a compound was tested against 60 cancer cell lines, hence the name NCI-60, but more recently this has been reduced to 59 cell lines, and there is some variation over time in the cancer cell lines making up this 59 (and sometimes it drifts from being 59 also). However, a constant is that there is always representative cell lines from leukemia, melanoma and cancers of the lung, colon, brain, ovary, breast, prostate and kidney. In a one-dose NCI compound test report, NCI report a number for each cell line, which they call "Growth Percent", which is its growth relative to the no-compound control, and relative to the time zero number of cells. This reported parameter allows detection of both growth inhibition (values between 0 and 100) and lethality (values less than 0). For example, an NCI "Growth Percent" value of 100 means no growth inhibition. Value of 40 means 60% growth inhibition. Value of 0 means no net growth over the course of the experiment. Value of −40 means 60% lethality. Value of −100 means all cells are dead. I don't present NCI one-dose data in this original format. Instead, if the NCI "Growth Percent" value for a cell is positive, it is manipulated: [100 minus this original NCI-60 "Growth Percent" data point], to yield the percentage "Growth Inhibition". If the original NCI "Growth Percent" value for a cell is negative, it is made positive to be the percentage of original cancer cells (at time zero) killed: "Percentage Killed" {and in these cases, of course, all growth has been inhibited, so percentage "Growth Inhibition" is then specified to be 100% for this cancer cell line}. In my one-dose figures, "Growth Inhibition" (0-100%) is presented on the x-axis and, if applicable, "Percentage Killed" (0-100%) further along on the x-axis. The latter is applicable when there is not just cancer growth inhibition but a reduction in the number of cancer cells from the start time i.e. when the compound is not merely slowing cancer growth, but is actively reducing the number of cancer cells from the starting number. In cases where there is only growth inhibition, only "Growth inhibition" is presented on the x-axis. In all cases, the greater the percentage number on the x-axis, for a given cancer cell line named on the y-axis, the greater the anti-cancer activity of this compound against this cancer cell line.

NCI-60 tests are performed at a controlled temperature of 37° C. [35].

To perform the anti-cancer testing reported: BMS-199264 hydrochloride was purchased from Sigma-Aldrich. BTB06584 was purchased from AdooQ Bioscience, Irvine, CA, USA. Compounds 19a (separated into 6a and 6b stereoisomers) and 31 were synthesized by reaction schemes disclosed herein. Almitrine dimesylate was purchased from Ak Scientific, Palo Alto, CA, USA. Tested compounds are available from NCI by NSC number which are: BTB06584 (NSC: 794220), BMS-199264 HCl (NSC: 795767), almitrine dimesylate (NSC: 800450), 6b (NSC: 801828), 6a (NSC: 801827), 31 (NSC: 802605).

FIG. 1: Anti-cancer activity of carboplatin in National Cancer Institute (NCI) one-dose (10 µM) assay. Data retrieved from NCI Developmental Therapeutics Program (DTP) screening database [32], database entry NSC: 241240. To retrieve this data, input NSC at dtp.cancer.gov/dtpstandard/dwindex/index.jsp. DTP database contains anti-cancer performance (or more typically lack thereof) for >800,000 compounds in the exact same experimental protocol. New entries become publically searchable after 3 years delay (to give time for compound submitters to secure IP protection, should they wish, before public disclosure by this database). This figure presents the anti-cancer performance of an FDA licensed cancer drug, carboplatin, one of the most used cancer drugs today, which is on the World Health Organisation (WHO) list of most Essential medicines, in exactly the same experimental protocol used for the novel cancer drugs of this disclosure, presented in later figures. This figure inclusion enables a direct like-for-like comparison between the new cancer drugs, disclosed by this disclosure, with a cancer drug in present, widespread clinical use.

FIG. 2: No anti-cancer activity of BTB06584 at 10 µM (NCI one-dose assay).

FIG. 3: Anti-cancer activity of BTB06584 at 100 µM (NCI one-dose assay).

FIG. 4: Anti-cancer activity of BMS-199264 hydrochloride at 10 µM (NCI one-dose assay).

FIG. 5: Anti-cancer activity of BMS-199264 hydrochloride at 100 µM (NCI one-dose assay).

Figure 6:
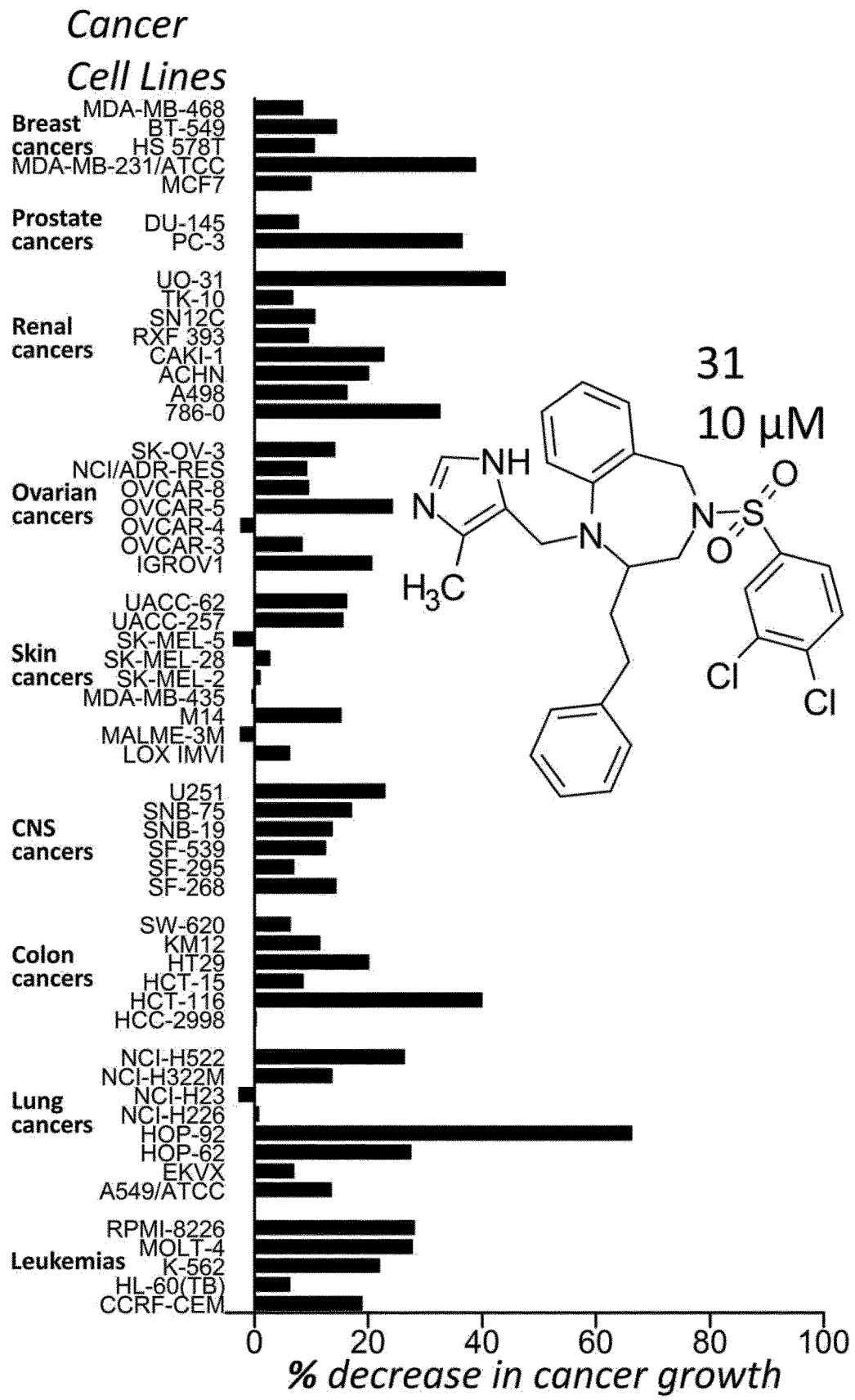
FIG. 6 shows anti-cancer activity of compound 31 in the NCI one-dose assay (10 µM).

FIG. 6: Anti-cancer activity of compound 31 at 10 µM (NCI one-dose assay).

Figure 7:
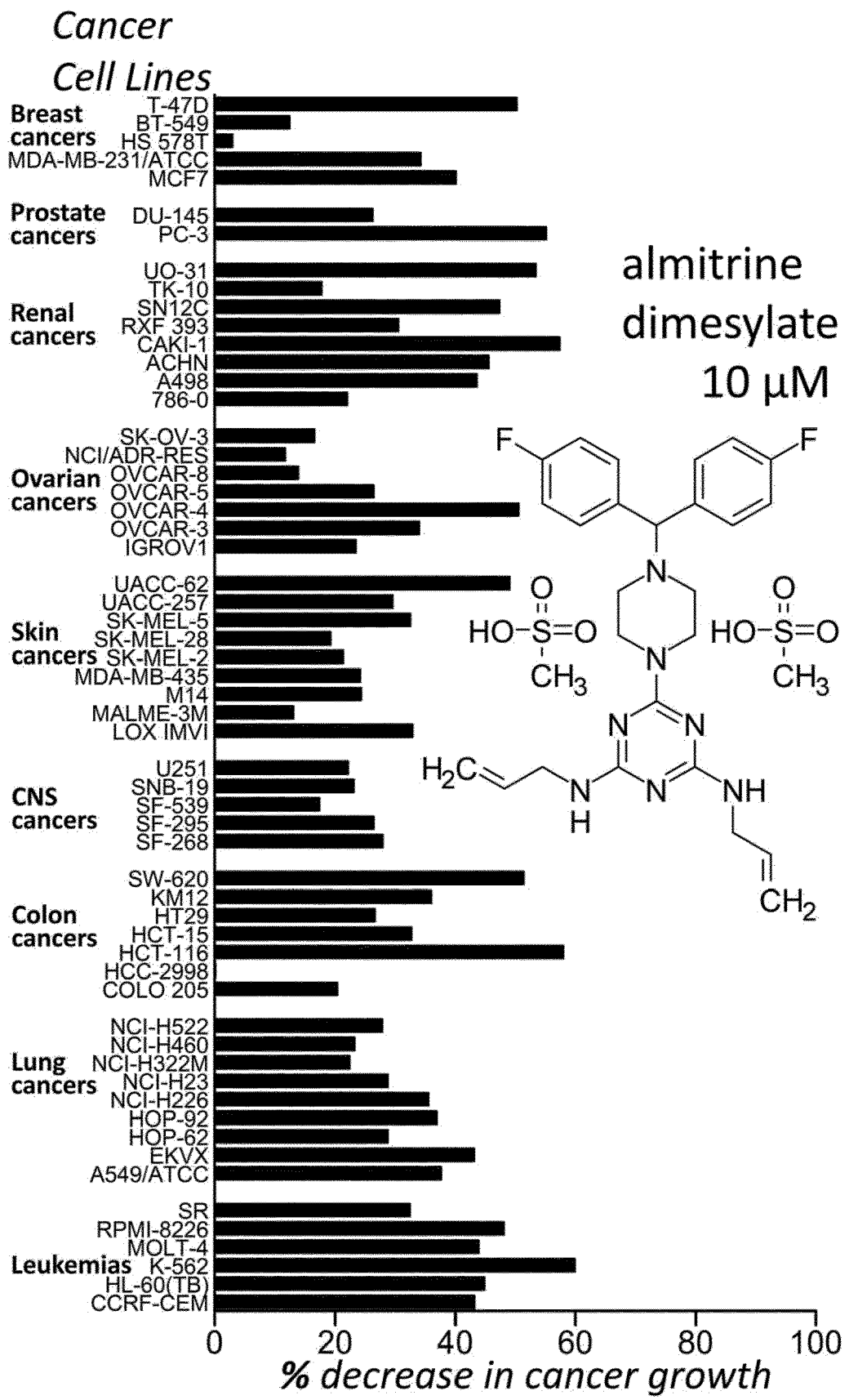
FIG. 7 shows anti-cancer activity of almitrine dimesylate in the NCI one-dose assay (10 µM).
Figure 8A:
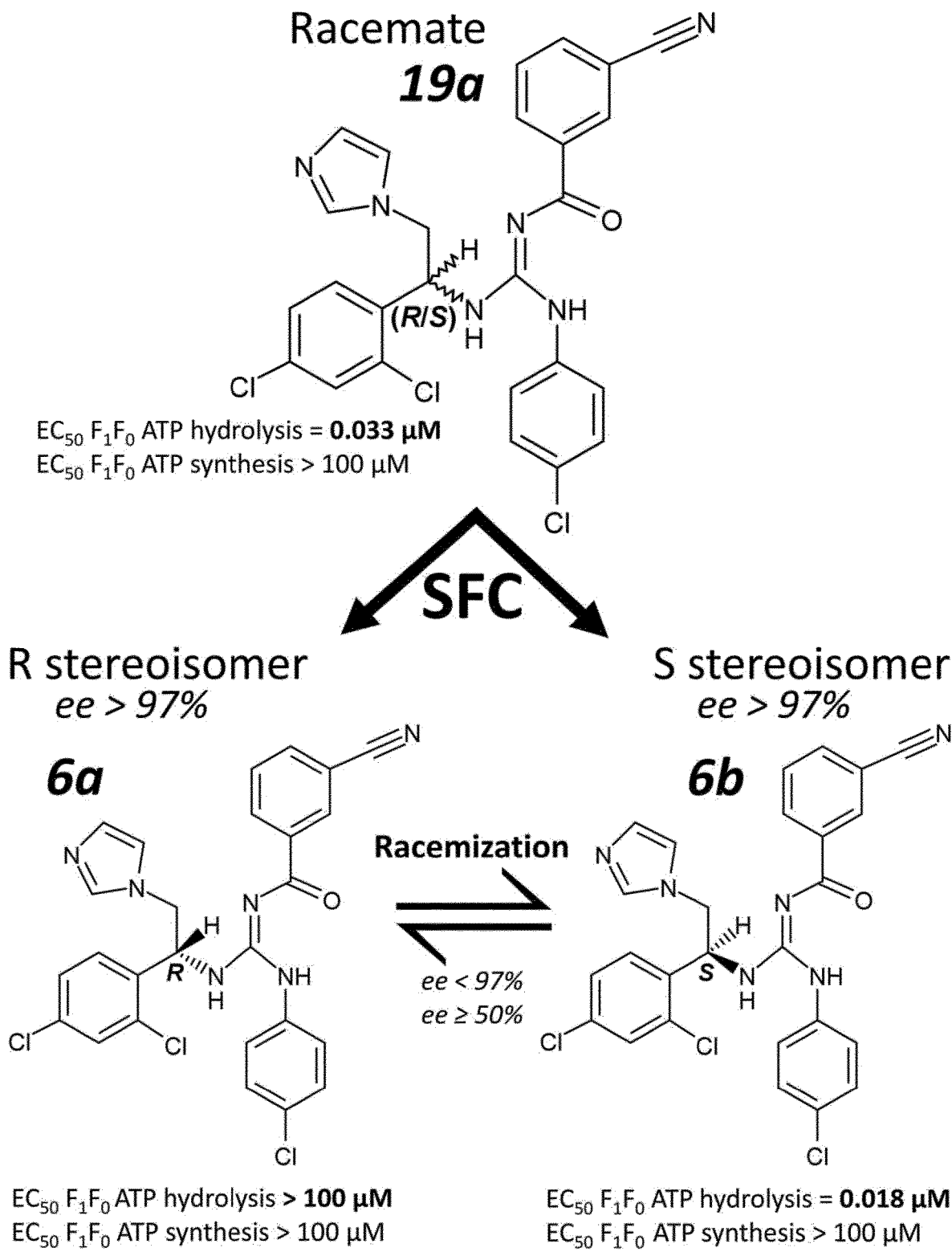
FIG. 8A shows structure and interrelation of compounds 19a, 6a and 6b.
Figure 8B:
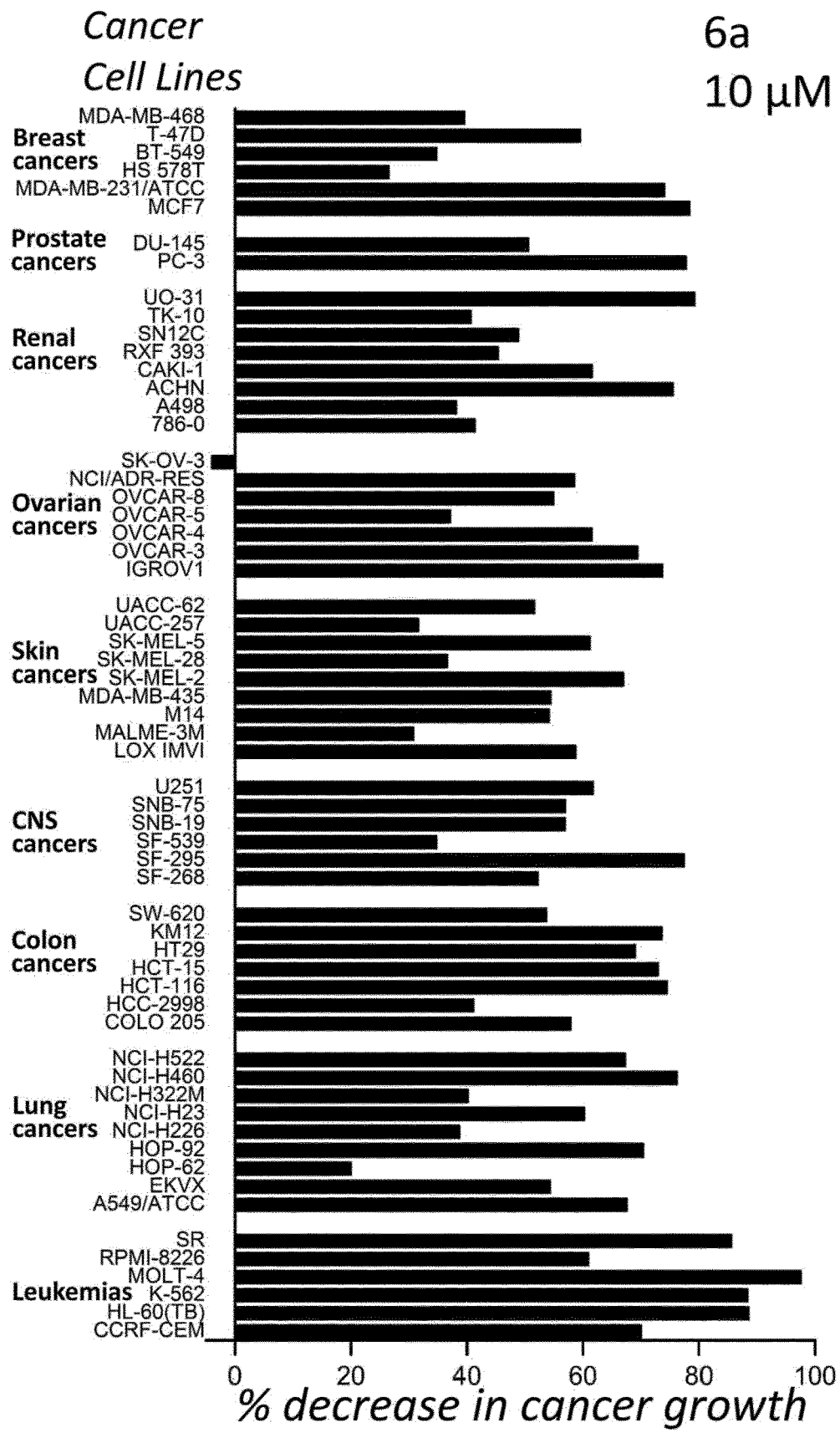
FIG. 8B shows anti-cancer activity of compound 6a in the NCI one-dose assay (10 µM).
Figure 8C:
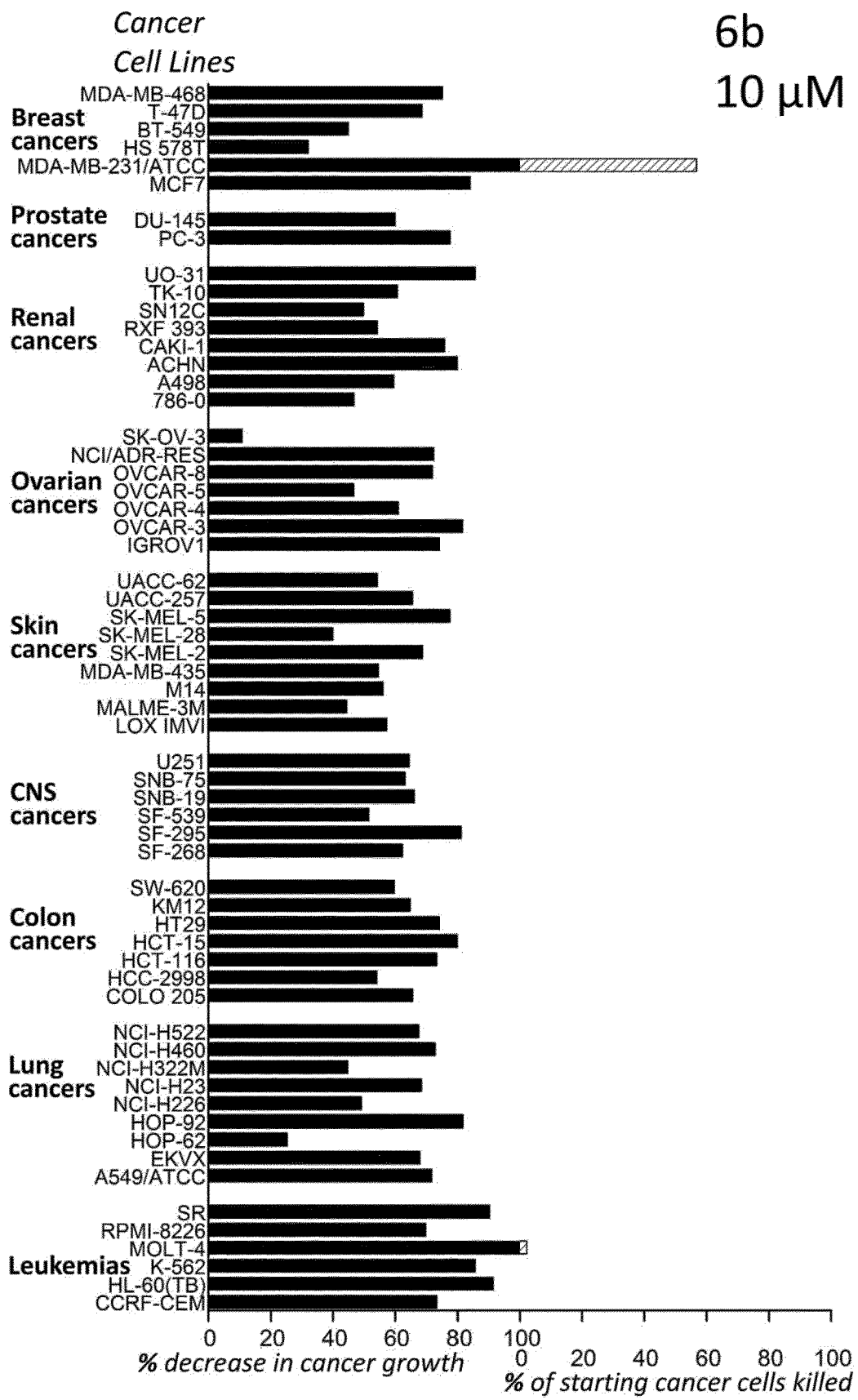
FIG. 8C shows anti-cancer activity of compound 6b in the NCI one-dose assay (10 µM).
Figure 8D:
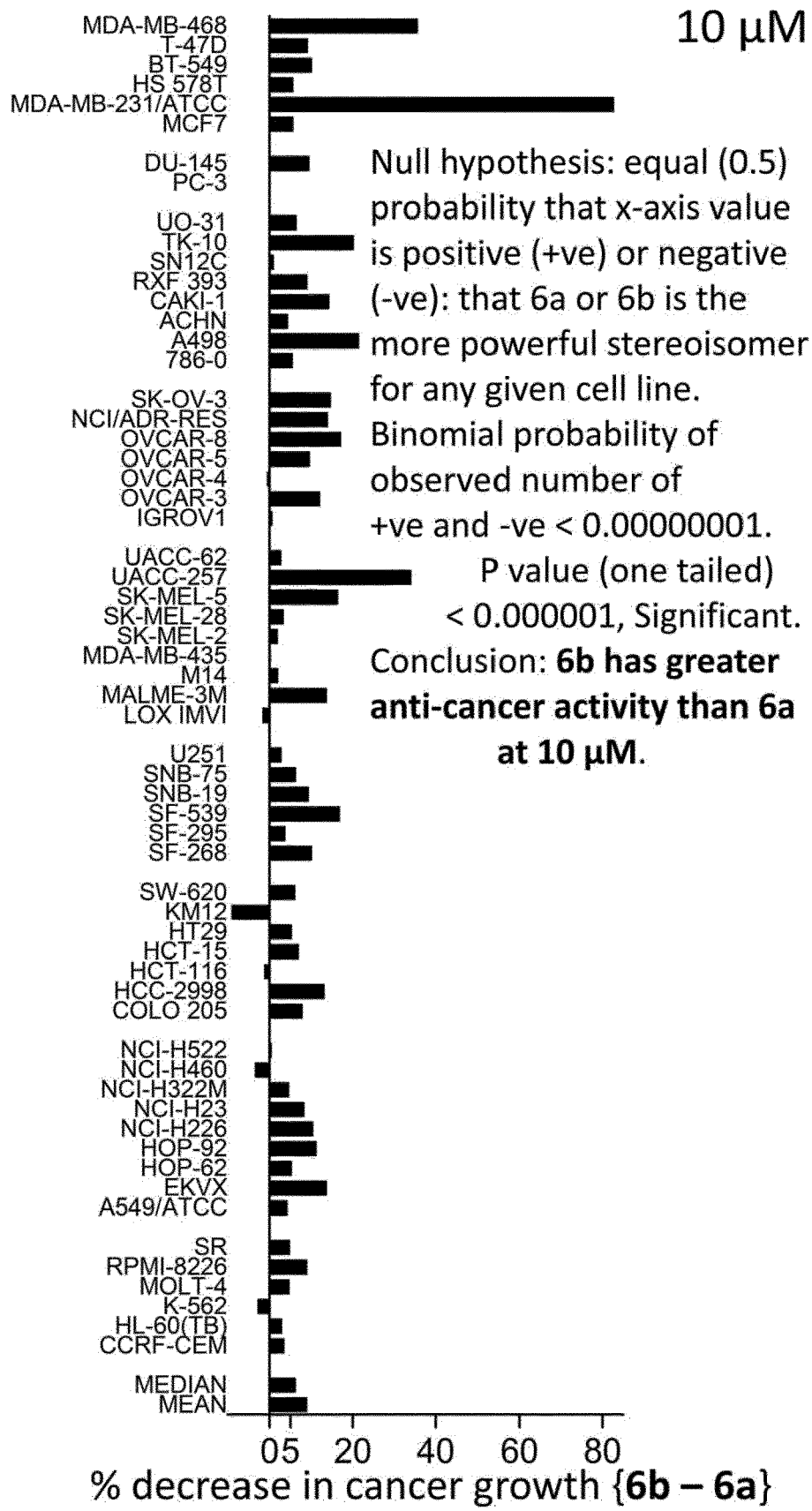
FIG. 8D shows differential in anti-cancer activity between 6a and 6b compounds in the NCI one-dose assay at 10 µM.
Figure 8E:
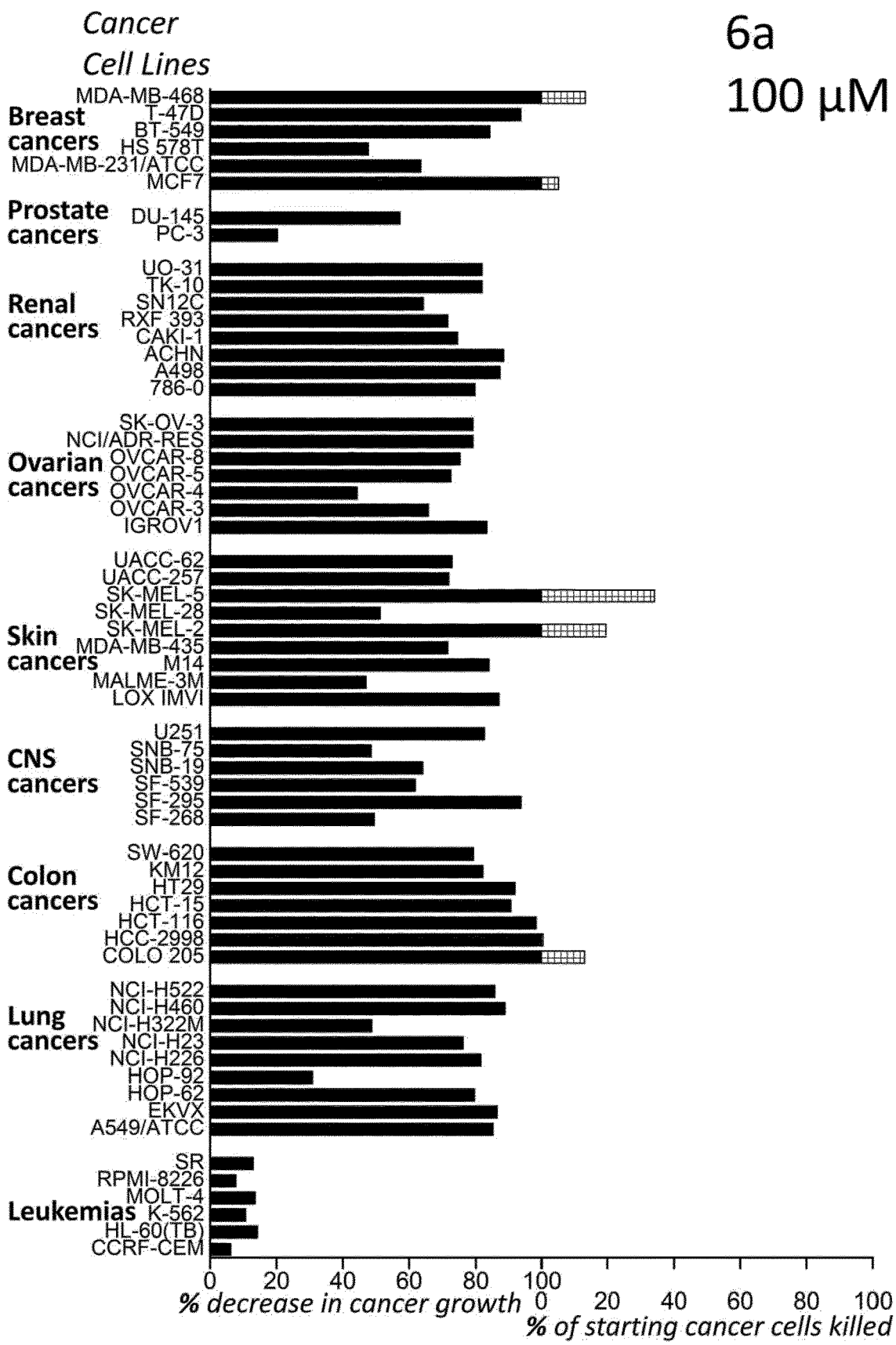
FIG. 8E shows anti-cancer activity of compound 6a in the NCI one-dose assay (100 µM).
Figure 8F:
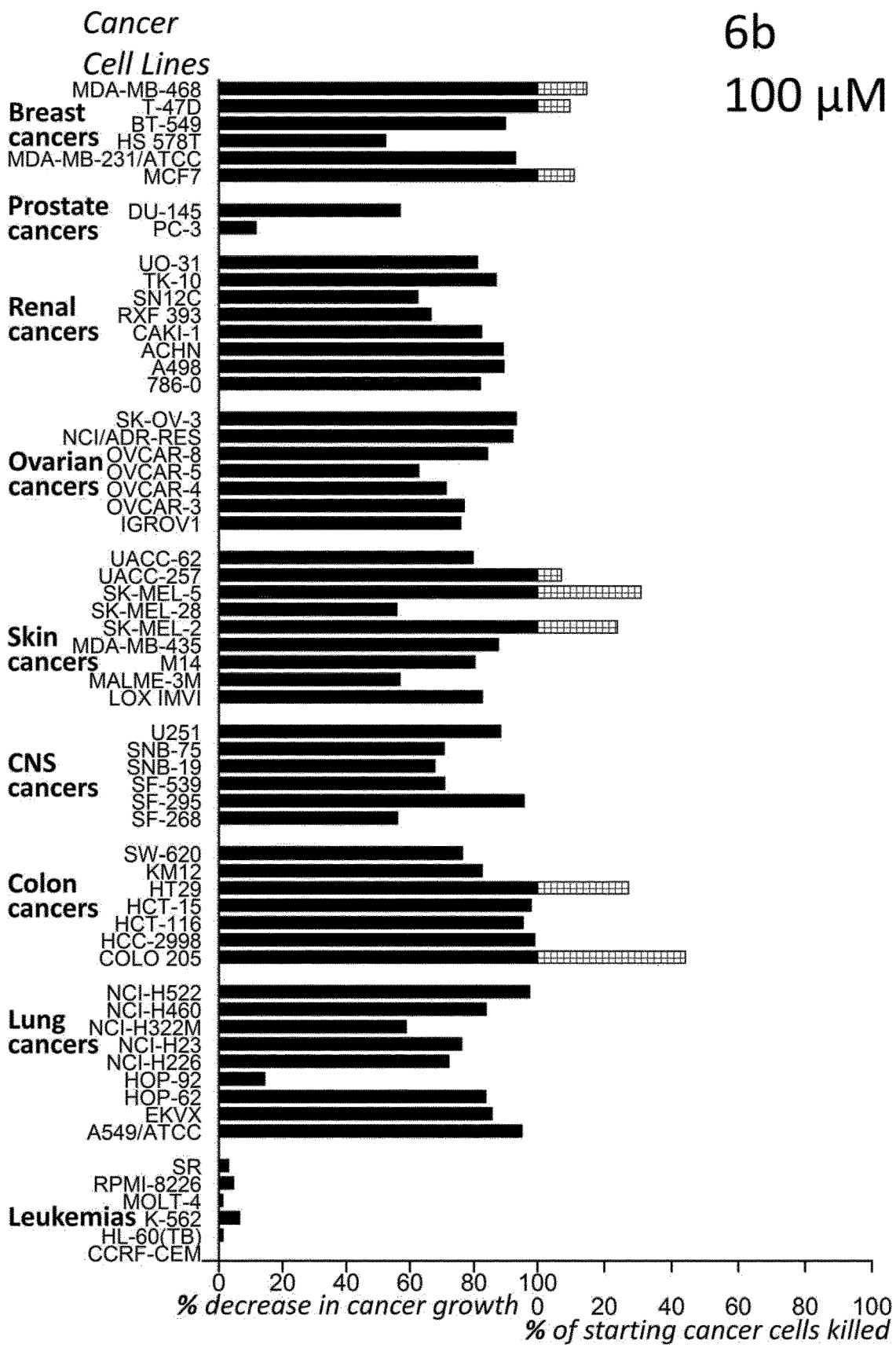
FIG. 8F shows anti-cancer activity of compound 6b in the NCI one-dose assay (100 µM).
Figure 10A:
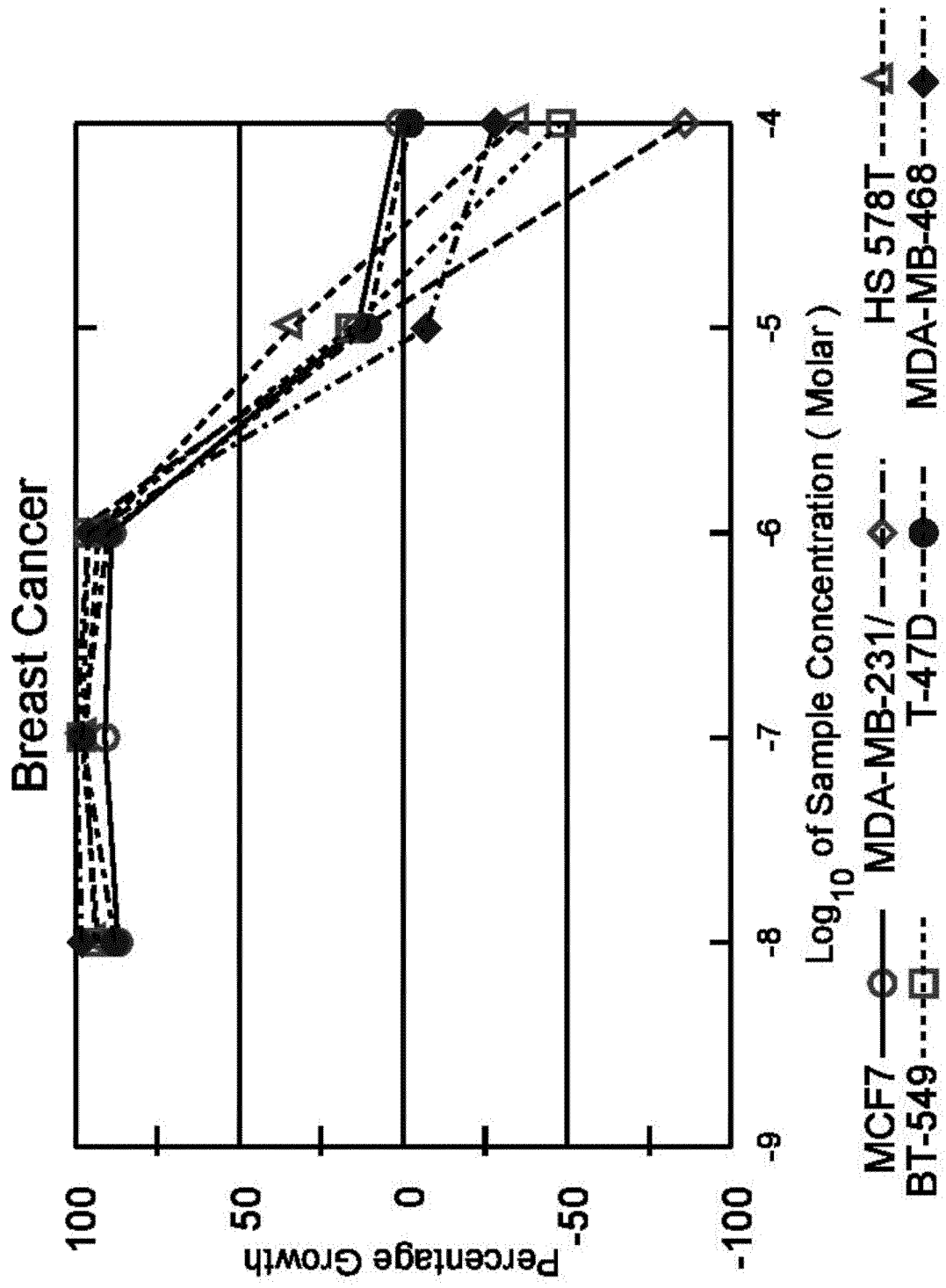
FIG. 10A to FIG. 10I show anti-cancer activity of BMS-199264 in the NCI five-dose assay, showing activity against cancer cell lines of the breast, prostate, kidney, ovary, skin, Central Nervous System (CNS), colon, lung, blood, respectively.
Figure 10B:
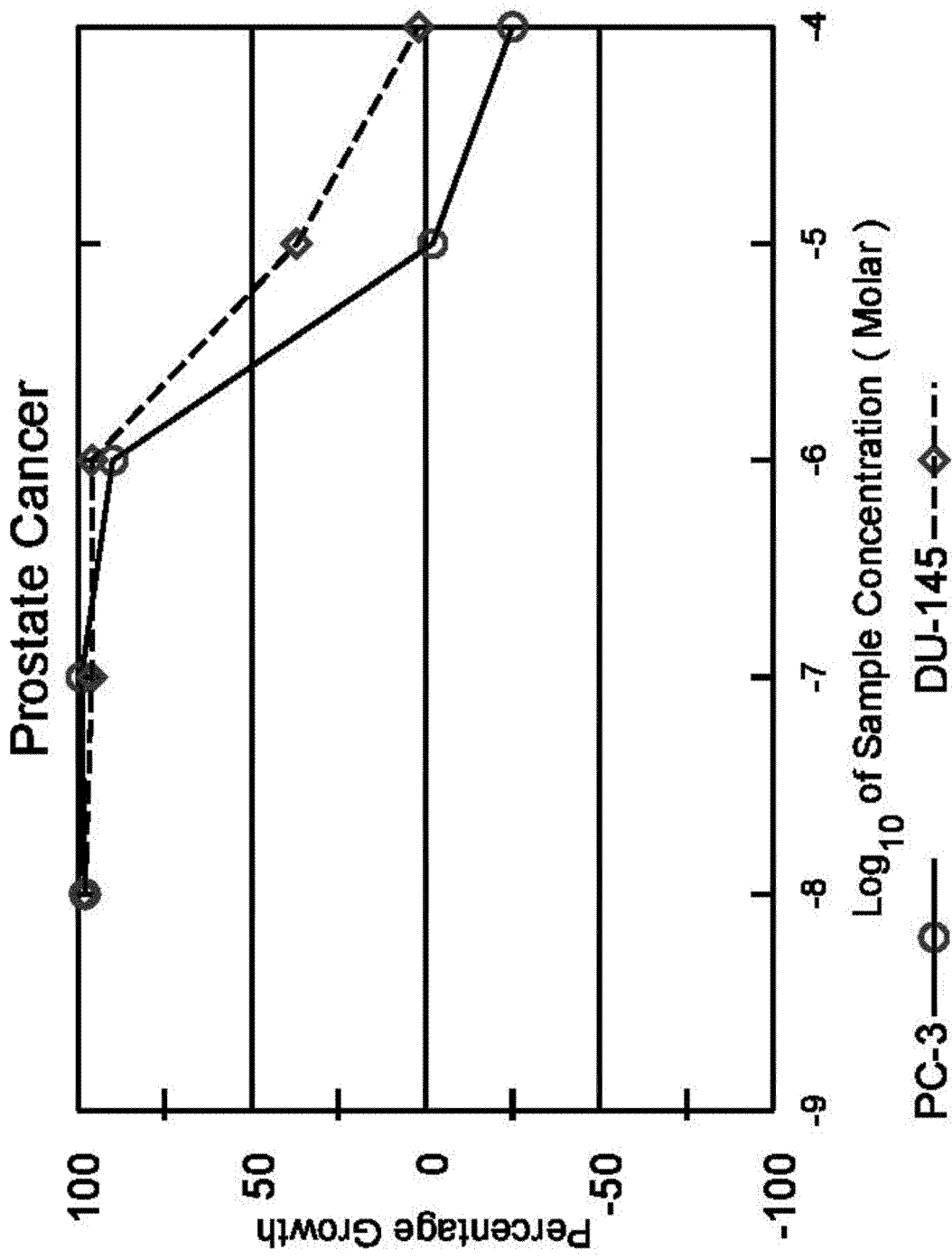
Figure 10C:
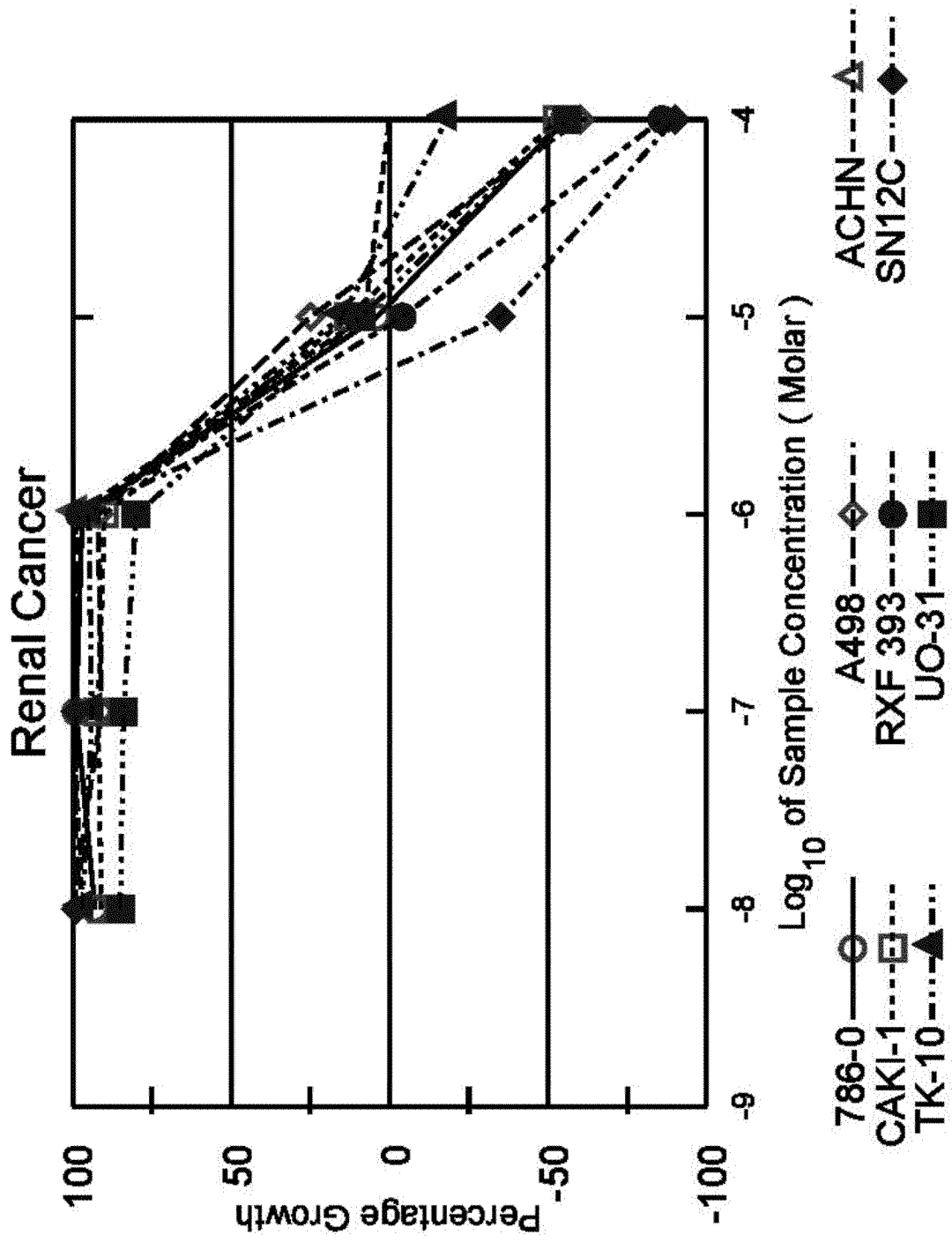
Figure 10D:
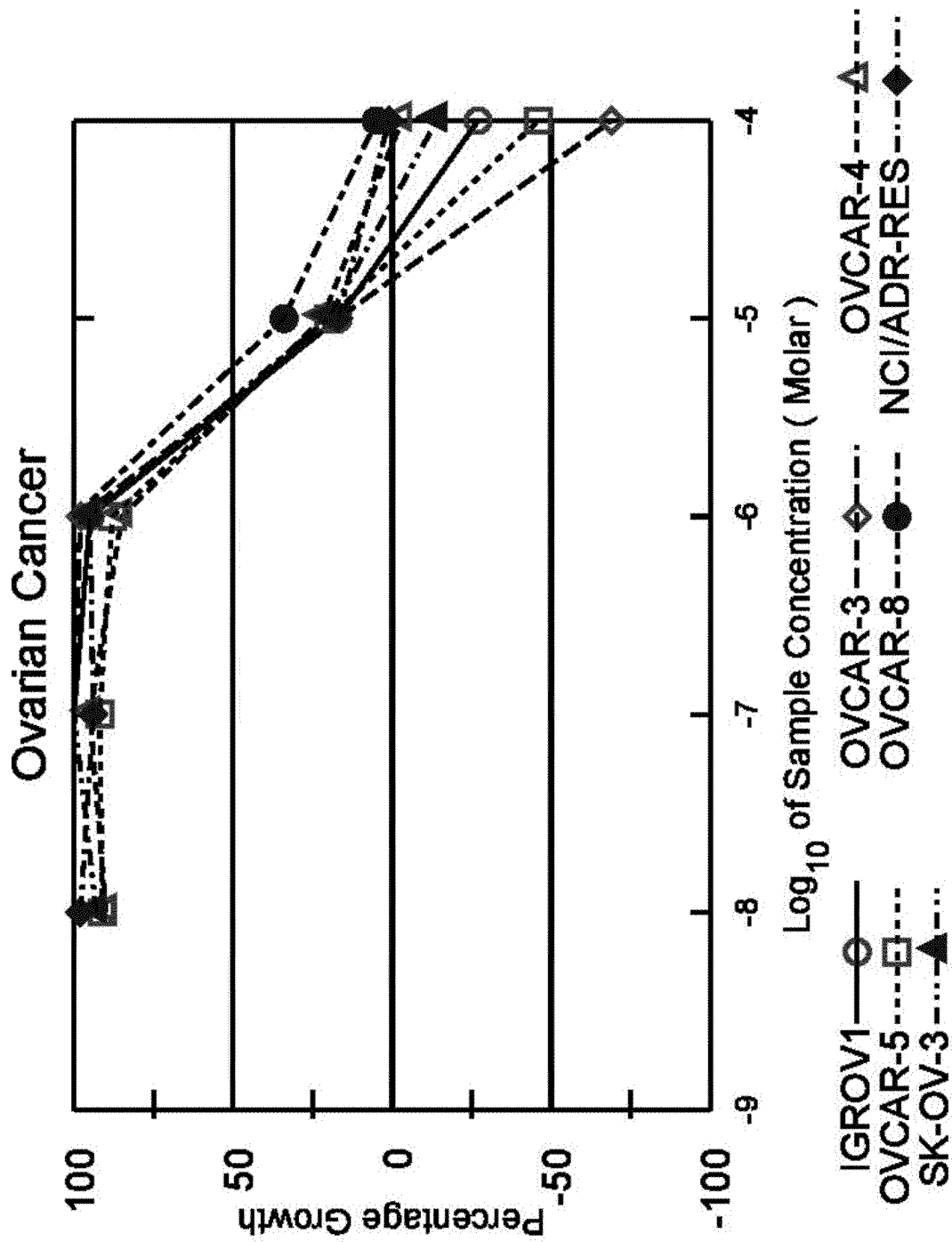
Figure 10E:
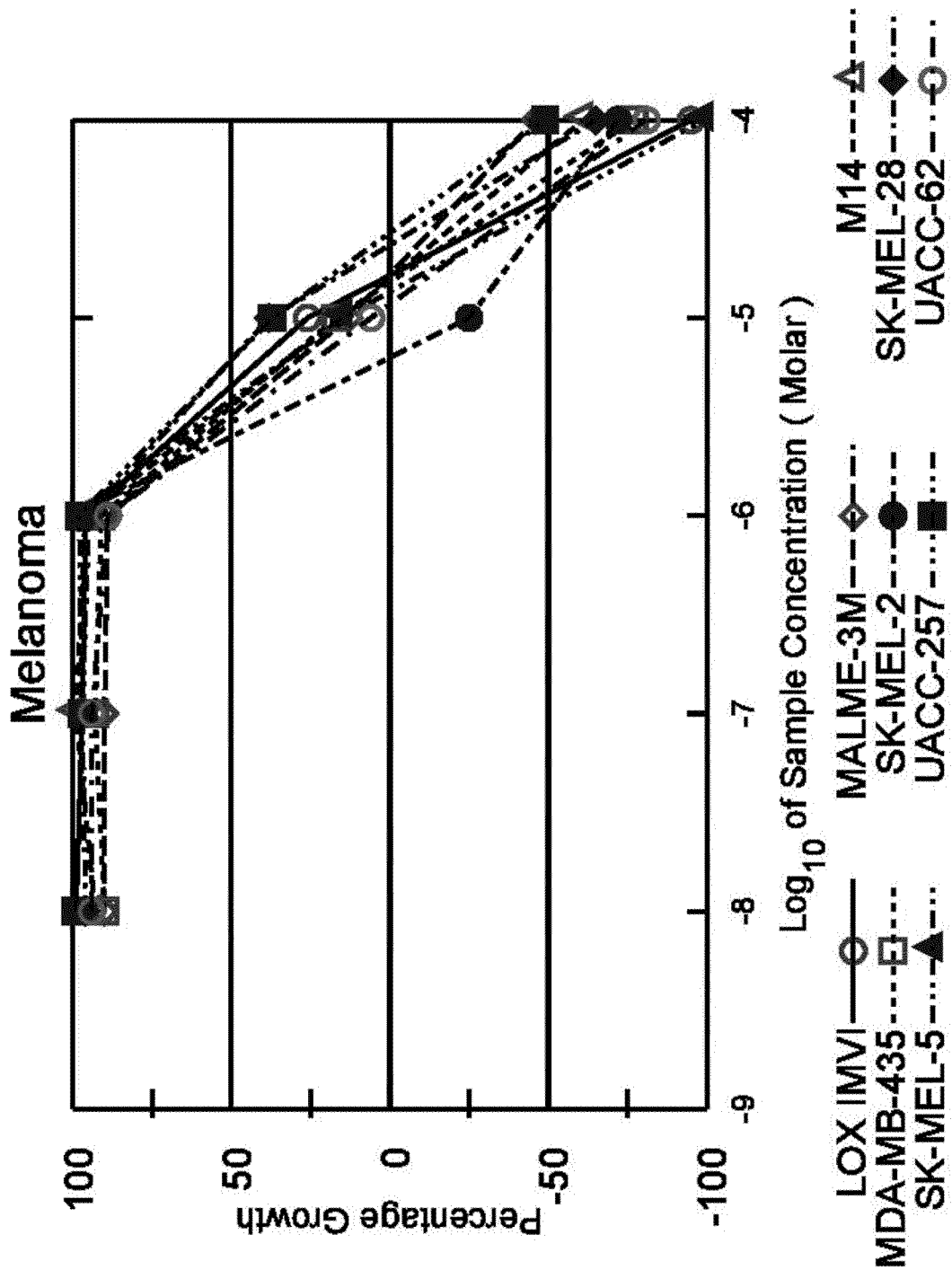
Figure 10F:
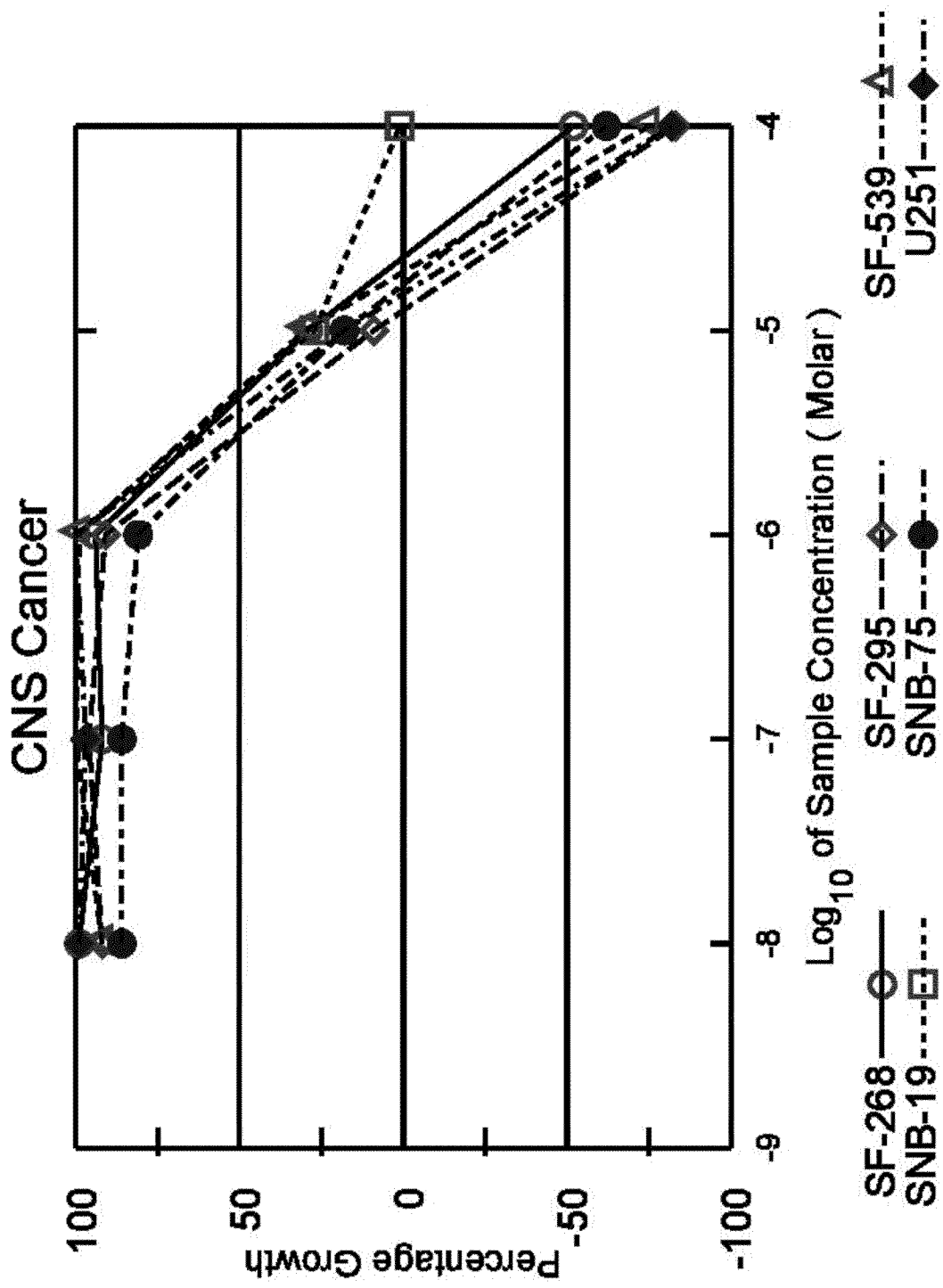
Figure 10G:
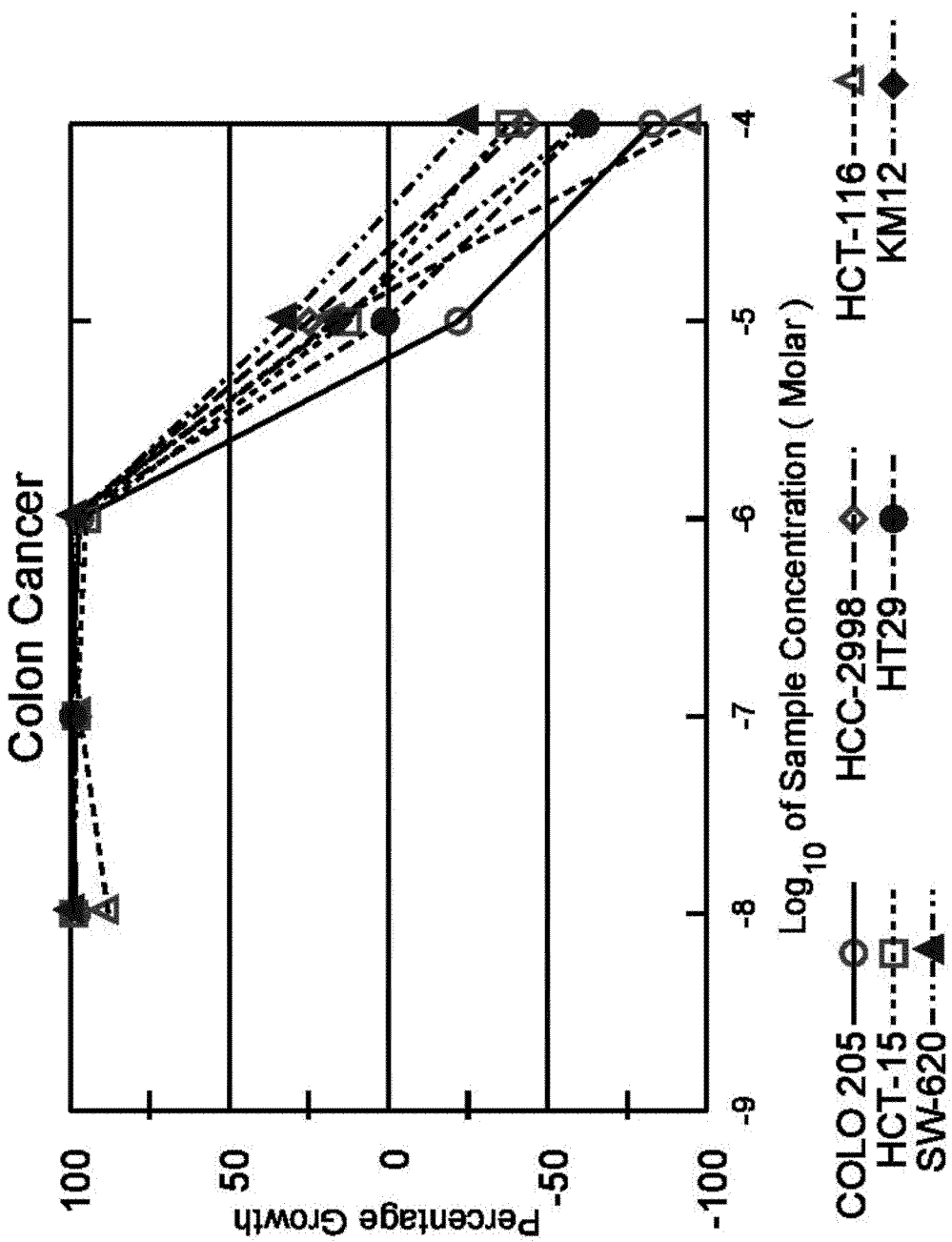
Figure 10H:
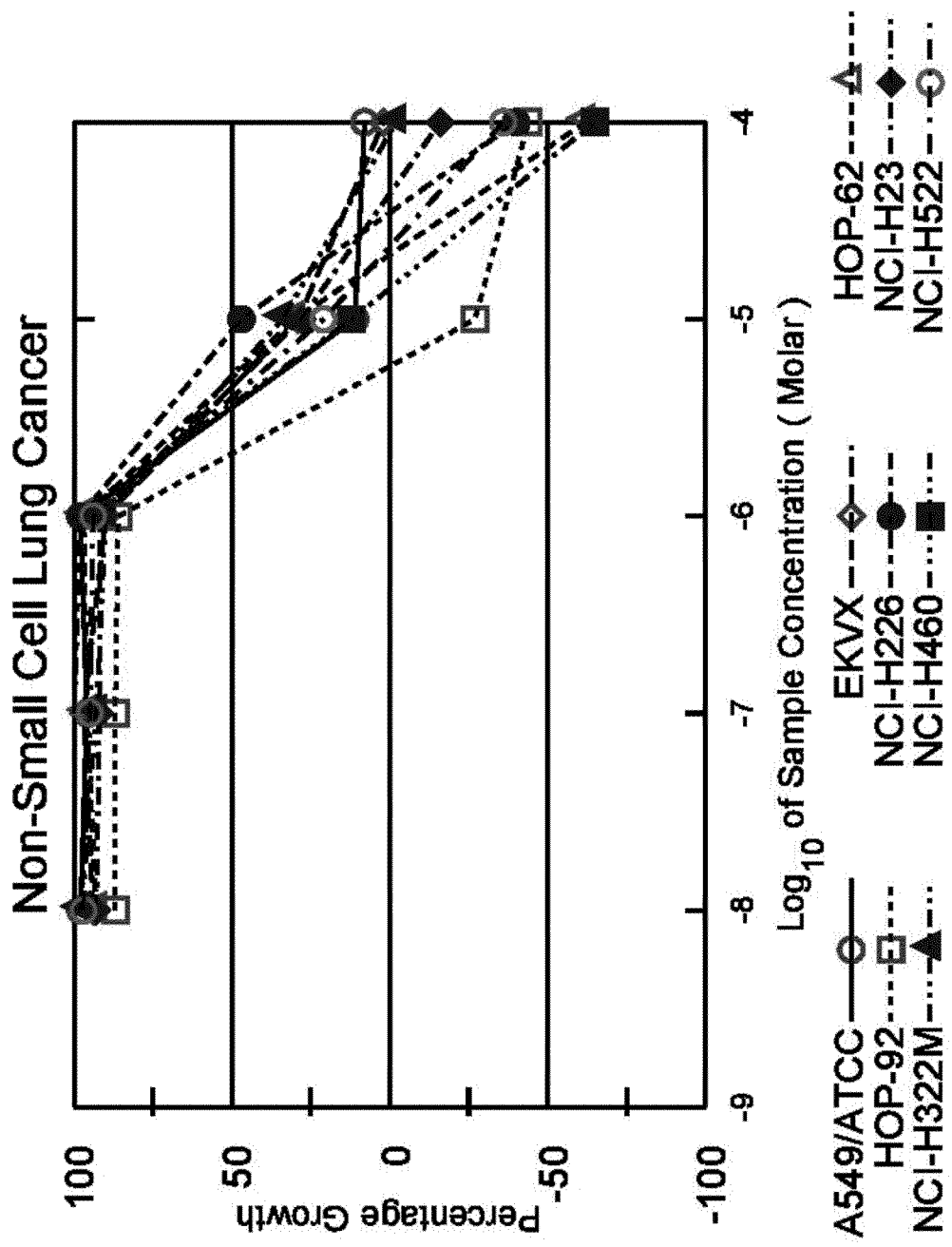
Figure 10I:
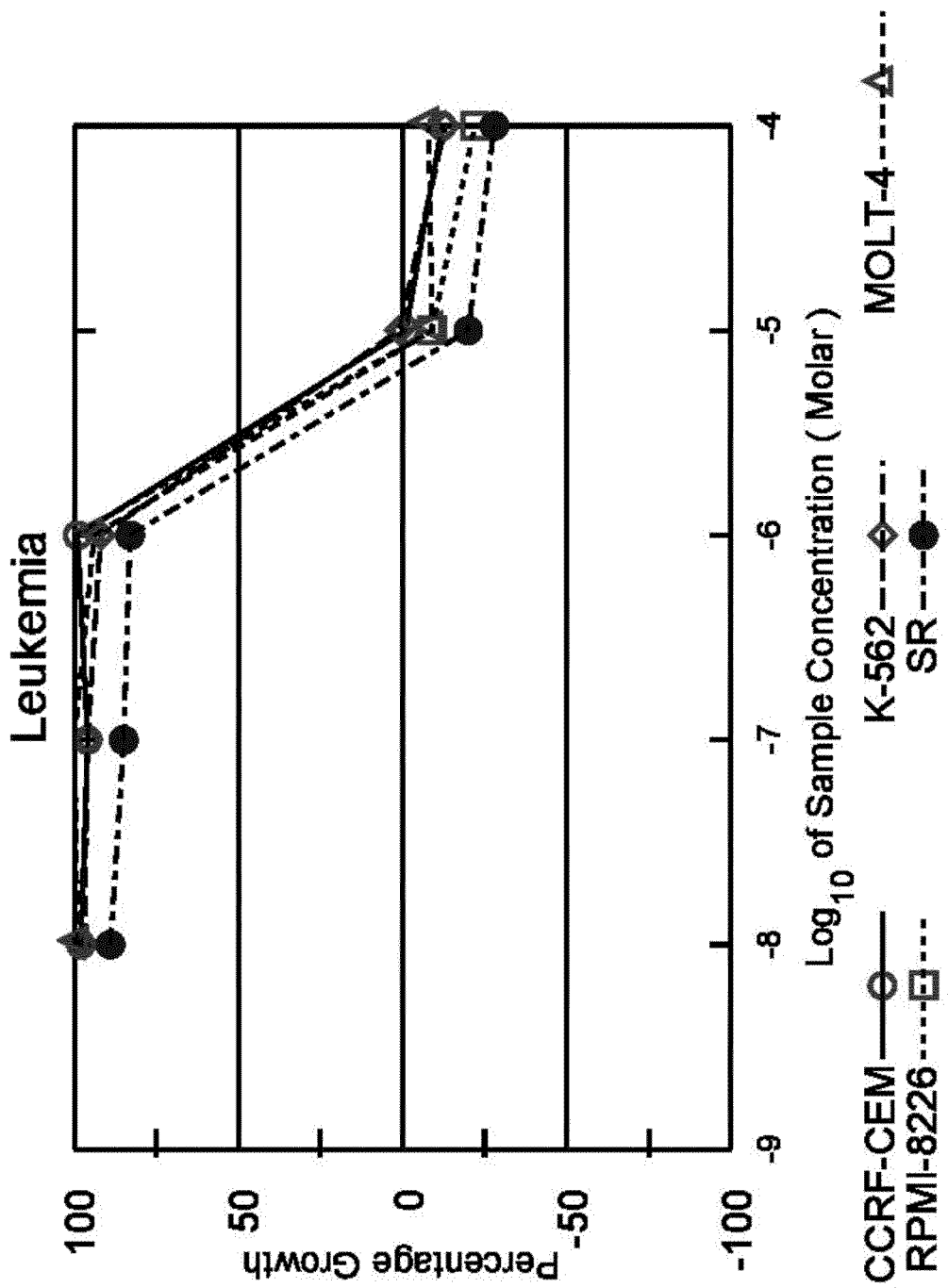
Figure 11A:
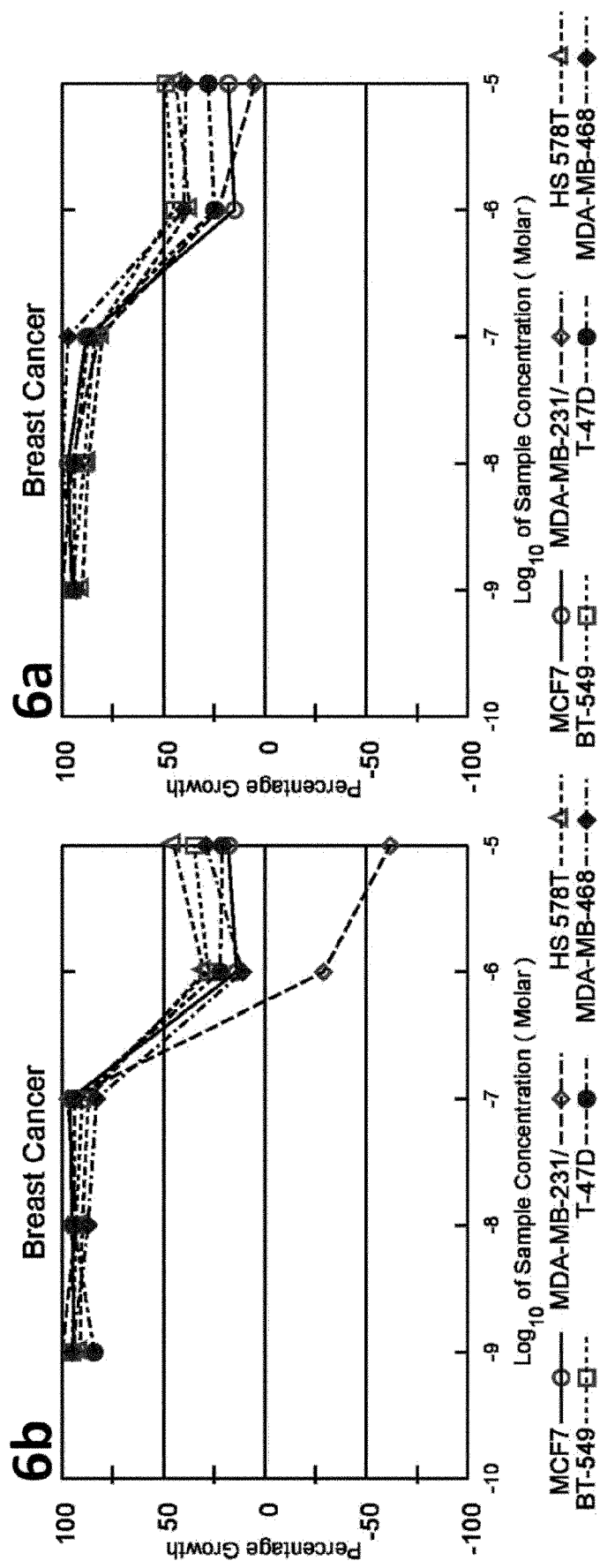
Figure 11B:
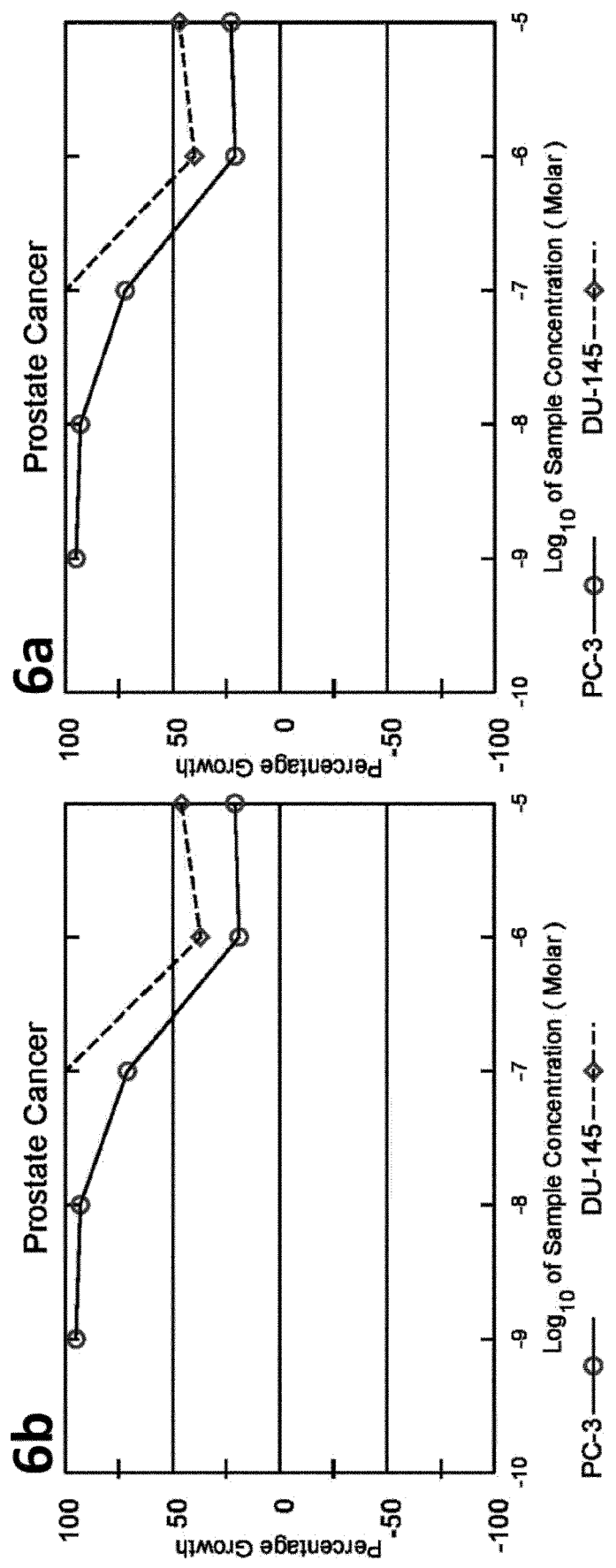
Figure 11C:
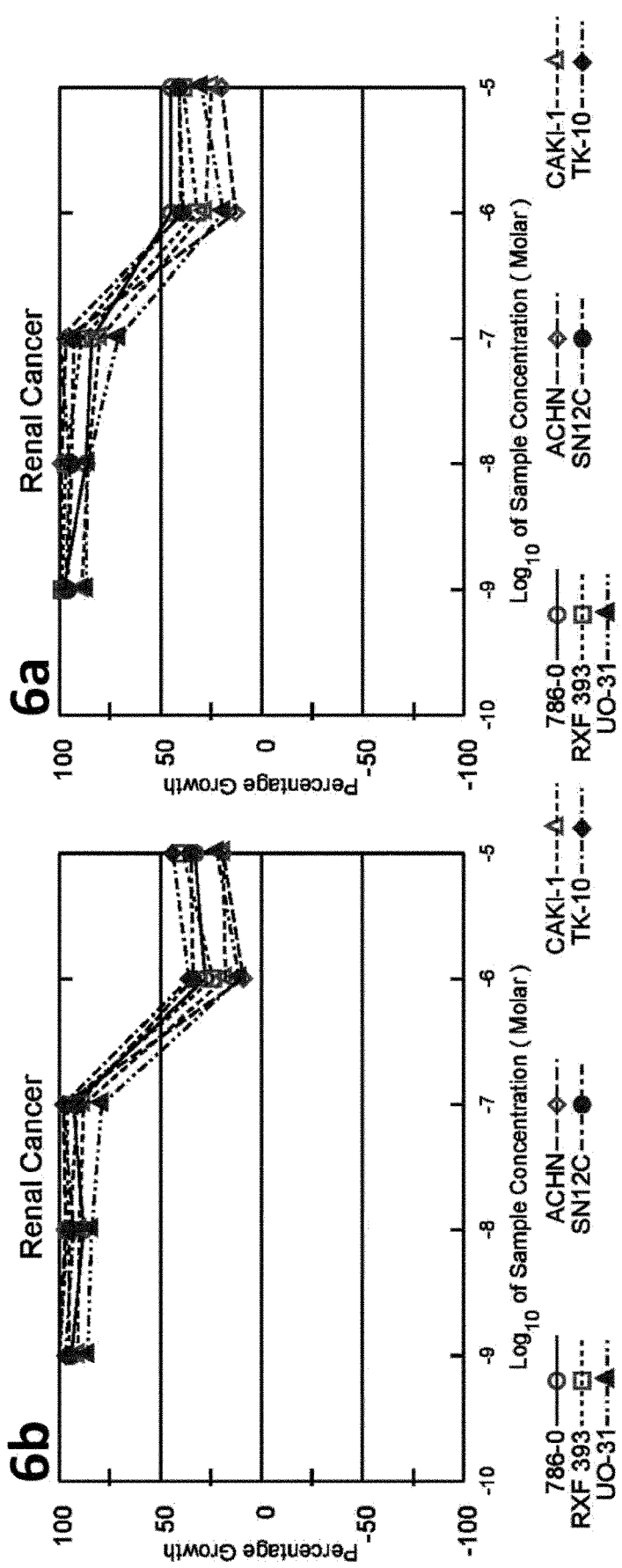
Figure 11D:
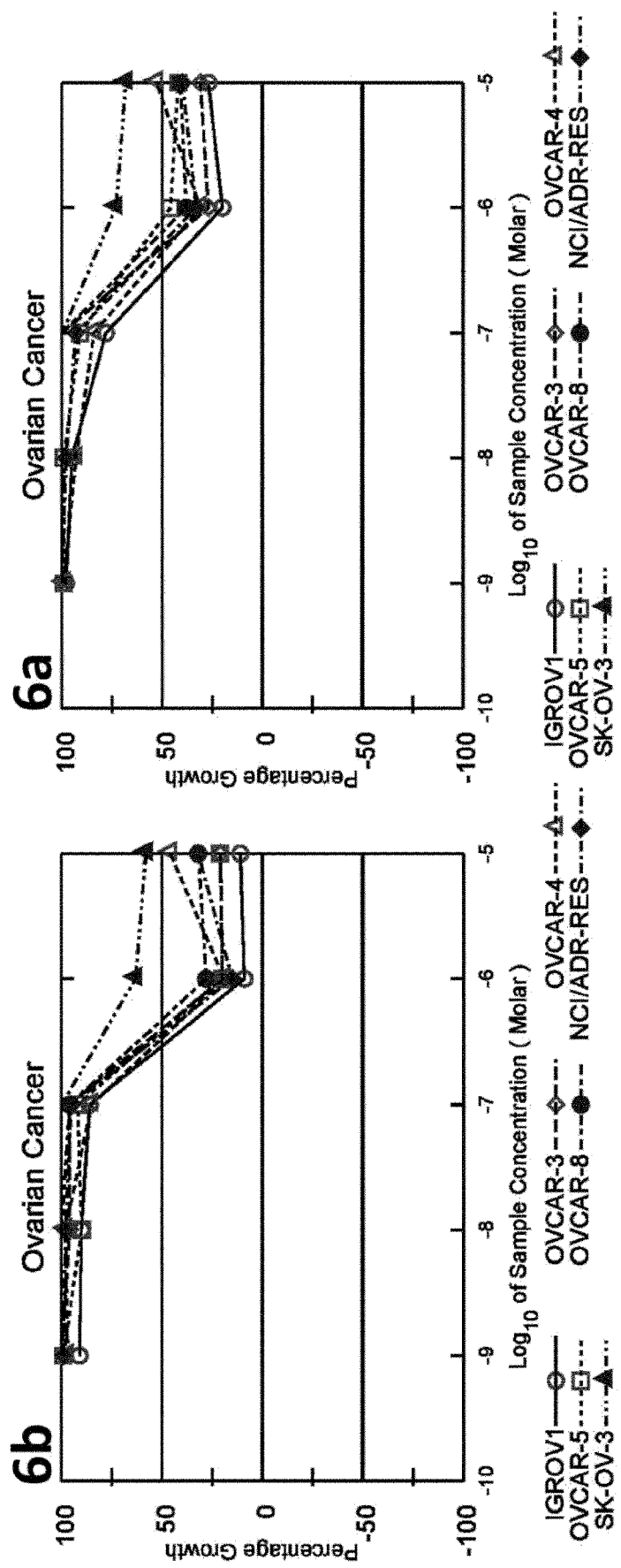
Figure 11E:
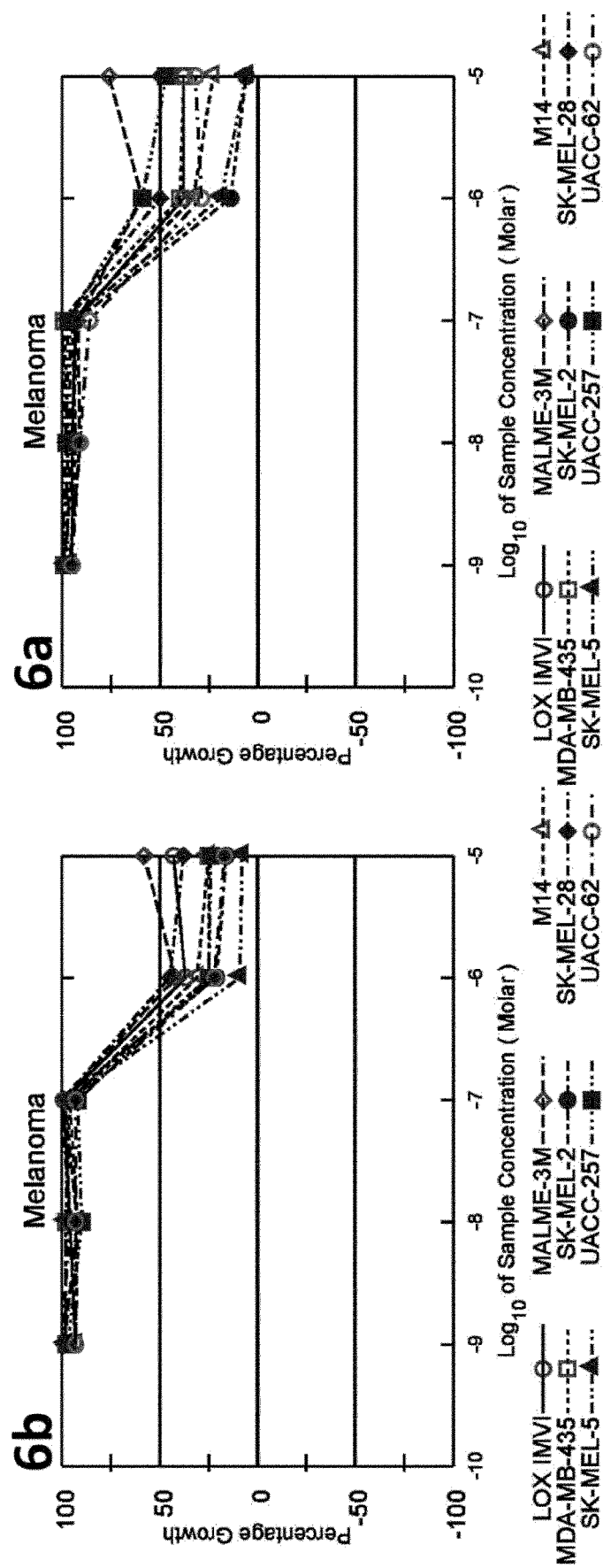
Figure 11F:
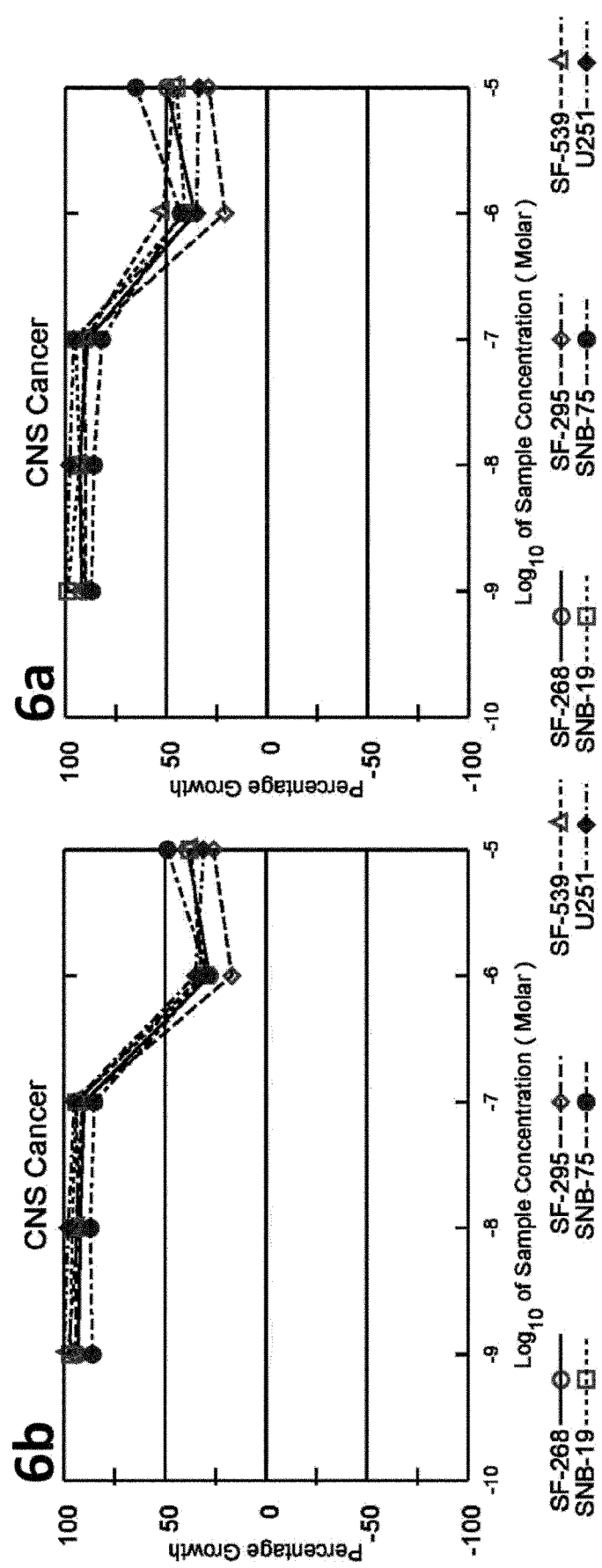
Figure 11G:
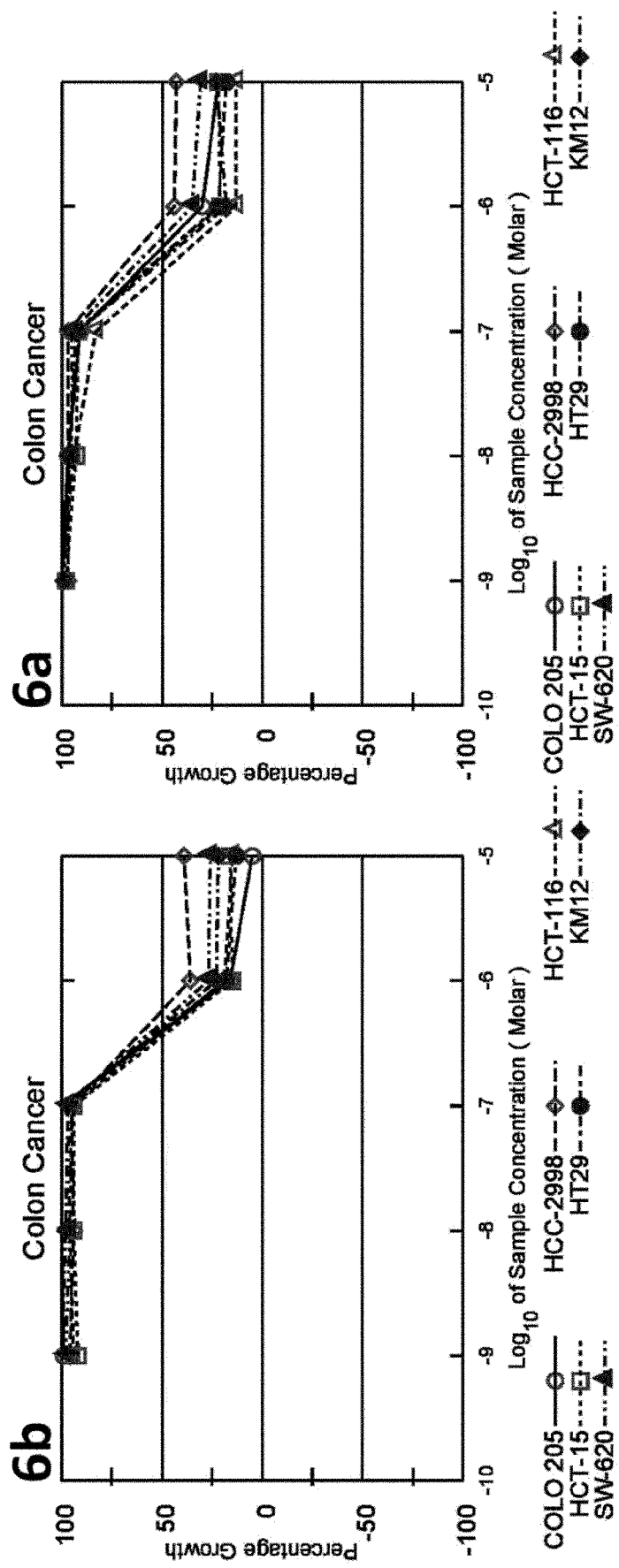
Figure 11H:
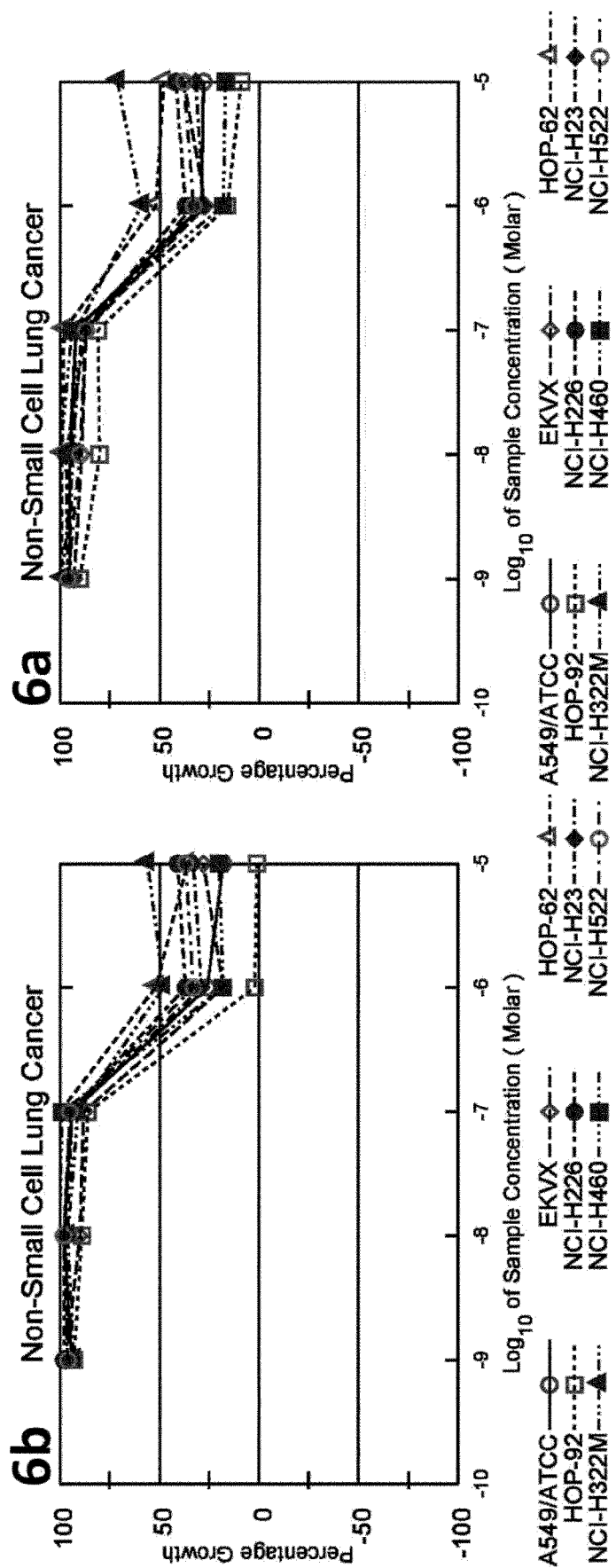
Figure 1I:
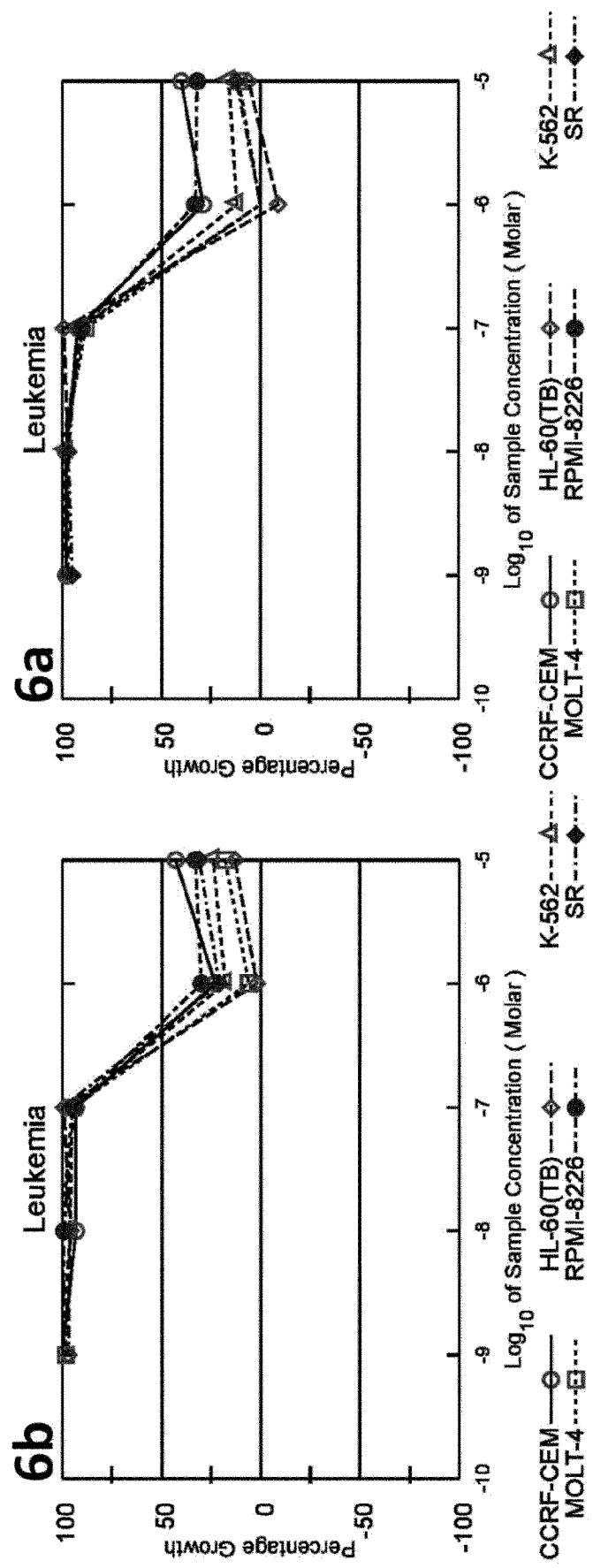

FIG. 7: Anti-cancer activity of almitrine dimesylate at 10 µM (NCI one-dose assay).

FIG. 8: (8A) A racemic mixture, or racemate, has equal amounts of the S and R enantiomers of a chiral molecule. Structure 19a is a racemate and (R/S) symbolises the chiral carbon as R or S. Structure 6a is its R stereoisomer, structure 6b is its S stereoisomer. The $EC_{50}$ $F_1F_0$ ATP hydrolase of the racemate (19a, 0.033 µM) is approximately half as potent as that of the isolated S stereoisomer (6b, 0.018 µM) because it contains half as much of the S stereoisomer per unit mass, because it also contains R stereoisomer ($EC_{50}$ $F_1F_0$ ATP hydrolase >100 µM) in a 50:50 ratio. Superfluid chromatography (SFC) was used to separate 19a into its component R and S stereoisomers, which don't and do potently inhibit $F_1F_0$ ATP hydrolase respectively ($EC_{50}$ values from SMPs in [5-6]), and two samples of opposite >97% enantiomeric excess (ee) was achieved: termed 6a and 6b respectively. These were independently tested in NCI one-dose (10 µM) testing: their results are shown in FIGS. (8B) and (8C) respectively. The anti-cancer activity of 6a and 6b was similar (Pearson correlation: R=0.8, significant at p<0.00001). This is because during the 48 hours of NCI one-dose testing, they underwent racemization and their ee eroded. Such that both samples ultimately contained a significant proportion of S stereoisomer and both exerted anti-cancer activity by inhibiting $F_1F_0$ ATP hydrolysis. Racemization is not instantaneous and so one sample, 6b, conferred greater/longer S stereoisomer exposure to the cancer cells than the other sample, 6a. Racemization isn't necessarily complete at testing end. These features explain why the 6b origin (>97% ee 6b at start) sample has greater anti-cancer activity than the 6a origin (>97% ee 6a at start) sample: 66% vs. 57% mean cancer growth inhibition, across all 59 cancer cell lines, respectively. During, and more certainly by end, of NCI one-dose testing, 6a and 6b have 97%>ee≥50% i.e. they are a racemate or scalemate. Although the fidelity of the (distinction between) 6a and 6b samples erodes during NCI testing, as they each converge (by epimerization) upon being 19a, I still use the 6a and 6b terms at times in this disclosure to refer to these samples during NCI testing. In addition, given that during NCI testing 6a→19a, and 6b→19a, I use the terms 6a, 6b and 19a interchangeably at other times during this disclosure. Racemization reduces, and increases, the anti-cancer activity of 6b and 6a respectively. (8D) 6b exerts greater anti-cancer activity than 6a. 6b is the S stereoisomer, 6a the R stereoisomer. However, also contemplated by, and componentry to, the present invention is if samples labelled 6b and 6a are the R and S stereoisomers respectively. (8E) and (8F) are the anti-cancer activities of 6a and 6b respectively in the NCI one-dose (100 µM) assay. In this assay, median cancer growth inhibition for both 6a and 6b >79%. With some and same cancer cell lines, for both 6a or 6b, anti-cancer activity is much less at 100 µM than 10 µM. Pearson correlation coefficient between 6a and 6b anti-cancer activity at 100 µM=0.9437 (p<0.00001).

FIG. 9: Anti-cancer potency (mean % decrease in cancer growth, as compared to no compound control, in NCI-60 one-dose testing) scales with inhibition of ($EC_{50}$) $F_1F_0$ ATP hydrolase, across diverse chemical structures. $EC_{50}$ values against ATP synthase, for BMS-199264 (N.B. $EC_{50}$ is for pure BMS-199264, not BMS-199264 HCl), 19a, 6a, 6b and 31 are from sub-mitochondrial (SMP) studies in [5-8], BTB06584 potency information (is not an $EC_{50}$) is from a whole cell study [13]. Compound 31 $EC_{50}$ for CYP2C9 is from [8].

6b and 6a anti-cancer activities are similar because of their epimerization in biological systems, which erodes their enantiomeric excess (ee) during NCI testing, making them converge upon being the racemate, 19a. Thus, during NCI testing, 6b $EC_{50} F_1F_0$ ATP hydrolase is not constant but in the range 0.033 µM≥$EC_{50}$ $F_1F_0$ ATP hydrolase ≤0.018 µM because $EC_{50}$ $F_1F_0$ ATP hydrolase→0.033 µM as 6b→19a, as racemization proceeds. Similarly, 6a $EC_{50}$ $F_1F_0$ ATP hydrolase→0.033 µM as 6a→19a.

Mean % cancer growth inhibition for BMS-199264 at 100 µM is >100% because for most cancer cell lines tested it doesn't just cause 100% cancer growth inhibition but, in addition, causes cancer regression, wherein the number of cancer cells at experiment end is less than at experiment start. BMS-199264 predominantly exerts anti-cancer activity at 10 µM by inhibiting $F_1F_0$ ATP hydrolase, and at 100 µM, by reducing $F_1F_0$ ATP synthesis.

31 has less anti-cancer activity than its $EC_{50}$ $F_1F_0$ ATP hydrolase value would predict because it is broken down by cytochrome P450 enzyme: CYP2C9, which it inhibits competitively (31 being consumed in the process). Average log 2 transcript intensity of CYP2C9, across all NCI-60 cell lines, is 3.539 [31-32]. Average log 2 transcript intensity of ATP5A1, the alpha subunit of $F_1$ ATP synthase, across all NCI-60 lines, is 9.871 [31-32]. There are 3 alpha subunits per ATP synthase [ I]. So, on average, approximately, there is a comparable amount of CYP2C9 and ATP synthase in an NCI-60 cancer cell line: 3.539:(9.871/3=3.29) 1. If we equate $EC_{50}$ as some measure of binding affinity then compound 31 has a greater affinity for binding ATP synthase in its reverse mode ($EC_{50}$=0.022 µM) than for binding CYP2C9 ($EC_{50}$=2 µM) (these $EC_{50}$ values come from different assays, thence this comparison isn't very robust). However, ATP synthase does not always operate in reverse, it likely has different operating propensities at different stages of the cell cycle, and compound 31 $EC_{50}$ $F_1F_0$ ATP synthesis is >30 µM. Thus, CYP2C9 can meaningfully reduce compound 31 inhibition of $F_1F_0$ ATP hydrolase, and thence its anti-cancer activity. Especially because CYP2C9, a cytochrome P450 enzyme, does not merely bind and sequester compound 31, but metabolises and inactivates compound 31 at a rate set by its kcat for compound 31. Compound 31 as substrate for an enzyme(s) of the cytochrome P450 enzyme, whilst itself having anti-cancer activity, means it can add to the anti-cancer action, for example potentiate the anti-cancer action, of other anti-cancer therapeutics which are also broken down by this system e.g. idarubicin.

At 10 µM, 6b (and 6a) exerts more anti-cancer activity than BMS-199264, despite having less effect on $F_1F_0$-ATP synthesis, because it inhibits $F_1F_0$-ATP hydrolysis more potently. FIG. 10: Anti-cancer activity of BMS-199264 hydrochloride. Results are from the NCI-60 five-dose in vitro assay [34-35] at the Developmental Therapeutics Program (DTP), at the National Cancer Institute (NCI, Bethesda, MD, USA). In this assay, which is well known to those of the art, a compound is tested, in vitro, against 59 different cancer cell lines, sourced from 9 different tissue types, across 5 different concentrations. 9 graphs in 9 sub-figures are presented (labelled 10A to 10I), one for each of the 9 tissue types. These graphs are as outputted by the NCI but changed from colour to black and white. On the y-axis of each is the aforementioned "Growth Percent" parameter used by NCI, which is growth relative to the no-compound control, and relative to the time zero number of cells. This parameter allows detection of both growth inhibition (values between 0 and 100) and lethality (values less than 0). $GI_{50}$ is the compound concentration that causes 50% growth inhibition of a cell line relative to the no-compound control. Each cancer cell line has a $GI_{50}$ value and the "mean GI50" of all 59 cell lines can be calculated: this mean GI50 for BMS-199264 hydrochloride is 3.9 µM.

FIG. 11: Anti-cancer activity of 6a and 6b in NCI-60 five-dose in vitro assay [34-35]. Mean GI50 for 6b is 0.446 µM. Mean GI50 for 6a is 0.666 µM.

Figure 12A:
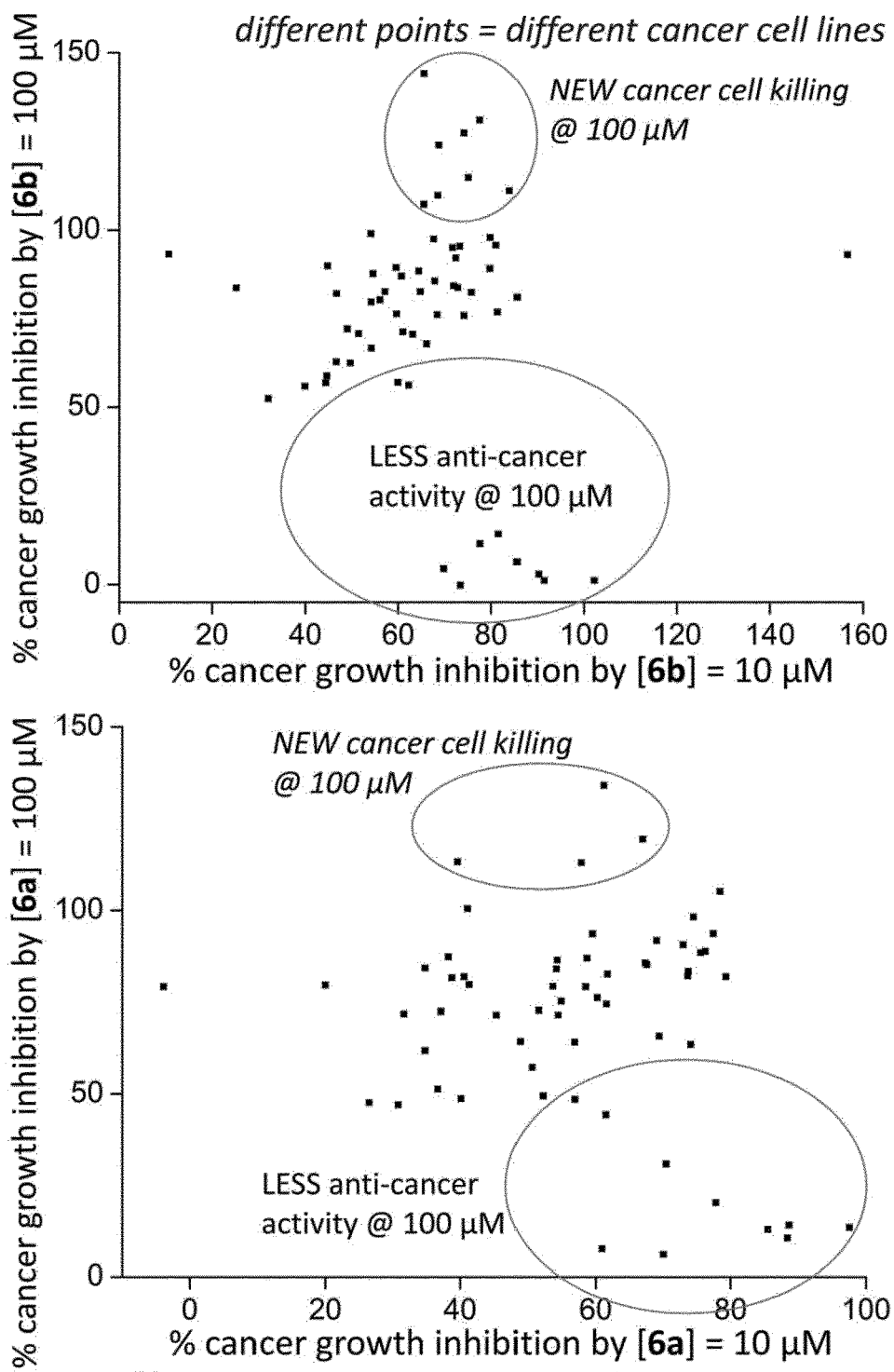
Figure 12C:
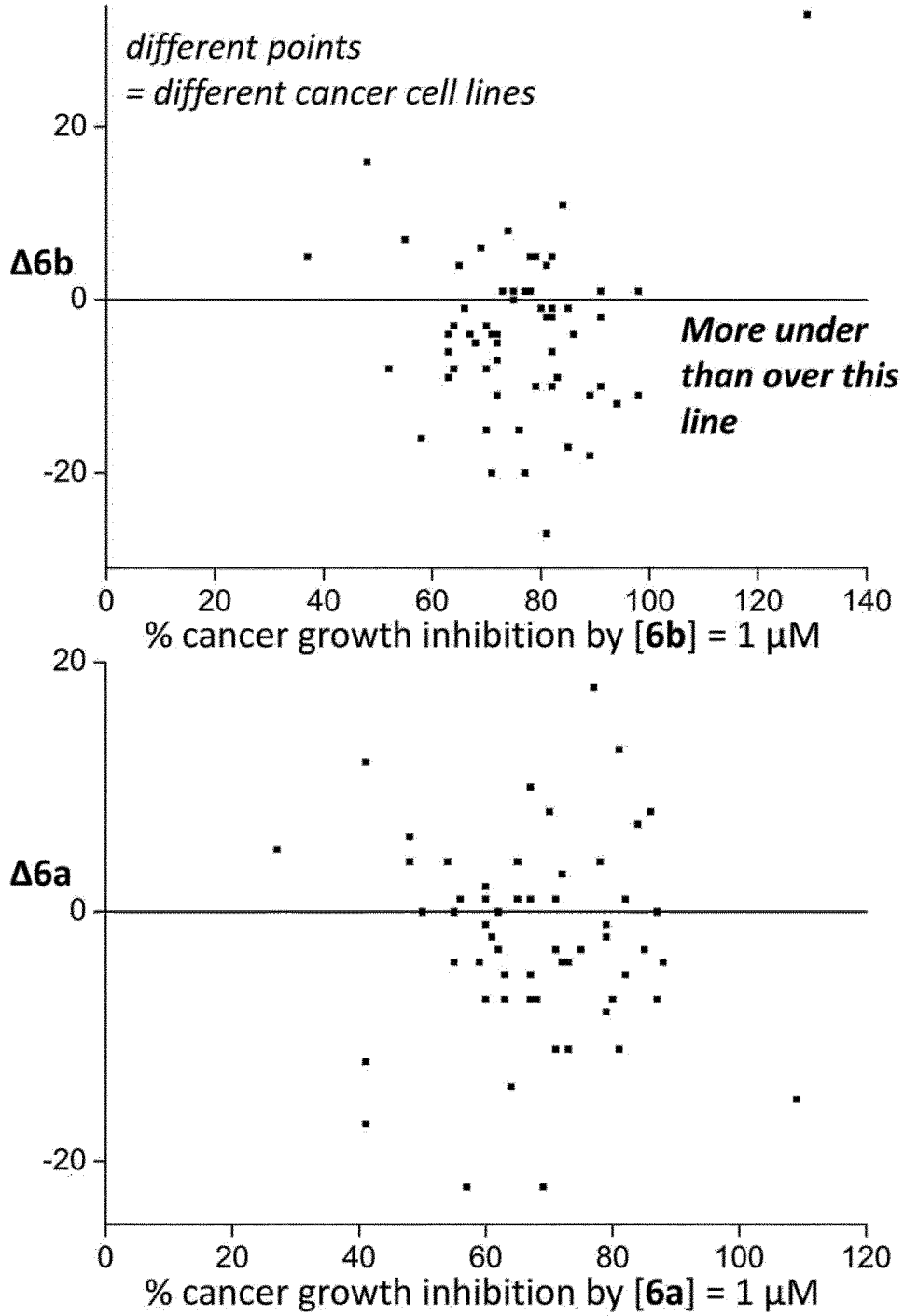
FIG. 12C recasts data from figures FIG. 11A to FIG. 11I.
Figure 13B:
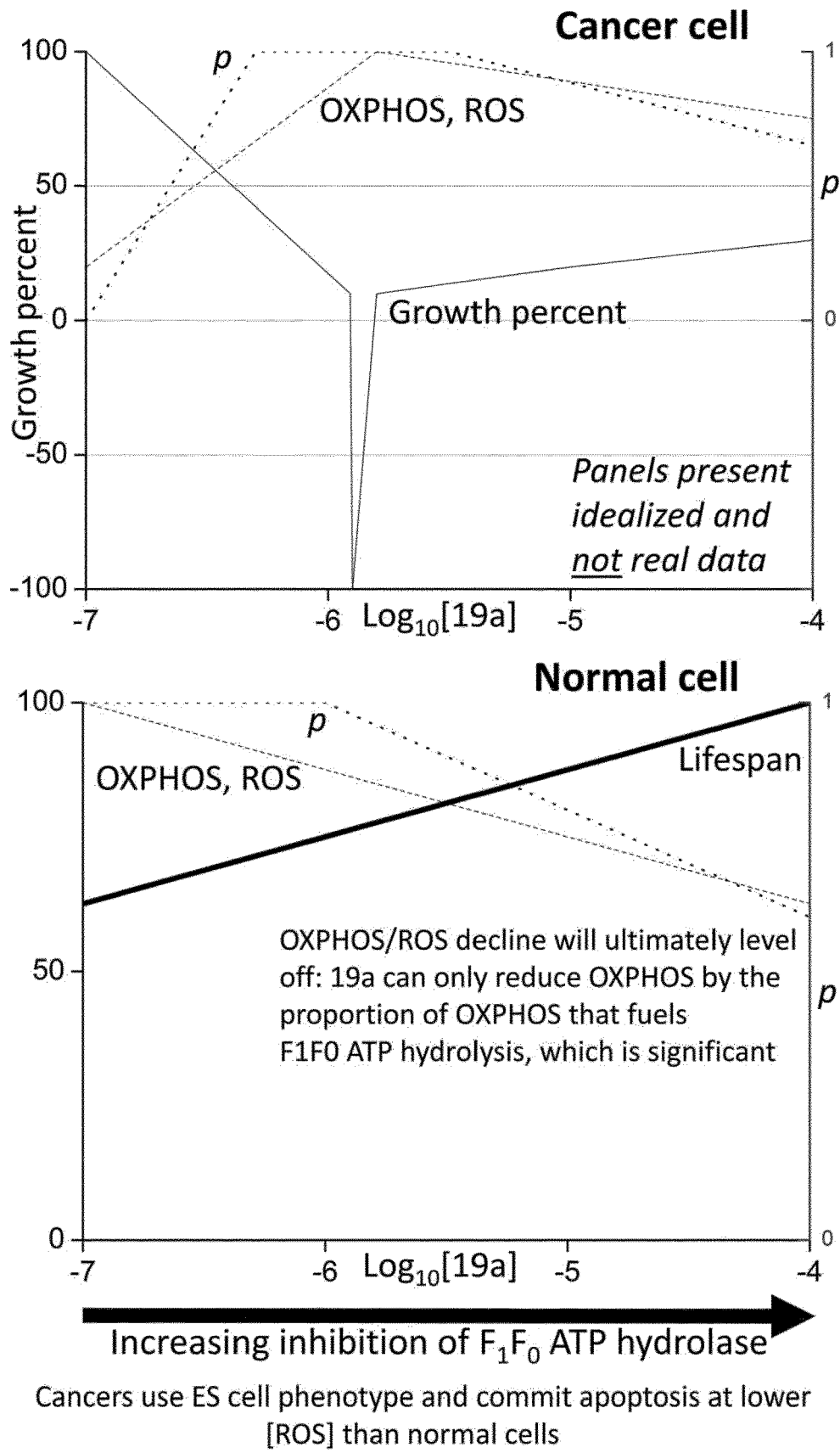

FIG. 12. Greater anti-cancer activity occurs with greater anti-cancer drug concentration. This is what someone of the art would expect. However, compounds 6a and 6b can, upon some (and overwhelmingly same) cancer cell lines, exert less anti-cancer activity at 100 µM than 10 µM in the NCI one-dose assay (FIGS. 12A and 12B) and can, upon some (and overwhelmingly same) cancer cell lines, exert less anti-cancer activity at 10 µM than 1 µM in the NCI five-dose assay (FIG. 12C). In 12A and 12B, most inhibited cancer cell lines at 10 µM are least inhibited at 100 µM. Next most inhibited cancer cell lines at 10 µM undergo cell death at 100 µM. Least inhibited cancer cell lines at 10 µM are more inhibited at 100 µM. Thus, to interpret, as one increases compound concentration, there are 3 zones passed, with their boundaries different for different cancer cell lines: (1) increased compound concentration increases anti-cancer activity, (2) compound causes cancer cell death, (3) increased compound concentration decreases anti-cancer activity. The anti-cancer activity of compounds 6a and 6b is highly correlated, which verifies the voracity of this data. 6b, as compared to 6a, is the stronger acting sample in NCI one-dose assay and, because it has the lower mean GI50, in the NCI five-dose assay also, wherein 6b has more cancer cell lines with less activity at 10 µM than 1 µM. Interpretation: 6a, and 6b, [compound] increase/decrease driven increase/decrease in anti-cancer activity is by action on same target. Data in FIGS. 12A and 12B is from data in FIG. 8. Data in FIG. 12C is from data in FIG. 11. FIG. 13. This diagram is an interpretation of experimental data in FIGS. 8, 11 and 12. It does not itself present real data. (13A) In FIG. 11, increasing concentration of 6a or 6b (both symbolised as 19a in the present figure) slows cancer proliferation, until a concentration of maximum slowing, after which further increase in compound concentration decreases cancer growth inhibition. The present diagram incorporates FIG. 11 data with an additional observation from FIG. 8, wherein high 6a and 6b doses decrease the cell number of some cancer cell lines, which I suggest is due to apoptosis. This observation is incorporated by a narrow dosage range that causes cancer cell death, the boundaries of which varies by cancer cell line, and it's narrowness explains why cancer cell killing is not observed for most cancer cell lines in the broadly separated doses of NCI five-dose testing. The diagram shows that increasing compound concentration increasingly blocks $F_1F_0$ ATP hydrolysis in cancer cells, which increasingly increases their OXPHOS rate, and thence reactive oxygen species [ROS]. Elevated [ROS] slows proliferation by ROS checkpoint blockade and atrophies DNA information fidelity, which reduces the number of possible cell divisions from limitless to a value increasingly convergent upon the Hayflick limit [96] of normal cells. At the inverted peak, the OXPHOS rate is so great, and [ROS] so elevated, apoptosis is triggered (by comparison, normal cells use this OXPHOS rate routinely). However, as compound concentration is increased beyond this point, greater $F_1F_0$ ATP hydrolysis inhibition makes OXPHOS more efficient (less ATP needs to be made because less ATP is hydrolysed), which reduces the OXPHOS rate and [ROS], and anti-cancer activity is less. (13B) Upper panel shows same diagram as (A), relating to a cancer cell, above an equivalent diagram for a normal cell, with equivalent x-axis. It shows that there are concentrations of an $F_1F_0$ ATP hydrolysis inhibitor(s) that harm cancer and help normal cells.

Cancers have, and need, lower intracellular [ROS] than normal cells. There are concentrations of $F_1F_0$ ATP hydrolysis inhibitor(s) that simultaneously raise [ROS] in cancer cells and decrease [ROS] in normal cells. In normal cells, greater $F_1F_0$ ATP hydrolysis inhibition makes OXPHOS more efficient (less ATP needs to be made because less ATP is hydrolysed), which reduces the OXPHOS rate and [ROS] and increases normal cell lifespan. $F_1F_0$ ATP hydrolysis inhibitor(s) conferred OXPHOS efficiency gain comes from, and so its maximum is dictated by, proportion of OXPHOS produced ATP hydrolysed by $F_1F_0$ ATP hydrolysis, which is high, and so lifespan (and healthspan) extension significant, especially if it reduces [ROS] sufficiently to reduce DNA mutation rate below DNA repair rate. Especially, if this [ROS] is sufficient to keep cells differentiated, maintaining tissue and organ function.

Figure 14A:
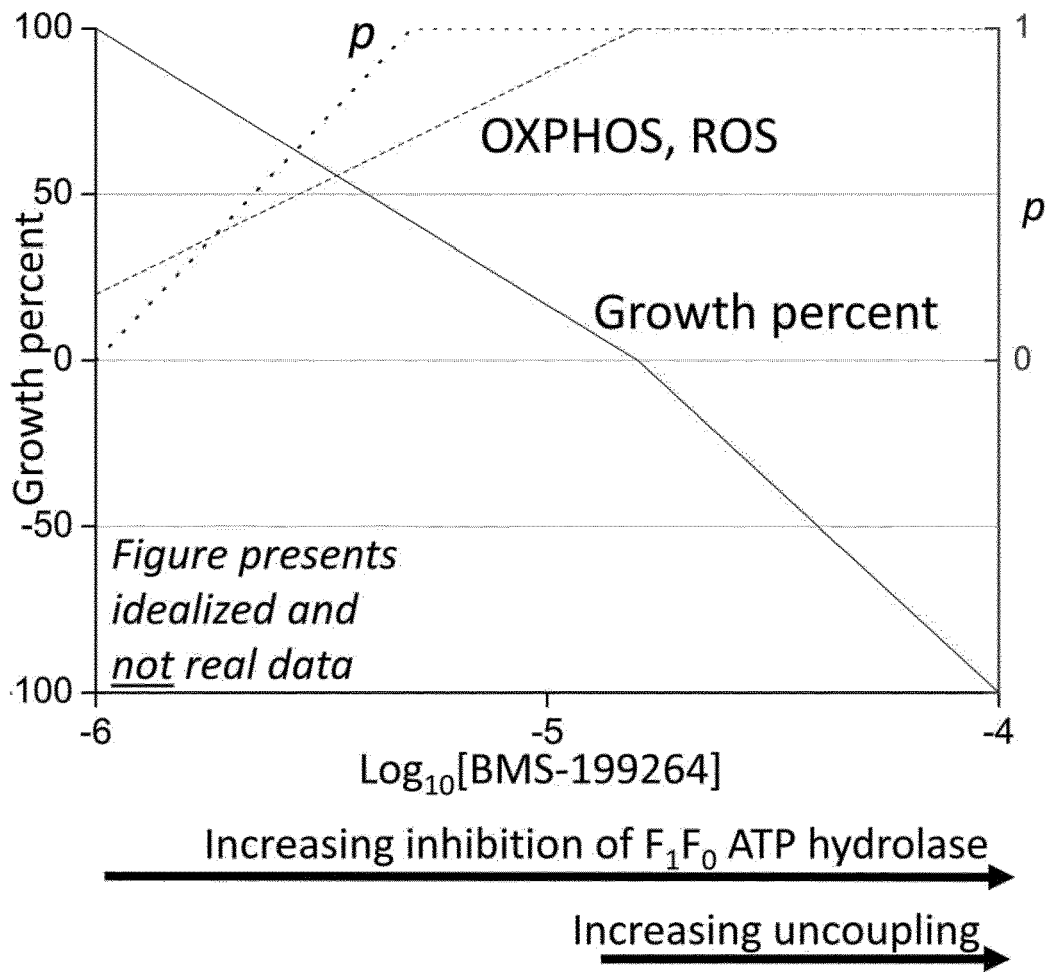
FIG. 14A and FIG. 14B interprets data from figures FIG. 10A to FIG. 10I.
Figure 14B:
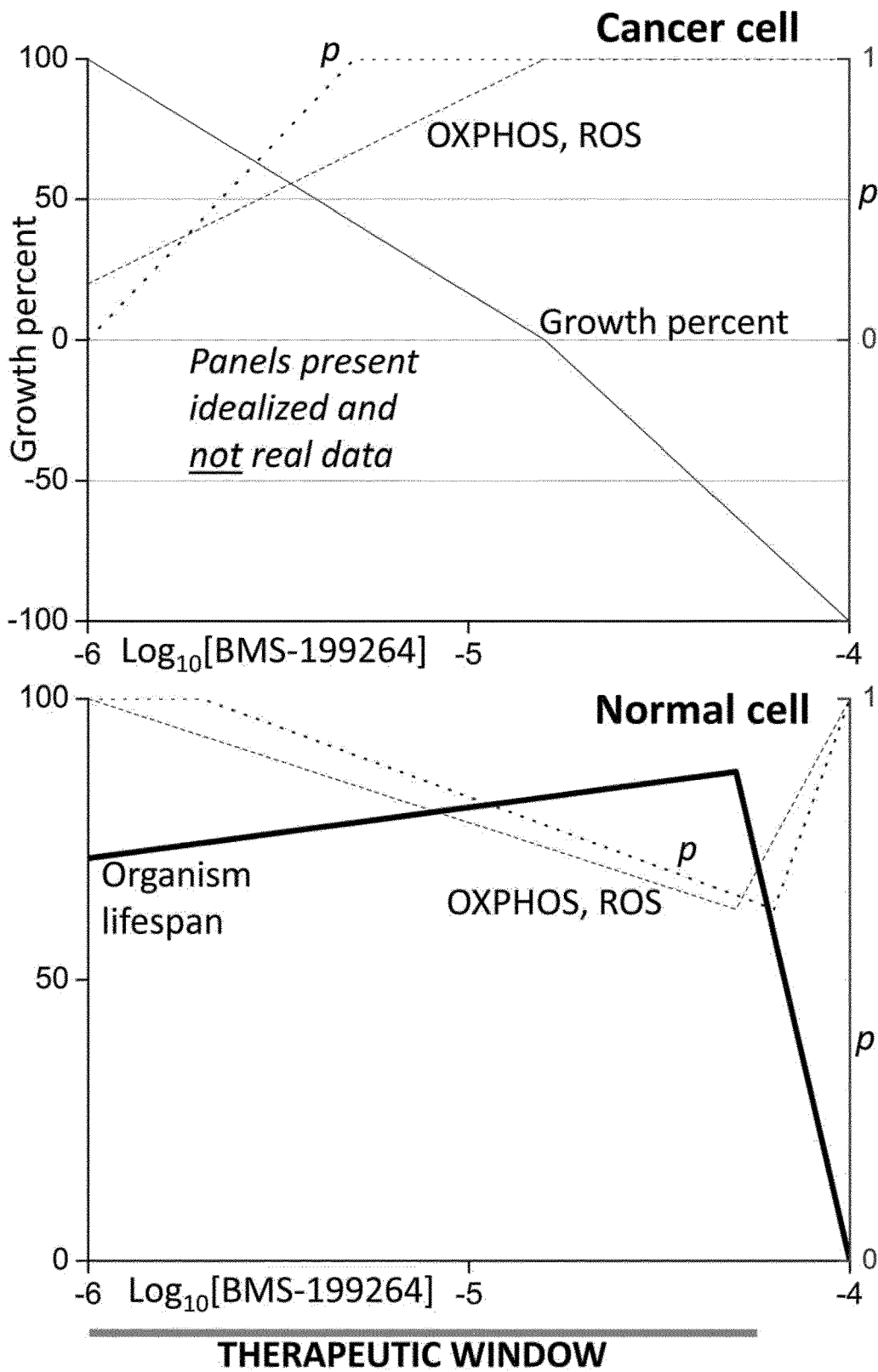

FIG. 14. This diagram is an interpretation of experimental data in FIG. 10. It does not itself present real data. BMS-199264 is distinct from compound 6b because, in addition to inhibiting $F_1F_0$ ATP hydrolysis, it can also significantly reduce $F_1F_0$ ATP synthesis at NCI tested concentrations. Background: BMS-199264 $EC_{50}F_1F_0$ ATP hydrolysis=0.48 µM, $EC_{50}$ $F_1F_0$ ATP synthesis=18 µM. (14A) Cancer cell. At lower [BMS-199264], anti-cancer activity is predominantly by inhibition of $F_1F_0$ ATP hydrolysis in cancer cells, which increases their OXPHOS rate, and thence reactive oxygen species [ROS]. Elevated [ROS] slows proliferation by ROS checkpoint blockade and atrophies DNA information fidelity, which reduces the number of possible cell divisions from limitless to a value, at increasing [BMS-199264], increasingly convergent upon the Hayflick limit [96] of normal cells. At higher [BMS-199264], anti-cancer activity is additionally by reduction of $F_1F_0$ ATP synthesis, principally by BMS-199264 conferred uncoupling of the proton motive force (refer FIG. 17), which increases cancer OXPHOS rate and intracellular [ROS]. So much that apoptosis ensues. (14B) Upper panel shows same diagram as (A), relating to a cancer cell, above equivalent diagram for a normal cell, with equivalent x-axis. It shows that lower [BMS-199264], which inhibits $F_1F_0$ ATP hydrolysis, harms cancer and helps normal cells. Thus, there is a therapeutic window. However, higher [BMS-199264], which significantly reduces $F_1F_0$ ATP synthesis, harms both cancer and normal cells. Greater [ROS] sensitivity of cancer, running an embryonic stem (ES) cell type phenotype, shown in relative positioning of plots upon equivalent x-axis.

Figure 15A:
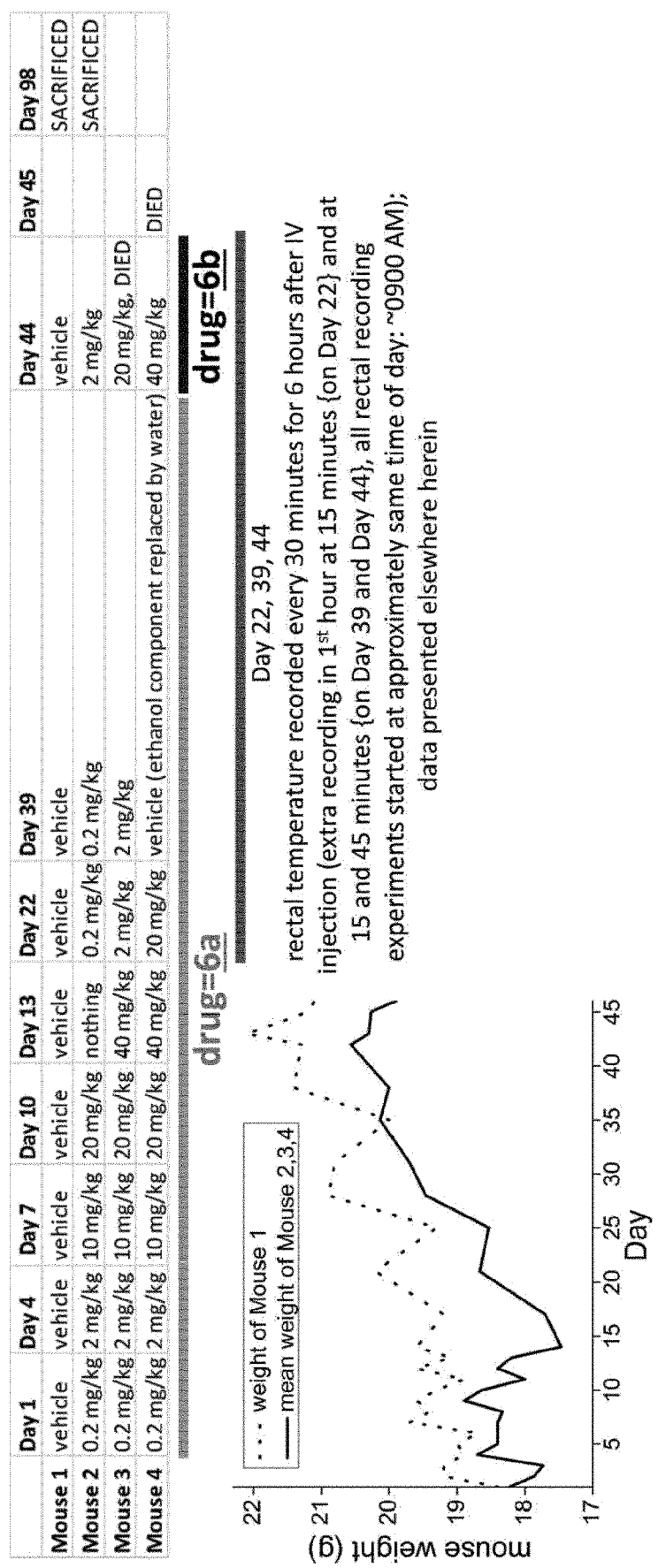
FIG. 15A and FIG. 15B presents in vivo mouse data for compounds 6a and 6b, which is interpreted by a diagram in FIG. 15C.
Figure 15B:
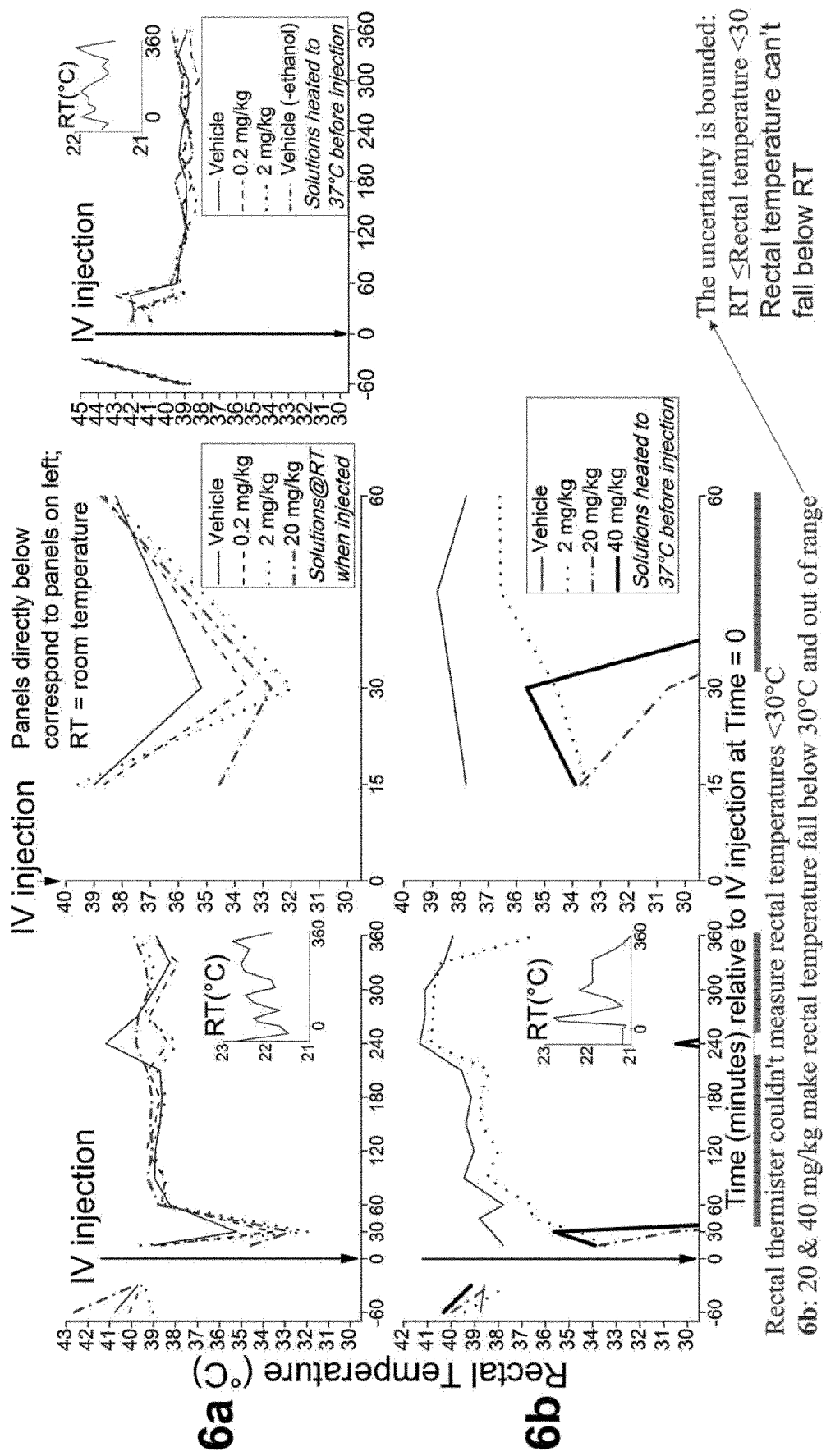

FIG. 15. In vivo study of compounds 6a and 6b, conducted at 22° C. room temperature. METHODOLOGY: 4 mice were used and in the presented table "Day" refers to the number of days since the 1$^{st}$ drug/vehicle dose on Day 1. Some experimental details: intravenous (IV) administration (tail vein), dosing volume=10 µl/g, solution (not suspension), sterilised (0.22 µm filter) vortexed vehicle=12.5% solutol, 12.5% ethanol, 75% water, IV solutions freshly prepared before injection except on days 22 and 39 when solutions prepared on previous dosing days were used (sub-optimal), Female Mus Musculus C57BL/6 strain, 6-8 weeks old at study start, mice sourced from Shanghai Lingchang Bio-Technology Co. Ltd, mice were observed/quarantined for a few days after arrival and before dosing, ad libitum Co$^{60}$ irradiation sterilized dry granule food & reverse osmosis autoclaved water, corn cob bedding, polysulfone individually ventilated cage (IVC, containing up to 5 animals): 325 mm×210 mm×180 mm, 12 hour light/dark cycle, 40-70% humidity, 20-26° C. room temperature, StudyDirector™ software (Studylog Systems, Inc. CA, USA) used to allocate/randomize control/treatment groups, animals marked by ear coding (notch), care and use of animals in accordance with the regulations of the Association for Assessment and Accreditation of Laboratory Animal Care (AAALAC), when recording rectal temperature: care was taken to ensure constant depth of probe insertion across different recordings, time was afforded for rectal probe temperature to equilibrate with rectal temperature, and time was afforded between recordings for probe temperature to reset.

RESULTS: FIGS. 15A) and (15B): For each animal, the 1$^{st}$ rectal temperature recording is typically of an atypically high body temperature, which is associated with the stress of being handled, which a mouse becomes habituated to during the course of the experiment. This handling effect has been reported in other rectal thermistor studies of rodents e.g. [97-98]. Mouse 3 rectal temperature was <30° C. by 45 minutes after 20 mg/kg IV injection of 6b, it died ~210 minutes after this IV injection, whilst drinking water, "choked on water" was reported observation, water temperature was at room temperature (RT)=~22° C. (so ingestion reduces body temperature, if it isn't already at RT). Mouse 4 rectal temperature was <30° C. by 45 minutes after 40 mg/kg IV injection of 6b, survived >6 hours, found dead the next day, did not survive the night. After IV of 6b: Mouse 3 and 4 exhibited hypoactivity and tachypnea, both signs of hypothermia [99], coinciding with their rectal temperature drop (<30° C.). Mouse 2 exhibited hypoactivity but recovered after 30 minutes, matching its recovery of rectal temperature. With 6b IV administration, there is a dose-dependent drop in rectal temperature.

Before 6b dosing experiments, Mouse 1, 2 and 3 had all survived IV injections of 6a. 6a doesn't potently reduce rectal temperature like 6b: the dose-dependent rectal temperature reduction (with hypoactivity reported over same timescale that rectal temperature is reduced) that 6a can cause is because of in vivo epimerization of 6a to 6b. Similarly, when 6b is the administered compound, in vivo epimerization of 6b to 6a reduces the effective dose of 6b and chemical modifications to the 6b compound structure to prevent or slow this epimerization are componentry to this invention: for example, a non-limiting example embodiment is to replace the hydrogen on the chiral carbon of 6b with deuterium. >40 mg/kg doses of 6a weren't trialed because I ran out of 6a compound. Indeed, I only had enough 6a to dose 2 of the 3 test mice with 40 mg/kg.

Vehicle control can cause a drop in rectal temperature because of its 12.5% ethanol content: 12.5% of 10 ul/g solution administered=1.25 ul/g ethanol=0.000989226 g/g=0.99 g/kg=1 g/kg ethanol (IV). 1.9 g/kg ethanol (intraperitoneal injection, IP) reduced rat body temperature by 1.6° C. (in 24.5 to 25° C. ambient temperature; raising temperature of IP injected ethanol solution to 37° C. didn't have major impact) [100]. Ideally, future studies should not use ethanol as a vehicle component. The problem is not its hypOthermia, which is safely mitigated by a higher ambient temperature [100]. But because at just a slightly higher ambient temperature than this, ethanol can cause hypERthermia [100]. And the ambient temperature that safely mitigates ethanol driven hypothermia, without causing ethanol driven hyperthermia, varies with the ethanol dose [100]. This [ethanol dose/ambient temperature/hypothermia/hyperthermia/safe rectal temperature] matrix can be mapped by experimentation, and indeed there is much in the literature already e.g. non-limiting examples: [100-106], to guide the best use of ethanol as a vehicle component in future studies. However, this experimentation can be avoided: alternative vehicle options, which are not a potent drug in and of themselves, as ethanol is, are well known to those of the art, e.g. see [107-108]: one or more of these can be employed as an alternative. When ethanol as vehicle is used, the fraction of rectal temperature drop accountable to the test drug can be calculated by subtracting any rectal temperature drop observed just with the ethanol containing vehicle control (assumes that ethanol and drug induced rectal temperature drops are additive and not potentiating). Drug induced rectal temperature reductions in this study, when they occur, are dose-dependent and well in excess of any rectal temperature drop observed when only ethanol containing vehicle control is injected.

The presented data shows that inhibiting the reverse mode of ATP synthase reduces body temperature. 6b potently inhibits the reverse mode of ATP synthase ($IC_{50}$=0.018 µM [5-6]), 6a does not ($IC_{50}$>100 µM [5-6]). 6b potently reduces rectal temperature, 6a does not (it does to a minor degree, which is evidence for in vivo epimerization of 6a to 6b, on a faster timescale than 6a clearance). A significant reduction in body temperature is lethal. Thence the maximal tolerated dose (MTD) of 6b, at room temperature=~22° C., is lower than the MTD of 6a. Body temperature cannot fall below ambient temperature and so the MTD of 6b is increased by ensuring ambient temperature is closer to the normal mouse body temperature, which ensures that mouse body temperature is maintained at an acceptable value. This brings greater alignment between the MTD of 6a and 6b, which in the case of 6a is very safe: $LD_{50}$>40 mg/kg (IV). This is safer than the FDA approved anti-depressants clomipramine HCl and imipramine HCl: $LD_{50}$ {mouse, IV} of 22 mg/kg and $LD_{50}$ {mouse, IV} of 27 mg/kg respectively (Register of Toxic Effects of Chemical Substances, RTECS). Some patients take these drugs daily, safely, for years.

Non-limiting example embodiments to maintain mice, or some other animal, including humans, at a life permissive body temperature, whilst having a compound of this disclosure in their body, include locating them in a temperature-controlled room or confinement. For example, in small animal experiments, a plant growth or egg incubator or similar type device. An embodiment is to administer a compound of this disclosure to an animal(s), including human(s), in a hot country, geography or climate e.g. Dubai or somewhere else in the Middle East, more preferably during summer when it has high daytime and night temperatures. There are many methods in the literature to keep rodents at elevated temperature, easing the cold stress they feel at typical room temperatures [62]: e.g. partially submerging water proof mouse cages into fish tanks, in use as water baths, heated by thermostatic electric fish tank heaters [111], or by heating cages with chemical reaction hand warmers [109-110]. Such methods, or any method with equivalent intention, when employed with an animal(s)/human(s) with a compound of this invention in its body, is componentry to this invention. Adaptive heating can be employed, which adjusts the heating element output (e.g. an infrared lamp, or any other heating element(s)) in response to the measured body temperature (e.g. by rectal temperature probe or by thermal imaging, or any other body temperature recording device(s)), to maintain a life-permissive body temperature, when a compound of this invention is in the body. With a compound of this disclosure, the need for (and amplitude of) ambient temperature intervention is more important for smaller than larger animals e.g. more so for a mouse (~20 g) than a rat (~150 g). If an experimenter has to work with a compound of this disclosure at typical room temperature (20-25° C.) then the test species, and individual(s), chosen should be as large as possible. All methods of maintaining body temperature within a temperature range that permits life, whilst having a compound of this invention in the body, are componentry to this invention. For (non-limiting) example, wearing clothes.

Figure 15C:
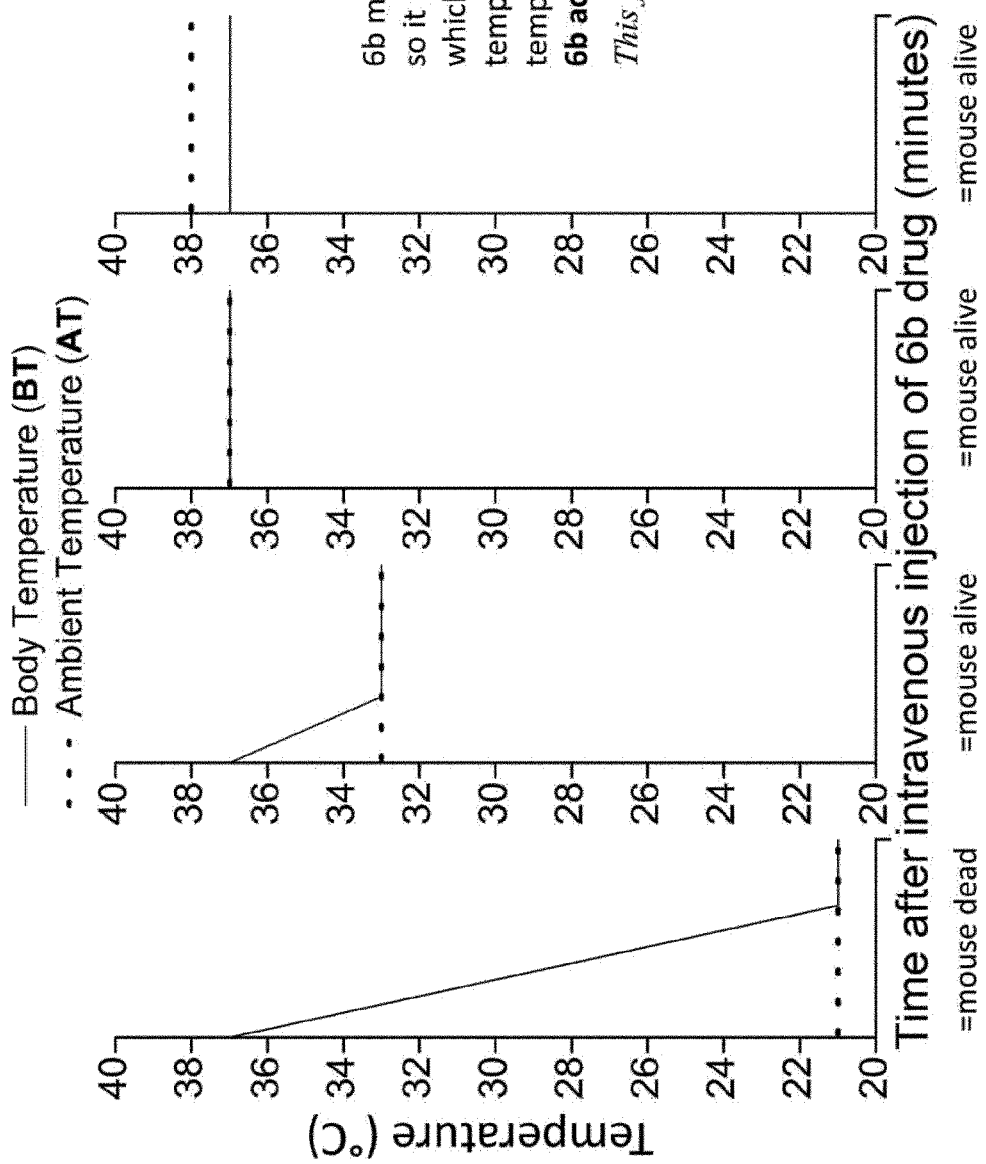

FIG. 15C): diagram, prediction, not real experimental data.

FIG. 16. The enantiomeric excess (ee) of 6a and 6b is stable in presented ee stability experiments. By contrast, as disclosed elsewhere herein, 6a and 6b significantly epimerize within 48 hours in a biological system (NCI-60 testing). This ee instability in biological media is an unexpected result. This finding is componentry to the invention of this disclosure, as are any modifications to the structure of 6a or 6b to slow their ee erosion due to epimerization/racemization. The ee instability is unexpected because it runs contrary to theory. The $2^{nd}$ order rate constant ($k_{gb}$) for general-base catalysed racemization can be predicted for 6a and 6b by theory from [112] (and its supplementary information, all incorporated by reference). Joined to the stereogenic carbon of 6a and 6b there is a phenyl group, alkyl and a guanidine group: $\Sigma\Delta\Delta G(R_1,R_2,R_3)=-9.81+2.8-19.1=-36.2$ kcal/mol. The value for the guanidine group (19.1) is not from [112] but from one of its authors, Dr. Andrew Leach, by personal communication, who sourced it by quantum mechanical calculation with the Gaussian 03 software package. The cross-conjugation correction [112] was not applied in this case because Dr. Leach wrote "I would not expect guanidine to be a conjugating group". $\log(k_{gb})=-0.11*\Sigma\Delta\Delta G(R_1,R_2,R_3)-9.81$, ∴ $K_{gb}=0.00000148593$ $M^{-1}s^{-1}$. This is not particularly fast. Racemization might occur faster for 6a and 6b in cells than predicted by theory because their high lipophibicity concentrates them in biological membranes. 6a log P=5.97, calculated from 6a structure using [25]. This means 6a accumulates ~1,000,000 times more in model-lipid octanol than water, which means 6a disproportionally accumulates in biological membranes, which drives it to high concentration, which permits significant intermolecular racemization. The protonable nitrogen atom of the 6a imidazole group pulls a proton off the stereogenic carbon of another 6a molecule, leaving a planar carboanion, and when a proton reattaches to this carbon there is an equal probability of it doing so from either side, and so there is a 50% chance that the stereochemistry changes. Thence, racemization proceeds at a faster rate than predicted by methodology of [112], the present state of the art in racemization theory/prediction. The same process can apply to 6b. Deuterium in place of hydrogen on the stereogenic carbon of 6b decreases the rate of this racemization, because a carbon-deuterium bond is stronger than a carbon-hydrogen bond (kinetic isotope effect, KIE) and this isotopologue of 6b is componentry to this invention. The difference in % cancer growth inhibition between 6a and 6b for each cell line at 10 μM drug dose (in NCI-60 one-dose testing) correlates with the difference in % cancer growth inhibition between 6a and 6b for each cell line at 1 μM drug dose (in NCI-60 five-dose testing). Pearson correlation coefficient, R=0.7919, p-value<0.00001, significant at p<0.05. This shows that there are cellular factors, which can vary between different cancer cell lines, determining the rate of 6a and/or 6b racemization. For example, this could be membrane volume and/or the level of expression of a racemase/epimerase enzyme(s), and/or an enzyme(s) that converts the drug into a form that can undergo enzyme-catalysed epimerisation. In NCI-60 one-dose testing at 10 μM, across cell lines tested, there is a positive correlation between % cancer growth inhibition of 6b and the product [(% cancer growth inhibition due to 6b)–(% cancer growth inhibition due to 6a)]. Pearson correlation coefficient, R=0.4167, p=0.000927, significant at p<0.05. Thus, when the anti-cancer performance of 6a is further behind the anti-cancer performance of 6b, anti-cancer performance of 6b is better. This suggests that for 6a to have greater anti-cancer activity, 6b needs to have less anti-cancer activity. Conversely, for 6b to have greater anti-cancer activity, 6a needs to have less anti-cancer activity. This is because what gives 6a its anti-cancer activity, racemization, takes away anti-cancer activity from 6b. Thus, in cancer cell lines that enable faster epimerization of 6a and 6b, there is greater 6a vs. 6b anti-cancer activity. This explains why, for NCI-60 one-dose (10 μM) assay, across the cell lines, there is a negative correlation (although not significant) between % cancer growth inhibition of 6a and the product [(% cancer growth inhibition due to 6b)–(% cancer growth inhibition due to 6a)]. Pearson correlation coefficient, R=−0.2136, but not significant at p<0.05. The same phenomenon (6a and 6b compete for anti-cancer activity, because what gives to 6a, racemization, takes away from 6b) is observed in NCI60 five-dose data at 1 μM. Across cell lines tested, there is a positive correlation between % cancer growth inhibition of 6b and the product [(% cancer growth inhibition due to 6b)–(% cancer growth inhibition due to 6a)]. Pearson correlation coefficient, R=0.3125, p=0.017949, significant at p<0.05. There is a negative correlation between % cancer growth inhibition of 6a and the product [(% cancer growth inhibition due to 6b)–(% cancer growth inhibition due to 6a)]. Pearson correlation coefficient, R=−0.4211, p=0.00111, significant at p<0.05.

FIG. 17: Mechanistic distinction from oligomycin enables therapeutic utility. Drawn molecules of this FIG. 17A) have an imidazole group, with a protonable nitrogen atom that can shuttle protons across the mitochondrial inner membrane (IM), dissipating the proton motive force (pmf, uncoupling). This figure presents experimental data (17B) using the HL-1 cardiac muscle cell line (cancer derived, but now very cardiac differentiated e.g. spontaneously contracts and beats like heart cells). Refer to the "Benchmark Drugs" first, which produce cellular effects well known to those of the art [3]. Oligomycin here refers to Oligomycin B. Oligomycin binds ATP synthase and blocks its forward, proton passing, ATP synthesizing, mode. This means less protons pass through ATP synthase, less pmf consumed per unit time, pmf increases, $\Psi_{IM}$ hyperpolarizes, electron flow along the respiratory chain slows, and $O_2$ consumption is decreased. Carbonilcyanide p-triflouromethoxyphenylhydrazone (FCCP) is an uncoupler that shuttles protons across the IM, dissipates pmf (as heat), pmf decreases, $\Psi_{IM}$ depolarizes, electron flow along the respiratory chain speeds, and $O_2$ consumption is increased. Distinct from oligomycin, three molecules of this figure increase, rather than decrease, $O_2$ consumption, which signifies their mechanistic distinction from oligomycin: they reduce ATP synthesis more by uncoupling than any inhibition of forward mode ATP synthase. They all contain a protonable nitrogen atom, with a basic pKa value conducive to uncoupling i.e. a pKa value reasonably close to {pH of mitochondrial intermembrane space+ pH of mitochondrial matrix)/2}. Although for VG025, its most conducive pKa is on its main ring rather than its imidazole. In a NADPH-linked sub-mitochondrial (SMP) assay of ATP synthesis, these molecules would decrease ATP production because they dissipate pmf as heat, and so there is less pmf available for ATP production. In interpretation, this uncoupling could be incorrectly attributed to inhibition of the forward mode of ATP synthase and so the full mechanistic distinction of these molecules from oligomycin could be missed. This has been the case with other imidazole containing compounds of this disclosure. Also with a protonable nitrogen in their imidazole, also with a pKa conducive to uncoupling, and wherein their inhibition of $F_1F_0$ ATP synthesis in the NADPH-linked SMP assay has been attributed to inhibiting the forward mode of ATP synthase [5-8]. But wherein their uncoupling is likely to be the more predominant factor (extrapolated from data of this figure) and wherein they do not inhibit the forward mode of ATP synthase much, if at all, in stark distinction to oligomycin. Uncoupling capability, which decreases with increased log P (refer next paragraph), explains why different molecules of the present figure exert different effects on $O_2$ consumption. The high log P value of VG019 means its uncoupling is minimal and its effect on $O_2$ consumption is zero (rounded) at a concentration (100 μM) it inhibits the reverse mode of ATP synthase, in stark distinction to oligomycin (3 μM), which dramatically decreases $O_2$ consumption (~40%), because, distinctly, it potently inhibits the forward mode of ATP synthase.

Log P=~3.2 is the optimal compromise for best passing a membrane: its hydrophobic core (selecting for high log P) and hydrophilic boundary layer (selecting for low log P) ([36], herein incorporated in its entirety). The imidazole containing molecules presented in this figure, and in this disclosure's drawings more generally, have log P>3.2 and present increased log P=decreased uncoupling. The uncoupling capability/liability of a molecule actually hinges on its intersection of pKa(s) and log P [36] but for the molecules in this disclosure's drawings, wherein the imidazole pKa values are, generally, all within a fairly narrow range, the more primary determinant to each molecule's uncoupling rate, relative to the others, is the molecule's log P value relative to the others.

The drawn molecules of this figure do inhibit the reverse mode of ATP synthase. When a respiratory chain inhibitor blocks electron flow, $\Psi_{IM}$ is maintained, not by proton pumping by the respiratory complexes, but by proton pumping by ATP synthase i.e. the reverse mode of ATP synthase. In the presented data, when the respiratory chain is blocked, the presented molecules depolarise $\Psi_{IM}$ because they block the reverse mode of ATP synthase. They do not affect $\Psi_{IM}$ by these means when the respiratory chain is operational. Because $\Psi_{IM}$ is not set/maintained by the reverse mode of ATP synthase in this case. Although the molecules with stronger uncoupling capability, they can shuttle more protons across the IM (dissipate more pmf) than the respiratory chain can increase its rate to replace, and they do depolarise $\Psi_{IM}$. When the respiratory chain is blocked, a stronger uncoupler in this figure depolarises TIM more. Because not only does it inhibit the generator of $\Psi_{IM}$ (reverse mode ATP synthase), it simultaneously erodes $\Psi_{IM}$ (uncoupling).

Oligomycin does inhibit the reverse mode of ATP synthase. But distinctly it inhibits its forward mode more [11]. So, using oligomycin, there is no margin to inhibit the reverse mode (anti-cancer), without adversely affecting cells using OXPHOS i.e. most normal cells. Contrast this with molecule VG019 of this figure, for example, which can inhibit the reverse mode of ATP synthase, and yet—in observed distinction to oligomycin—does not affect cells using OXPHOS: it does not change their $O_2$ consumption or $\Psi_{IM}$ (at 100 μM). This grants it, in distinction to oligomycin, anti-cancer selectivity. Other molecules of this disclosure have even greater cancer selectivity. For example, a preferred embodiment (refer disclosure section: "Preferred Embodiments") inhibits $F_1F_0$ ATP hydrolysis >5,556 times more than $F_1F_0$ ATP synthesis, in NADH-linked and NADPH-linked SMP assays [5-6], whilst oligomycin—inversely-inhibits $F_1F_0$ ATP hydrolysis less than $F_1F0$ ATP synthesis in such assays [11].

Computational calculations of log P and pKa were made using [25]. The data presented in this Figure is from [12] (herein incorporated in entirety), but the analysis/(re)interpretation is novel. As is the process/method of using these molecules as anti-cancer therapeutics, which is componentry to this invention. The imidazole of the drawn molecules is 4-yl. Permutations, with 5-yl instead, are also disclosed by this invention as anti-cancer therapeutics.

Example Embodiments of the Invention

The Drawings present embodiments of the invention. Further examples are enumerations of Markush Formulas (I), (II), (III), (IV), (V) and (VI), presented henceforth. Note: none of these formulae share Markush symbols, which can be, for example, symbols of the type: Rx, wherein x is an integer, well known to those of the art. They each have their own, as specified for each, in their own sections of this disclosure.

In this disclosure, the term "Formula [X]" is used when a statement is true for Formula (I), (II), (III), (IV), (V) and (VI), and all are being referred to independently. A compound of Formula [X] is a compound of Formula (I), or Formula (II), or Formula (III), or Formula (IV), or Formula (V), or Formula (VI), or any compound presented in this disclosure's Drawings.

This invention is described using these example embodiments but it isn't limited to these. These merely illustrate the invention. Compounds of other structures, which are identified as therapeutic inhibitors by the rationale and methods of the present invention, are also encompassed by the present invention.

Encompassed by this invention are methods of treating a subject suffering from a medical disease or disorder by administering an effective amount of at least one compound of Formula (I), (II), (III), (IV), (V) or (VI) or a pharmaceutically-acceptable salt, solvate, hydrate or prodrug thereof, or a pharmaceutical composition(s) comprising one or compounds of Formula (I), (II), (III), (IV), (V) or (VI), for use in a method of treatment of the human or animal body by therapy, particularly for use in a method of treating, ameliorating, preventing or combating a disease or disorder selected from (i) cancer;
(ii) cancer that metabolizes much of its glucose and/or glutamine to lactate, for example a cancer exhibiting the Warburg effect and/or a cancer that can be discriminated from surrounding tissue by PET imaging (e.g. $^{18}$F-FDG PET);
(iii) cachexia, cancer driven cachexia or weight loss;
(iv) disease or disorder that causes a higher than normal body temperature such as high environmental temperature, ingesting an uncoupler (e.g. 2,4-dinitrophenol), infection, sepsis, stroke, fever, pyrexia, hyperpyrexia, hyperthermia, malignant hyperthermia, neuroleptic malignant syndrome, serotonin syndrome, thyroid storm, heatstroke, thermoregulatory disorder(s), Kawasaki syndrome, drug or drug withdrawal induced hyperthermia, idiosyncratic drug reaction, fever of unknown or uncertain origin, reaction to incompatible blood product(s), metabolic disorder(s), cancer, injury;
(v) Tumour Associated Macrophages (TAMs) or any macrophage associated disease or disorder such as Macrophage Activation Syndrome (MAS), HIV, AIDS, HIV-associated neurocognitive disorders (HAND), HIV associated cancers, AIDS-defining cancers, non-AIDS defining cancers;
(vi) virus neuroinvasion via macrophages, as used for example by HIV and SARS coronavirus;
(vii) neurocognitive or neurodegenerative diseases/disorders, for example those caused by a virus;
(viii) acute or chronic or systemic inflammation or any inflammatory disease/disorder/syndrome or any autoinflammatory disease/disorder/syndrome or any autoimmune disease/disorder/syndrome;
(ix) low or less than desired metabolic/bioenergetic efficiency in a subject, or low or less than desired physical or mental performance, or low or less than desired body weight;
(x) diseases or disorders treatable by conferring hypothermia in a subject for some medical or other purpose which can include slowing a chemical reaction(s) rate in a subject for therapeutic benefit, preventing/minimizing brain and/or tissue damage, deep hypothermic circulatory arrest for surgery, hypothermia for a surgical purpose, hypothermia for cardiac and/or cardiovascular surgery and/or brain surgery (neurosurgery), Emergency Preservation and Resuscitation (EPR), preserving detached body parts such as limbs and/or organs (for example during organ storage and/or transplant), protective hypothermia, targeted temperature management, therapeutic hypothermia, hypothermia therapy for neonatal encephalopathy, birth asphyxia, haemorrhage, hypovolemia, decompression sickness, burn injury(s) including skin burn, inflammation, allergic reaction, anaphylaxis, tissue/organ rejection, hypoxia, hypoxemia, anoxemia, anoxia, anemia, hypervolemia, altitude sickness, obstructed airway, asthma attack, hypoxia in a body/tissue/organ, hypoglycemia, reperfusion injury (ischemia-reperfusion injury), upon release of a ligature or tourniquet, uraemia, crush syndrome, compartment syndrome, traumatic brain and/or spinal cord injury, major trauma, infection, bacterial and/or viral infection(s) (e.g. meningitis), sepsis, septic shock, ischemic brain/heart/kidney injury, neuroprotection and/or cardioprotection and/or tissue protection during/after a stroke and/or ischemia and/or cardiac arrest and/or resuscitation and/or a period(s) of poor blood flow anywhere in a subject;
(xi) poisoning by a toxic amount of a compound(s) in a subject e.g. carbon monoxide/methanol/heavy metal/pesticide poisoning, snake/spider/bee/insect/lizard venom, metabolic poison(s), bacterial toxin(s), endotoxemia or drug/substance overdose e.g. heroin, ethanol, prescription medication(s) or over the counter medication(s);
(xii) accelerated aging disease or progeroid syndrome including Werner syndrome, Bloom syndrome, Rothmund-Thomson syndrome, Cockayne syndrome, xeroderma pigmentosum, trichothiodystrophy, combined xeroderma pigmentosum-Cockayne syndrome, restrictive dermopathy, Wiedemann-Rautenstrauch syndrome, Hutchinson-Gilford progeria syndrome (progeria);
(xiii) disease or disorder of ageing (incidence increases with increased age/senescence) and/or a disease/disorder associated with elevated reactive oxygen species including degenerative diseases, neurodegenerative diseases, amyotrophic lateral sclerosis (ALS), Parkinson's disease, Alzheimer's disease, Huntington's disease, spinocerebellar ataxias, Friedreich's ataxia, dementia, Batten disease, polyglutamine diseases, osteoporosis, atherosclerosis, cardiovascular disease, myocardial infarction, cerebrovascular disease, stroke, heart failure, chronic obstructive pulmonary disease (COPD), hypertension, arthritis, cataracts, type 2 diabetes, andropause, sarcopenia, age-related macular degeneration (AMD), hearing loss, movement disability, cancer;
(xiv) aging, wherein these compounds slow ageing, extend lifespan and healthspan;
(xv) skin aging;
(xvi) cardiovascular diseases and conditions associated with ischemia and associated conditions including, without limitation, ischemia-reperfusion injury, myocardial ischemia, ischemic heart disease, chronic stable angina pectoris, myocardial infarction, congestive heart failure, an acute coronary syndrome, muscle cell damage, necrosis, cardiac arrhythmias, non-Q wave MI, unstable angina, high blood pressure, coronary artery disease, ischemic hypoxia, cyanosis, gangrene, acute limb ischemia, stroke, ischemic stroke, brain ischemia, vascular dementia, transient ischemic attack (TIA), ischemic colitis, mesenteric ischemia, angina pectoris, ischemic heart disease, ischemic neuropathy, hypoxic-ischemic encephalopathy, cerebral hypoxia, brain hypoxia, ischemia resulting from vascular occlusion, cerebral infarction, stroke and related cerebral vascular diseases (including cerebrovascular accident and transient ischemic attack), muscle cell damage, necrosis; or
(xvii) acute inflammation, chronic inflammation, systemic inflammation, inflammation because of infection or foreign bodies or injury or chemical or toxin or drug or stress or frostbite or burn or ionising radiation, inflammatory diseases/disorders/syndromes, Macrophage Activation Syndrome (MAS), autoinflammatory diseases/disorders/syndromes, age-related chronic inflammatory diseases ("inflammaging"), autoimmune diseases/disorders/syndromes, diseases/disorders of the innate immune system, sore throat, sore throat associated with cold or flu or fever, high-intensity exercise associated inflammation, ulcerative colitis, inflammatory bowel disease (IBD), irritable bowel syndrome (IBS), rheumatoid arthritis, osteoarthritis, psoriatic arthritis, atopic dermatitis, allergic airway inflammation, asthma, inflammation associated depression, exercise-induced acute inflammation, atherosclerosis, allergy, hay fever, anaphylaxis, inflammatory myopathies, drug-induced inflammation, systemic inflammatory response syndrome, sepsis-related multiple organ dysfunction/multiple organ failure, microbial infection, acute brain/lung/hepatic/renal injuries, acne vulgaris, celiac disease, celiac sprue, chronic prostatitis, colitis, diverticulitis, glomerulonephritis, hidradenitis suppurativa, hypersensitivities, interstitial cystitis, Mast Cell Activation Syndrome, mastocytosis, otitis, pelvic inflammatory disease (PID), reperfusion injury, rheumatic fever, rhinitis, sarcoidosis, transplant rejection, parasitosis, eosinophilia, type III hypersensitivity, ischaemia, chronic peptic ulcer, tuberculosis, Crohn's disease, hepatitis, chronic active hepatitis, immune hepatitis, ankylosing spondylitis, diverticulitis, fibromyalgia, systemic lupus erythematous (SLE), Alzheimer's disease, Parkinson's disease, neurodegenerative disease, cardiovascular disease, chronic obstructive pulmonary disease, bronchitis, acute bronchitis, appendicitis, acute appendicitis, bursitis, colitis, cystitis, dermatitis, encephalitis, gingivitis, meningitis, infective meningitis, myelitis, nephritis, neuritis, periodontitis, chronic periodontitis, phlebitis, prostatitis, RSD/CRPS, rhinitis, sinusitis, chronic sinusitis, tendonitis, testiculitis, tonsillitis, urethritis, vasculitis, respiratory bronchiolitis-associated interstitial lung disease and desquamative interstitial pneumonia, interstitial lung disease, Lofgren syndrome, Heerfordt syndrome, monocytosis, liver fibrosis, steatohepatitis, nonalcoholic steatohepatitis, silicosis, histiocytoses, Langerhans' cell histiocytosis, haemophagocytic lymphohistiocytosis, pulmonary langerhans cell histiocytosis, obesity, type II diabetes, gout, pseudogout, organ transplant rejection, epidermal hyperplasia, chronic fatigue syndrome, graft versus host disease (GVHD), lymphadenopathy, familial mediterranean fever (FMF), TNF receptor-associated periodic syndrome (TRAPS), Hyperimmunoglobulinemia D with recurrent fever syndrome (HIDS), cryopyrin associated periodic syndrome (CAPS), Blau syndrome, Majeed syndrome, deficiency of interleukin-1 receptor antagonist (DIRA), mevalonate kinase deficiency, pyogenic-arthritis-pyoderma gangrenosum and acne syndrome (PAPA), periodic fever aphthous stomatitis pharyngitis adenitis (PFAPA) syndrome, Behcet's disease, Still's disease, Crohn's disease, Schnitzler's syndrome, Sweet's syndrome, NLRP12-associated autoinflammatory disorders, deficiency of interleukin-1 receptor antagonist (DIRA), pyoderma gangrenosum, cystic acne, aseptic arthritis, periodic Fever Associated with mevalonate kinase deficiency (hyperimmunoglobulin D Syndrome), Pyogenic Arthritis Pyoderma Gangrenosum Acne (PAPA) syndrome, Periodic Fever Aphthous Stomatitis, Pharyngitis and Adenopathy (PFAPA) syndrome, Adult-Onset Still's Disease (AOSD), Systemic Juvenile Idiopathic Arthritis (sJIA), Chronic Recurrent Multifocal Osteomyelitis (CRMO), Synovitis Acne Pustulosis Hyperostosis Osteitis (SAPHO) syndrome, Cryopyrin associated Periodic Syndrome (CAPS), Familial cold auto inflammatory syndrome (FCAS), Muckle-Wells syndrome (MWS), Familial cold urticarial, Neonatal onset multisystemic inflammatory disorder (NOMID), hereditary Periodic Fever Syndromes, Periodic Fever Syndromes, systemic autoinflammatory diseases, Addison's disease, Agammaglobulinemia, Alopecia areata, Amyloidosis, Ankylosing spondylitis, Anti-GBM/Anti-TBM nephritis, Antiphospho lipid syndrome, autoimmune angioedema, autoimmune dysautonomia, autoimmune encephalomyelitis, autoimmune hepatitis, autoimmune inner ear disease (AIED), autoimmune myocarditis, autoimmune pancreatitis, autoimmune retinopathy, autoimmune urticaria, axonal & neuronal neuropathy (AMAN), Baló disease, Behcet's disease, benign mucosal pemphigoid, Bullous pemphigoid, Castleman disease (CD), Celiac disease, Chagas disease, chronic inflammatory demyelinating polyneuropathy (CIDP), chronic recurrent multifocal osteomyelitis (CRMO), Churg-Strauss, Cicatricial pemphigoid, Cogan's syndrome, cold agglutinin disease, congenital heart block, coxsackie myocarditis, CREST syndrome, Berger's disease, dermatitis herpetiformis, dermatomyositis, Devic's disease (neuromyelitis optica), discoid lupus, Dressler's syndrome, endometriosis, eosinophilic esophagitis (EoE), eosinophilic fasciitis, erythema nodosum, essential mixed cryoglobulinemia, Evans syndrome, fibromyalgia, fibrosing alveolitis, giant cell arteritis (temporal arteritis), giant cell myocarditis, glomerulonephritis, Goodpasture's syndrome, granulomatosis with polyangiitis, Graves' disease, Guillain-Barre syndrome, Hashimoto's thyroiditis, hemolytic anemia, immune hemolytic anemia, Henoch-Schonlein purpura (HSP), Herpes gestationis or pemphigoid gestationis (PG), hypogammalglobulinemia, IgA Nephropathy, IgG4-related sclerosing disease, Immune thrombocytopenic purpura (ITP), Inclusion body myositis (IBM), Interstitial cystitis (IC), juvenile arthritis, juvenile diabetes (Type 1 diabetes), juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multiple sclerosis, Myasthenia gravis, Myositis, Narcolepsy, Neuromyelitis optica, Neutropenia, Ocular cicatricial pemphigoid, Optic neuritis, Palindromic rheumatism (PR) PANDAS, Paraneoplastic cerebellar degeneration (PCD), Paroxysmal nocturnal hemoglobinuria (PNH), Parry Romberg syndrome, Pars planitis (peripheral uveitis), Parsonnage-Turner syndrome, Pemphigus, peripheral neuropathy, perivenous encephalomyelitis, Pernicious anemia (PA), POEMS syndrome, Polyarteritis nodosa, Polyglandular syndromes type I, II, III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Type 1 diabetes, Ulcerative colitis (UC), Undifferentiated connective tissue disease (UCTD), Uveitis, Vasculitis, Vitiligo, Wegener's granulomatosis (or Granulomatosis with Polyangiitis (GPA)), idiopathic thrombocytopenia purpura, splenomegaly.

Example (I)

Summary of Formula (I)

This invention embodiment relates to compounds having the following formula:

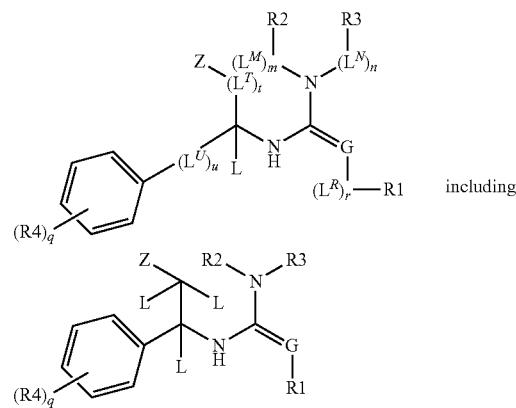

Formula (I)

including

-continued

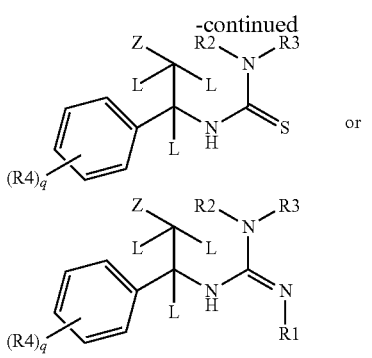

or a pharmaceutically-acceptable salt, solvate, hydrate or prodrug thereof, wherein:

- $L^M$, $L^N$, $L^U$, $L^T$ and $L^R$ are each independently selected from a single bond or $CR^V_2$, wherein each $R^V$ is independently selected from hydrogen, alkyl, or substituted alkyl (non-limiting examples: $CF_3$, $CCl_3$), or deuterated alkyl (non-limiting example: $CD_3$), or aminoalkyl, or thioalkyl, or alkoxy, or halogen, or haloalkyl, or haloalkoxy;
- m, n, u, t, and r are each independently selected from 0, 1, 2, 3 and 4;
- L is independently at each point of its use alkyl, or substituted alkyl (non-limiting examples: $CF_3$, $CCl_3$), or deuterated alkyl (non-limiting example: $CD_3$), or aminoalkyl, or thioalkyl, or alkoxy, or halogen, or haloalkyl, or haloalkoxy or any atom or isotope permitted by valence (including any accompanying hydrogens by valence e.g. (non-limiting) OH, $NH_2$, SH, $SiH_3$, $PH_2$ etc.);
- $R_1$ is $R_{extra}$, hydrogen, cyano, $-SO_2R_8$, $-C(=O)R_9$, or heteroaryl;
- $R_{extra}$ is selected from L (defined earlier), alkyl, substituted alkyl, alkenyl, substituted alkenyl, alkylene, substituted alkylene, alkynyl, substituted alkynyl, alkoxy, thioalkyl, aminoalkyl, carbamyl, sulfonyl, sulfonamide, cycloalkyl, (cycloalkyl)alkyl, hydroxyalkyl, haloalkyl, haloalkoxy, alkoxyalkyl, morpholinylalkyl, aryl, arylalkyl, heterocyclo, heteroaryl, (heterocyclo)alkyl, acyl, alkoxycarbonyl, substituted amino;
- $R_2$ is (i) independently hydrogen, L (defined earlier), alkyl, or substituted alkyl, or (ii) taken together with $R_3$ forms a heterocyclo;
- $R_3$ is (i) independently alkyl, substituted alkyl, L, alkylthio, aminoalkyl, carbamyl, $B_B$-aryl, $B_B$-heterocyclo, $B_B$-heteroaryl, or $B_B$-cycloalkyl, or (ii) taken together with $R_2$ forms a heterocyclo;
- Z is heteroaryl;
- $B_B$ is a bond, $C_{1-4}$alkylene, $C_{2-4}$alkenylene, substituted $C_{1-4}$alkylene, substituted $C_{2-4}$alkenylene, $-C(=O)NR_{19}-$, $-C_{1-4}$alkylene-$C(=O)NR_{19}-$, or substituted $C_{1-4}$alkylene-$C(=O)NR_{19}-$;
- $R_4$ at each occurrence is selected independently of each other $R_4$ from the group consisting of halogen, alkyl, haloalkyl, nitro, cyano, haloalkoxy, $OR_{25}$, $SR_{25}$, $NR_{25}R_{26}$, $NR_{25}SO_2R_{27}$, $SO_2R_{27}$, $SO_2NR_{25}R_{26}$, $CO_2R_{26}$, $C(=O)R_{26}$, $CHNR_{25}R_{26}$, $OC(=O)R_{25}$, $-OC(=O)NR_{25}R_{26}$, $NR_{25}C(=O)R_{26}$, $NR_{25}CO_2R_{26}$, aryl, heteroaryl, heterocyclo and cycloalkyl;
- $R_8$ is alkyl, substituted alkyl, aryl, or heteroaryl;
- $R_9$ is $-NR_{10}R_{11}$, alkyl, substituted alkyl, alkoxy, alkylthio, cycloalkyl, aryl, heteroaryl, heterocycle, or $-CO_2R_{12}$;
- $R_{10}$ and $R_{11}$, are (i) independently selected from hydrogen, alkyl, substituted alkyl, alkoxy, heterocyclo, cycloalkyl, aryl, and heteroaryl; or (ii) taken together form a hetero cyclo or heteroaryl;
- $R_{12}$ and $R_{19}$ are hydrogen or alkyl;
- $R_{25}$ and $R_{26}$ are independently selected from hydrogen, alkyl, or substituted alkyl, or taken together form a heterocyclo or heteroaryl ring;
- $R_{27}$ is alkyl or substituted alkyl, and
- q is 0, 1, 2, or 3.

Preferred Compounds of Formula (I)

Preferred methods are to use, and preferred compounds are, compounds with the following formula, or pharmaceutically-acceptable salts, solvates, hydrates or prodrugs thereof,

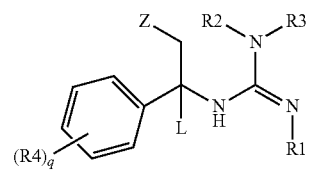

and even more preferred methods are to use, and preferred compounds are, compounds with the following formula, or pharmaceutically-acceptable salts, solvates, hydrates or prodrugs thereof,

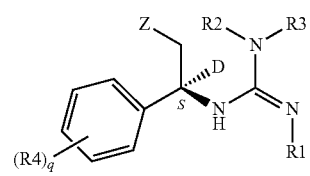

other preferred methods are to use, and preferred compounds are, compounds with the following formula, or pharmaceutically-acceptable salts, solvates, hydrates or prodrugs thereof,

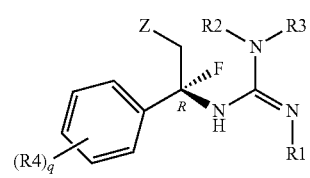

in which, in the preceding three structures shown:

- L is hydrogen, or methyl, or $CF_3$, or $CD_3$, or deuterium (D);
- D is deuterium (enrichment, for example, exceeding 40% deuterium incorporation at shown position, and optionally at other positions also);
- S symbolises the S stereoisomer, for example, in enantiomeric excess (ee) exceeding 70%;
- R symbolises the R stereoisomer, for example, in enantiomeric excess (ee) exceeding 70% (following IUPAC naming rules the chiral carbon of the fluorine (F)

analogue is labelled R rather than S, but note that the arrangement of which bond is up, bold wedge, and down, dashed, around the stereogenic carbon is the same as the preceeding structures labelled S at their chiral carbon, it is this molecule arrangement that is salient, and that is disclosed, rather than a mere label in a naming convention. This clarification won't be repeated at every place to which it applies in this disclosure, at every point at which there is an F in place of an H on the chiral carbon, or any other higher order of priority atom (by IUPAC rules), e.g. (non-limiting) any other halogen, because this clarification here itself is likely superfluous: all this is very clear to someone of the art. So, when there is said to be an enantiomeric excess (ee) in this disclosure in relation to this example embodiment, Formula (I), it applies to this molecular configuration, this arrangement of solid/dashed wedges, about the chiral carbon, whether this be S or R by IUPAC naming rules);

Z is triazolyl optionally substituted with one to two $R_7$ or imidazolyl optionally substituted with one to two $R_7$ and/or having fused thereto a benzene ring in turn optionally substituted with one to two $R_7$;

$R_1$ is cyano or —C(=O)$R_9$;

$R_2$ is hydrogen, alkyl, or benzyl;

$R_3$ is aryl or arylalkyl optionally substituted with alkyl, halogen, trifluoromethyl, OCF$_3$, cyano, nitro, amino, hydroxy, or methoxy;

$R_4$ is halogen, alkyl, trifluoromethyl, or OCF$_3$;

$R_7$ is alkyl, carbamyl or carbamylC$_{1-4}$alkyl;

$R_9$ is —NR$_{10}$R$_{11}$, alkyl, substituted alkyl, alkoxy, alkylthio, cycloalkyl, aryl, heteroaryl, heterocycle, or —CO$_2$R$_{12}$;

$R_{10}$ and $R_{11}$ are (i) independently selected from hydrogen, alkyl, substituted alkyl, alkoxy, heterocyclo, cycloalkyl, aryl, and heteroaryl; or (ii) taken together form a heterocyclo or heteroaryl;

$R_{12}$ is hydrogen or alkyl; and q is 0, 1, 2, or 3.

Further preferred are compounds having the following formula, or pharmaceutically-acceptable salts, solvates, hydrates or prodrugs thereof,

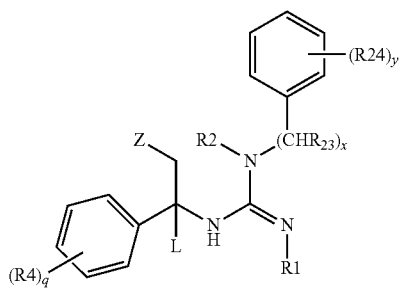

and even more preferred are compounds having the following formula, or pharmaceutically-acceptable salts, solvates, hydrates or prodrugs thereof,

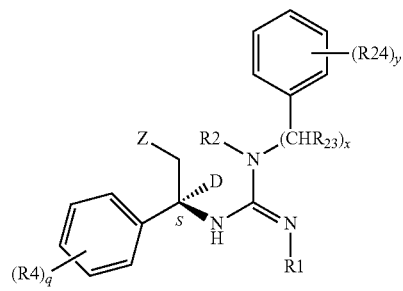

other preferred compounds are those with the following formula, or pharmaceutically-acceptable salts, solvates, hydrates or prodrugs thereof,

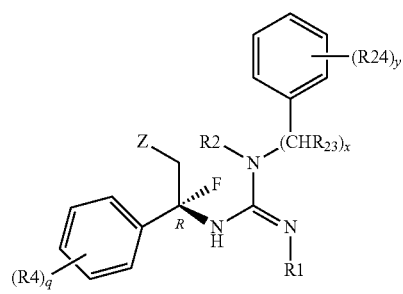

in which, for the preceding three structures shown:

z is 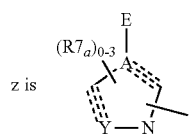

and more preferably

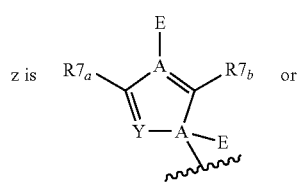

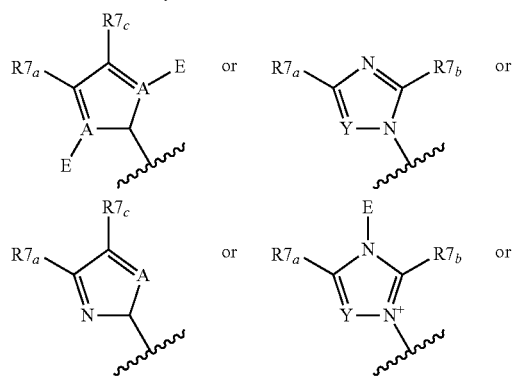

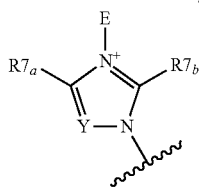

L is hydrogen, or methyl, or CF$_3$, or CD$_3$, or deuterium (D);

D is deuterium (enrichment, for example, exceeding 40% deuterium incorporation at shown position, and optionally at other positions also);

S symbolises the S stereoisomer, for example, in enantiomeric excess (ee) exceeding 70%;

A is nitrogen (N), or N$^+$, or carbon;

E is absent, or alkyl, or substituted alkyl, or deuterated alkyl, or aminoalkyl, or thioalkyl, or alkoxy or any atom or isotope permitted by valence (including any accompanying hydrogens by valence e.g. (non-limiting) OH, NH$_2$, SH, SiH$_3$, PH$_2$ etc.), for example hydrogen, deuterium or fluorine;

Y is N, CH or CR$_{7c}$;

R$_1$ is cyano or —C(=O)R$_9$;

R$_2$ is hydrogen or C$_{1-4}$alkyl;

R$_4$ is halogen, C$_{1-4}$alkyl, trifluoromethyl; or OCF$_3$;

R$_{7a}$, R$_{7b}$, and R$_{7c}$ are independently E (defined earlier), hydrogen, alkyl, carbamyl or carbamylC$_{1-4}$alkyl, or R$_{7a}$ and R$_{7c}$ join to form an optionally substituted fused phenyl ring;

R$_9$ is —NR$_{10}$R$_{11}$, alkyl, substituted alkyl, alkoxy, alkylthio, cycloalkyl, aryl, heteroaryl, heterocycle, or —CO$_2$R$_{12}$;

R$_{10}$ and R$_{11}$ are (i) independently selected from hydrogen, alkyl, substituted alkyl, alkoxy, heterocyclo, cycloalkyl, aryl, and heteroaryl; or (ii) taken together form a heterocyclo or heteroaryl;

R$_{12}$ is hydrogen or alkyl;

R$_{23}$ is hydrogen, alkyl, hydroxyalkyl, or phenyl;

R$_{24}$ is alkyl, halogen, trifluoromethyl, cyano, halogen, hydroxy, OCF$_3$, methoxy, phenyloxy, benzyloxy, cyano, or acyl, or two R$_{24}$ groups join to form a fused cycloalkyl or benzene ring;

q is 1 or 2;

x is 0, 1, or 2; and y is 0, 1, 2, or 3.

More preferred are compounds having the following formula, or pharmaceutically-acceptable salts, solvates, hydrates or prodrugs thereof,

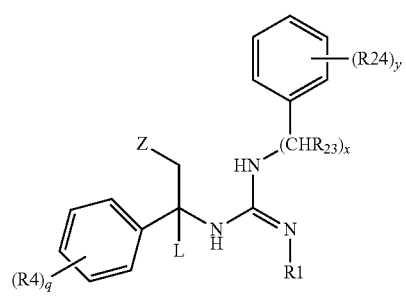

and even more preferred are compounds having the following formula, or pharmaceutically-acceptable salts, solvates, hydrates or prodrugs thereof,

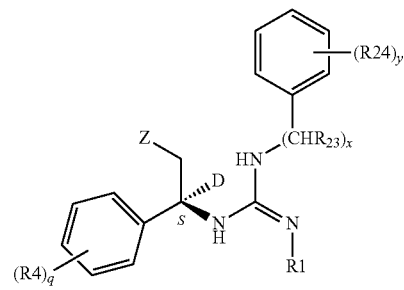

other preferred compounds are those with the following formula, or pharmaceutically-acceptable salts, solvates, hydrates or prodrugs thereof,

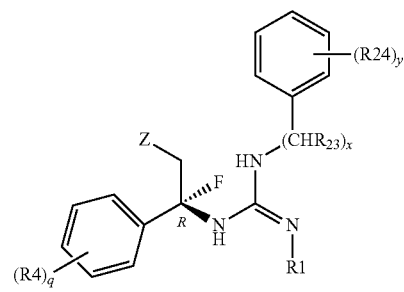

in which, for the preceding three structures shown:

z is 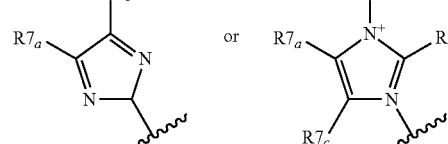

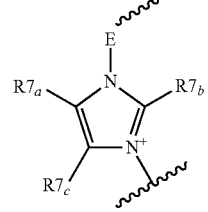

L is hydrogen, or methyl or deuterium;

D is deuterium (enrichment, for example, exceeding 40% deuterium incorporation at shown position, and optionally at other positions also);

S symbolises the S stereoisomer, for example, in enantiomeric excess (ee) exceeding 70%;

R$_1$ is cyano or —C(=O)R$_9$;

R$_4$ is halogen, C$_{1-4}$alkyl, trifluoromethyl, or OCF$_3$;

R$_{7c}$ is hydrogen or R$_7$ and R$_{7c}$ join to form a fused benzene ring optionally substituted with $C_{1-4}$alkyl or —$(CH_2)_{1-2}$—NHC(=O)$C_{1-4}$alkyl,
$R_{7b}$ is hydrogen, $C_{1-4}$alkyl, or —$(CH_2)_{1-2}$—NHC(=O)$C_{1-4}$alkyl;
$R_9$ is a) —$NR_{10}R_{11}$
b) $C_{1-8}$alkyl optionally substituted with one to two of:
  i) $SR_{13}$, $OR_{13}$, $NR_{13a}R_{13b}$, halogen, trifluoromethyl, $CO_2R_{13a}$, and C(=O)$NR_{13a}R_{13b}$;
  ii) cycloalkyl optionally substituted with one to two of C(=O)H, $C_{1-4}$acyl, alkenyl, carbamyl, and/or phenyl in turn optionally substituted with halogen;
  iii) phenyl or napthyl optionally substituted with one to two of halogen, nitro, amino, alkyl, hydroxy, $C_{1-4}$alkoxy, or having fused thereto a five or six membered heterocyclo;
  iv) pyridinyl, thiophenyl, furanyl, tetrahydrofuranyl, or azepinyl, optionally substituted with alkyl or having fused thereto a five to six membered carbocyclic ring optionally substituted with keto or $C_{1-4}$alkoxy;
c) $C_{1-4}$alkoxy;
d) $C_{1-4}$alkylthio;
e) $CO_2$alkyl;
f) 3 to 6 membered cycloalkyl optionally having up to four substituents selected from alkyl, halogen, cyano, alkenyl, acyl, alkylthio, carbamyl, and/or phenyl in turn optionally substituted with halogen; or having an aryl fused thereto;
g) phenyl optionally substituted with one to four of halogen, cyano, trifluoromethyl, nitro, hydroxy, $C_{1-4}$alkoxy, haloalkoxy, $C_{1-6}$alkyl, $CO_2$alkyl, $SO_2$alkyl, $SO_2NH_2$, amino, NH($C_{1-4}$alkyl), N($C_{1-4}$alkyl)$_2$, NHC(=O)alkyl, C(=O)alkyl, and/or $C_{1-4}$ alkyl in turn optionally substituted with one to three of trifluoromethyl; hydroxy, cyano, phenyl, pyridinyl; and/or a five or six membered heteroaryl or heterocyle in turn optionally substituted with keto or having a benzene ring fused thereto;
h) pyridinyl, thiazolyl, furanyl, thiophenyl, and pyrrolyl optionally substituted with one to two of halogen, alkyl, and phenyl in turn optionally substituted with halogen or trifluoromethyl;
$R_{10}$ is hydrogen, alkyl, or alkoxy;
$R_{11}$ is alkyl, substituted alkyl, alkoxy, heterocyclo, cycloalkyl, aryl, or heteroaryl;
or $R_{10}$ and $R_{11}$, taken together form a heterocyclo or heteroaryl;
$R_{23}$ is hydrogen, alkyl, hydroxyalkyl, or phenyl;
$R_{24}$ is alkyl, halogen, trifluoromethyl, cyano, halogen, hydroxy, $OCF_3$, methoxy, phenyloxy, benzyloxy, cyano, or acyl, or two $R_{24}$ groups join to form a fused cycloalkyl or benzene ring;
q is 0, 1, or 2;
x is 0 or 1; and
y is 0, 1, or 2.

Most preferred are compounds as immediately defined above wherein, $R_1$ is cyano or —C(=O)$R_9$; $R_9$ is optionally substituted phenyl or phenyl $C_{1-4}$alkyl; x is 0 or 1; and q and y are 1 or 2. For this preferred structure, its S stereoisomer is preferred. And further preferred is for its L group to be deuterium.

Example Embodiments of Formula (I)

Compounds from [5-6], selected as specific anti-cancer therapeutics by the invention of this disclosure, selected because they inhibit the reverse, more than the forward, mode of ATP synthase. $EC_{50}$ and $IC_{50}$ used interchangeably. $EC_{50}$ values for $F_1F_0$ ATP hydrolysis, and $F_1F_0$ ATP synthesis, in NADH-linked and NADPH-linked sub-mitochondrial (SMP) assays respectively, sourced from [5-6], are presented. [5-6] refer to these $EC_{50}$ values as $IC_{50}$ values for inhibiting $F_1F_0$ ATP hydrolase (reverse mode) and $F_1F_0$ ATP synthase (forward mode). However, this in incorrect. Because, as identified by the invention of this disclosure, explained herein, although these molecules inhibit $F_1F_0$ ATP hydrolase, their reducing of $F_1F_0$ ATP synthesis is not (predominantly) because of inhibiting $F_1F_0$ ATP synthase, but by uncoupling. More preferred molecules of this invention have a low $EC_{50}$ for $F_1F_0$ ATP hydrolysis, and a higher $EC_{50}$ for $F_1F_0$ ATP synthesis, and their ratio difference is large.

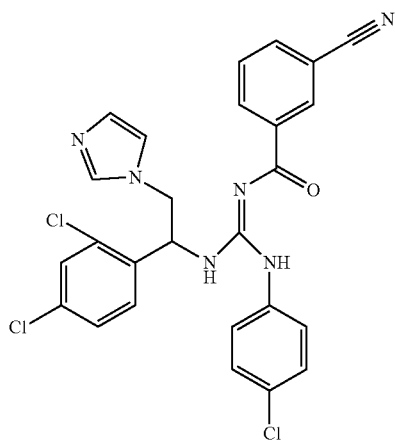

Racemate
$EC_{50} F_1F_0$ ATP hydrolase = 0.333 ± 0.02 (μM)
$EC_{50} F_1F_0$ ATP synthesis > 100 (μM)
$EC_{50}$ Ratio > 3,030

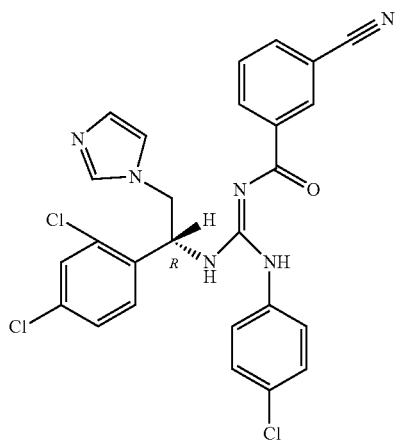

R stereoisomer
$EC_{50} F_1F_0$ ATP hydrolase > 100 (μM)
$EC_{50} F_1F_0$ ATP synthesis > 100 (μM)

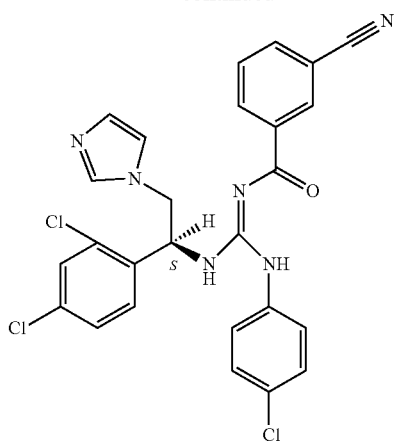

S Stereoisomer Preferred
$EC_{50} F_1F_0$ ATP hydrolasee = 0.018 ± 0.016 (μM)
$EC_{50} F_1F_0$ ATP synthesis > 100 (μM)
$EC_{50}$ Ratio > 5,556
In rat: orally bioavailable (47%), i.v. half-life (2.1 hours),
$C_{max}$ = 21 μM, volume of distribution $V_{SS}$ = 2.37 L/kg Further example embodiments of Formula (I), with SMP data, reinterpreted (as aforementioned, these molecules don't significantly inhibit $F_1F_0$ ATP synthase but do reduce $F_1F_0$ ATP synthesis by uncoupling), from [5], $EC_{50} F_1F_0$ ATP hydrolase = 0.082 ± 0.03 (μM)
$EC_{50} F_1F_0$ ATP synthesis > 100 (μM)
$EC_{50}$ Ratio > 1,220

$EC_{50} F_1F_0$ ATP hydrolase = 2.41 (μM)
$EC_{50} F_1F_0$ ATP synthesis > 100 (μM)
$EC_{50}$ Ratio > 41.5

$EC_{50} F_1F_0$ ATP hydrolase = 0.71 ± 0.34 (μM)
$EC_{50} F_1F_0$ ATP synthesis > 100 (μM)
$EC_{50}$ Ratio > 141

$EC_{50} F_1F_0$ ATP hydrolase = 0.60 ± 0.16 (μM)
$EC_{50} F_1F_0$ ATP synthesis > 100 (μM)
$EC_{50}$ Ratio > 167

Further Examples [5]

| R1 | R2 | EC$_{50}$ F$_1$F$_0$ ATP hydrolase (µM) |
|---|---|---|
| 4-Cl | CN | 8.8 |
| 2-Cl | CN | 2.23 |
| 2,3-Cl$_2$ | CN | 2.49 ± 0.72 |
| 3-Cl | CN | 9.17 |
| 4-Cl | C(=O)4-CN—Ph | 0.28 |
| 4-Cl | C(=O)Et | 2.27 |

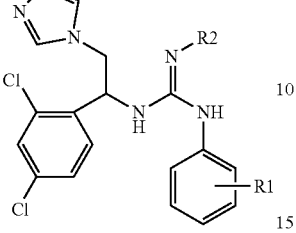

Further example, with synthesis step, effectively without a protonable element in its imidazole, which diminishes the molecule's ability to uncouple the proton motive force:

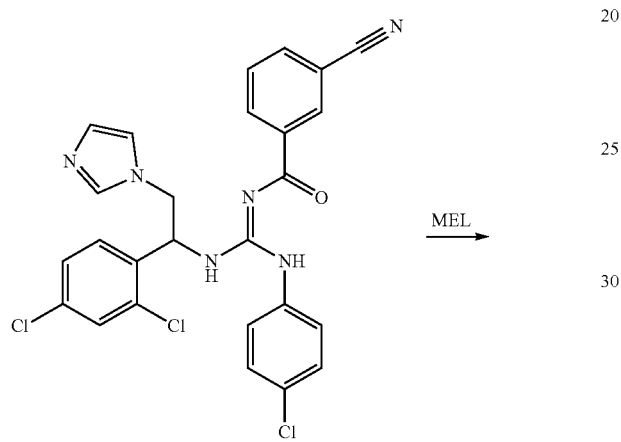

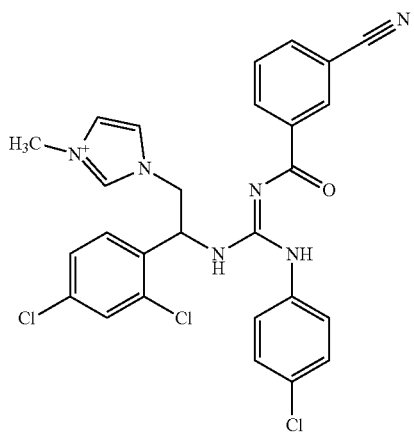

General Compound Synthesis

A general synthetic route applicable to some compounds of the invention is set out in Scheme 1 below.

Scheme 1

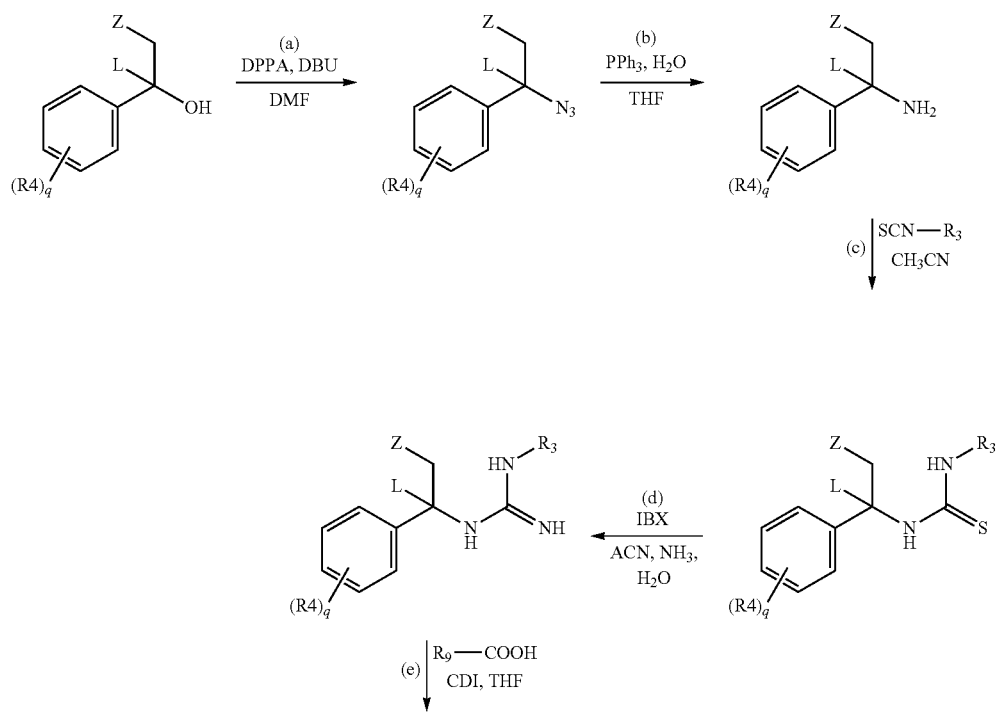

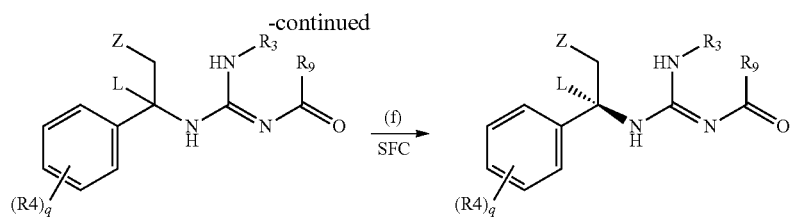

The person skilled in the art is able to make modifications to this general synthetic route, based on the common general knowledge, the chemical reaction literature, and/or the content of prior art disclosures cited herein, in order to synthesise compounds of the invention where necessary.

Specific Compound Synthesis

Racemate 19a [5] was synthesised by the following synthesis route, Scheme 2, and separated into component stereoisomers using superfluid chromatography (SFC). Starting reagents for this synthesis were sourced commercially using the LabNetwork (www.labnetwork.com), which is a website that permits one to search for chemical suppliers for inputted structures/chemical names e.g. there are numerous suppliers listed on LabNetwork for the starting compound, Compound 1.

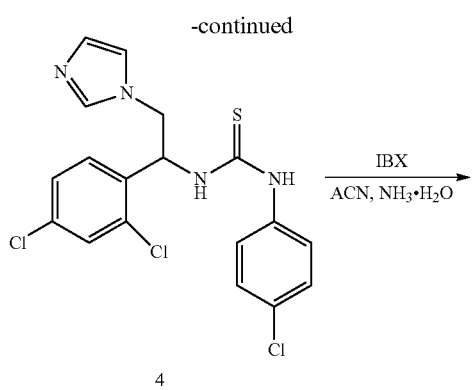

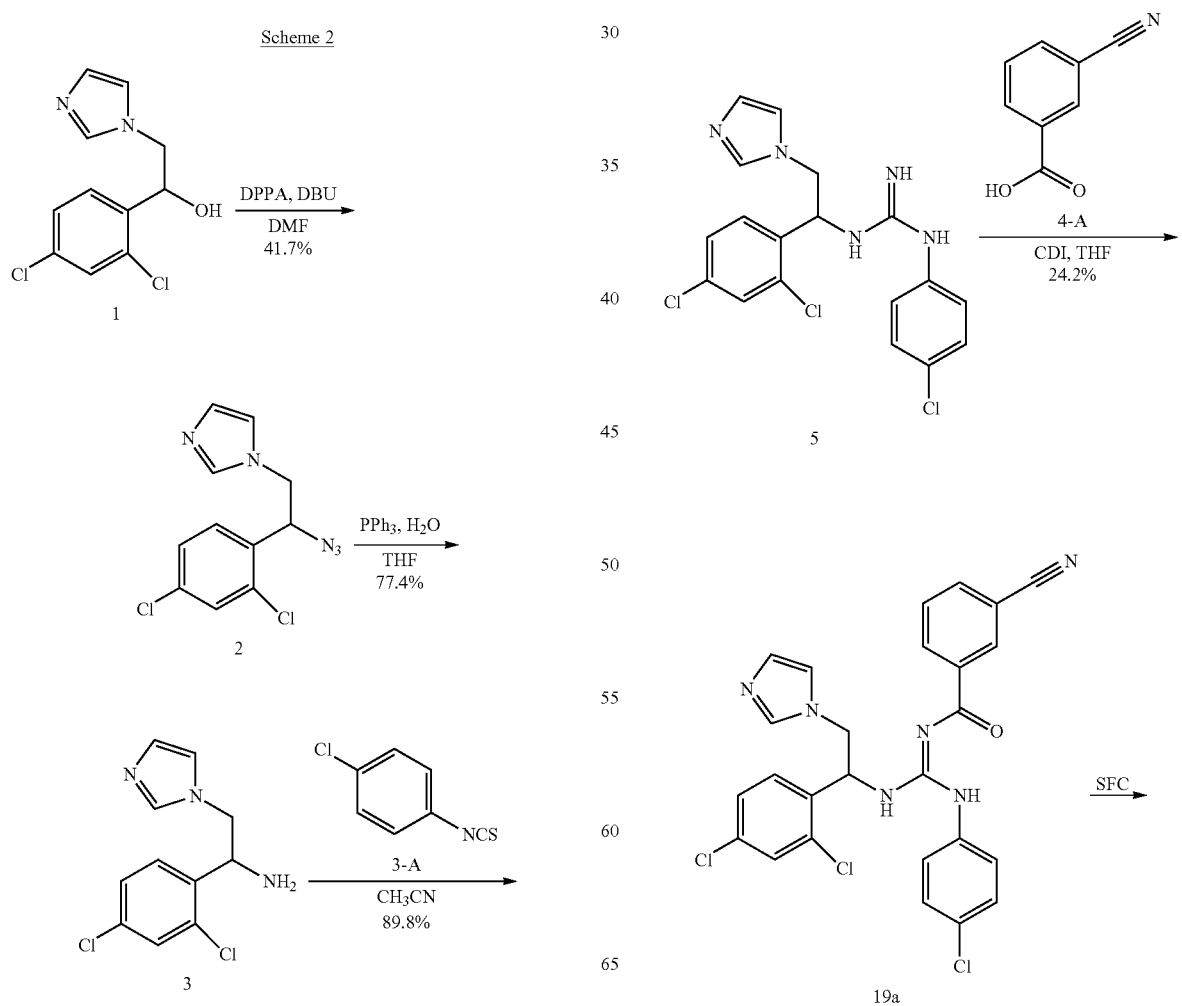

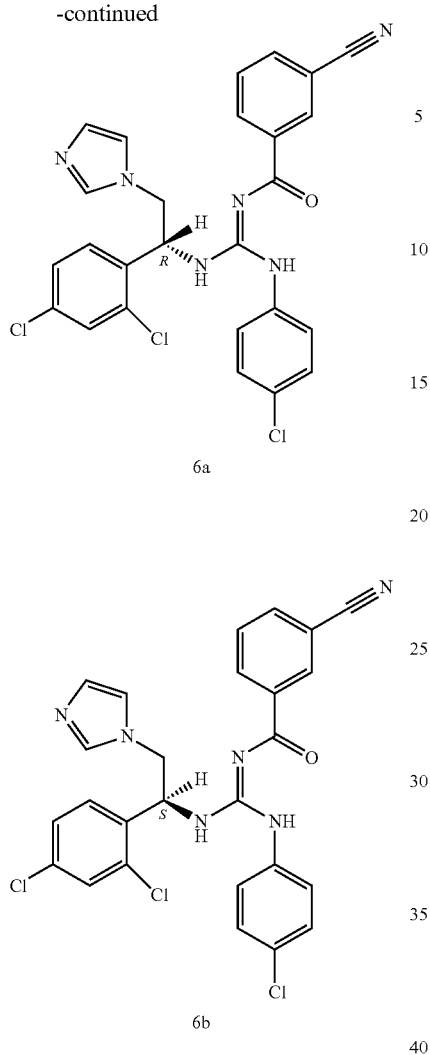

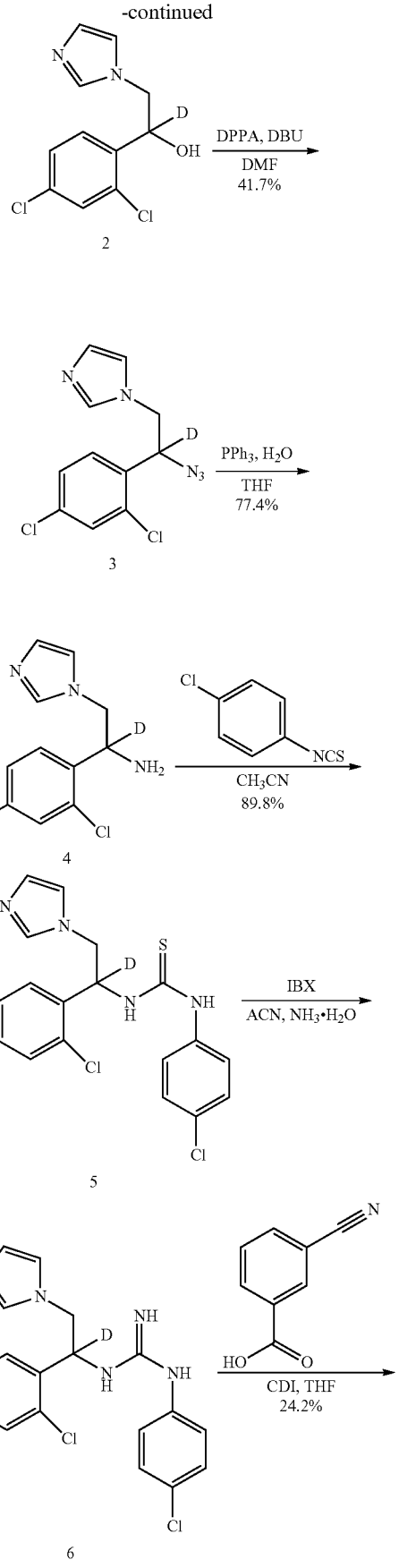

The reaction scheme below, Scheme 3, is modified from that presented above, in order to produce a deuterated analogue, with deuterium in place of hydrogen on the chiral carbon. The scheme is provided for the purpose of illustrating the invention, and should not be regarded in any manner as limiting the scope or the spirit of the invention. This illustrating, not limiting, feature applies to all the compound synthesis schemes of this disclosure. The starting compound in the scheme below, Compound 1, is available from multiple suppliers listed on LabNetwork (e.g. Manchester Organics Ltd., UK).

Scheme 3

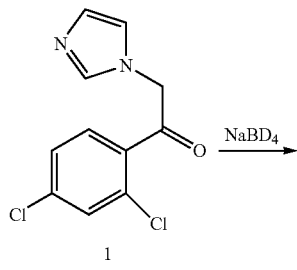

87
-continued

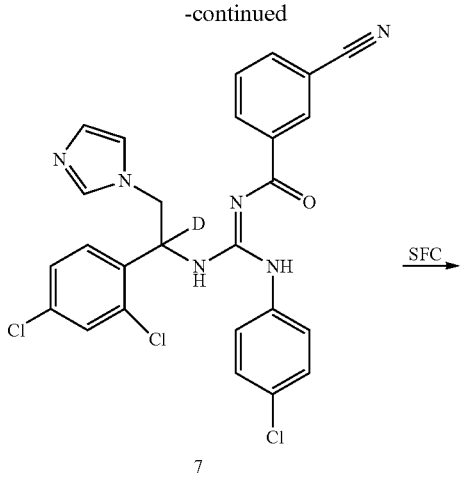

7

SFC →

88
-continued

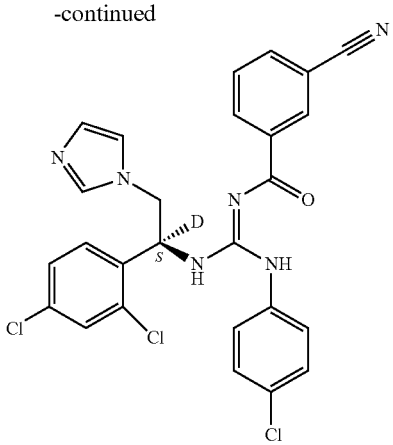

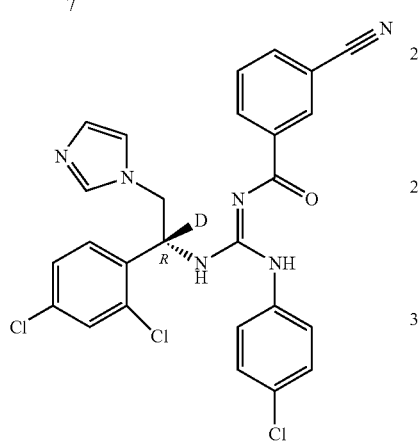

Compound 4 in Scheme 3 is of the form of Compound 1, the starting compound, in the molecule synthesis embodiments of [P1] (presented in its "Process of Preparation" section), BUT with the exception that is deuterated on its chiral carbon. This deuterated form can be substituted into the synthesis schemes described in [P1] to produce deuterated molecules, with deuterium on their chiral carbon, which are componentry to the present invention, and in a non-limiting embodiment, one of more of these new compositions of matter are used as anti-cancer medicines. Solvents, temperatures, pressures, and other reaction conditions may readily be selected by one of ordinary skill in the art. Starting materials are commercially available or can be readily prepared by one of ordinary skill in the art using known methods. Further methods to synthesize Compound 4, of Scheme 3 above, are given below in Scheme 4.

Scheme 4

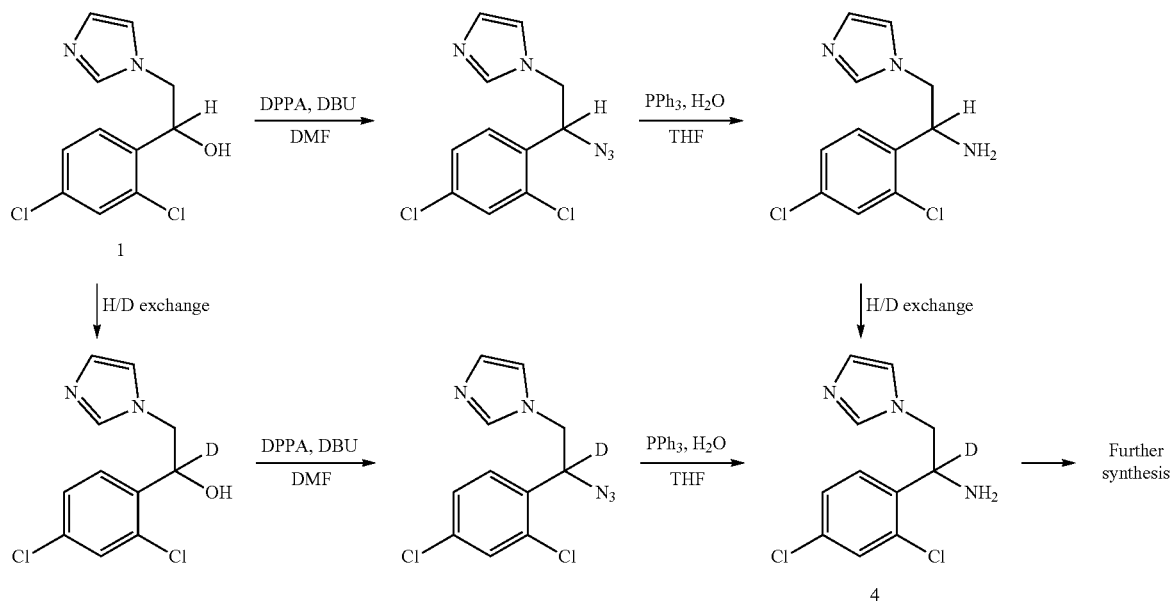

{deuterium can be incorporated at other positions also, not shown, depending on the particular deuteration reaction used}

Compound 1 in Scheme 4 is available from multiple suppliers listed on LabNetwork (e.g. Apollo Scientific Ltd., Stockport, UK). Conducting Scheme 4, the aim is to obtain a higher degree of deuterium incorporation on the chiral carbon than natural abundance: for Compound 4 ultimately, and for Compound 1 first if the lower arm of the synthesis route is used. In both cases, the greater the deuterium incorporation, the better. Deuterium incorporation at other positions of each molecule is permissible and within the scope of the invention, as is elevated deuterium incorporation only at the chiral carbon. Reactions described in [L, H, G, K, M, J1, J2, J3, I, F, S] deuterate (herein defined as replace hydrogen with deuterium) the α-carbon to a secondary alcohol and so the chiral carbon of Compound 1. Reactions described in [A, B, P, E1, E2, F] deuterate the α-carbon to primary amines, thence can deuterate the chiral carbon of Compound 4. Reactions described in [N] deuterate sp3 carbons, thence can deuterate the chiral carbon of Compounds 1 and 4. Reactions described in [O1, O2] can deuterate the β-carbon to phenyl groups and so can deuterate the chiral carbon of Compounds 1 and 4. Reactions described in [R1, R2, Q1, Q2] can deuterate widely, upon aromatic and alkyl molecular components, and thence can deuterate the chiral carbon of Compounds 1 and 4. Reactions described in [D] deuterate the β-carbon to tertiary amines, thence can deuterate the chiral carbon of Compounds 1 and 4. The teaching of [D] is especially preferred for use in the present context. Whichever option(s) is chosen, solvents, temperatures, pressures, and other reaction conditions may readily be selected by one of ordinary skill in the art. The level of deuteration can be modulated by modulating the reaction time: greater deuterium incorporation by longer reaction time. One can do multiple cycles of one or more of these reactions until the desired level of deuterium incorporation occurs, monitored by $^1$H and/or $^2$H NMR (e.g. deuterium incorporation quantified by decrease of $^1$H NMR integral intensity at specified position(s) compared to starting material) and/or mass spectrometry. Some of the reactions cited herein use commercially available catalysts e.g. 10% Pd/C catalyst [O1, O2, Q1, R1, R2], and/or Pt/C catalyst [R1, R2, Q1, Q2], or shvo catalyst [D], or RuCl$_2$(P(Ph)$_3$)$_3$ (CAS no: 15529-49-4) [A], or 5% Ru/C catalyst [K], or Ru-macho catalyst [G, M], all available from Sigma-Aldrich. Others teach, or cite literature teaching, how to prepare the catalyst to use. The aforementioned list of synthesis options, to make Compound 4 in Scheme 4, is not exhaustive. A person skilled in the art will know how to find further options. For example using computational tools, including artificial intelligence (AI, non-limiting e.g. [A11, A12, A13]), to search the chemical reaction literature/databases, e.g. (non-limiting) the Reaxys or CAS databases, and their own skill in the art to find, plan and prioritise synthesis routes. 2-(1H-imidazol-1-yl)-1-phenylethanamine is commercially available on LabNetwork and can be deuterated at its chiral carbon (and optionally at other positions also) by one or more of the aforementioned methods disclosed herein for deuterating the chiral carbon of 1-(2,4-dichlorophenyl)-2-(imidazol-1-yl)ethanamine. Before or after deuteration, its phenyl group can be (non-limiting) alkylated, halogenated, or CF$_3$ added (non-limiting example: at the IUPAC 2.5 positions), at desired position(s) by methods well known to those of the art. Then it can be a starting compound in the synthesis schemes of [P1] and used to produce deuterated compositions of matter that are componentry to this invention, which in non-limiting embodiments, are used singly or in a combination in anti-cancer therapy, in an animal or human. Alternatively, the final products, rather than starting materials, of the synthesis schemes of [P1] can be deuterated, to produce deuterated compositions of matter that are componentry to this invention, which in non-limiting embodiments, are used singly or in a combination in anti-cancer therapy, in an animal or human. Reactions described in [A, B, E1, E2, F] can deuterate the α-carbon to secondary amines, and thence the chiral carbon of Compound 19a, in Scheme 2 presented previously, and the chiral carbon of other molecules with the scaffold of [P1], as presented in the abstract of [P1]. These compounds can also be deuterated at their chiral carbon, and in further embodiments at further or other position(s), by reactions described in [N], which deuterate sp3 carbons. And/or by reactions described in [O1, O2], which can deuterate the β-carbon to phenyl groups. And/or by reactions described in [R1, R2, Q1, Q2], which deuterate aromatic and alkyl molecular components. And/or by reactions described in [D], which can deuterate the β-carbon to tertiary amines. Some of these reactions are stereoretentive [F, N, E1, E2] and thus can be used, optionally, after stereoisomer enrichment. Others are not, e.g. [Q1, Q2], and so should be used before any enantiomeric excess (ee) enrichment step. All patents and papers cited by the present disclosure, and their supplementary materials, are herein incorporated by reference, and are componentry, to the present disclosure.

The reaction scheme below, Scheme 5, differs from Scheme 2 in order to produce methylated analogues, with methyl in place of hydrogen on the chiral carbon.

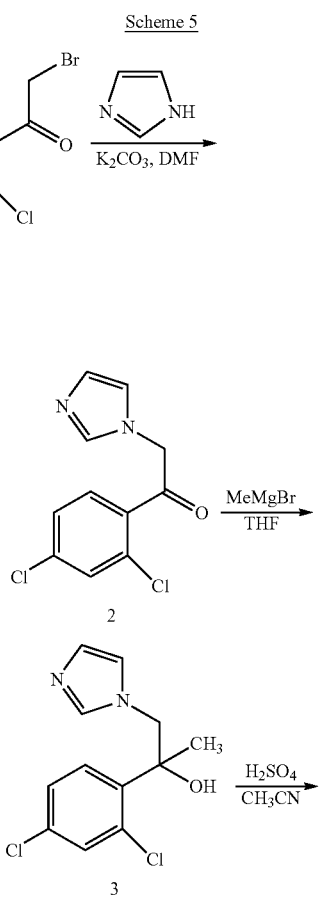

Scheme 5

-continued

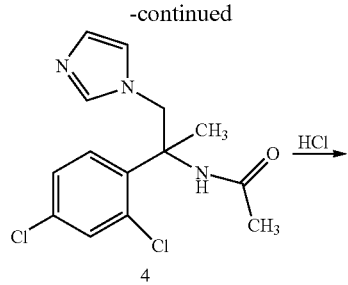
4

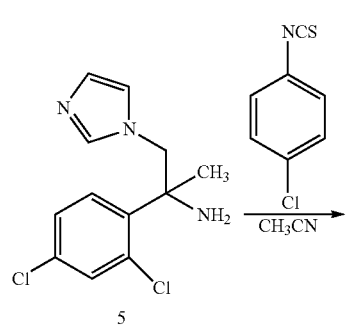
5

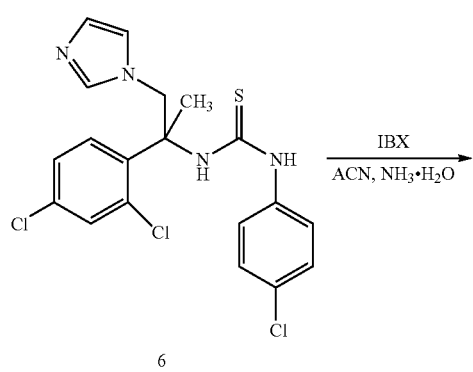
6

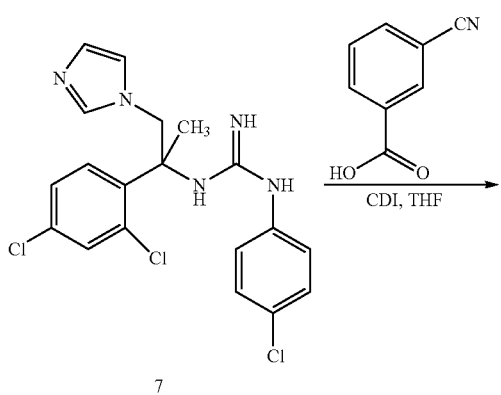
7

-continued

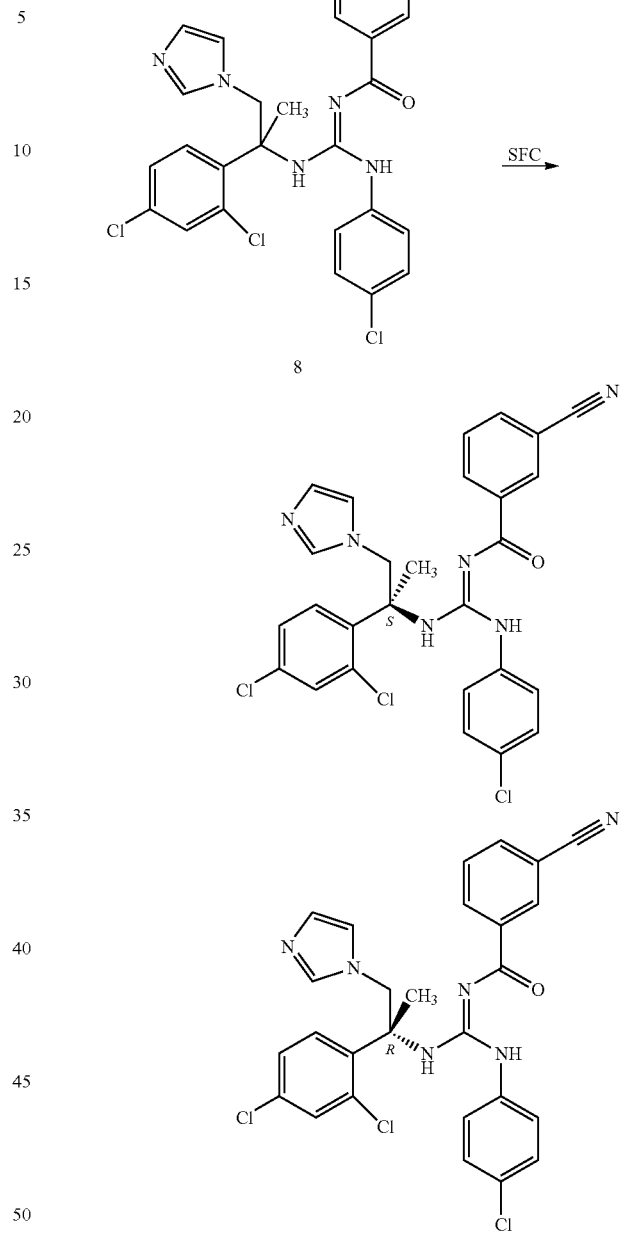
8

Compound 5 in Scheme 5 is of the form of Compound 1, the starting compound, in the molecule synthesis embodiments of [P1] (presented in its "Process of Preparation" section), BUT with the exception that is methylated on its chiral carbon. This methylated form can be substituted into the synthesis schemes described in [P1] to produce methylated molecules, with methyl on their chiral carbon, that are componentry to the present invention, and in a non-limiting embodiment, one of more of these new compositions of matter are used as anti-cancer medicines. Solvents, temperatures, pressures, and other reaction conditions may readily be selected by one of ordinary skill in the art. Starting materials are commercially available or can be readily prepared by one of ordinary skill in the art using known methods.

The reaction scheme below, Scheme 6, differs from Scheme 2 in order to produce fluorinated analogues, with fluorine in place of hydrogen on the chiral carbon.
Scheme 6
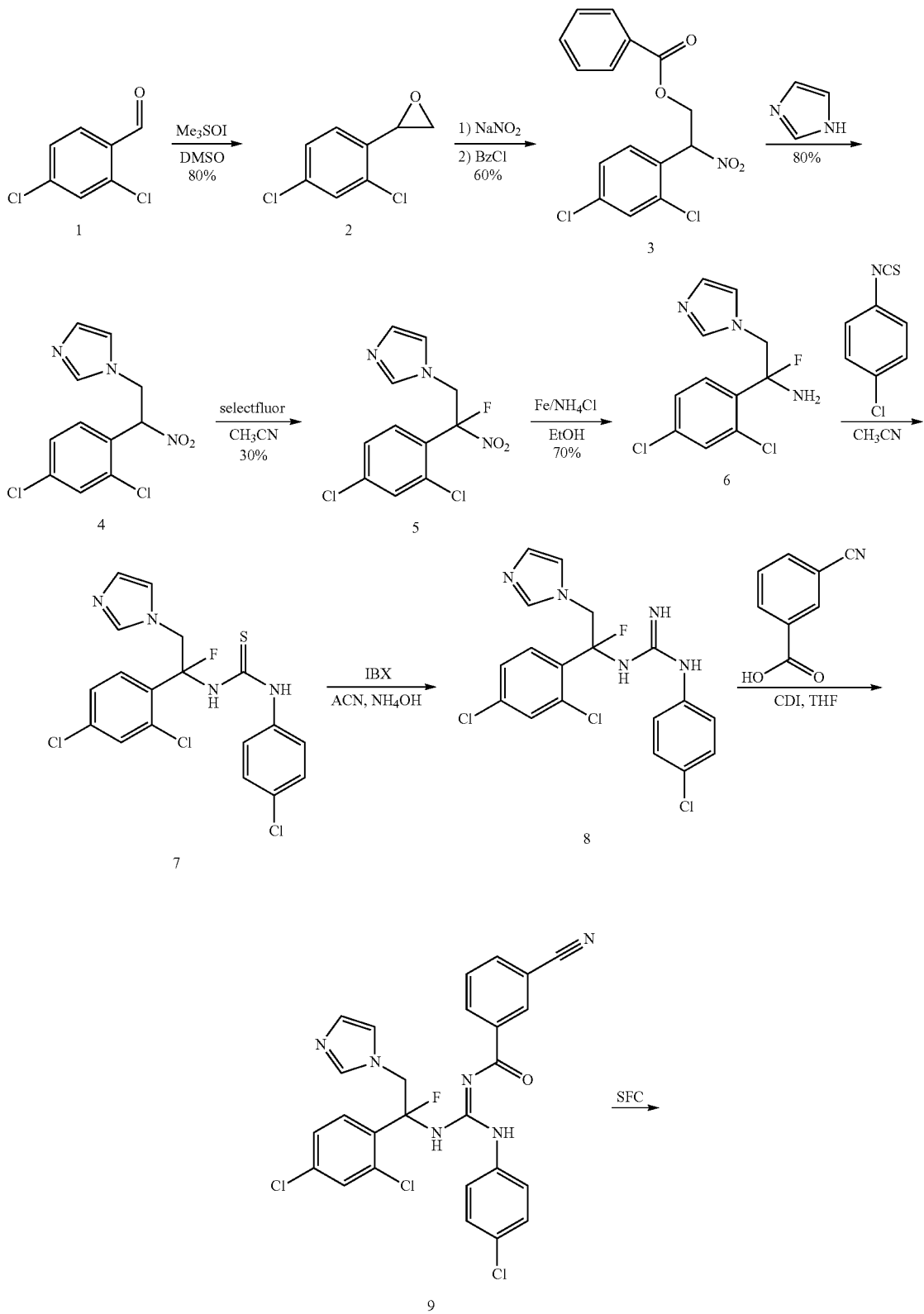

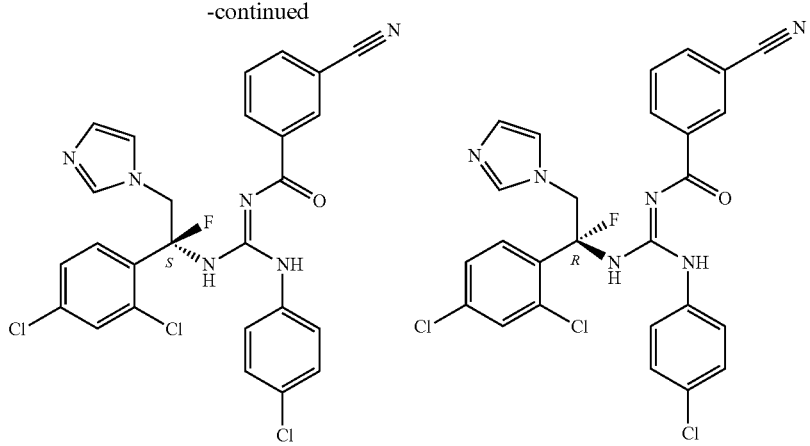

Compound 6 in Scheme 6 is of the form of Compound 1, the starting compound, in the molecule synthesis embodiments of [P1] (presented in its "Process of Preparation" section), BUT with the exception that is fluorinated on its chiral carbon. This fluorinated form can be substituted into the synthesis schemes described in [P1] to produce fluorinated molecules, with fluorine on their chiral carbon, that are componentry to the present invention, and in a non-limiting embodiment, one of more of these new compositions of matter are used as anti-cancer medicines. Solvents, temperatures, pressures, and other reaction conditions may readily be selected by one of ordinary skill in the art. Starting materials are commercially available or can be readily prepared by one of ordinary skill in the art using known methods.

Example (II)

Summary of Formula (II)

This invention embodiment relates to compounds having the formula:

Formula (II)

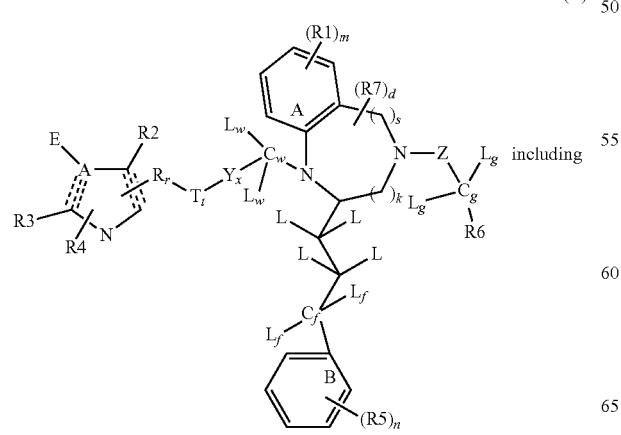

-continued or pharmaceutically-acceptable salts, solvates, hydrates or prodrugs thereof, wherein:

L is independently at each point of use alkyl, or substituted alkyl, or deuterated alkyl, or aminoalkyl, or thioalkyl, or alkoxy, or halogen, or haloalkyl, or haloalkoxy, or any atom or isotope permitted by valence (including any accompanying hydrogens by valence e.g. (non-limiting) OH, $NH_2$, SH, $SiH_3$, $PH_2$ etc.), for example hydrogen, or deuterium, or fluorine;

A is nitrogen (N), or $N^+$, or carbon;

E is absent, or alkyl, or substituted alkyl, or deuterated alkyl, or aminoalkyl, or thioalkyl, or alkoxy or any atom or isotope permitted by valence (including any accompanying hydrogens by valence e.g. (non-limiting) OH, $NH_2$, SH, $SiH_3$, $PH_2$ etc.), for example hydrogen, or deuterium or fluorine;

C is carbon;

x, w, f, g are independently selected to be 0, 1, 2 or 3;

d is a selected integer between 0 and 7;

k and s are independently selected to be 1, 2, or 3;

The 5-sided ring structure is attached by any one of its available ring atoms, and none, one or two of its bonds can be a double bond, for example at locations shown by the "single or double bond" symbol;

$R_1$ and $R_5$ are attached to any available carbon atom of phenyl rings A and B, respectively, and at each occurrence are independently selected from hydrogen, deuterium, alkyl, substituted alkyl, trifluoromethoxy, halogen, cyano, nitro, $OR_8$, $NR_8R_9$, $C(=O)R_8$, $CO_2R_8$, $C(=O)NR_8R_9$, $NR_8C(=O)R_9$, $NR_8C(=O)OR_9$, S(O)$_o$R$_9$, NR$_8$SO$_2$R$_9$, SO$_2$NR$_8$R$_9$, cycloalkyl, heterocycle, aryl, and heteroaryl, and/or two of R$_1$ and/or two of R$_5$ join together to form a fused benzo ring; R$_2$, R$_3$ and R$_4$ are independently selected from E (defined earlier), hydrogen, or deuterium, or alkyl, or deuterated alkyl, and substituted alkyl, or one of R$_2$, R$_3$ and R$_4$ is a bond to R, T or Y and the other of R$_2$, R$_3$ and R$_4$ are independently selected from hydrogen, alkyl, and substituted alkyl;

Z and Y are independently selected from C(=O), —CO$_2$—, —SO$_2$—, —CH$_2$—, —CH$_2$C(=O)—, and —C(=O)C(=O)—, or Z may be absent;

R and T are selected from —CH$_2$—, —C(=O)—, and —CH[(CH$_2$)$_p$(Q)]—, wherein Q is NR$_{10}$R$_{11}$, OR$_{10}$ or CN;

R$_6$ is selected from thienyl, alkyl, alkenyl, substituted alkyl, substituted alkenyl, aryl, substituted aryl, cycloalkyl, heterocyclo, heteroaryl and aryl optionally substituted with a lower aliphatic group or one or more functional groups selected independently from the group consisting of —NH$_2$, —OH, phenyl, halogen, (C$_1$-C$_4$)alkoxy or —NHCOCH$_3$;

R$_7$ is selected from L (defined earlier), hydrogen, alkyl, substituted alkyl, alkenyl, substituted alkenyl, aminoalkyl, halogen, cyano, nitro, keto (=O), hydroxy, alkoxy, alkylthio, C(=O)H, acyl, CO$_2$H, alkoxycarbonyl, carbamyl, sulfonyl, sulfonamidyl, cycloalkyl, heterocycle, aryl, and heteroaryl;

R$_8$ and R$_9$ are independently selected from hydrogen, alkyl, substituted alkyl, C$_{2-4}$alkenyl optionally substituted, cycloalkyl, heterocycle, aryl, and heteroaryl, or R$_8$ and R$_9$ taken together to form a heterocycle or heteroaryl, except R$_9$ is not hydrogen when attached to a sulfonyl group as in SO$_2$R$_9$;

R$_{10}$ and R$_{11}$ are independently selected from hydrogen, alkyl, and substituted alkyl;

m and n are independently selected from 0, 1, 2 and 3 o, p and q are independently 0, 1 or 2; and r and t are 0 or 1.

Preferred Compounds of Formula (II)

Preferred methods are to use, and preferred compounds are, compounds with the following formula, or pharmaceutically-acceptable salts, solvates, hydrates or prodrugs thereof,

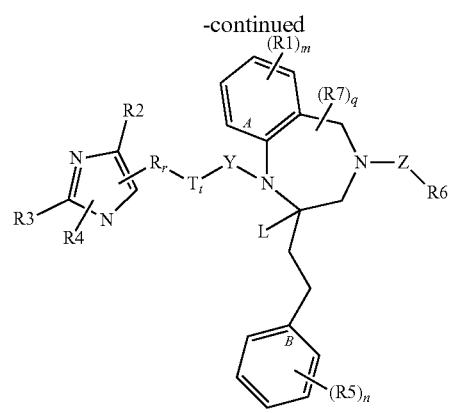

including

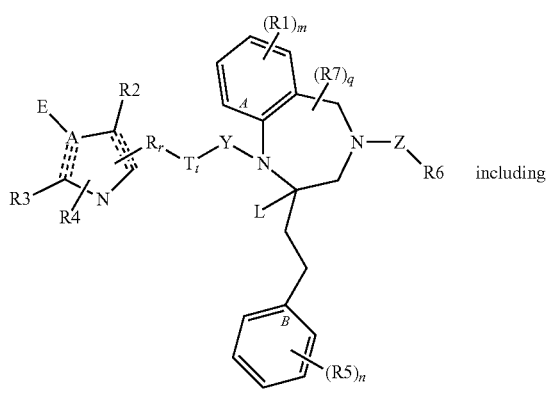

-continued wherein:

L is hydrogen, or deuterium, or methyl, or fluorine;

A is nitrogen (N), or N$^+$, or carbon;

E is absent, or alkyl, or substituted alkyl, or deuterated alkyl, or aminoalkyl, or thioalkyl, or alkoxy or any atom or isotope permitted by valence (including any accompanying hydrogens by valence e.g. (non-limiting) OH, NH$_2$, SH, SiH$_3$, PH$_2$ etc.), for example hydrogen or deuterium;

R$_1$ and R$_5$ are attached to any available carbon atom of phenyl ring A and phenyl ring B, respectively, and at each occurrence are independently selected from hydrogen, deuterium, alkyl, aralkyl, aminoalkyl, halogen, cyano, nitro, hydroxy, alkoxy, trifluoromethoxy, alkylthio, NH$_2$, NH(alkyl), N(alkyl)$_2$, C(=O)H, acyl, CO$_2$H, alkoxycarbonyl, carbamyl, sulfonyl, sulfonamide, cycloalkyl, heterocycle, aryl, and heteroaryl, and/or two of R$_1$ and/or two of R$_5$ join together to form a fused benzo ring;

R$_2$, R$_3$ and R$_4$ are independently selected from hydrogen and alkyl;

Z is —CO$_2$—, —SO$_2$—, or is absent;

Y, R and T are selected from —CH$_2$— and —C(=O)—,

R$_6$ is selected from:

C$_{1-4}$alkyl or C$_{1-4}$alkenyl optionally substituted with up to three of halogen, aryl and CO$_2$C$_{1-6}$alkyl;

phenyl optionally substituted with up to three Rig and/or having fused thereto a benzo-ring or a five to six membered heteroaryl;

heteroaryl selected from thiophenyl, imidazolyl, pyrazolyl, and isoxazolyl wherein said heteroaryl is optionally substituted with up to two R$_{12}$, R$_7$ is selected from hydrogen, alkyl, substituted alkyl, alkenyl, substituted alkenyl, aminoalkyl, halogen, cyano, nitro, keto (=O), hydroxy, alkoxy, alkylthio, C(=O)H, acyl, CO$_2$H, alkoxycarbonyl, carbamyl, sulfonyl, sulfonamide, cycloalkyl, heterocycle, aryl, and heteroaryl;

R$_{12}$ at each occurrence is independently selected from each other R$_{12}$ from the group consisting of C$_{1-6}$alkyl, halogen, nitro, cyano, hydroxy, alkoxy, NHC(=O) alkyl, —CO$_2$alkyl, —SO$_2$phenyl, aryl, five to six membered monocyclic heteroaryl, and phenyloxy or benzyloxy in turn optionally substituted with halogen, hydroxyl, C$_{1-4}$alkyl, and/or O(C$_{1-4}$alkyl); m and n are independently selected from 0, 1, 2 or 3; and q is 0, 1 or 2; and r and t are 0 or 1.

More preferred are compounds having the following formula, or pharmaceutically-acceptable salts, solvates, hydrates or prodrugs thereof,

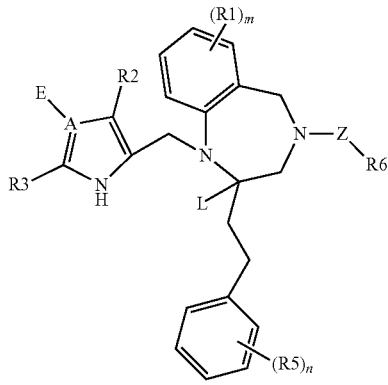

wherein $R_1$ and $R_5$ are attached to any available carbon atom of phenyl ring A and phenyl ring B, respectively, and at each occurrence are independently selected from alkyl, halogen, cyano, hydroxy, alkoxy, $NH_2$, NH(alkyl), N(alkyl)$_2$, C(=O)H, acyl, $CO_2H$, alkoxycarbonyl, and/or two of $R_1$ and/or two of $R_5$ join together to form a fused benzo ring;

$R_2$, $R_3$ and $R_4$ are independently selected from hydrogen and lower alkyl;

Z is —$CO_2$—, —$SO_2$—, or is absent;

$R_6$ is selected from: $C_{1-4}$alkyl or $C_{1-4}$alkenyl optionally substituted with up to three of halogen, aryl and $CO_2C_{1-6}$alkyl;

phenyl optionally substituted with up to three $R_{12}$ and/or having fused thereto a benzo ring or a five to six membered heteroaryl;

heteroaryl selected from thiophenyl, imidazolyl, pyrazolyl, and isoxazolyl, wherein said heteroaryl is optionally substituted with up to two $R_{12}$, $R_{12}$ at each occurrence is independently selected from each other $R_{12}$ from the group consisting of $C_{1-6}$ alkyl, halogen, nitro, cyano, hydroxy, alkoxy, NHC(=O) alkyl, —$CO_2$alkyl, —$SO_2$phenyl, aryl, five to six membered monocyclic heteroaryl, and phenyloxy or benzyloxy in turn optionally substituted with halogen, hydroxyl, $C_{1-4}$ alkyl, and/or O($C_{1-4}$ alkyl); and m and n are independently selected from 0, 1, or 2.

Even more preferred are compounds as immediately defined above wherein $R_6$ is selected from $C_{1-4}$alkyl, trifluoromethyl, benzyl, $C_{2-3}$alkenyl substituted with phenyl,

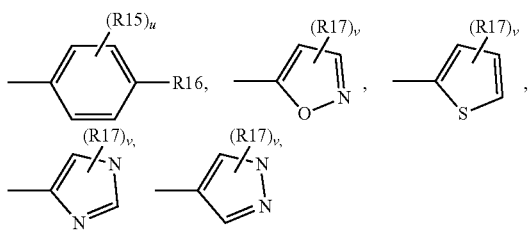

wherein:

$R_{15}$ is halogen, alkyl, nitro, cyano, hydroxy, alkoxy, NHC(=O)alkyl, and/or two $R_{15}$ groups are taken together to form a fused benzo ring or a five to six membered heteroaryl;

$R_{16}$ is selected from hydrogen, deuterium, halogen, alkyl, nitro, cyano, hydroxy, alkoxy, NHC(=O)alkyl, and phenyloxy or benzyloxy in turn optionally substituted with 1 to 3 of hydrogen, deuterium, halogen, cyano, and $C_{1-4}$alkoxy;

$R_{17}$ is selected from alkyl, alkoxy, $CO_2C_{1-6}$alkyl, and $SO_2$phenyl;

and u and v are independently 0, 1 or 2.

Most preferred compounds of Formula (II) are those having the formula:

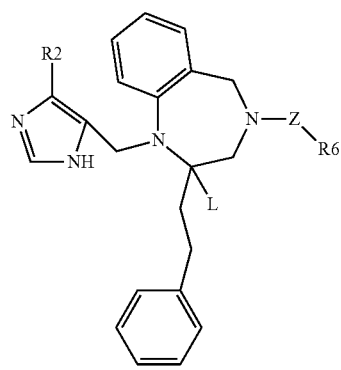

wherein

L is deuterium;

$R_2$ is hydrogen or $CH_3$;

Z is —$CO_2$—, —$SO_2$—, or is absent; and $R_6$ is selected from the groups recited immediately above, most preferably

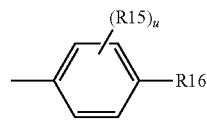

Example Embodiments of Formula (II)

Compounds from [8, 12], selected as specific anti-cancer therapeutics by the invention of this disclosure, selected because they inhibit the reverse, more than the forward, mode of ATP synthase. $EC_{50}$ and $IC_{50}$ used interchangeably. $EC_{50}$ values for $F_1F_0$ ATP hydrolysis, and $F_1F_0$ ATP synthesis, in NADH-linked and NADPH-linked sub-mitochondrial (SMP) assays respectively, sourced from [8], are presented. [8] refer to these $EC_{50}$ values as $IC_{50}$ values for inhibiting $F_1F_0$ ATP hydrolase (reverse mode) and $F_1F_0$ ATP synthase (forward mode). However, this in incorrect. Because, as identified by the invention of this disclosure, explained herein, although these molecules inhibit $F_1F_0$ ATP hydrolase, their reducing of $F_1F_0$ ATP synthesis is not (predominantly) because of inhibiting $F_1F_0$ ATP synthase, but by uncoupling.

Further Examples [ 2]

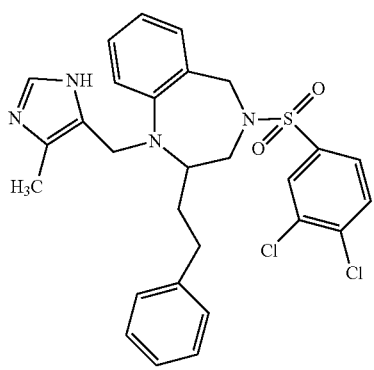

EC$_{50}$F$_1$F$_0$ ATP hydrolase > 0.022 (μM)
EC$_{50}$F$_1$F$_0$ ATP synthesis > 30 (μM)
Ec$_{50}$ Ratio > 1,364

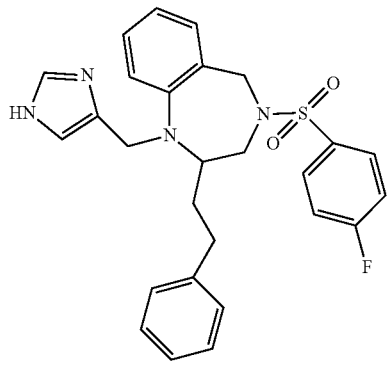

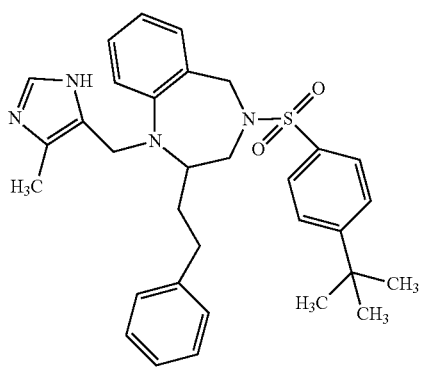

EC$_{50}$F$_1$F$_0$ ATP hydrolase > 0.077 (μM)
EC$_{50}$F$_1$F$_0$ ATP synthesis > 30 (μM)
Ec$_{50}$ Ratio > 390

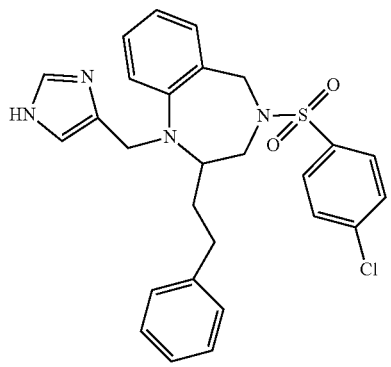

| R6 | R5 | Imidazole | EC$_{50}$ F$_1$F$_0$ ATP hydrolase (μM) |
|---|---|---|---|
| 4-F—Ph | SO$_2$ | 5-yl | 0.221 |
| Ph | SO$_2$ | 5-yl | 0.282 |
| 4-OH—Ph | SO$_2$ | 5-yl | 0.667 |
| 4-OMe—Ph | SO$_2$ | 5-yl | 0.077 |
| 2,5-di-Cl—Ph | SO$_2$ | 5-yl | 0.158 |
| 4-(AcNH)—Ph | SO$_2$ | 5-yl | 2.981 |
| 4-CN—Ph | SO$_2$ | 5-yl | 0.255 |
| 2-Cl-4-CN—Ph | SO$_2$ | 5-yl | 0.939 |
| 3-NO$_2$—Ph | SO$_2$ | 5-yl | 0.423 |
| Naphth-1-yl | SO$_2$ | 5-yl | 0.338 |
| Thiophen-2-yl | SO$_2$ | 5-yl | 0.636 |
| Benzofurazan-7-yl | SO$_2$ | 5-yl | 1.777 |
| Quinolin-8-yl | SO$_2$ | 5-yl | 2.935 |
| Bn | SO$_2$ | 5-yl | 2.405 |
| CF$_3$ | SO$_2$ | 5-yl | 0.077 |
| 4-t-Bu—Ph | SO$_2$ | 5-yl | 0.008 |
| 4-t-Bu—Ph | CH$_2$ | 5-yl | 2.138 |
| 4-t-Bu—Ph | CH$_2$ | 4-Me-5-yl | 2.352 |
| 4-t-Bu—Ph | SO$_2$ | 2-yl | >10 |
| 4-F—Ph | SO$_2$ | 2-Me-5-yl | 9.623 |
| 4-F—Ph | SO$_2$ | 4-Me-5-yl | 0.151 |

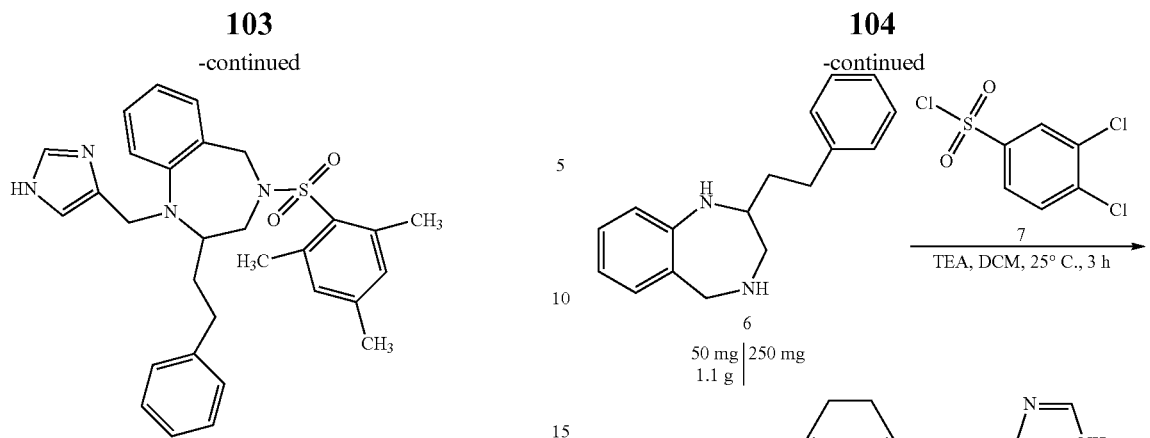

Scheme IIa is route used for synthesizing Compound 31 [8], starting reagents were sourced commercially using the LabNetwork (www.labnetwork.com).

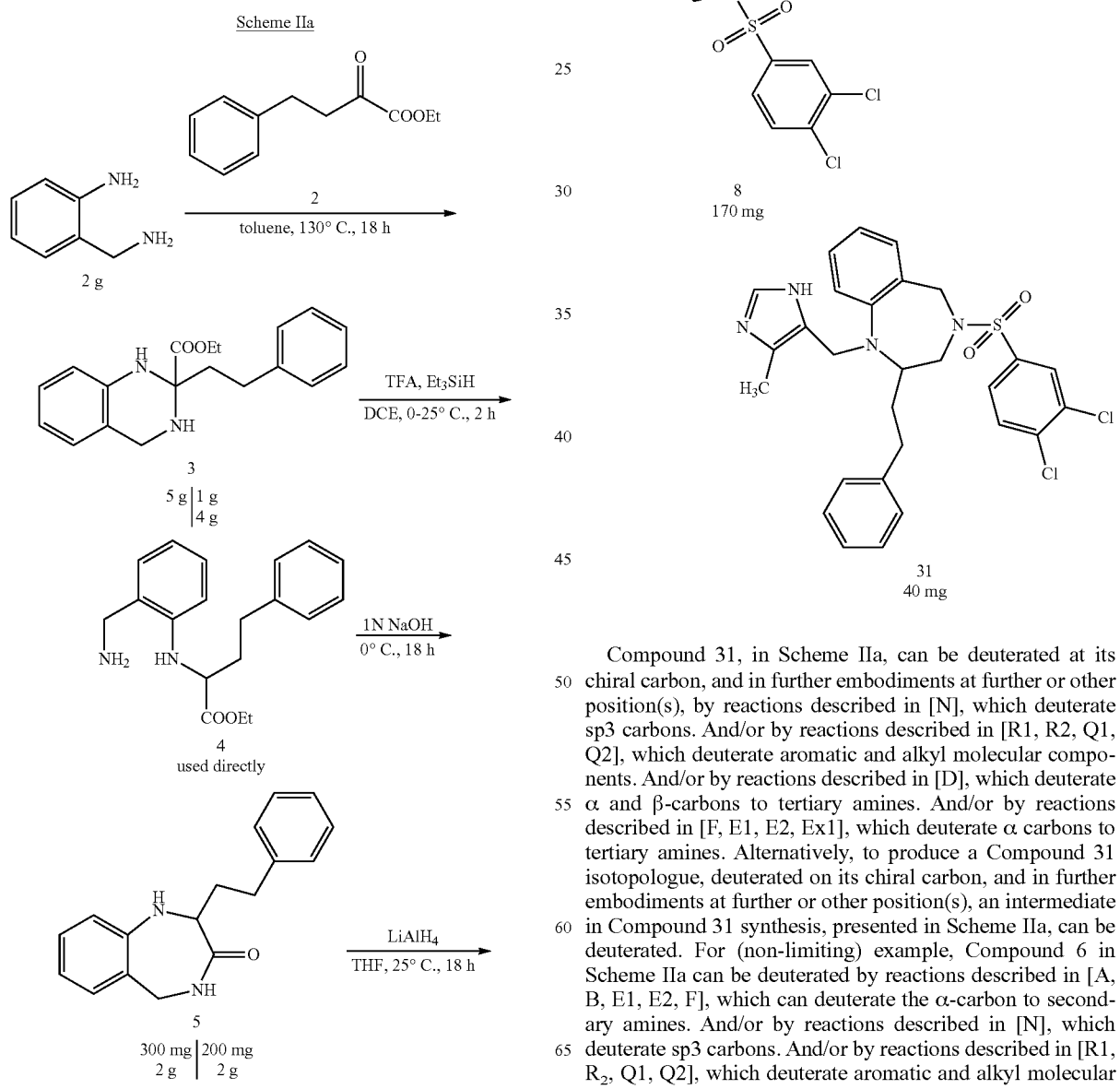

Compound 31, in Scheme IIa, can be deuterated at its chiral carbon, and in further embodiments at further or other position(s), by reactions described in [N], which deuterate sp3 carbons. And/or by reactions described in [R1, R2, Q1, Q2], which deuterate aromatic and alkyl molecular components. And/or by reactions described in [D], which deuterate α and β-carbons to tertiary amines. And/or by reactions described in [F, E1, E2, Ex1], which deuterate α carbons to tertiary amines. Alternatively, to produce a Compound 31 isotopologue, deuterated on its chiral carbon, and in further embodiments at further or other position(s), an intermediate in Compound 31 synthesis, presented in Scheme IIa, can be deuterated. For (non-limiting) example, Compound 6 in Scheme IIa can be deuterated by reactions described in [A, B, E1, E2, F], which can deuterate the α-carbon to secondary amines. And/or by reactions described in [N], which deuterate sp3 carbons. And/or by reactions described in [R1, R2, Q1, Q2], which deuterate aromatic and alkyl molecular components. A deuterated Compound 6 can be inputted into synthesis schemes of [P2], in place of Compound 10 in Scheme III in the "Process of Preparation" section of [P2], to make deuterated isotopologues with the scaffold of [P2]. These are componentry to the present invention as new compositions of matter, and in non-limiting embodiments are used singly or in combination, optionally in co-therapy with an FDA and/or EMA approved medicine(s) and/or treatment(s), for example a licensed cancer treatment, as anti-cancer therapeutics. Throughout this disclosure, deuteration methods conveyed are illustrative rather than limiting. All stereoisomers of all the compounds of the present invention are contemplated, either in admixture or in pure or substantially pure form.

Example (III)

Summary of Formula (III)

This invention embodiment relates to compounds having the following formula:

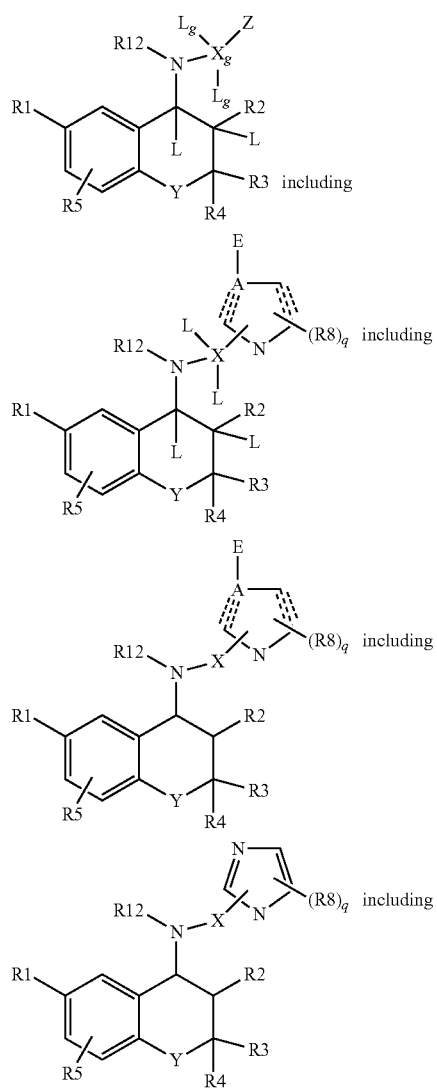

Formula (III)

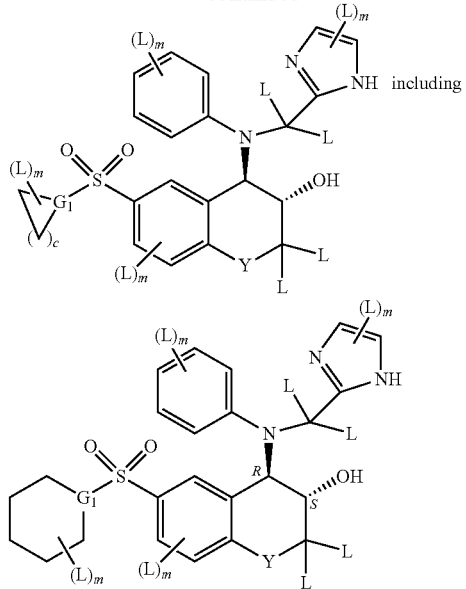

or their enantiomers, diastereomers, pharmaceutically-acceptable salts, solvates, hydrates or prodrugs thereof, wherein:

Optionally, one or more places have deuterium in place of hydrogen, at an artificially high level of deuterium incorporation, in excess of the naturally occurring abundance;

Optionally, one or more places have fluorine, or other halogen, or methyl, or alkyl, or substituted alkyl, in place of hydrogen;

Z is heteroaryl;

g is selected from 0, 1, 2, 3, 4;

L is independently at each point of its use hydrogen, alkyl, or substituted alkyl (non-limiting example: $CF_3$), or deuterated alkyl (non-limiting example: $CD_3$), or aminoalkyl, or thioalkyl, or alkoxy, or halogen, or haloalkyl, or haloalkoxy or any atom or isotope permitted by valence (including any accompanying hydrogens by valence e.g. (non-limiting) OH, $NH_2$, SH, $SiH_3$, $PH_2$ etc.);

$G_1$ is N or C;

c is selected from 1, 2, 3, 4, 5, 6, 7, 8, 9;

m is independently at each point of use selected from 0, 1, 2, 3, 4, 5, 6, as valence permits;

$R_2$ is hydrogen, L (defined earlier), hydroxy, or —OC(O)R14;

R14 is hydrogen, alkyl, haloalkyl, aryl, arylalkyl, cycloalkyl or (cycloalkyl)alkyl;

R3 and R4 are each independently hydrogen, or L (defined earlier), or $CF_3$, or chlorine or other halogen, or alkyl, or substituted alkyl, or deuterated alkyl, or arylalkyl, or R3 and R4 taken together with the carbon atom to which they are attached form a 3- to 7-membered carbocyclic ring;

R5 is independently at each point of use hydrogen, L (defined earlier), alkyl, halogen, heterocyclo, nitrile, haloalkyl or aryl;

R12 is selected from hydrogen, aryl, heteroaryl, heterocyclo;

X is alkyl;

Y is a single bond, $—CH_2—$, $—C(O)O$, S or $—N(R_{14})—$;

A is nitrogen (N), or $N^+$, or carbon;

E is absent, or alkyl, or substituted alkyl (non-limiting example: $CF_3$), or deuterated alkyl, or aminoalkyl, or thioalkyl, or alkoxy or any atom or isotope permitted by valence (including any accompanying hydrogens by valence e.g. (non-limiting) OH, $NH_2$, SH, $SiH_3$, $PH_2$ etc.), for example hydrogen, or deuterium, or fluorine;

R8 is independently selected at each point of use from E (defined earlier), hydrogen, alkyl, halogen, carbamyl, carbamyl$C_{1-4}$alkyl, substituted alkyl or two R8 groups join to form an optionally substituted fused phenyl ring;

q is 0, 1, 2, 3 or 4.

R1 is selected from L (defined earlier), hydrogen, deuterium, CN, $SO_2$-piperidine, $SO_2$-piperidine substituted with 0-10 of $R_5$, $R_9$, cyano, halogen, alkyl, substituted alkyl, alkenyl, substituted alkenyl, alkylene, substituted alkylene, alkynyl, substituted alkynyl, alkoxy, thioalkyl, aminoalkyl, carbamyl, sulfonyl, sulfonamide, cycloalkyl, (cycloalkyl)alkyl, hydroxyalkyl, haloalkyl, haloalkoxy, alkoxyalkyl, morpholinylalkyl, aryl, arylalkyl, heterocyclo, heteroaryl, (heterocyclo)alkyl, acyl, alkoxycarbonyl, substituted amino; Most preferably $R_1$ is smaller than 300 Daltons;

R9 is

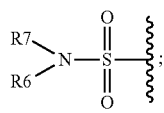

R6 and R7 are independently hydrogen, L (defined earlier), R1 (provided R1 is not R9), alkyl, cycloalkyl, aryl, arylalkyl, haloalkyl, hydroxyalkyl, hydroxyalkyl substituted with a carboxylic ester or carboxylic acid, alkoxyalkyl, thioalkyl, (cycloalkyl)alkyl, morpholinylalkyl, heterocyclo or (heterocyclo)alkyl; or R6 and R7 taken together with the nitrogen atom to which they are attached form a 5- to 7-membered mono or bicyclic ring including fused rings such as
- 1-pyrrolidinyl, 1-piperidinyl, 1-azepinyl, 4-morpholinyl, 4-thiamorpholinyl, 4-thiamorpholine dioxide, 1-piperazinyl, 4-alkyl-1-piperazinyl, 4-arylalkyl-1-piperazinyl, 4-diarylalkyl-1-piperazinyl; or 1-piperazinyl, 1-pyrrolidinyl, 1-piperidinyl or 1-azepinyl substituted with one or more L (defined earlier), alkyl, alkoxy, alkylthio, halo, trifluoromethyl, hydroxy, aryl, arylalkyl, —COOR14 or —CO-substituted amino;
- or R5 and R6 taken together with the atoms to which they are attached form a 5- to 7-membered ring optionally substituted with aryl;
- Encompassed by this invention are methods of administering a therapeutically effective amount of any compound(s) of [P6], or a pharmaceutically-acceptable salt, solvate, hydrate or prodrug thereof, optionally in a pharmaceutical composition(s), optionally in co-therapy with another anti-cancer treatment(s), to treat/ameliorate/prevent/combat cancer in a subject. Especially preferred for this use are compounds of [P6] with 3S, 4R stereochemistry.

Preferred Compounds of Formula (III)

Preferred methods are to use, and preferred compounds are, compounds of Formula (III), their enantiomers, diastereomers, pharmaceutically-acceptable salts, solvates, hydrates or prodrugs thereof, in which:
Z is triazolyl optionally substituted with one to two R8 or imidazolyl optionally substituted with one to two R8 and/or having fused thereto a benzene ring in turn optionally substituted with one to two R8;
Y is oxygen;
R2 is hydroxyl;
R3 and R4 are methyl or chlorine;
R1 is R9;
$G_1$ is nitrogen;
R6 and R7 are alkyl; or R6 and R7 taken together with the nitrogen atom to which they are attached ($G_1$=N) form a 6-membered ring;
X is alkyl;
R12 is aryl or heterocyclo;
A is N;
E is absent, or deuterium, or hydrogen;
R5 and R8 are hydrogen;
Stereochemistry is 3S, 4R;

Example Embodiments of Formula (III)

Immediately below, compounds from [7], selected as specific anti-cancer therapeutics by the invention of this disclosure. $EC_{50}$ values for $F_1F_0$ ATP hydrolysis, and $F_1F_0$ ATP synthesis, in NADH-linked and NADPH-linked sub-mitochondrial (SMP) assays respectively. [7] refers to these $EC_{50}$ values as $IC_{50}$ values for inhibiting $F_1F_0$ ATP hydrolase (reverse mode) and $F_1F_0$ ATP synthase (forward mode). However, this in incorrect. Because, as identified by the invention of this disclosure, explained herein, although these molecules inhibit $F_1F_0$ ATP hydrolase, their reducing of $F_1F_0$ ATP synthesis is not (predominantly) because of inhibiting $F_1F_0$ ATP synthase, but by uncoupling. The structure on the left is BMS-199264. It does not harm ex vivo rat heart at a concentration (10 μM [11]) that it exerts anti-cancer activity (discovery of this disclosure).

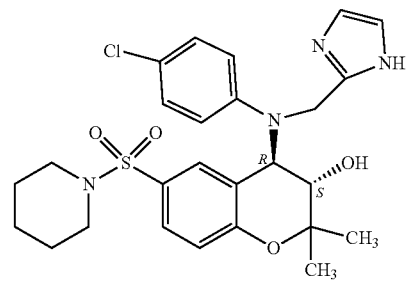

$EC_{50} F_1F_0$ ATP hydrolase = 0.48 ± 0.23 (μM)
$EC_{50} F_1F_0$ ATP synthesis = 18 ± 9.5 (μM)
$EC_{50}$ Ratio = 38
10 μM doesn't harm ex vivo rat heart

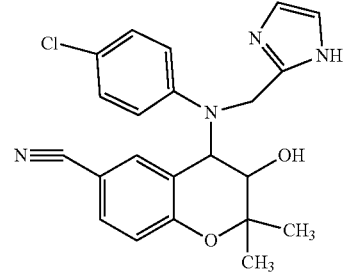

3S,4R
$EC_{50} F_1F_0$ ATP hydrolase = 0.24 ± 0.13 (μM)
$EC_{50} F_1F_0$ ATP synthesis = 3.8 ± 2.1 (μM)
3R,4S
$EC_{50} F_1F_0$ ATP hydrolase = 0.48 ± 0.23 (μM)
$EC_{50} F_1F_0$ ATP synthesis = 4 ± 0.45 (μM)

For the following example embodiment, with synthesis scheme (as 2 possible salts shown, Scheme IIIa), the starting material is BMS-199264, which is available commercially. For example from Sigma-Aldrich, a chemical and reagents vender well known to those of the art.

Scheme IIIa

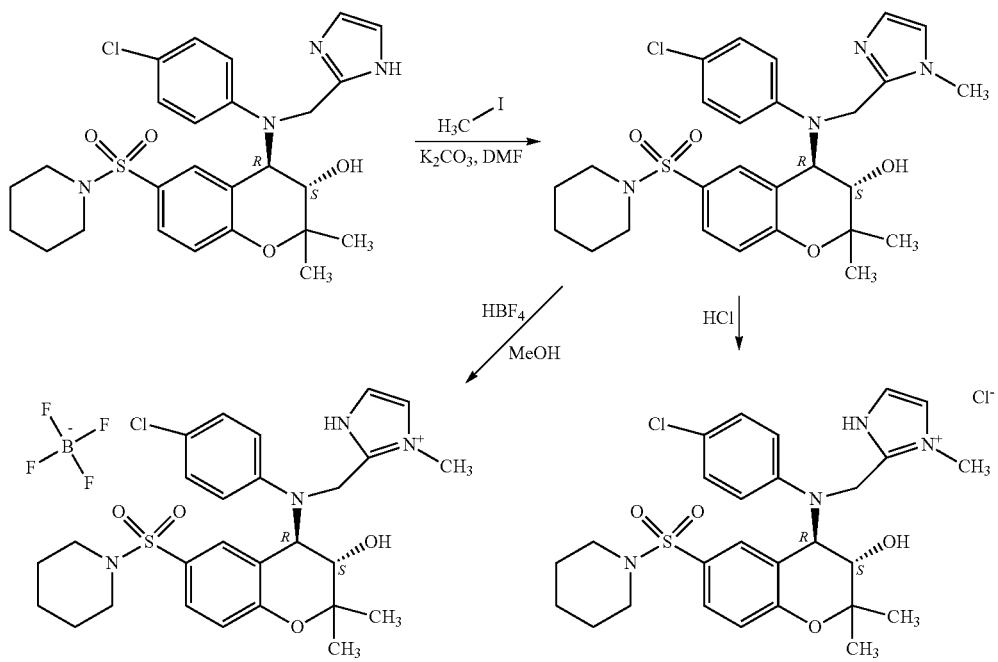

Further Example Embodiment

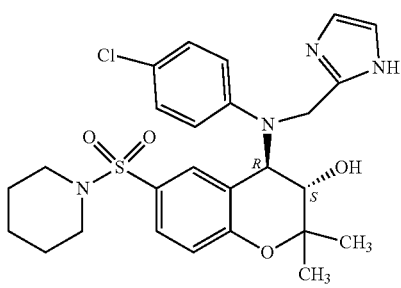

The following example embodiment does not uncouple the proton motive force (pmf) because its imidazole group, unlike BMS-199264, for example, does not have a protonable element.

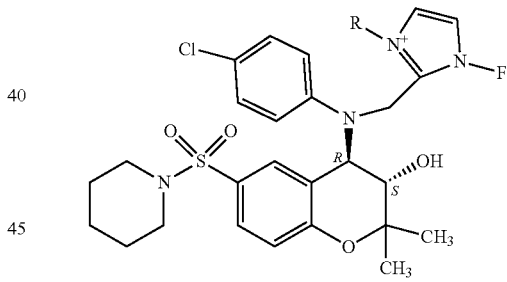

The following example embodiment (log P=3.79, calculated from structure [31]) uncouples the proton motive force (pmf) less than BMS-199264 (log P=4.35, calculated from structure [31]) because its log P is further removed from the log P=~3.2 optimum for uncoupling [32].

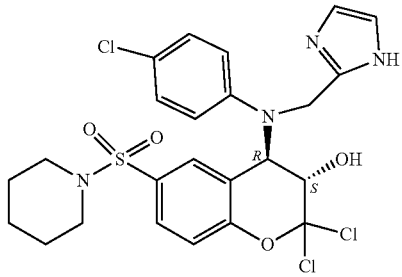

BMS-199264, and/or its analogues, can be deuterated by reactions described in [R1, R2, Q1, Q2], which deuterate aromatic and alkyl molecular components. Furthermore, there is a great wealth of reactions available to deuterate their aromatic rings, and those skilled in the art will know these. For (non-limiting) example, refer [Ex2]. Carbon 1 of BMS-199264, a chiral centre, can be deuterated by reactions described in [D, F, E1, E2, Ex1], which deuterate α carbons to tertiary amines, and/or by reactions described in [N], which deuterate sp3 carbons, and/or by reactions described in [I, M, G, H], which deuterate α and β-carbons to an OH group. Carbon 6 of BMS-199264, a chiral centre, can be deuterated by reactions described in [L, H, G, A, K, M, J1, J2, J3, I, F, S], which deuterate the α-carbon to an OH group, and/or by reactions described in [D], which deuterate α and β-carbons to tertiary amines, and/or by reactions described in [N], which deuterate sp3 carbons. The scaffold of [P6] is presented in its abstract. Deuterated isotopologues of this [P6] scaffold, for (non-limiting) example deuterated BMS-199264, are componentry to the present invention as new compositions of matter, and in non-limiting embodiments are used singly or in combination, optionally in co-therapy with an FDA and/or EMA approved medicine(s) and/or treatment(s), for example a licensed cancer treatment, as anti-cancer therapeutics.

Example (IV)

Background

Well known to those of the art: amino acids have the following structure, wherein the R group is different in different amino acids.

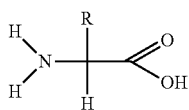

Summary of Formula (IV)

This invention embodiment relates to compounds having the following formula:

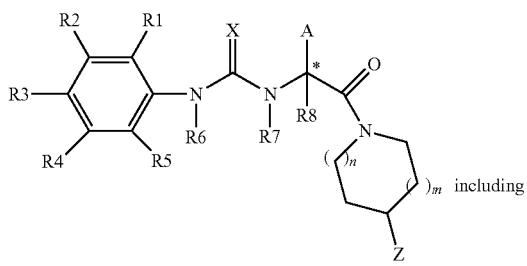

Formula (IV) including

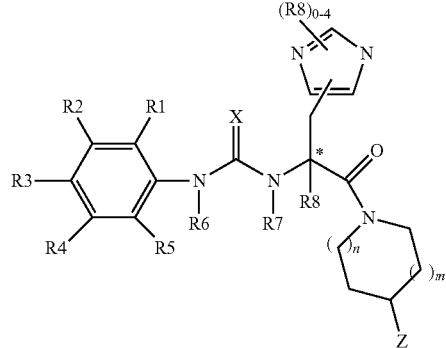

or their enantiomers, diastereomers, pharmaceutically-acceptable salts, solvates, hydrates or prodrugs thereof, wherein:

X is selected from O or S;

A is selected from hydrogen, deuterium, alkyl, substituted alkyl, cycloalkyl, heterocycle, aryl, heteroaryl, aminoalkyl, thioalkyl, alkoxy and an R group of a proteogenic amino acid, or other amino acid synthesized or used by a living system (non-limiting example of such a system: a human), which is optionally isotopically enriched, and/or substituted by alkyl, substituted alkyl, deuterated alkyl, halogen, cycloalkyl, heterocycle, aryl, heteroaryl, aminoalkyl, thioalkyl, alkoxy, haloalkyl, haloalkoxy, or any atom or isotope permitted by valence (including any accompanying hydrogens by valence e.g. (non-limiting) OH, $NH_2$, SH, $SiH_3$, $PH_2$ etc.);

n and m are 0, 1, or 2;

$R_1$ through $R_5$ are independently selected from hydrogen, halogen, $NO_2$, CN, $C_{1-8}$alkyl, substituted $C_{1-8}$alkyl, $C_{3-8}$cycloalkyl, aryl, heterocyclo, heteroaryl, $OR_9$, $SR_9$, $COR_{11}$, $CO_2R_{11}$, $CONR_9R_{10}$ or $NR_9R_{10}$;

$R_6$ and $R_7$ are independently hydrogen, alkyl or substituted alkyl;

$R_8$ is hydrogen, deuterium, $C_{1-8}$alkyl, substituted $C_{1-8}$alkyl, deuterated $C_{1-8}$alkyl, aryl, heterocyclo, heteroaryl, aminoalkyl, thioalkyl, alkoxy, halogen, haloalkyl, haloalkoxy, or any atom or isotope permitted by valence (including any accompanying hydrogens by valence e.g. (non-limiting) OH, $NH_2$, SH, $SiH_3$, $PH_2$ etc.);

Z is hydrogen, alkyl, substituted alkyl, cycloalkyl, aryl, heterocyclo, heteroaryl, $COR_{11}$, $CO_2R_{11}$, $SO_2R_{11}$, $S(O)R_{11}$ or $CONR_9R_{10}$;

$R_9$ and $R_{10}$ are independently hydrogen, $C_{1-8}$alkyl, substituted $C_{1-8}$alkyl, $C_{3-10}$cycloalkyl, aryl, heterocyclo, heteroaryl, $COR_{13}$, $SO_2R_{13}$ or $S(O)R_{13}$; and $R_{11}$, $R_{12}$ and $R_{13}$ are independently hydrogen, $C_{1-8}$alkyl, substituted $C_{1-8}$alkyl, $C_{3-10}$cycloalkyl, aryl, heterocyclo or heteroaryl;

wherein each occurrence of $R_9$-$R_{13}$ is chosen independently.

Preferred Compounds of Formula (IV)

Preferred methods are to use, and preferred compounds are, compounds of Formula (IV), their enantiomers, diastereomers, pharmaceutically-acceptable salts, solvates, hydrates or prodrugs thereof, in which:

$R_2$, $R_3$ and $R_4$ are all hydrogen; and/or $R_6$ and $R_7$ are both hydrogen; and/or n and m are both 1; and/or $R_1$ and $R_5$ are both $C_{1-8}$ alkyl, preferably both $R_1$ and $R_5$ are isopropyl groups.

Other preferred methods use, and preferred compounds are, compounds of Formula (IV), their enantiomers, diastereomers, pharmaceutically-acceptable salts, solvates, hydrates or prodrugs thereof, in which:

Z is $C_{1-8}$alkyl, $C_{2-8}$alkenyl, $C_{1-8}$halo alkyl, cycloalkyl, aryl, arylalkyl, heteroaryl, heteroarylalkyl —$COR_{11}$, —$CO_2R_{11}$, —$SO_2R_{11}$, —$S(O)R_{11}$ or —$CONR_9R_{10}$; especially preferable is benzyl, —$C(O)_2H$ or —$C(O)_2C_{1-8}$alkyl;

$R_9$ is hydrogen;

$R_{10}$ is $C_{1-8}$alkyl or $C_{3-10}$cycloalkyl; aryl or arylalkyl; and $R_{11}$ is hydrogen, $C_{1-8}$alkyl, $C_{3-10}$cycloalkyl, $C_{3-10}$heterocycloalkyl, $C_{3-10}$aryl or $C_{3-10}$arylalkyl.

Other preferred methods use, and preferred compounds are, compounds of Formula (IV), their enantiomers, diastereomers, pharmaceutically-acceptable salts, solvates, hydrates or prodrugs thereof, in which:

A is hydrogen, deuterium, $C_{1-8}$alkyl, heteroaryl, aryl, or alkyl substituted with heterocyclo, aryl, OH, SH, $ST^1$, —$C(O)$, H, $T^3$-$NT^5T^6$, -$T^8$-$C(O)_tT^9$-$NT^5T^6$ or $T^3$-$N(T^2)T^4NT^5T^6$, $T^1$ is alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl;

$T^2$ and $T^3$ are each independently a single bond, -$T^8$-$S(O)_t$-$T^9$-, -$T^8$-$C(O)$-$T^9$-, -$T^{18}$-$C(S)$-$T^9$, -$T^8$-O—$C(O)$-$T^9$-, -$T^8$-$C(O)_tT^9$-$T^8$-$C(=NT^{10}$-$T^9$- or -$T^8$-$C(O)$—$C(O)$-$T^9$-;

$T^5$, $T^6$, $T^7$, $T^8$ and $T^9$ are independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alky, each group optionally substituted where valence allows by one to three groups selected from halo, cyano, nitro, OH, oxo, —SH, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl, —$OT^{11}$, —$ST^{11}$, —$C(O)_tH$, —$C(O)_tT^{11}$, —O—$C(O)T^{11}$, $T^8C(O)_tN(T^{12})T^{11}$, —$SO_3H$, —$S(O)_tT^{11}$, $S(O)_tN(T^{12})T^{11}$, -$T^{13}$-$NT^{11}T^{12}$, -$T^{13}$-$N(T^{12})$-$T^4$-$NT^{11}T^{22}$, -$T^{13}$-$N(T^{11})$-$T^{12}$-$T^{11}$ and -$T^{13}$-$N(T^{18})$-$T^{14}$-H; or $T^8$ and $T^9$ are each independently a single bond, alkylene, alkenylene or alkynylene;

$T^{11}$ is alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl;

$T^{12}$ is halo, cyano, nitro, OH, oxo, —SH, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl, —$C(O)_tH$ or —$SO_3H$;

$T^{13}$ and $T^{14}$ are each independently a single bond, —$S(O)_t$—, —$C(O)$—, —$C(S)$—, —O—, —S—, —O—$C(O)$—, —$C(O)_t$—, —$C(NT^{13})$— or —$C(O)C(O)$;

wherein each occurrence of $T^1$-$T^{14}$ is chosen independently; and t is 1 or 2.

Preferred compounds of the foregoing section are those in which A is hydrogen, deuterium, $C_{1-8}$alkyl, hydroxyalkyl, heterocycloalkyl, heteroaryl alkyl, aryl, arylalkyl, or alkyl substituted with a group selected from SH, $ST^4$, —$C(O)_tH$, $T^6$-$NT^8T^9$, -$T^{11}$-$C(O)_tT^{12}$-$NT^8T^9$ and $T^6$-$N(T^5)T^7NT^8T^9$.

More preferred are those compounds in which A is hydrogen, deuterium, methyl, $CH_2(CH_3)_2$, —$(CH_2)_2(CH_3)_2$, —$CH(CH_3)CH_2(CH_3)$, —$(CH_2)OH$, hydroxyethyl, $(CH_2)_2SCH_3$, —$CH_2SH$, phenyl, —$CH_2$(phenyl), —$CH_2$(p-hydroxyphenyl), —$CH_2$(indole), —$(CH_2)C(O)NH_2$, —$(CH_2)_2C(O)NH_2$, —$(CH_2)_2C(O)OH$, —$CH_2C(O)OH$, —$(CH_2)_4NH_2$, $(CH_2)_3(=NH)CNH_2$, or —$CH_2$(imidazole). Especially preferred A groups are $CH(CH_3)CH_2(CH_3)$, phenyl, phenyl alkyl or —$CH_2$(2-indole).

Alternatively preferred methods use, and preferred compounds are, compounds of Formula (IVb), their enantiomers, diastereomers, pharmaceutically-acceptable salts, solvates, hydrates or prodrugs thereof, in which:

Formula (IVb)

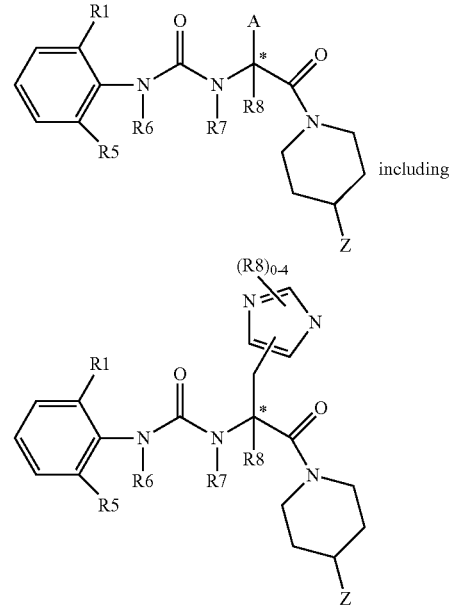

including wherein:

A is hydrogen, deuterium, $C_{1-8}$alkyl, heteroaryl, aryl, or alkyl substituted with heterocyclo, aryl, OH, SH, $ST^1$, —$C(O)_tH$, $T^3$-$NT^5T^6$, -$T^8$-$C(O)_tT^9$-$NT^5T^6$ or $T^3$-$N(T^2)T^4NT^5T^6$;

$R^1$ and $R^5$ are independently $C_{1-8}$alkyl optionally substituted where valence allows;

$R^6$ and $R^7$ are independently hydrogen or $C_{1-8}$alkyl;

$R^8$ is hydrogen, halogen, deuterium, $C_{1-8}$alkyl or substituted $C_{1-8}$alkyl;

Z is hydrogen, $C_{1-8}$alkyl, $C_{2-8}$alkenyl, $C_{1-8}$haloalkyl, cycloalkyl, aryl, arylalkyl, heteroaryl, heteroarylalkyl —$COR^{11}$, —$CO_2R^{11}$, —$SO_2R^{11}$, —$S(O)R^{11}$ or —$CONR^9R^{10}$;

$R^9$ is hydrogen, $R^{10}$ is $C_{1-8}$alkyl or $C_{3-10}$cycloalkyl; aryl or arylalkyl;

$R^{11}$ is hydrogen, $C_{1-8}$alkyl, $C_{3-10}$cycloalkyl, $C_{3-10}$heterocycloalkyl, $C_{3-10}$aryl or $C_{3-10}$arylalkyl.

$T^1$ is alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl;

$T^2$ and $T^3$ are each independently a single bond, -$T^8$-$S(O)_t$-$T^9$-, -$T^8$-$C(O)$-$T^9$-, -$T^{18}$-$C(S)$-$T^9$-, -$T^8$-O-$T^9$-, -T⁸-S-T⁹-, -T⁸-O—C(O)-T⁹-, -T⁸-C(O)$_t$T⁹-, -T⁸-C(=NT¹⁰-T⁹- or -T⁸-C(O)—C(O)-T⁹-;

T⁵, T⁶, T⁷, T⁸ and T⁹ are independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alky, each group optionally substituted where valence allows by one to three groups selected from halo, cyano, nitro, OH, oxo, —SH, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl, —OT¹¹, —C(O)$_t$H, —C(O)$_t$T¹¹, —O—C(O)T¹¹, T⁸C(O)$_t$N(T¹²)T¹¹, —SO₃H, —S(O)$_t$T¹¹, S(O)$_t$N(T¹²)T¹¹, -T¹³-NT¹¹T¹², -T¹³-N(T¹²)-T⁴-NT¹¹T²², -T¹³-N(T¹¹)-T¹²-T¹¹ and -T¹³-N(T¹⁸)-T¹⁴-H; or T⁸ and T⁹ are each independently a single bond, alkylene, alkenylene or alkynylene;

T¹¹ is alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl;

T¹² is halo, cyano, nitro, OH, oxo, —SH, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl, —C(O)$_t$H or —SO₃H;

T¹³ and T¹⁴ are each independently a single bond, —S(O)S, —C(O)—, —C(S)—, —O—, —S—, —O—C(O)—, —C(O)$_t$, —C(=NT¹³)- or —C(O)—C(O)—; and t is 1 or 2.

More preferred methods/compounds use/are:

A is hydrogen, deuterium, methyl, —CH₂(CH₃)₂, —(CH₂)₂(CH₃)₂, —CH(CH₃)CH₂(CH₃), (CH₂)OH, hydroxyethyl, —(CH₂)₂SCH₃, —CH₂SH, phenyl, —CH₂(phenyl), —CH₂(p-hydroxyphenyl), —CH₂(indole), —(CH₂)C(O)NH₂, —(CH₂)₂C(O)NH₂, —(CH₂)₂C(O)OH, —CH₂C(O)OH, —(CH₂)₄NH₂, —(CH₂)₃(=NH)CNH₂ or —CH₂(imidazole).

Especially preferred methods/compounds use/are:

A is —CH(CH₃)CH₂(CH₃), phenyl, CH₂(phenyl) or —CH₂(2-indole).

Also, especially preferred methods/compounds use/are:

R⁸ is hydrogen and the configuration about the carbon marked with the * is S, provided A is not H. Also preferred: R⁸ is deuterium and the configuration about the carbon marked with the * is S, provided A is not H or deuterium.

Other preferred methods/compounds use/are:

R¹ and R⁵ are both isopropyl; and/or R⁶R⁷ and R⁹ are all hydrogen; and/or Z is CH₂(phenyl), —C(O)₂H or —C(O)₂C₁₋₈alkyl.

Example Embodiments of Formula (IV)

In the following scheme, Scheme X, all reactants are commercially available e.g. Compound 2 is available from Oxchem Corporation, IL, USA.

Scheme X

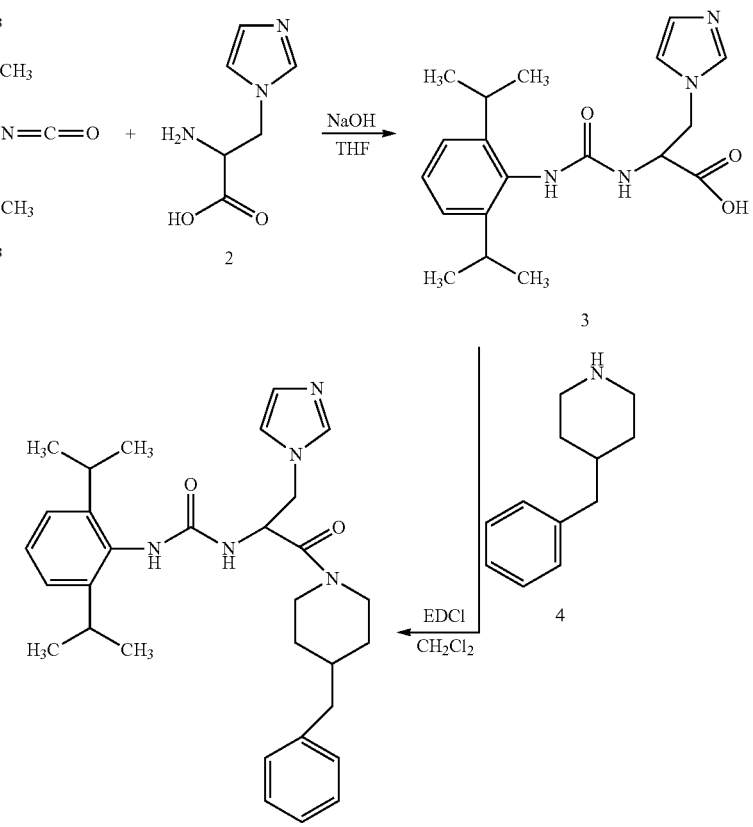

Using Scheme X, above, with different amino acids as the Compound 2 input, gives different Compound 5 products (all reactants are commercially available e.g. Compound 2b is available from Aurora Fine Chemicals LLC, San Diego, USA, Compound 2c and 2d from Sigma-Aldrich).

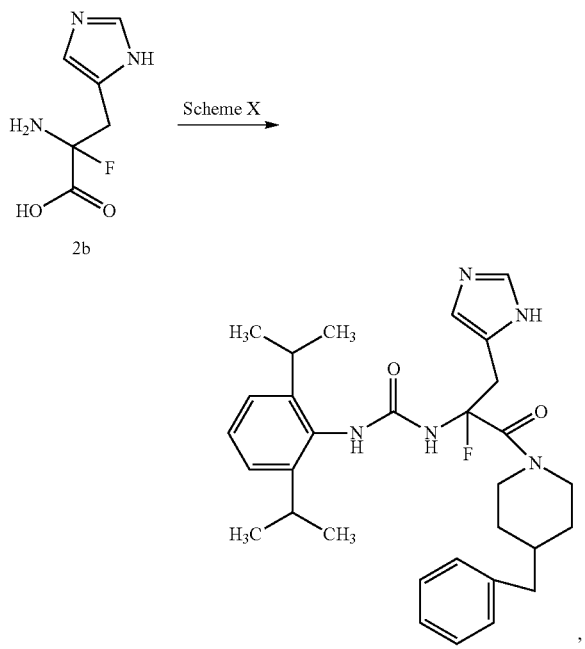

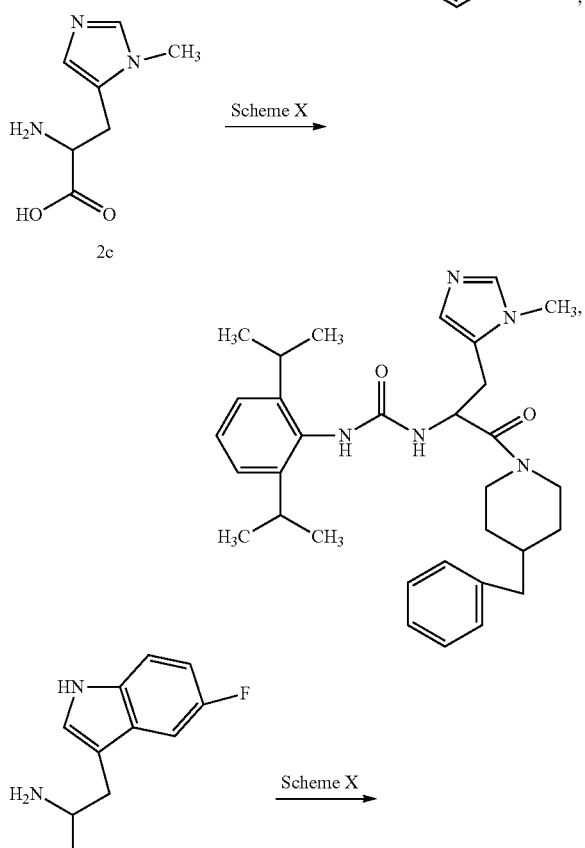

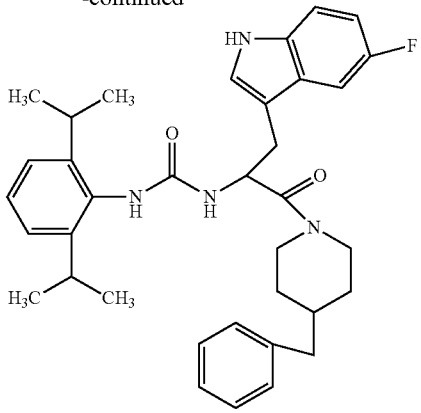

Following is Structure IV, from Scheme I, in the "Process of Preparation" section of [P3], symbol definitions are as in [P3]. Scheme I in [P3] is a more general form of Scheme X above.

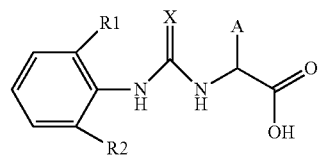

IV

This Structure IV can be deuterated, as can final compounds of the scaffold of [P3] (scaffold presented in its abstract), at its chiral carbon, and in further embodiments at further or other position(s), by reactions described in [A, B, E1, E2, F], which can deuterate the α-carbon to secondary amines. And/or by reactions described in [Ex3], which can deuterate the α-carbon to a carbonyl, using pyrrolidine (available from Sigma-Aldrich) as catalyst, and/or by reactions described in [Ex4], which deuterate ketones. And/or by reactions described in [N], which deuterate sp3 carbons. And/or by reactions described in [R1, R2, Q1, Q2], which deuterate aromatic and alkyl molecular components. Deuterated Compound IV structure(s) can be inputted into the synthesis Scheme I of [P3], in place of an undeuterated Compound IV form compound(s), to make deuterated isotopologue(s) with the scaffold of [P3], its scaffold is shown in its abstract. Alternatively, to achieve this aim, a compound(s) of Structure III form in Scheme I of [P3] can be deuterated at its chiral carbon, and in further embodiments at further or other position(s), by reactions described in [A, B, P, E1, E2, F], which deuterate the α-carbon to primary amines. And/or by a methodology used to deuterate amino acids, of which many are known to those of the art (non-limiting e.g. [AA1-AA6, B]), because Structure III (of [P3]) is of the amino acid form. Indeed, deuterated (and/or other isotopically enriched e.g. $^{13}C$ and/or $^{15}N$) amino acids can be sourced commercially, e.g. (non-limiting) from Sigma-Aldrich or Cambridge Isotope Laboratories Inc., and used in Scheme I of [P3] to produce isotopically enriched compound embodiments of the present invention. For (illustrative, non-limiting) example, Cambridge Isotope Laboratories Inc. sell histidine enriched (97-99%) for $^{13}C$, $^{15}N$, $^{2}H$ at the respective positions of C, N and H in histidine (item number: CDNLM-6806-PK). Sigma-aldrich sell this also (item number: 750158 ALDRICH). Deuterated (and other isotopically enriched) compound embodiments of the scaffold of [P3] (scaffold presented in its abstract), most preferably deuterated at their chiral carbon (which in an embodiment is $^{13}C$ at enriched, non-natural abundance, e.g. {non-limiting}>70% $^{13}C$ incorporation), are componentry to the present invention as new compositions of matter. And in non-limiting embodiments, these are used singly or in combination, optionally in co-therapy with an FDA and/or EMA approved medicine(s) and/or treatment(s), for example a licensed cancer treatment, as anti-cancer therapeutics.

Example (V)

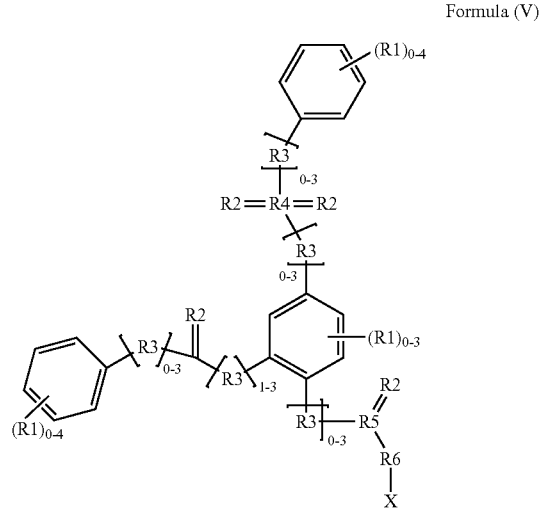

Formula (V)

R2 = O, S, Se
R3 = O, C, S, Se, Si
R4 = S, Se
R5 = N, C
R6 = R3, X

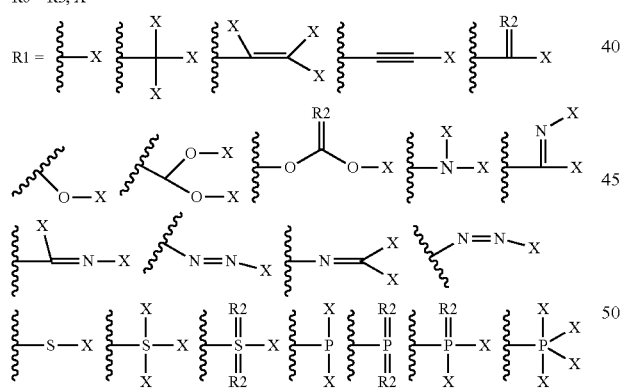

X = absent, H, Deuterium, OH (hydroxyl), SH (thiol), =O (keto), CN (cyano), halogen, $CH_3$ (methyl), methoxy ($OCH_3$), trifluoromethyl, $OCF_3$, $NH_2$ (amino), NOOH (nitro), =N—OH, COOH (carboxyl), COH (formyl), N=O (nitroso), O—N=O (nitrosooxy), alkyl($C_{1-4}$), alkoxy($C_{1-4}$), haloalkyl($C_{1-4}$), alkylthio($C_{1-4}$), hydroxyalkyl($C_{1-4}$), aminoalkyl($C_{1-4}$), cycloalkyl ($C_{1-4}$), haloalkoxy($C_{1-4}$), alkenyl($C_{1-4}$), alkynyl($C_{1-4}$), alkoxycarbonyl($C_{1-4}$), substituted alkyl($C_{1-4}$) {which is an alkyl with between 1 and 4 carbons and one or more independent substituents of X}

Molecular permutations of BTB06584. Enumerations of this Markush structure, and their pharmaceutically-acceptable salts, solvates, hydrates and prodrugs thereof, are disclosed as anti-cancer molecules: the process/method of their use as anti-cancer molecules is disclosed by this invention. As valence permits: R1 is selected from the options of R1 (independently in each case of R1), X is selected from the options of X (independently in each case of X), R2 is selected from the options of R2 (independently in each case of R2), R3 is selected from the options of R3 (independently in each case of R3), R4 is selected from the options of R4 (independently in each case of R4). In other embodiments one or more phenyl groups has one or more of its double bonds replaced with a single bond. In other embodiments, one or more phenyl groups is replaced with cyclohexane, each with the same possible substitutions as the phenyl it replaces. Hydrogen atoms aren't shown in this figure, but in further embodiments one or more hydrogen atoms is replaced with deuterium. In further embodiments: any possible isotopic substitution at one or more places.

Example Embodiments of Formula (V)

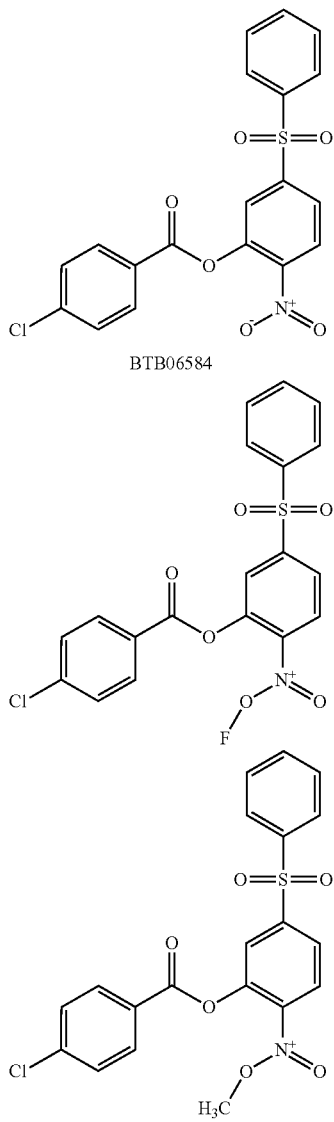

BTB06584

BTB06584, and/or its analogues, can be deuterated by reactions described in [R1, $R_2$, Q1, Q2], which deuterate aromatic and alkyl molecular components. Furthermore, there is a great wealth of reactions available to deuterate their aromatic rings, and those skilled in the art will know these. For (non-limiting) example, refer [Ex2]. Deuterated isotopologues of Formula (V), for (non-limiting) example deuterated BTB06584, are componentry to the present invention as new compositions of matter, and in non-limiting embodiments are used singly or in combination, optionally in co-therapy with an FDA and/or EMA approved medicine(s) and/or treatment(s), for example a licensed cancer treatment, as anti-cancer therapeutics.

Example (VI)

Encompassed by this embodiment are methods of treating a subject suffering from cancer by administering an effective amount of at least one compound of Formula (VI) or a pharmaceutically-acceptable salt, solvate, hydrate or prodrug thereof, or a pharmaceutical composition(s) comprising one or compounds of Formula (VI).

Summary of Formula (VI)

This invention embodiment relates to compounds having the following formula:

Formula (VI)

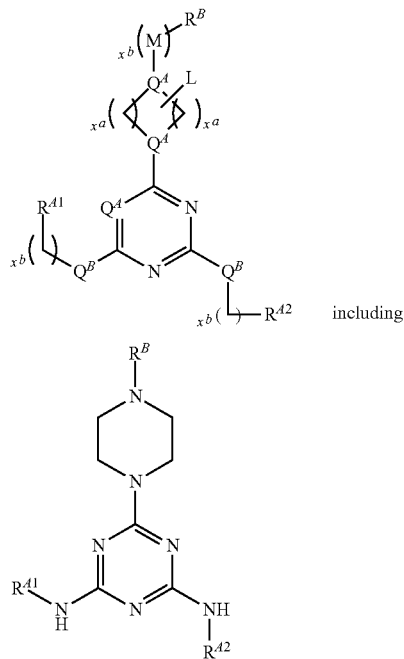

including or a pharmaceutically-acceptable salt, solvate, hydrate or prodrug thereof, wherein:

each $Q^A$ is independently selected from N and CH;

each $Q^B$ is independently selected from NH and $CH_2$;

M is independently selected from O, NH and $CH_2$;

$x^a$ is independently at each point of use selected from 1, 2, 3, 4, or 5; $x^b$ is independently at each point of use selected from 0, 1, 2, 3, 4, or 5; L represents 0-5 optional substituents on the ring independently selected from alkyl, substituted alkyl, deuterated alkyl, aminoalkyl, thioalkyl, alkoxy, halogen, haloalkyl, haloalkoxy, or any atom or isotope permitted by valence (including any accompanying hydrogens by valence e.g. (non-limiting) OH, $NH_2$, SH, $SiH_3$, $PH_2$ etc.);

$R^{A1}$ and $R^{A2}$ are each independently selected from the groups

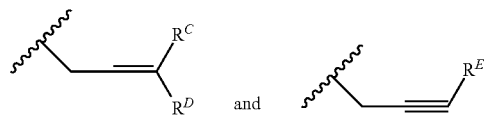

wherein $R^C$ and RP are each independently selected from hydrogen, deuterium, halogen and alkyl, and wherein $R^E$ is hydrogen, deuterium, or alkyl;

$R^B$ is selected from $R^{B1}$, hydrogen and deuterium;

wherein $R^{B1}$ is selected from phenyl, benzyl, heteroaryl, pyridyl, pyrimidyl and pyrazinyl optionally substituted with one or more substituents $R^{B2}$;

wherein each $R^{B2}$ is independently selected from halogen, alkyl, alkoxy, nitro, amino, methoxy and polyhalogen alkyl;

or $R^B$ is a phenylalkyl of the formula:

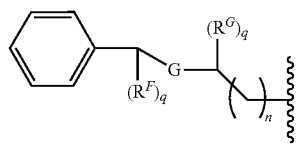

wherein $R^F$ and $R^G$ are hydrogen or alkyl, G is a carbon-carbon double bond or a carbon-carbon single bond, n is 0 or 1 and q is 0 or 1 provided that where q is 0, G is a carbon-carbon double bond and where q is 1, G is a carbon-carbon single bond, or $R^B$ is a diphenylalkyl of the formula

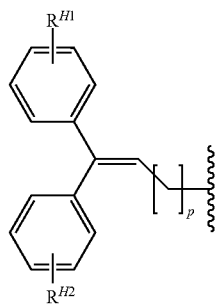

wherein $R^{H1}$ and $R^{H2}$ each independently represent 1-5 optional substituents on each ring, and wherein each $R^{H1}$ and $R^{H2}$, when present, is independently selected at each point of use from hydrogen, L (defined earlier) or halogen, and p is 0, 1 or 2;

or $R^B$ is the group

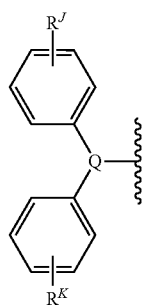

Wherein Q is CH or N, $R^J$ and $R^K$ each independently represent 1-5 optional substituents on each ring, and wherein each $R^J$ and each $R^K$, when present, is independently selected from L (defined earlier), halogen, alkyl, alkoxy, nitro, amino and polyhalogen alkyl.

In some embodiments, when one or both of $R^J$ and $R^K$ is alkoxy, this alkoxy group may be methoxy.

It is to be understood that in the compounds of general Formula (VI), wherein $R^{A1}$ and/or $R^{A2}$ are alkenyl moieties having different substituents at the position $R^C$ and $R^D$, that compound may exist in cis or trans isomeric forms both of which are considered to be within the scope of the present invention. All isotopic forms of Formula (VI) are within the scope of the present invention.

Preferred Embodiments of Formula (VI)

For Formula (VI), the symbols $R^C$ and $R^D$ as defined in subgroups $R^{A1}$ and $R^{A2}$, may be hydrogen, halogen (suitably fluorine, chlorine or bromine), alkyl, suitably "lower alkyl" (herein now defined) having from 1 to 5 carbon atoms, such as methyl, ethyl, propyl, isopropyl, butyl, isobutyl, tert butyl, pentyl and the like, most preferably methyl; and the moiety $R^E$ may be hydrogen, or lower alkyl having from 1 to 5 carbon atoms such as methyl, ethyl, propyl, butyl, or pentyl, most suitably methyl.

The subgroup $R^B$ may be hydrogen; phenyl; or substituted phenyl. The substituted phenyl group may include one or more of the preferred substituents in any of the available positions for substitution, however, mono substitution in the 4-position of the phenyl nucleus is especially preferred. Suitable substituents for the phenyl nucleus include halogen, preferably fluorine, chlorine or bromine; lower alkyl, lower alkoxy, and poly halogen lower alkyl (i.e. substituted alkyl) wherein the alkyl moiety contains from 1 to 5 carbon atoms, especially preferred however are methyl, methoxy, and trifluoromethyl; and nitro and amino.

Where the subgroup $R^B$ represents substituted pyridyl, substituted pyrimidyl, or substituted pyrazinyl, the substituting group may be located on one or more of the available carbon atoms in the nucleus, and may be the same or different. Preferred among the substituting groups are lower alkyl or lower alkoxy having from 1 to 5 carbon atoms such as methyl, ethyl, butyl or penty; or methoxy, propoxy, butoxy or pentoxy.

Where the moiety $R^B$ represents substituted benzyl, the benzyl moiety may be substituted in one or more of the available positions on the phenyl nucleus thereof. Among the preferred substituents are halogen (suitably fluorine, chlorine or bromine), lower alkoxy having from 1 to 5 carbon atoms, especially preferred is methoxy and most preferred being di- and tri-methoxy; or alkylenedioxy suitably lower alkylenedioxy such as methylenedioxy, ethylenedioxy, propylenedioxy and the like, most suitably, the alkylenedioxy moiety is attached across the 3- and 4-positions of the phenyl nucleus, although the bridging of other carbon atoms in the phenyl nucleus is to be considered within the scope of the present invention.

The moieties $R^F$ and $R^G$ may be hydrogen, or lower alkyl of 1 to 5 carbon atoms, most preferred however being methyl.

The groups $R^{H1}$ and $R^{H2}$ may be independently hydrogen, or halogen suitably fluorine, chlorine or bromine.

Preferred embodiments of Formula (VI) include wherein $R^C$ and $R^D$ are methyl, $R^E$ is methyl and $R^B$ is selected from chlorophenyl, methylphenyl, methoxyphenyl, trifluorophenyl, chlorophenyl, dimethoxybenzyl, trimethoxybenzyl, methylenedioxybenzyl and ethylenedioxybenzyl.

In some embodiments $R^B$ is the group

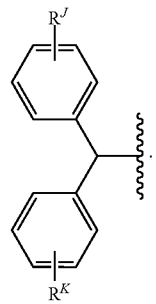

In some embodiments, $R^B$ is the group

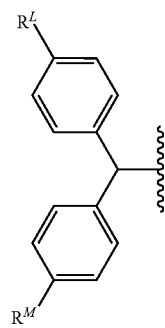

wherein $R^L$ and $R^M$ are each independently selected from halogen, alkyl, alkoxy, nitro, amino and polyhalogen alkyl.

Synthesis of Structures of Formula (VI)

Synthesis routes for example embodiments of Formula (VI) are in [P7], which is herein incorporated in entirety by reference. One or more chemical enumerations/structures from [P7], in use as an anti-cancer therapeutic, is componentry to the present invention. Indeed, encompassed by this embodiment are methods of treating a subject suffering from cancer by administering an effective amount of at least one compound from [P7] or a pharmaceutically-acceptable salt, solvate, hydrate or prodrug thereof, or a pharmaceutical composition(s) comprising one or compounds from [P7].

Example Embodiments of Formula (VI)

Invention embodiments include compounds of Formula (VI), whether a decoupler or not, and any compound(s) of any formula, which has decoupling activity (changes $F_1F_0$ ATP synthase stoichiometry), in use for anti-cancer therapy.

Decoupler Drugs as Anti-Cancer Medicines

Enumerations of Formulas I-V exert anti-cancer activity by inhibiting, and so reducing, $F_1F_0$ ATP hydrolysis. The present embodiment also exerts anti-cancer activity by reducing $F_1F_0$ ATP hydrolysis. However, not by inhibition of $F_1F_0$ ATP hydrolysis, but by making $F_1F_0$ ATP hydrolysis more efficient! Such that less ATP is hydrolysed per unit proton motive force (pmf) generated i.e. $F_1F_0$ ATP hydrolysis is reduced. The shared feature of these embodiments is that cancer function is impaired, and cancer danger reduced, by reducing $F_1F_0$ ATP hydrolysis in cancer cells. The present embodiment relates to and discloses the method/use of a "decoupler" drug(s) as an anti-cancer therapeutic e.g. (non-limiting) almitrine, which is a compound of Formula (VI). Disclosed experimental data shows that almitrine exerts anti-cancer activity (FIG. 7).

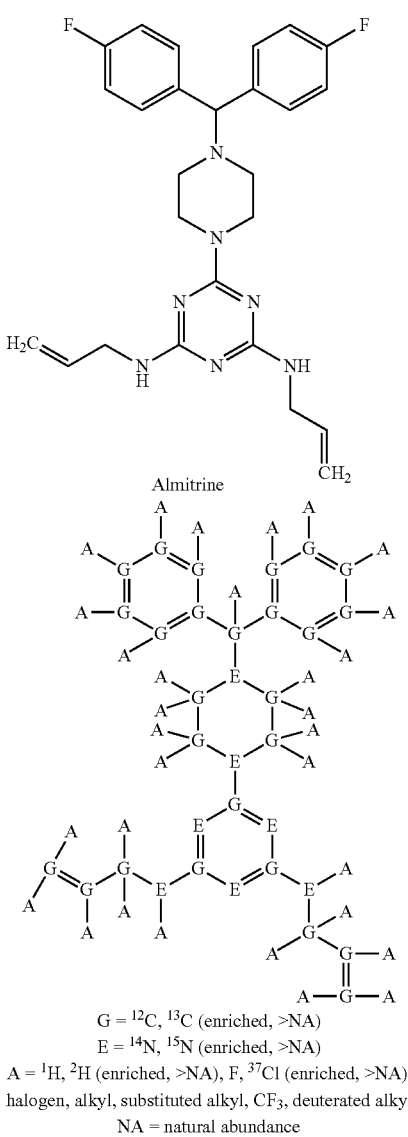
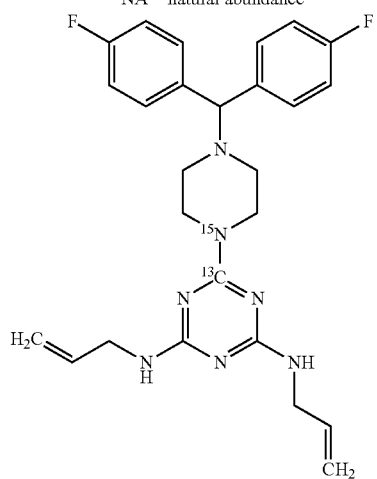

Decoupler drugs modify the H⁺/ATP stoichiometry of ATP synthase, so modifying the ATP/O ratio, without significantly changing $\Psi_{IM}$ [113-116]. Such drugs symmetrically modify the forward and reverse modes of ATP synthase: they make the forward mode less efficient (less ATP synthesized per protons passed) and the reverse mode more efficient (more protons pumped per ATP hydrolysed). In other words, they reduce the (fractional) ATP yield/cost of a proton passing through ATP synthase energetically "downhill"/"uphill", in relation to the direction of the proton motive force (pmf). In isolated mitochondria, the almitrine conferred decrease in $F_1F_0$ ATP synthesis and hydrolysis is maximal at ~60%, no matter how great the almitrine concentration [114]. Almitrine can double the stoichiometry: double the number of protons required/pumped for/by ATP synthesis/hydrolysis. Almitrine reduces the amount of ATP that $F_1F_0$ ATP synthase synthesizes, but it also reduces the amount of ATP that $F_1F_0$ ATP synthase hydrolyses, which is normally, without almitrine, significant. Indeed, this disclosure discloses a new fundamental biological discovery, with supporting in vivo experimental data (FIG. 15): $F_1F_0$ ATP hydrolysis isn't a bug but a feature, substantial and essential to heat generation and homeothermy. Almitrine reduces ATP synthesis and hydrolysis and these aspects largely offset and intracellular [ATP] remains within survivable limits. Almitrine reduces inefficiency (heat generation) but simultaneously increases inefficiency (heat generation). Making the forward mode of ATP synthase less efficient might be bad for normal cells, as it might be for cancer cells that use OXPHOS, but this decoupler action disproportionally affects cells with a higher respiratory rate [114], which could disproportionally affect cancer cells. Although decouplers make the reverse mode of ATP synthase more efficient, this action still exerts anti-cancer activity on cancers using ATP synthase in reverse. Because these cancers use this mode for its inefficiency: to consume ATP, to permit high glycolytic and PPP flux, to enable high [NADPH] and low [ROS]. So, slowing/reducing this $F_1F_0$ ATP hydrolysis exerts anti-cancer activity. The same cancer can be disrupted by both almitrine actions, upon the forward and reverse modes of ATP synthase, at different stages of the cell cycle.

In normal cells, almitrine decreases ATP synthesis, but decreases ATP hydrolysis also, and so [ATP] is maintained. In cancer cells residing in hypoxia, thence forced to survive with a lower OXPHOS rate, which already rely upon high $IF_1$ expression (many cancers overexpress $IF_1$ [23-24]) to block ATP hydrolysis and buoy [ATP], almitrine conferred decrease in ATP synthesis strikes them disproportionally.

Comparing FIGS. 1 and 7, one observes that in standardized NCI one-dose testing [16-17], almitrine dismesylate (10 μM) exerts greater anti-cancer activity than carboplatin (10 μM), which is an FDA approved chemotherapeutic, one of the most used chemotherapies today, and is on the World Health Organisation (WHO) list of essential medicines. Furthermore, almitrine dismesylate is less toxic to normal cells than carboplatin. In mice, intraperitoneal injection (IP) $LD_{50}$ (dosage at which 50% of test mice die)=118 mg/kg for carboplatin [117] and =370 mg/kg for almitrine dismesylate [118].

In humans, 200 mg per day of oral almitrine dismesylate has been trialed for sleep apnea, which is a drive to snoring [119]. In humans, oral almitrine dismesylate has been used for decades, totaling millions of patient months of almitrine administration, for chronic obstructive pulmonary disease (COPD), often at 200 mg oral almitrine dismesylate per day [120, 121]. A single 200 mg oral almitrine dismesylate dose (70% orally bioavailable) renders a mean cmax plasma concentration of 286 ng/ml=0.6 μM [121]. Because almitrine volume of distribution (VD)=17 l/kg [121], and human volume=~1 l/kg [122], corresponding almitrine tissue concentration (assuming uniform)=(0.6*17)=~10 μM, which is an almitrine concentration that exerts anti-cancer activity in NCI testing (FIG. 7). Almitrine has a long lifetime in the body and 24 hours after 200 mg oral almitrine dimesylate, plasma [almitrine] is still ~50 ng/ml [121] which will compound with the next daily 200 mg almitrine dimesylate dose and drive almitrine tissue concentrations >10 µM. A different human study [123] recorded mean cmax plasma concentration, post a single 150 mg oral almitrine dimesylate dose, to be 379 ng/ml, and an even higher volume of distribution for almitrine. In clinical use for COPD, a plasma concentration of 300 ng/ml almitrine is the directive [120], which corresponds to an anti-cancer tissue concentration (~10 µM) of almitrine. Non-limiting anti-cancer embodiments of this invention are almitrine dosages/formulations/compositions/salts/patterns of administration (e.g. sequential administration scheme) already used in humans (for example, as reported in the literature). Furthermore, higher or lower almitrine doses for anti-cancer therapy, optionally administered intravenously and/or with layoff periods (no drug administered), are further embodiments of this invention. An invention embodiment is a method of trialing almitrine as an anti-cancer drug in human cancer patients without first performing Phase I trials with almitrine or first trialing almitrine in healthy human subjects.

Almitrine acts upon BK potassium channels in chemoreceptors, within the caratoid bodies, and acts as a respiratory stimulant, which increases blood and tissue oxygenation, decreasing their $[CO_2]$ [125, 126]. This respiratory stimulation should exert an additional anti-cancer effect in vivo because increasing $[O_2]$ in blood and tissues increases their [ROS], especially in combination with ROS inducing [chemo/radio] therapies (permitting their use at lower doses, reducing their side effects). This synergises with the almitrine conferred reduction in $F_1F_0$ ATP hydrolysis in cancer cells, which corrupts the system cancers use to maintain low intracellular [ROS] at key stage(s) of the cell cycle, which is paramount to their "limitless replicative potential" (Hallmark of cancer [26]) and thence danger. Almitrine will be especially valuable against cancers (e.g. lung, breast) that can disrupt breathing and/or reduce $O_2$ delivery to tissues. Embodiments of this invention are to use almitrine, or any other drug(s) that modifies ATP synthase stoichiometry (a decoupler), as an anti-cancer medicine, optionally in co-therapy with one or more FDA and/or EMA approved drug(s), e.g. a cancer drug(s), and/or in co-therapy with any other compound(s) embodiments of the present invention e.g. a compound(s) of Formula (I-V) herein. Almitrine dimesylate is also known as almitrine bismesylate or almitrine dimethanesulfonate. All pharmaceutical salts of almitrine are contemplated as anti-cancer therapeutics, as is almitrine in complex with another drug(s) e.g. almitrine-raubasine.

When used chronically, almitrine can have side effects [120]. A 30 year national pharmacovigilance survey in France, representing several million patient months of almitrine treatment [124], showed that upon multi-year use (mean onset of adverse reactions=11 months), some patients receiving oral almitrine exhibited weight loss (795 cases) and peripheral neuropathy (2,304 cases) [120]. Although these side effects didn't present in all patients and only in a minority of cases that they did present were they categorised as serious (<10%) [120]. Almitrine has never been FDA approved. Almitrine has now been withdrawn from use in France, Portugal and Poland, where it was previously approved to treat chronic obstructive pulmonary disease (COPD). This withdrawal was because of the aforementioned two side effects and because alternative treatments emerged and because "available efficacy data, including data which became available since the initial marketing authorisation, showed only very limited clinical efficacy of almitrine in its approved indications" [120]. Although almitrine does increase arterial pO2, this does not translate to significant clinical benefit for COPD sufferers [120].

Almitrine's anti-cancer activity was unknown prior to this disclosure, despite almitrine being around since the early 1970 s. Its anti-cancer activity is unexpected to a person of the art. Especially because another respiratory stimulant, doxapram, has been publically shown by others to have no anti-cancer activity in the same one-dose (10 µM) NCI-60 test in which, disclosed herein, almitrine dimesylate (10 µM) exerts anti-cancer activity. Doxapram in NCI-60 (10 µM) testing: mean % cancer growth inhibition=−3.7% (median=−2.3%) i.e. negative numbers show cancer growth promotion (!) rather inhibition, as compared to no drug control, NSC: 760347 in [16]. Thence, the discovery of almitrine conferred anticancer activity, disclosed herein, is unforeseen by a person of the art, novel and componentry to the invention of this disclosure. The risk-reward axis for almitrine is sufficient for an anti-cancer drug. Especially when used acutely, because most of almitrine's side-effects only occur with chronic use. Acute almitrine use for cancer treatment has a different risk-reward axis than chronic almitrine use for COPD treatment (for which it is ineffective [120]), especially because almitrine's side-effects are mostly associated with chronic use, and because cancer can be an immediately life-threatening disease for too many patients, with too few life-saving options. Indeed, the merit of anti-cancer treatment merits the risk of higher almitrine dosages than 200 mg per day.

Intravenous delivery of 459±155 mg almitrine, infused within 24 hours, caused reversible lactic acidosis and hepatic dysfunction in 30% of 25 patients [127]. The other 70% of patients had no ill effects, and unaltered plasma [lactate]. The side-affected minority correlated with an impaired liver function parameter, increased plasma [bilirubin], prior to almitrine administration. Thus, this side-affected cohort is largely predictable. Most side-affected were women, but not all women were affected (N.B. women can have a smaller liver relative to body size e.g. refer [128]). The liver converts lactate to glucose by the Cori cycle [1] and an impaired/overwhelmed liver cannot process the elevated plasma lactate that almitrine administration can cause [115], which renders lactate acidosis. An embodiment of this invention is to select a cancer patient's almitrine dosage dependent upon their liver function. That is, in a further (non-limiting) embodiment, assessed by measuring plasma [bilirubin]. For non-limiting example: if (plasma [bilirubin]>17 µM) {the patient should not be administered high almitrine dosage(s)}. Patients with better liver function are at less risk of almitrine driven lactic acidosis [127] and can endure higher almitrine dosages. Another embodiment is to record plasma [lactate], and/or a liver function assay chemical(s) (non-limiting e.g. bilirubin), whilst a cancer patient is administered with almitrine, or a course of almitrine administrations, and to lower the administered almitrine dosage/frequency if these plasma concentrations become abnormal. An invention embodiment is to use almitrine, and a drug(s)/treatment(s) treating/mitigating lactic acidosis, in anti-cancer therapy. Another embodiment is almitrine for anti-cancer therapy, given with a dosage adjustment dependent upon initial body weight, before treatment, and optionally reducing the dosage if significant weight loss occurs. Almitrine in co-therapy with a high(er) calorie diet, as an anti-cancer treatment, is another embodiment. Almitrine in co-therapy with a drug to treat or mitigate peripheral neuropathy (e.g. {non-limiting} gabapentin, duloxetine, pregabalin etc.), as an anti-cancer treatment, is an embodiment of this invention. An embodiment is to use almitrine for anti-cancer therapy and to monitor the almitrine recipient, or for the almitrine recipient to self-monitor, for weight loss and/or signs of neuropathy, and/or odd neurological sensations, especially in the body periphery e.g. the limbs. An embodiment is to use almitrine for anti-cancer therapy under medical supervision. Wherein, in animal or human, almitrine dosage, frequency, route and duration of administration is directed/recommended, and/or almitrine is administered, by a medically qualified professional(s) e.g. a doctor or vet or nurse or pharmacist. In an embodiment, an oncologist or other cancer specialist or a medically qualified professional that has undergone additional training and/or qualification and/or residency in oncology beyond a degree in human and/or veterinary medicine. And optionally wherein one or more of the dosage, frequency, route and duration of almitrine administration is modulated in the light of cancer progression/regression/stasis during the course of almitrine administration.

Mechanistic studies in animals [129-130] have identified that it might not be almitrine itself that causes almitrine associated neuropathy but instead difluorobenzhydrylpiperadine (DFBP), which is the major almitrine metabolite formed in humans. DFBP also causes weight loss in [129] and so DFBP could also be the basis to almitrine associated weight loss (reported in [120]), or this could just be a function of altered feeding behaviour as a function of the DFBP generated neuropathy. To render DFBP from almitrine, the bond between almitrine's nitrogen, at atom number 11, and carbon, at atom number 9, must be broken. An embodiment of this invention is almitrine isotopically enriched (greater than natural abundance, e.g. {non-limiting}>70%) for $^{15}N$ at Atom Number 11, and/or isotopically enriched for $^{13}C$ at Atom Number 9, which will make this bond stronger by the kinetic isotope effect (KIE), which will reduce the rate of DFBP formation, and reduce neuropathy (Atom Numbers as labelled by [25]). Kinetic isotope effect (KIE) is the change in the rate of a chemical reaction when one (or more) of the atoms in the reactants is replaced with its isotope. Heavier isotopes form stronger bonds that require higher energy to break them, which ultimately slows down the chemical reaction rate. Other atom(s) of almitrine enriched (greater than natural abundance, e.g. {non-limiting}>70%) with their heavier, stable respective isotope(s) (e.g. {non-limiting} $^{2}H$ replacements of $^{1}H$) is also componentry to the present invention. As is one or more hydrogen atom(s) upon almitrine, or an aforementioned almitrine isotopologue, replaced by fluorine (or other halogen), especially near the N11-C9 bond that breaks to release DFBP, preferably upon the piperazine ring. The use of one or more of the new compositions of matter of this disclosure, to treat a condition for which almitrine has been used in humans, for (non-limiting) example, chronic obstructive pulmonary disease (COPD), is componentry to this invention. As is their use as an anti-cancer treatment.

Following reactions are illustrative, not restrictive: almitrine could be deuterated, upon its piperazine ring and/or other loci, by reactions described in [N], which deuterate sp3 carbons.

And/or by reactions described in [R1, $R_2$, Q1, Q2] which deuterate widely, upon aromatic and alkyl molecular components. And/or by reactions described in [O1, O2], which deuterate α- and β-carbons to phenyl groups. And/or by reactions described in [D], which deuterate α- and β-carbons to tertiary amines. And/or by reactions described in [F, E1, E2, Ex1], which deuterate α-carbons to tertiary amines. And/or by reactions described in [A, B, E1, E2, F], which deuterate α-carbons to secondary amines. Whichever option(s) is chosen, solvents, temperatures, pressures, and other reaction conditions can be selected by one of ordinary skill in the art. Deuteration can be modulated by modulating reaction time: greater deuterium incorporation by longer reaction time. One can do multiple cycles of one or more of these reactions until the desired level of deuterium incorporation occurs, monitored by $^{1}H$ and/or $^{2}H$ NMR and/or mass spectrometry.

Encompassed by this invention are methods of administering an effective amount of almitrine (and/or one or more of its metabolites), or a pharmaceutically-acceptable salt, solvate, hydrate or prodrug thereof, or a pharmaceutical composition(s) comprising almitrine (and/or one or more of its metabolites), optionally in co-therapy with another anti-cancer treatment(s), to treat/ameliorate/prevent/combat cancer in a subject. Encompassed by this invention are methods of administering an effective amount of GAL021 [125-126] and/or any compound(s) of [P8], or a pharmaceutically-acceptable salt, solvate, hydrate or prodrug thereof, or a pharmaceutical composition(s) comprising GAL021 [125-126] and/or any compound(s) of [P8], optionally in co-therapy with another anti-cancer treatment(s), to treat/ameliorate/prevent/combat cancer in a subject. Encompassed by this invention are methods of administering an effective amount of a (e.g. chemoreceptor) respiratory stimulant(s), or a pharmaceutically-acceptable salt, solvate, hydrate or prodrug thereof, or a pharmaceutical composition(s) comprising a respiratory stimulant(s), optionally in co-therapy with another anti-cancer treatment(s), to treat/ameliorate/prevent/ combat cancer in a subject. Encompassed by this invention are methods of administering an effective amount of a compound(s) that increases pO2 in the subject's blood, or a pharmaceutically-acceptable salt, solvate, hydrate or prodrug thereof, or a pharmaceutical composition(s) comprising a compound(s) that increases pO2 in the subject's blood, optionally in co-therapy with another anti-cancer treatment(s), to treat/ameliorate/prevent/combat cancer in the subject.

A method of treating, ameliorating, preventing or combating cancer in a subject wherein the method comprises the subject taking, or being administered, a therapeutically effective amount of almitrine and/or other compound(s) of Formula VI (and/or a pharmaceutical composition(s) containing a therapeutically effective amount of almitrine and/or other compound(s) of Formula VI herein). Almitrine and/or other compound(s) of Formula VI, (and/or a pharmaceutical composition(s) containing almitrine and/or other compound(s) of Formula VI) for use in the treatment/amelioration/prevention/combat of cancer in a subject. The use of almitrine, and/or other compound(s) of Formula VI, in the manufacture of a medicament for the therapeutic and/or prophylactic treatment of cancer, optionally in a ready-to-use drug form, optionally in a package together with instructions for its anti-cancer use. Almitrine, and/or other compound(s) of Formula VI, for use in a method for the treatment/amelioration/prevention/combat of cancer and/or ischemia and/or stroke (reduces ATP hydrolysis and maintains intracellular [ATP] when $O_2$ and glucose is in short supply because of a vascular occlusion or similar) in a subject.

Definitions Used to Specify Formulas (I), (II), (III), (IV), (V) and (VI)

The initial definition provided for a group or term herein applies to that group or term throughout the present specification, individually or as part of another group, unless otherwise indicated.

The term "alkyl" refers to straight or branched chain hydrocarbon groups having 1 to 21 carbon atoms, preferably 1 to 8 carbon atoms. Lower alkyl groups, that is, alkyl groups of 1 to 4 carbon atoms, are most preferred.

The term "substituted alkyl" refers to an alkyl group as defined above having one, two, three, or four substituents selected from the group consisting of halogen, trifluoromethyl, alkenyl, alkynyl, nitro, cyano, keto (=O), OR$_a$, SR$_a$, NR$_a$R$_b$, NR$_a$SO$_2$, NR$_a$SO$_2$R$_c$, SO$_2$R$_c$, SO$_2$NR$_a$R$_b$, CO$_2$R$_a$, C(=O)R$_a$, C(=O)NR$_a$R$_b$, OC(=O)R$_a$, —OC(=O)NR$_a$R$_b$, NR$_a$C(=O)R$_b$, NR$_a$CO$_2$R$_b$, =N—OH, =N—O-alkyl, aryl, heteroaryl, heterocyclo and cycloalkyl, wherein R$_a$ and R$_b$ are selected from hydrogen, alkyl, alkenyl, cycloalkyl, heterocyclo, aryl, and heteroaryl, and R$_c$ is selected from hydrogen, alkyl, cycloalkyl, heterocyclo aryl and heteroaryl. When a substituted alkyl includes an aryl, heterocyclo, heteroaryl, or cycloalkyl substituent, said ringed systems are as defined below and thus may in turn have zero to four substituents (preferably 0-2 substituents), also as defined below. When either R$_a$, R$_b$ or R$_c$ is an alkyl, said alkyl may optionally be substituted with 1-2 of halogen, trifluoromethyl, alkenyl, alkynyl, nitro, cyano, keto (=O), OH, O(alkyl), phenyloxy, benzyloxy, SH, S(alkyl), NH$_2$, NH(alkyl), N(alkyl)$_2$, NHSO$_2$, NHSO$_2$(alkyl), SO$_2$(alkyl), SO$_2$NH$_2$, SO$_2$NH(alkyl), CO$_2$H, CO$_2$(alkyl), C(=O)H, C(=O)alkyl, C(=O)NH$_2$, C(=O)NH(alkyl), C(=O)N(alkyl)$_2$, OC(=O)alkyl, OC(=O)NH$_2$, —OC(=O)NH(alkyl), NHC(=O)alkyl, and/or NHCO$_2$(alkyl).

"Alkyl" when used in conjunction with another group such as in arylalkyl refers to a substituted alkyl in which at least one of the substituents is the specifically named group. For example, the term arylalkyl includes benzyl, or any other straight or branched chain alkyl having at least one aryl group attached at any point of the alkyl chain. As a further example, the term carbamylalkyl includes the group —(CH$_2$)$_n$—NH—C(=O)alkyl, Wherein n is 1 to 12.

The term "alkenyl" refers to straight or branched chain hydrocarbon groups having 2 to 21 carbon atoms and at least one double bond. Alkenyl groups of 2 to 6 carbon atoms and having one double bond are most preferred.

The term "alkynyl" refers to straight or branched chain hydrocarbon groups having 2 to 21 carbon atoms and at least one triple bond. Alkynyl groups of 2 to 6 carbon atoms and having one triple bond are most preferred.

The term "alkylene" refers to bivalent straight or branched chain hydrocarbon groups having 1 to 21 carbon atoms, preferably 1 to 8 carbon atoms, e.g., {—CH$_2$—}$_n$, Wherein n is 1 to 12, preferably 1-8. Lower alkylene groups, that is, alkylene groups of 1 to 4 carbon atoms, are most preferred. The terms "alkenylene" and "alkynylene" refer to bivalent radicals of alkenyl and alknyl groups, respectively, as defined above.

When reference is made to a substituted alkylene, alkenylene, or alkynylene group, these groups are substituted with one to four substituents as defined above for alkyl groups. A substituted alkylene, alkenylene, or alkynylene may have a ringed substituent attached in a spiro fashion as in

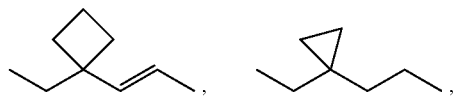

and so forth.

The term "alkoxy" refers to an alkyl or substituted alkyl group as defined above having one, two or three oxygen atoms (—O—) in the alkyl chain. For example, the term "alkoxy" includes the groups —O—C$_{1-12}$alkyl, —C$_{1-6}$alkylene-O—C$_{1-6}$alkyl, —C$_{1-4}$alkylene-O-phenyl, and so forth.

The term "thioalkyl" or "alkylthio" refers to an alkyl or substituted alkyl group as defined above having one or more sulphur (—S—) atoms in the alkyl chain. For example, the term "thioalkyl" or "alkylthio" includes the groups —(CH$_2$)$_n$—S—CH$_2$aryl, —(CH$_2$)$_n$—S-aryl, etc. etc.

The term "aminoalkyl" or "alkylamino" refers to an alkyl or substituted alkyl group as defined above having one or more nitrogen (—NR'—) atoms in the alkyl chain. For example, the term "aminoalkyl" includes the groups —NR'—C$_{1-12}$alkyl and —CH$_2$—NR'-aryl, etc. (where R' is hydrogen, alkyl or substituted alkyl as defined above). "Amino" refers to the group —NH$_2$.

When a subscript is used as in C$_{1-8}$alkyl, the subscript refers to the number of carbon atoms the group may contain. Zero when used in a subscript denotes a bond, e.g., C$_{0-4}$ alkyl refers to a bond or an alkyl of 1 to 4 carbon atoms. When used with alkoxy, thioalkyl or aminoalkyl, a subscript refers to the number of carbon atoms that the group may contain in addition to heteroatoms. Thus, for example, monovalent. C$_{1-2}$aminoalkyl includes the groups —CH$_2$—NH$_2$, —NH—CH$_3$, —(CH$_2$)$_2$—NH$_2$, —NH—CH$_2$—CH$_3$, —CH$_2$—NH$_2$—CH$_3$, and —N—(CH$_3$)$_2$. A lower aminoalkyl comprises an aminoalkyl having one to four carbon atoms.

The alkoxy, thioalkyl, or aminoalkyl groups may be monovalent or bivalent. By "monovalent" it is meant that the group has a valency (i.e., power to combine with another group), of one, and by "bivalent" it is meant that the group has a valency of two. For example, a monovalent alkoxy includes groups such as —O—C$_{1-12}$alkyl, —C$_{1-6}$alkylene-O—C$_{1-6}$alkyl, etc., whereas a bivalent alkoxy includes groups such as —O—C$_{1-2}$alkylene-, C$_{1-6}$alkylene-O—C$_{1-6}$alkylene-, etc.

The term "acyl" refers to a carbonyl

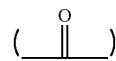

linked to an organic group i.e.

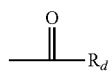

wherein R$_d$ may be selected from alkyl, alkenyl, substituted alkyl, substituted alkenyl, aryl, heterocyclo, cycloalkyl, or heteroaryl, as defined herein.

The term "alkoxycarbonyl" refers to a group having a carboxy or ester group

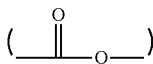

linked to an organic radical, i.e.,

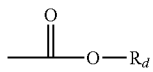

Wherein $R_d$ is as defined above for acyl.

The term "carbamyl" refers to a functional group in which a nitrogen atom is directly bonded to a carbonyl, i.e., as in —$NR_eC(=O)R^f$ or —$C(=O)NR_eR_f$, wherein $R_e$ and $R_f$ can be hydrogen, alkyl, substituted alkyl, alkenyl, substituted alkenyl, alkoxy, cycloalkyl, aryl, heterocyclo, or heteroaryl, or they may join to form a ring.

The term "sulfonyl" refers to a sulphoxide group (i.e., —$S(O)_{1-2}$) linked to an organic radical $R_e$, as defined above.

The term "sulfonamide" or "sulfonamido" refers to the group —$S(O)_2NR_eR_f$, wherein $R_e$ and $R_f$ are as defined above. Preferably when one of $R_e$ and $R_f$ is optionally substituted heteroaryl or heterocycle (as defined below), the other of $R_e$ and $R_f$ is hydrogen or alkyl.

The term "cycloalkyl" refers to fully saturated and partially unsaturated hydrocarbon rings of 3 to 9, preferably 3 to 7 carbon atoms. The term "cycloalkyl" includes such rings having zero to four substituents (preferably 0-2 substituents), selected from the group consisting of halogen, alkyl, substituted alkyl (e.g., trifluoromethyl), alkenyl, substituted alkenyl, alkynyl, nitro, cyano, keto, $OR_d$, $SR_d$ $NR_dR_e$ $NR_cSO_2$, $NR_cSO_2R_e$, C(=O)H, acyl, —$CO_2H$, alkoxycarbonyl, carbamyl, sulfonyl, sulfonamide, —OC(=O)$R_d$, =N—OH, =N—O-alkyl, aryl, heteroaryl, heterocyclo, a 4 to 7 membered carbocyclic ring, and a five or six membered ketal, e.g., 1,3-dioxolane or 1,3-dioxane, wherein $R_c$, $R_d$ and $R_e$ are defined as above. The term "cycloalkyl" also includes such rings having a phenyl ring fused thereto or having a carbon-carbon bridge of 3 to 4 carbon atoms. Additionally, when a cycloalkyl is substituted with a further ring, i.e., aryl, arylalkyl, heteroaryl, heteroarylalkyl, heterocyclo, heterocycloalkyl, cycloalkylalkyl, or a further cycloalkyl ring, such ring in turn may be substituted with one to two of $C_{0-4}$alkyl optionally substituted with halogen, trifluoromethyl, alkenyl, alkynyl, nitro, cyano, keto (=O), OH, O(alkyl), phenyloxy, benzyloxy, SH, S(alkyl), NH$_2$, NH(alkyl), N(alkyl)$_2$, NHSO$_2$, NHSO$_2$(alkyl), SO$_2$(alkyl), SO$_2$NH$_2$, SO$_2$NH(alkyl), CO$_2$H, CO$_2$(alkyl), C(=O)H, C(=O)alkyl, C(=O)NH$_2$, C(=O)NH(alkyl), C(=O)N(alkyl)$_2$, OC(=O)alkyl, —OC(=O)NH$_2$, —OC(=O)NH(alkyl), NHC(=O)alkyl, and NHCO$_2$(alkyl).

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes OCF$_3$.

The term "aryl" refers to phenyl, biphenyl, 1-naphthyl, 2-naphthyl, and anthracenyl, with phenyl being preferred. The term "aryl" includes such rings having zero to four substituents (preferably 0-2 substituents), selected from the group consisting of halo, alkyl, substituted alkyl (e.g., trifluoromethyl), alkenyl, substituted alkenyl, alkynyl, nitro, cyano, $OR_d$, $SR_d$, $NR_dR_e$, $NR_dSO_2$, $NR_dSO_2R_e$, C(=O)H, acyl, —CO$_2$H, alkoxycarbonyl, carbamyl, sulfonyl, sulfonamide, —OC(=O)$R_d$, heteroaryl, heterocyclo, cycloalkyl, phenyl, benzyl, napthyl, including phenylethyl, phenyloxy, and phenylthio, wherein $R_c$, $R_d$ and $R_e$ are defined as above. Additionally, two substituents attached to an aryl, particularly a phenyl group, may join to form a further ring such as a fused or spiro-ring, e.g., cyclopentyl or cyclohexyl or fused heterocycle or heteroaryl. When an aryl is substituted with a further ring, such ring in turn may be substituted with one to two of $C_{0-4}$alkyl optionally substituted with halogen, trifluoromethyl, alkenyl, alkynyl, nitro, cyano, keto (=O), OH, O(alkyl), phenyloxy, benzyloxy, SH, S(alkyl), NH$_2$, NH(alkyl), N(alkyl)$_2$, NHSO$_2$, NHSO$_2$(alkyl), SO$_2$(alkyl), SO$_2$NH$_2$, SO$_2$NH(alkyl), CO$_2$H, CO$_2$(alkyl), C(=O)H, C(=O)alkyl, C(=O)NH$_2$, C(=O)NH(alkyl), C(=O)N(alkyl)$_2$, OC(=O)alkyl, —OC(=O)NH$_2$, —OC(=O)NH(alkyl), NHC(=O)alkyl, and NHCO$_2$(alkyl).

The term "heterocyclo" refers to substituted and unsubstituted non-aromatic 3 to 7 membered monocyclic groups, 7 to 11 membered bicyclic groups, and 10 to 15 membered tricyclic groups, in which at least one of the rings has at least one heteroatom selected from O, S and N. Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. The heterocyclo ring may contain zero to four substituents (preferably 0-2 substituents), selected from the group consisting of halo, alkyl, substituted alkyl (e.g., trifluoromethyl), alkenyl, substituted alkenyl, alkynyl, nitro, cyano, keto, $OR_d$, $SR_d$, $NR_dR_e$, $NR_dSO_2$, $NR_dSO_2R_c$, SO$_2R_d$, C(=O)H, acyl, —CO$_2$H, alkoxycarbonyl, carbamyl, sulfonyl, sulfonamide, —OC(=O)$R_d$, =N—OH, =N—O-alkyl, aryl, heteroaryl, cycloalkyl, a five or six membered ketal, e.g., 1,3-dioxolane or 1,3-dioxane, or a monocyclic 4 to 7 membered non aromatic ring having one to four heteroatoms, wherein $R_c$, $R_d$ and $R_e$ are defined as above. The term "heterocyclo" also includes such rings having a phenyl ring fused thereto or having a carbon-carbon bridge of 3 to 4 carbon atoms. Additionally, when a heterocyclo is substituted with a further ring, i.e., aryl, arylalkyl, heteroaryl, heteroarylalkyl, cycloalkyl, cycloalkylalkyl, heterocycloalkyl, or a further heterocyclo ring, such ring in turn may be substituted with one to two of $C_{0-4}$alkyl optionally substituted with halogen, trifluoromethyl, alkenyl, alkynyl, nitro, cyano, keto (=O), OH, O(alkyl), phenyloxy, benzyloxy, SH, S(alkyl), NH$_2$, NH(alkyl), N(alkyl)$_2$, NHSO$_2$, NHSO$_2$(alkyl), SO$_2$(alkyl), SO$_2$NH$_2$, SO$_2$NH(alkyl), CO$_2$H, CO$_2$(alkyl), C(=O)H, C(=O)alkyl, C(=O)NH$_2$, C(=O)NH(alkyl), C(=O)N(alkyl)$_2$, OC(=O)alkyl, —OC(=O)NH$_2$, —OC(=O)NH (alkyl), NHC(=O)alkyl, and NHCO$_2$(alkyl).

Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

The term "heteroaryl" refers to substituted and unsubstituted aromatic 5 to 7 membered monocyclic groups, 9 or 10 membered bicyclic groups, and 11 to 14 membered tricyclic groups which have at least one heteroatom selected from O, S and N in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero to four substituents (preferably 0-2 substituents), selected from the group consisting of halo, alkyl, substituted alkyl (e.g., trifluoromethyl), alkenyl, substituted alkenyl, alkynyl, nitro, cyano, $OR_d$, $SR_d$, $NR_dR_e$, $NR_dSO_2$, $NR_dSO_2R_c$, $SO_2R_d$, C(=O)H, acyl, $CO_2H$, alkoxycarbonyl, carbamyl, sulfonyl, sulfonamide, —OC(=O)$R_d$, heterocyclo, cycloalkyl, aryl, or a monocyclic 4 to 7 membered aromatic ring having one to four heteroatoms, including phenylethyl, phenyloxy, and phenylthio, wherein $R_c$, $R_d$ and $R_e$ are defined as above. Additionally, when a heteroaryl is substituted with a further ring, i.e., aryl, arylalkyl, heterocyclo, heterocycloalkyl, cycloalkyl, cycloalkylalkyl, heteroarylalkyl, or a further heteroaryl ring, such ring in turn may be substituted with one to two of $C_{0-4}$ alkyl optionally substituted with halogen, trifluoromethyl, alkenyl, alkynyl, nitro, cyano, keto (=O), OH, O(alkyl), phenyloxy, benzyloxy, SH, S(alkyl), $NH_2$, NH(alkyl), N(alkyl)$_2$, $NHSO_2$, $NHSO_2$(alkyl)$_n$, $SO_2$(alkyl), $SO_2NH_2$, $SO_2NH$(alkyl), $CO_2H$, $CO_2$(alkyl), C(=O)H, C(=O)alkyl, C(=O)$NH_2$, C(=O)NH(alkyl), C(=O)N(alkyl)$_2$, OC(=O)alkyl, —OC(=O)$NH_2$, OC(=O)NH(alkyl), NHC(=O)alkyl, and $NHCO_2$(alkyl).

Exemplary monocyclic heteroaryl groups include pyrrolyl, pyrazolyl, pyrazolinyl, imidazolyl, oxazolyl, isoxazolyl, thiazolyl

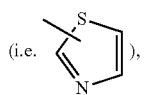

thiadiazolyl, isothiazolyl, furanyl, thienyl, oxadiazolyl, pyridyl, pyrazinyl, pyridinyl, pyrimidinyl, pyridazinyl, triazinyl and the like.

Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

When the term "unsaturated" is used herein to refer to a ring or group, the ring or group may be fully unsaturated or partially unsaturated.

The phrase "optionally substituted" is intended to include substituted or unsubstituted possibilities. Accordingly, the phrase "each group of which may be optionally substituted means that each group includes both substituted and unsubstituted groups.

The use of the phrase "Where valence allows" means that the groups may be substituted only to the degree and nature allowed by valency of the group. This is commonly understood by those of skill in the art. For example, a hydrogen substituent cannot be further substituted nor can a phenyl group be directly substituted by an oxo group due to limits on valency.

The term "substituted amino" refers to a group of the formula —$NZ^2Z^3$ wherein $Z^2$ is hydrogen, alkyl, cycloalkyl, aryl, arylalkyl, (cycloalkyl)alkyl, morpholinylalkyl, heterocyclo or (heterocyclo)alkyl and $Z^3$ is hydrogen, alkyl, cycloalkyl, aryl, arylalkyl, haloalkyl, hydroxyalkyl, alkoxyalkyl, thioalkyl, (cycloalkyl)alkyl or hydroxyalkyl further substituted with a carboxylic ester or carboxylic acid, with the proviso that when $Z^2$ is hydrogen, then $Z^3$ is other than hydrogen; or $Z^2$ and $Z^3$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl; or 1-pyrrolidinyl, 1-piperidinyl, 1-azepinyl substituted with alkyl, alkoxy, alkylthio, halo, trifluoromethyl or hydroxy.

The term "heterocyclo" or "hetero" also includes such monocyclic and bicyclic rings wherein an available carbon atom is substituted with a ($C_1$-$C_4$)-alkyl, aryl, ($C_1$-$C_4$)-alkylthio, ($C_1$-$C_4$)-alkoxy, halo, nitro, keto, cyano, hydroxy, azo, thiazo, amino, —NH—($C_1$-$C_4$)-alkyl, —N(($C_1$-$C_4$)-alkyl)$_2$, —$CF_3$, (aminoester)alkyl, carboxylic acid, carboxylic ester, —$OCHF_2$ or ($C_1$-$C_4$)-alkoxy further substituted with a carboxylic acid or such monocyclic and bicyclic rings wherein two or three available carbons have substituents selected from methyl, methoxy, methylthio, halo, —$CF_3$, nitro, hydroxy, amino and —$OCHF_2$.

Stereoisomers

All stereoisomers of Formula [X], such as those, for example, which may exist due to asymmetric carbons, including enantiomeric forms (which may exist even in the absence of asymmetric carbons) and diastereomeric forms, are contemplated and within the scope of this invention. Individual stereoisomers of the compounds of this invention may, for example, be substantially free of other isomers, or may be admixed, for example, as racemates or with all other or other selected, stereoisomers. The chiral centers of the present invention can have the S or R configuration as defined by the IUPAC 1974 Recommendations.

For the molecules presented in this invention's Description and Drawings: the present invention contemplates all polymorphs, metabolites, isotopologues, geometric/conformational isomers, rotamers, atropisomers, stereoisomers, optically active forms, tautomers, keto-enol tautomers, cis- and trans-isomers, E and Z isomers, R- and S-enantiomers, diastereomers, isomers, (D)-isomers, (L)-isomers, the racemic mixtures thereof, other mixtures thereof and isotopic variants (e.g. deuterium in place of hydrogen in some or all places upon the molecule {s}) as falling within the scope of the invention. All such isomers, as well as mixtures thereof, are intended to be included in this invention. As well as analogues and pharmaceutically/physiologically acceptable salts/ethers/esters/solvates/hydrates/chelates/complexes/ metal complexes/mixtures/prodrugs/particles/radionuclides/derivatives/carriers/crystalline forms/liposomes thereof. Unless indicated otherwise, chemical structures and graphical representations of compounds herein encompass all stereoisomers. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. The present invention is not limited to any particular mechanism, nor to any understanding of the action of the agents being administered.

The invention also embraces isotopically labelled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

Salts, Solvates, Prodrugs

Throughout the specification, groups and substituents thereof may be chosen by one skilled in the field to provide stable moieties and compounds.

The compounds of Formula [X] form salts which are also within the scope of this invention. Reference to a compound of the Formula [X] herein is understood to include reference to salts thereof, unless otherwise indicated.

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of ordinary skill in the art, "salts" of the compounds of the present invention may be derived from inorganic or organic acids and bases. For therapeutic use, salts of the compounds of the present invention are contemplated as being pharmaceutically acceptable (i.e., non-toxic, physiologically acceptable). However, salts of acids and bases that are non-pharmaceutically acceptable may also find use, for example, in the preparation, isolation or purification of a pharmaceutically acceptable compound.

The term "salt(s)", as employed herein, denotes acidic and/or basic salts formed with inorganic and/or organic acids and bases. In addition, when a compound of Formula [X] contains both a basic moiety, such as, but not limited to an amine or a pyridine or imidazole ring, and an acidic moiety, such as, but not limited to a carboxylic acid, zwitterions ("inner salts") may be formed and are included within the term "salt(s)" as used herein.

Salts of the compounds of the Formula [X] may be formed, for example, by reacting a compound of the Formula [X] with an amount of acid or base, such as an equivalent amount, in a medium such as one in which the salt precipitates or in an aqueous medium followed by lyophilization.

The compounds of Formula [X] which contain a basic moiety, such as, but not limited to an amine or a pyridine or imidazole ring, may form salts with a variety of organic and inorganic acids. Exemplary acid addition salts include acetates (such as those formed with acetic acid or trihalo acetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methane-sulfonates (formed with methanesulfonic acid), 2-naphthalene-sulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of Formula [X] which contain an acidic moiety, such as, but not limited to a carboxylic acid, may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydro-abietyl)ethylenediamine], N-methyl D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e. g., decyl, lauryl, myristyl and stearyl chlorides, bromides and iodides), aralkyl halides (e.g., benzyl and phenethyl bromides), and others.

Compounds of the Formula [X], and salts thereof, may exist in their tautomeric form (for example, as an amide or imino ether). All such tautomeric forms are contemplated herein as part of the present invention.

In addition, compounds of the Formulas [X] may have prodrug forms. Any compound that will be converted in vivo to provide the bioactive agent (i.e., a compound of Formula [X]) is a prodrug within the scope and spirit of the invention.

For example, pro-drug compounds of the Formulas [X] may be carboxylate ester moieties. A carboxylate ester may be conveniently formed by esterifying any of the carboxylic acid functionalities found on the disclosed ring structure(s).

Various forms of prodrugs are well known in the art. For examples of such prodrug derivatives, see:
a) *Design of Prodrugs*, edited by H. Bundgaard, (Elsevier, 1985), and *Methods in Enzymology*, Vol. 42, p. 309-396, edited by K. Widder, et. al. (Academic Press, 1985);
b) *A Textbook of Drug Design and Development*, edited by Krosgaard-Larsen and H. Bundgaard, Chapter 5, "Design and Application of Prodrugs," by H. Bundgaard, p. 113-191 (1991);
c) H. Bundgaard, *Advanced Drug Delivery Reviews*, Vol. 8, p. 1-38 (1992);
d) H. Bundgaard, et al., *Journal of Pharmaceutical Sciences*, Vol. 77, p. 285 (1988); and
e) N. Kakeya, et. al., *Chem. Phar. Bull.*, Vol. 32, p. 692 (1984).

It should further be understood that solvates (e.g., hydrates) of the compounds of Formula [X] are also within the scope of the present invention. Methods of solvation are generally known in the art.

Chelates, metal complexes, mixtures, radio-nuclides and liposomes of Formula [X] are within the scope of this invention.

Dosage

As used herein, the term "effective amount" refers to the amount of a compound sufficient to effect beneficial or desired results. An effective amount can be administered in one or more administrations, applications or dosages and is not intended to be limited to a particular formulation or administration route.

The effective amount of a compound of the present invention may be determined by one of ordinary skill in the art. The specific dose level and frequency of dosage for any particular subject may vary and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

An exemplary effective amount of compounds of Formula [X] may be within the dosage range of about 0.001 to about 300 mg/kg, preferably about 0.2 to about 50 mg/kg and more preferably about 0.5 to about 25 mg/kg (or from about 1 to about 2500 mg, preferably from about 5 to about 2000 mg) on a regimen in single or 2 to 4 divided daily doses. But more exactly it depends upon the compound used, the condition and its advancement/severity, the route of administration, type of dosing (e.g. pulse or consistent etc.), what other treatments are undertaken alongside or previously (e.g. chemotherapeutics, surgery, radiotherapy etc.), the age, sex, condition, previous/other diseases of the patient, pharmacokinetics of compound in that patient, response to treatment and exceptions to this dosage range may be contemplated by the present invention, and they might be changed during treatment to find the optimum. Optimal dosages to be administered to a subject may be determined by those skilled in the art. When the compounds described herein are co-administered with another agent, the effective amount may be less than when the agent is used alone.

Pharmaceutical Composition

As used herein, the term "pharmaceutical composition" refers to the combination of an active agent with a carrier, inert or active, making the composition especially suitable for diagnostic or therapeutic use in vivo. Disclosed is a pharmaceutical composition of a therapeutically effective amount of a compound(s) of Formula [X] or a pharmaceutically acceptable salt thereof, and one or more pharmaceutically acceptable carriers, additives and/or diluents.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, Pa. [1975].

Administration

The compounds of Formula [X] may be administered by any means suitable for the condition to be treated. For example: oral, parenteral, enteral, infusion, injection, sublingual, topical, rectal, transdermal, intramuscular and inhalation. The compound may be delivered orally, such as in the form of tablets, capsules, granules, microgranules, pellets, soft-gels, powders, or liquid formulations including syrups, liquids, solutions, elixirs, suspensions, emulsions or magmas; sublingually; bucally; transdermally; parenterally, such as by subcutaneous, intravenous, intramuscular or intrasternal injection or infusion (e.g., as sterile injectable aqueous or non-aqueous solutions or suspensions); nasally such as by inhalation spray; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavouring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavours, colouring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

Co-Administration

As used herein, the term "co-administration" refers to the administration of at least two agent(s) (e.g., a compound of the present invention) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

PATENTS, OR PATENT APPLICATIONS, CITED

[P1] Atwal K S, Grover G J, Ding C Z, Stein P D, Lloyd J, Ahmad S, Hamann L G, Green D, Ferrara F N, inventors; Bristol-Myers Squibb Co., assignee. (1-phenyl-2-heteroaryl) ethyl-guanidine compounds as inhibitors of mitochondrial FIFO ATP hydrolase. U.S. Pat. No. 6,916,813. 2005 Jul. 12.
[P2] Ding C, Hamann L, Stein P, Pudzianowski A, inventors; Ding Charles Z., Hamann Lawrence G., Stein Philip D., Pudzianowski Andrew T., assignee. Benzodiazepine inhibitors of mitochondrial FIFO ATP hydrolase and methods of inhibiting FIFO ATP hydrolase. U.S. patent application Ser. No. 10/461,736. 2003 Jun. 13.
[P3] Hamann L G, Pudzianowski A T, inventors; Bristol-Myers Squibb Company, assignee. N-substituted phenylurea inhibitors of mitochondrial FIFO ATP hydrolase. U.S. Pat. No. 6,846,836. 2005 Jan. 25.
[P4] Glick G D, inventor; University of Michigan, assignee. Methods and compositions for treating diseases and conditions associated with mitochondrial function. U.S. patent application Ser. No. 11/726,219. 2009 Nov. 5.
[P5] Glick G, inventor; University of Michigan, assignee. Methods and compositions for treating diseases and conditions associated with mitochondrial function. U.S. patent application Ser. No. 11/110,228. 2005 Dec. 8.
[P6] Ding C Z, Atwal K S, inventors; Bristol-Myers Squibb Company, assignee. Sulfonamido substituted benzopyran derivatives. U.S. Pat. No. 5,869,478. 1999 Feb. 9.
[P7] Regnier G, Canevari R, Laubie M, inventors; En Nom Collectif Science Union, Medicale Rech France, assignee. S-triazine compounds. U.S. Pat. No. 3,647,794. 1972 Mar. 7.
[P8] Dax S L, Woodward R, Peng S, inventors; Galleon Pharmaceuticals Inc, assignee. Compounds as respiratory stimulants for treatment of breathing control disorders or diseases. U.S. Pat. No. 9,351,972. 2016 May 31.

NON-PATENT REFERENCES

[1] Stryer L, Berg J M, Tymoczko J L (2002) Biochemistry, 4$^{th}$ Ed. New York, NY: W H Freeman.
[2] Alberts B, Johnson A, Lewis J, Raff M, Roberts K, Walter P (1994) Molecular Biology Of The Cell, 3$^{rd}$ Ed. New York, NY: Garland Publishing.
[3] Nicholls D G, Ferguson S (2013) Bioenergetics. Academic Press. [4] Hong S, Pedersen P L (2008) ATP synthase and the actions of inhibitors utilized to study its roles in human health, disease, and other scientific areas. Microbiology and Molecular Biology Reviews 72(4):590-641.
[5] Atwal K S, Ahmad S, Ding C Z, Stein P D, Lloyd J, Hamann L G, Green D W, Ferrara F N, Wang P, Rogers W L, Doweyko L M, Miller A V, Bisaha S N, Schmidt J B, Li L, Yost K J, Lan H J, Madsen C S (2004) N-[1-Aryl-2-(1-imidazolo)ethyl]-guanidine derivatives as potent inhibitors of the bovine mitochondrial $F_1F_0$ ATP hydrolase. Bioorg. Med. Chem. Lett. 141027-1030.
[6] Bisaha S N, Malley M F, Pudzianowski A, Monshizadegan H, Wang P, Madsen C S, Gougoutas J Z, Stein P D (2005) A switch in enantiomer preference between mitochondrial F 1 F 0-ATPase chemotypes. Bioorganic & medicinal chemistry letters 15(11):2749-51.
[7] Atwal K S, Wang P, Rogers W L, Sleph P, Monshizadegan H, Ferrara F N, Traeger S, Green D W, Grover G J (2004) Small molecule mitochondrial $F_1F_0$ ATPase hydrolase inhibitors as cardioprotective agents. Identification of 4-(N-arylimidazole)-substituted benzopyran derivatives as selective hydrolase inhibitors. J. Med. Chem. 471081-1084. INCLUDING this paper's supplementary material.
[8] Hamann L G, Ding C Z, Miller A V, Madsen C S, Wang P, Stein P D, Pudzianowski A T, Green D W, Monshizadegan H, Atwal K S (2004) Benzodiazepine-based selective inhibitors of mitochondrial $F_1F_0$ ATP hydrolase. Bioorg. Med. Chem. Lett. 141031-1034.
[9] Grover G J, Marone P A, Koetzner L, Seto-Young D (2008) Energetic signalling in the control of mitochondrial F 1 F 0 ATP synthase activity in health and disease. The international journal of biochemistry & cell biology 40(12):2698-2701.
[10] Grover G J, Malm J (2008) Pharmacological Profile of the Selective Mitochondrial F1F0 ATP Hydrolase Inhibitor BMS-199264 in Myocardial Ischemia. Cardiovascular therapeutics 26(4):287-296.
[11] Grover G J, Atwal K S, Sleph P G, Wang F L, Monshizadegan H, Monticello T, Green D W (2004) Excessive ATP hydrolysis in ischemic myocardium by mitochondrial F1F0-ATPase: effect of selective pharmacological inhibition of mitochondrial ATPase hydrolase activity. American Journal of Physiology-Heart and Circulatory Physiology 287(4):H1747-H1755.
[12] Ivanes F (2013) New mechanisms of protection of cardiomyocytes from ischemia/reperfusion injury (Doctoral dissertation, Universite Claude Bernard-Lyon I).
[13] Ivanes F, Faccenda D, Gatliff J, Ahmed A A, Cocco S, Cheng C H K, & Campanella M (2014) The compound BTB06584 is an IF1-dependent selective inhibitor of the mitochondrial F1Fo-ATPase. British journal of pharmacology 171(18):4193-4206.
[14] Salomon A R, Voehringer D W, Herzenberg L A, Khosla C (2000) Understanding and exploiting the mechanistic basis for selectivity of polyketide inhibitors of F0F1-ATPase. Proceedings of the National Academy of Sciences. 97(26):14766-71.
[15] Kramar R, Hohenegger M, Srour A N, Khanakah G. Oligomycin toxicity in intact rats. Inflammation Research. 1984 Dec. 1; 15(5):660-3.
[16] National Cancer Institute (NCI) Developmental Therapeutics Program (DTP) Screening Data Database https://dtp.cancer.gov/dtpstandard/dwindex/index.jsp. Accessed on 29/06/17
[17] Gao C, Shen Y, Jin F, Miao Y, Qiu X (2016) Cancer stem cells in small cell lung cancer cell line H446: higher dependency on oxidative phosphorylation and mitochondrial substrate-level phosphorylation than non-stem cancer cells. PloS one. 11(5):e0154576.
[18] Cuezva J M, Krajewska M, de Heredia M L, Krajewski S, Santamaria G, Kim H, Zapata J M, Marusawa H, Chamorro M, Reed J C (2002) The bioenergetic signature of cancer. Cancer research. 62(22):6674-81.
[19] Aldea M, Clofent J, De Arenas C N, Chamorro M, Velasco M, Berrendero J R, Navarro C, Cuezva J M (2011) Reverse phase protein microarrays quantify and validate the bioenergetic signature as biomarker in colorectal cancer. Cancer letters. 311(2):210-8.

[20] Hjerpe E, Brage S E, Carlson J, Stolt M F, Schedvins K, Johansson H, Shoshan M, Avail-Lundqvist E (2013) Metabolic markers GAPDH, PKM2, ATP5B and BEC-index in advanced serous ovarian cancer. BMC clinical pathology. 13(1):30.

[21] Johnson K M, Chen X, Boitano A, Swenson L, Opipari Jr A W, Glick G D (2005) Identification and validation of the mitochondrial F1F0-ATPase as the molecular target of the immunomodulatory benzodiazepine Bz-423. Chemistry & biology. 12(4):485-96.

[22] Forrest M D (2015) Why cancer cells have a more hyperpolarised mitochondrial membrane potential and emergent prospects for therapy. bioRxiv. 025197.

[23] Sgarbi G, Barbato S, Costanzini A, Solaini G, Baracca A. The role of the ATPase inhibitor factor 1 (IF1) in cancer cells adaptation to hypoxia and anoxia. Biochimica et Biophysica Acta (BBA)—Bioenergetics. 2018 Feb. 1; 1859(2):99-109. (epublished 31 Oct. 2017)

[24] Yin T, Lu L, Xiong Z, Wei S, Cui D (2015) ATPase inhibitory factor 1 is a prognostic marker and contributes to proliferation and invasion of human gastric cancer cells. Biomedicine & Pharmacotherapy. 70:90-6.

[25] Marvin cheminformatics suite (version 16.3.21; academic license; ChemAxon Kft., Budapest, Hungary; www.chemaxon.com)

[26] Hanahan D, Weinberg R A (2000) The hallmarks of cancer. Cell. 100(1):57-70.

[27] Walenta S, Wetterling M, Lehrke M, Schwickert G, Sundfor K, Rofstad E K, Mueller-Klieser W (2000) High lactate levels predict likelihood of metastases, tumor recurrence, and restricted patient survival in human cervical cancers. Cancer research. 60(4):916-21.

[28] Paull K D, Shoemaker R H, Hodes L, Monks A, Scudiero D A, Rubinstein L, Plowman J, Boyd M R (1989) Display and analysis of patterns of differential activity of drugs against human tumor cell lines: development of mean graph and COMPARE algorithm. JNCI: Journal of the National Cancer Institute. 81(14):1088-92.

[29] https://dtp.cancer.gov/databases_tools/compare.htm. Accessed on 29/06/17

[30] Holbeck S L, Collins J M, Doroshow J H (2010) Analysis of Food and Drug Administration-approved anticancer agents in the NCI60 panel of human tumor cell lines. Molecular cancer therapeutics. 9(5):1451-60.

[31] Reinhold W C, Sunshine M, Liu H, Varma S, Kohn K W, Morris J, Doroshow J, Pommier Y (2012) CellMiner: a web-based suite of genomic and pharmacologic tools to explore transcript and drug patterns in the NCI-60 cell line set. Cancer research. 72(14):3499-511.

[32] discover.nci.nih.gov/cellminer/home.do. Accessed on 29/06/17

[33] Gholami A M, Hahne H, Wu Z, Auer F J, Meng C, Wilhelm M, Kuster B (2013) Global proteome analysis of the NCI-60 cell line panel. Cell reports. 4(3):609-20.

[34] Shoemaker R H (2006) The NCI60 human tumour cell line anticancer drug screen. Nature Rev. Cancer 6:813-23.

[35] NCI-60 Screening Methodology. Details of both the one-dose and five-dose assays. dtp.cancer.gov/discovery_development/nci-60/methodology.htm (accessed on 25 Jun. 2017).

[36] Martineau L C (2012) Simple thermodynamic model of unassisted proton shuttle uncoupling and prediction of activity from calculated speciation, lipophilicity, and molecular geometry. Journal of theoretical biology. 303: 33-61.

[37] Jacques V, Czarnik A W, Judge T M, Van der Ploeg L H, DeWitt S H (2015) Differentiation of antiinflammatory and antitumorigenic properties of stabilized enantiomers of thalidomide analogs. Proceedings of the National Academy of Sciences. 112(12):E1471-9.

[38] Houston M A, Augenlicht L H, Heerdt B G (2011) Stable differences in intrinsic mitochondrial membrane potential of tumor cell subpopulations reflect phenotypic heterogeneity. International journal of cell biology 2011.

[39] Heerdt B G, Houston M A, Augenlicht L H (2005) The intrinsic mitochondrial membrane potential of colonic carcinoma cells is linked to the probability of tumor progression. Cancer Res. 65:9861-9867.

[40] Heerdt B G, Houston M A, Augenlicht L H. Growth properties of colonic tumor cells are a function of the intrinsic mitochondrial membrane potential. Cancer Res. 2006; 66(3):1591-6.

[41] Bonnet S, Archer S L, Allalunis-Turner J, Haromy A, Beaulieu C, Thompson R, Lee C T, Lopaschuk G D, Puttagunta L, Bonnet S, Harry G. A mitochondria-K+ channel axis is suppressed in cancer and its normalization promotes apoptosis and inhibits cancer growth. Cancer cell. 2007 Jan. 31; 11(1):37-51.

[42] Ye X Q, Wang G H, Huang G J, Bian X W, Qian G S, Yu S C. Heterogeneity of mitochondrial membrane potential: a novel tool to isolate and identify cancer stem cells from a tumor mass?. Stem Cell Reviews and Reports. 2011 Mar. 1; 7(1):153-60.

[43] Lee D G, Choi B K, Kim Y H, Oh H S, Park S H, Bae Y S, Kwon B S. The repopulating cancer cells in melanoma are characterized by increased mitochondrial membrane potential. Cancer Letters. 2016 Nov. 28; 382(2): 186-94.

[44] Boonstra J, Post J A (2004) Molecular events associated with reactive oxygen species and cell cycle progression in mammalian cells. Gene. 337:1-3.

[45] Fantin V R, St-Pierre J, Leder P (2006) Attenuation of LDH-A expression uncovers a link between glycolysis, mitochondrial physiology, and tumor maintenance. Cancer cell 9(6):425-434.

[46] Christofk H R, Vander Heiden M G, Harris M H, Ramanathan A, Gerszten R E, Wei R, & Cantley L C (2008) The M2 splice isoform of pyruvate kinase is important for cancer metabolism and tumour growth. Nature 452(7184):230-233.

[47] Bonnet S, Archer S L, Allalunis-Turner J, Haromy A, Beaulieu C et al. (2007) A mitochondria-K+ channel axis is suppressed in cancer and its normalization promotes apoptosis and inhibits cancer growth. Cancer cell 11(1): 37-51.

[48] Wadhwa R, Sugihara T, Yoshida A, Nomura H, Reddel R R, et al. (2000) Selective toxicity of MKT-077 to cancer cells is mediated by its binding to the hsp70 family protein mot-2 and reactivation of p53 function. Cancer Res. 60:6818-6821.

[49] Schulz T J, Thierbach R, Voigt A, et al (2006) Induction of oxidative metabolism by mitochondrial frataxin inhibits cancer growth: Otto Warburg revisited. J. Biol. Chem. 281:977-81.

[50] Devi G S, Prasad M H, Saraswathi I, Raghu D, Rao D N, Reddy P P (2000) Free radicals antioxidant enzymes and lipid peroxidation in different types of leukemias. Clin. Chim. Acta. 293:53-62

[51] Szatrowski, T. P., & Nathan, C. F. (1991). Production of large amounts of hydrogen peroxide by human tumor cells. Cancer research, 51(3), 794-798.

[52] Lu W, Hu Y, Chen G, Chen Z, Zhang H, Wang F, Feng L, Pelicano H, Wang H, Keating M J, Liu J (2012) Novel role of NOX in supporting aerobic glycolysis in cancer cells with mitochondrial dysfunction and as a potential target for cancer therapy. PLoS biology. 10(5):e1001326.

[53] Block K, Gorin Y. Aiding and abetting roles of NOX oxidases in cellular transformation. Nature Reviews Cancer. 2012 Sep. 1; 12(9):627-37.

[54] Ben-Porath I, Thomson M W, Carey V J, Ge R, Bell G W, Regev A, Weinberg R A (2008) An embryonic stem cell-like gene expression signature in poorly differentiated aggressive human tumors. Nature genetics. 40(5): 499.

[55] Chung S, Dzeja P P, Faustino R S, Perez-Terzic C, Behfar A, Terzic A (2007) Mitochondrial oxidative metabolism is required for the cardiac differentiation of stem cells. Nat. Clin. Pract. Cardiovasc Med. 4: S60-S67.

[56] Teslaa T, Teitell M A (2014) Pluripotent stem cell energy metabolism: an update. The EMBO journal e201490446.

[57] Hong Y, Stambrook P J (2004) Restoration of an absent G1 arrest and protection from apoptosis in embryonic stem cells after ionizing radiation. PNAS 101(40):14443-14448.

[58] Gordon C J (1991) Toxic-induced hypothermia and hypometabolism: Do they increase uncertainty in the extrapolation of toxicological data from experimental animals to humans? Neuroscience & Biobehavioral Reviews. 15(1):95-8.

[59] Zamzami N, Kroemer G (2001) The mitochondrion in apoptosis: how Pandora's box opens. Nat. Rev. Mol. Cell Biol. 2:67-71

[60] Donadelli M, Dando I, Dalla Pozza E, Palmieri M (2015) Mitochondrial uncoupling protein 2 and pancreatic cancer: A new potential target therapy. World journal of gastroenterology: WJG 21(11):3232.

[61] Ayyasamy V, Owens K M, Desouki M M, Liang P, Bakin A, Thangaraj K, et al. (2011) Cellular Model of Warburg Effect Identifies Tumor Promoting Function of UCP2 in Breast Cancer and Its Suppression by Genipin. PLoS ONE 6(9):e24792. doi:10.1371/journal.pone.0024792.

[62] Gordon C J (2012) Thermal physiology of laboratory mice: Defining thermoneutrality. Journal of Thermal Biology. 37(8): 654-85.

[63] Bindu B, Bindra A, Rath G (2017) Temperature management under general anesthesia: Compulsion or option. Journal of anaesthesiology, clinical pharmacology. 33(3):306.

[64] Bell E F (1983) Infant incubators and radiant warmers. Early human development. 8(3-4):351-75.

[65] Parsons K (2014) Human thermal environments: the effects of hot, moderate, and cold environments on human health, comfort, and performance. CRC press.

[67] R Core Team (2013). R: A language and environment for statistical computing. R Foundation for Statistical Computing, Vienna, Austria. R-project.org/[68] Ward T H, Cummings J, Dean E, Greystoke A, Hou J M, Backen A, Ranson M, Dive C (2008) Biomarkers of apoptosis. British journal of cancer. 99(6):841.

[67] R Core Team (2013). R: A language and environment for statistical computing. R Foundation for Statistical Computing, Vienna, Austria. URL http://www.R-project.org/

[68] Ward T H, Cummings J, Dean E, Greystoke A, Hou J M, Backen A, Ranson M, Dive C (2008) Biomarkers of apoptosis. British journal of cancer. 99(6):841.

[69] Yin T, Lu L, Xiong Z, Wei S, Cui D (2015) ATPase inhibitory factor 1 is a prognostic marker and contributes to proliferation and invasion of human gastric cancer cells. Biomedicine & Pharmacotherapy. 70:90-6.

[70] Zheng J, Ramirez V D (2000) Inhibition of mitochondrial proton F0F1-ATPase/ATP synthase by polyphenolic phytochemicals. British journal of pharmacology. 130(5): 1115-23.

[71] Zhu A, Lee D, Shim H. Metabolic positron emission tomography imaging in cancer detection and therapy response (2011) In Seminars in oncology (Vol. 38, No. 1, pp. 55-69). W B Saunders.

[72] Zhang L, Martins A F, Mai Y, Zhao P, Funk A M, Clavijo Jordan M V, Zhang S, Chen W, Wu Y, Sherry A D. Imaging Extracellular Lactate In Vitro and In Vivo Using CEST MRI and a Paramagnetic Shift Reagent (2017) Chemistry-A European Journal. 23(8):1752-6.

[73] Chen L Q, Pagel M D (2015) Evaluating pH in the Extracellular Tumor Microenvironment Using CEST MRI and Other Imaging Methods. Advances in radiology.

[74] Anderson M, Moshnikova A, Engelman D M, Reshetnyak Y K, Andreev O A (2016) Probe for the measurement of cell surface pH in vivo and ex vivo. Proceedings of the National Academy of Sciences. 201608247.

[75] Manzoor A A, Schroeder T, Dewhirst M W (2008) One-stop-shop tumor imaging: buy hypoxia, get lactate free. The Journal of clinical investigation. 118(5):1616.

[76] Ng J, Shuryak I (2015) Minimizing second cancer risk following radiotherapy: current perspectives. Cancer management and research. 7:1.

[77] Lin M T, Beal M F (2006) Mitochondrial dysfunction and oxidative stress in neurodegenerative diseases. Nature. 443(7113):787-95

[78] Umphred D A, Lazaro R T, Roller M, Burton G, editors Neurological rehabilitation. Elsevier Health Sciences; 2013 Aug. 7

[79] Kang Y S, Jung H J, Oh J S, Song D Y (2016) Use of PEGylated Immunoliposomes to Deliver Dopamine Across the Blood-Brain Barrier in a Rat Model of Parkinson's Disease. CNS Neuroscience & Therapeutics. 22(10):817-23.

[80] Di Gioia S, Trapani A, Mandracchia D, De Giglio E, Cometa S, Mangini V, Arnesano F, Belgiovine G, Castellani S, Pace L, Lavecchia M A (2015) Intranasal delivery of dopamine to the striatum using glycol chitosan/sulfobutylether-β-cyclodextrin based nanoparticles. European Journal of Pharmaceutics and Biopharmaceutics. 94:180-93.

[81] Oorschot D E. Total number of neurons in the neostriatal, pallidal, subthalamic, and substantia nigral nuclei of the rat basal ganglia: a stereological study using the cavalieri and optical dissector methods. J. Comp. Neurol. 1996; 366:580-599.

[82] Naoi M, Maruyama W (1999) Cell death of dopamine neurons in aging and Parkinson's disease. Mechanisms of ageing and development. 111(2):175-88

[83] Garedew A, Henderson S O, Moncada S (2010) Activated macrophages utilize glycolytic ATP to maintain mitochondrial membrane potential and prevent apoptotic cell death. Cell Death & Differentiation. 17(10):1540-50.

[84] Mantovani A, Marchesi F, Malesci A, Laghi L, Allavena P (2017) Tumour-associated macrophages as treatment targets in oncology. Nature reviews Clinical oncology.

[85] Colotta F, Allavena P, Sica A, Garlanda C, Mantovani A (2009) Cancer-related inflammation, the seventh hallmark of cancer: links to genetic instability. Carcinogenesis. 30(7):1073-81.

[86] Honeycutt J B, Wahl A, Baker C, Spagnuolo R A, Foster J, Zakharova O, Wietgrefe S, Caro-Vegas C, Madden V, Sharpe G, Haase A T (2016) Macrophages sustain HIV replication in vivo independently of T cells. The Journal of clinical investigation. 126(4):1353.

[87] Arainga M, Edagwa B, Mosley R L, Poluektova L Y, Gorantla S, Gendelman H E. A mature macrophage is a principal HIV-1 cellular reservoir in humanized mice after treatment with long acting antiretroviral therapy (2017) Retrovirology. 14(1):17.

[88] Appelberg K S, Wallet M A, Taylor J P, Cash M N, Sleasman J W, Goodenow M M. HIV-1 Infection Primes Macrophages through STAT Signaling to Promote Enhanced Inflammation and Viral Replication (2017) AIDS Research and Human Retroviruses.

[89] Burdo T H, Lentz M R, Autissier P, Krishnan A, Halpern E, Letendre S, Rosenberg E S, Ellis R J, Williams K C (2011) Soluble CD163 made by monocyte/macrophages is a novel marker of HIV activity in early and chronic infection prior to and after anti-retroviral therapy. Journal of Infectious Diseases. 204(1):154-63.

[90] Yamasaki K, Chuang V T, Maruyama T, Otagiri M (2013) Albumin-drug interaction and its clinical implication. Biochimica et Biophysica Acta (BBA)—General Subjects. 1830(12):5435-43.

[91] Karimi M, Sahandi Zangabad P, Ghasemi A, Amiri M, Bahrami M, Malekzad H, Ghahramanzadeh Asl H, Mandieh Z, Bozorgomid M, Ghasemi A, Rahmani Taji Boyuk M R (2016) Temperature-responsive smart nanocarriers for delivery of therapeutic agents: applications and recent advances. ACS applied materials & interfaces. 8(33): 21107-33.

[92] Ta T, Porter T M (2013) Thermosensitive liposomes for localized delivery and triggered release of chemotherapy. Journal of controlled release. 169(1-2):112-25.

[93] Zangabad P S, Mirkiani S, Shahsavari S, Masoudi B, Masroor M, Hamed H, Jafari Z, Taghipour Y D, Hashemi H, Karimi M, Hamblin M R (2017) Stimulus-responsive liposomes as smart nanoplatforms for drug delivery applications. Nanotechnology reviews.

[94] Kneidl B, Peller M, Winter G, Lindner L H, Hossann M (2014) Thermosensitive liposomal drug delivery systems: state of the art review. International journal of nanomedicine. 9:4387.

[95] Sun T, Zhang Y S, Pang B, Hyun D C, Yang M, Xia Y (2014) Engineered nanoparticles for drug delivery in cancer therapy. Angewandte Chemie International Edition. 53(46):12320-64.

[96] Hayflick L (1965) The limited in vitro lifetime of human diploid cell strains. Experimental cell research. 37(3):614-36.

[97] Cabanac A, Briese E (1992) Handling elevates the colonic temperature of mice. Physiology & behavior. 51(1):95-8.

[98] Michel C, Cabanac M (1999) Opposite effects of gentle handling on body temperature and body weight in rats. Physiology & behavior. 67(4):617-22.

[99] McCullough L, Arora S (2004) Diagnosis and treatment of hypothermia. American family physician. 70(12):2325-32.

[100] Freund G (1973) Hypothermia after acute ethanol and benzyl alcohol administration. Life sciences. 13(4):345-9.

[101] Lomax P, Bajorek J G, Chesarek W A, Chaffee R R (1980) Ethanol-induced hypothermia in the rat. Pharmacology. 21(4):288-94.

[102] Myers R D (1981) Alcohol's effect on body temperature: hypothermia, hyperthermia or poikilothermia? Brain research bulletin. 7(2):209-20.

[103] Kalant H, Le A D (1983) Effects of ethanol on thermoregulation. Pharmacology & therapeutics. 23(3): 313-64.

[104] Malcolm R D, Alkana R L (1983) Temperature dependence of ethanol lethality in mice. Journal of Pharmacy and Pharmacology. 35(5):306-11.

[105] Briese E, Hernandez L (1996) Ethanol anapyrexia in rats. Pharmacology Biochemistry and Behavior. 54(2): 399-402.

[106] Lomax P, Bajorek J G, Bajorek T A, Chaffee R R (1981) Thermoregulatory mechanisms and ethanol hypothermia. European journal of pharmacology. 71(4):483-7.

[107] Gad S C, Spainhour C B, Shoemake C, Pallman D R, Stricker-Krongrad A, Downing P A, Seals R E, Eagle L A, Polhamus K, Daly J (2016) Tolerable levels of nonclinical vehicles and formulations used in studies by multiple routes in multiple species with notes on methods to improve utility. International journal of toxicology 2:95-178.

[108] Gad S C, Cassidy C D, Aubert N, Spainhour B, Robbe H (2006) Nonclinical vehicle use in studies by multiple routes in multiple species. International journal of toxicology. 25(6):499-521.

[109] Gordon C J, Puckett E T, Repasky E S, Johnstone A F (2017) A Device that Allows Rodents to Behaviorally Thermoregulate when Housed in Vivariums. Journal of the American Association for Laboratory Animal Science. 56(2):173-6.

[110] Boily P (2009) Role of voluntary motor activity on menthol-induced hyperthermia in mice. Journal of Thermal Biology. 34(8):420-5.

[111] Gaskill B N, Rohr S A, Pajor E A, Lucas J R, Garner J P (2009) Some like it hot: mouse temperature preferences in laboratory housing. Applied Animal Behaviour Science. 116(2):279-85.

[112] Ballard A, Ahmad H O, Narduolo S, Rosa L, Chand N, Cosgrove D A, Varkonyi P, Asaad N, Tomasi S, Buurma N J, Leach A G (2018) Quantitative Prediction of Rate Constants for Aqueous Racemization To Avoid Pointless Stereoselective Syntheses. Angewandte Chemie. 130(4): 994-7.

[A] Takahashi M, Oshima K, Matsubara S (2005) Ruthenium catalyzed deuterium labelling of α-carbon in primary alcohol and primary/secondary amine in D2O. Chemistry letters. 34(2):192-3.

[B] Chatterjee B, Krishnakumar V, Gunanathan C (2016) Selective α-Deuteration of Amines and Amino Acids Using D2O. Organic letters. 18(22):5892-5.

[C] Michelotti A, Rodrigues F, Roche M (2017) Development and Scale-Up of Stereoretentive α-Deuteration of Amines. Organic Process Research & Development. 21(11):1741-4.

[D] Neubert L, Michalik D, Balm S, Imm S, Neumann H, Atzrodt J, Derdau V, Holla W, Beller M (2012) Ruthenium-catalyzed selective α,β-deuteration of bioactive amines. Journal of the American Chemical Society. 12; 134(29):12239-44.

[E1] Taglang C, Martinez-Prieto L M, del Rosal I, Maron L, Poteau R, Philippot K, Chaudret B, Perato S, Sam Lone A, Puente C, Dugave C (2015) Enantiospecific C? H Activation Using Ruthenium Nanocatalysts. Angewandte Chemie International Edition. 54(36):10474-7.

[E2] Pieters G, Taglang C, Bonnefille E, Gutmann T, Puente C, Berthet J C, Dugave C, Chaudret B, Rousseau B (2014)

Regioselective and stereospecific deuteration of bioactive aza compounds by the use of ruthenium nanoparticles. Angewandte Chemie International Edition. 53(1):230-4.

[F] Bhatia S, Spahlinger G, Boukhumseen N, Boll Q, Li Z, Jackson J E (2016) Stereoretentive H/D Exchange via an Electroactivated Heterogeneous Catalyst at sp3 C—H Sites Bearing Amines or Alcohols. European Journal of Organic Chemistry. 24:4230-5.

[G] Chatterjee B, Gunanathan C (2015) Ruthenium Catalyzed Selective a- and α, ß-Deuteration of Alcohols Using $D_2O$. Organic letters. 17(19):4794-7.

[H] Khaskin E, Milstein D (2013) Simple and Efficient Catalytic Reaction for the Selective Deuteration of Alcohols. ACS Catalysis. 3(3):448-52.

[I] Bai W, Lee K H, Tse S K, Chan K W, Lin Z, Jia G (2015) Ruthenium-catalyzed deuteration of alcohols with deuterium oxide. Organometallics. 34(15):3686-98.

[J1] Breno K L, Tyler D R (2001) C—H Bond Activation in Aqueous Solution: A Linear Free Energy Relationship Investigation of the Rate-Limiting Step in the H/D Exchange of Alcohols Catalyzed by a Molybdocene. Organometallics. 20(18):3864-8.

[J2] Balzarek C, Weakley T J, Tyler D R (2000) C—H Bond Activation in Aqueous Solution: Kinetics and Mechanism of H/D Exchange in Alcohols Catalyzed by Molybdocenes. Journal of the American Chemical Society. 122 (39):9427-34.

[J3] Balzarek C, Tyler D R (1999) Intra- and Intermolecular H/D Exchange in Aqueous Solution Catalyzed by Molybdocenes. Angewandte Chemie International Edition. 38(16):2406-8.

[K] Maegawa T, Fujiwara Y, Inagaki Y, Monguchi Y, Sajiki H (2008) A convenient and effective method for the regioselective deuteration of alcohols. Advanced Synthesis & Catalysis. 350(14-15):2215-8.

[L] Bossi G, Putignano E, Rigo P, Baratta W (2011) Pincer Ru and Os complexes as efficient catalysts for racemization and deuteration of alcohols. Dalton Transactions. 40(35):8986-95.

[M] Zhang L, Nguyen D H, Raffa G, Desset S, Paul S, Dumeignil F, Gauvin R M (2016) Efficient deuterium labelling of alcohols in deuterated water catalyzed by ruthenium pincer complexes. Catalysis Communications. 84:67-70.

[N] Palmer W N, Chirik P J (2017) Cobalt-Catalyzed Stereoretentive Hydrogen Isotope Exchange of C (sp3)-H Bonds. ACS Catalysis. 7(9):5674-8.

[O1] Sajiki H, Aoki F, Esaki H, Maegawa T, Hirota K (2004) Efficient C—H/C-D Exchange Reaction on the Alkyl Side Chain of Aromatic Compounds Using Heterogeneous Pd/C in $D_2O$. Organic letters. 6(9):1485-7.

[O2] Esaki H, Aoki F, Umemura M, Kato M, Maegawa T, Monguchi Y, Sajiki H (2007) Efficient H/D Exchange Reactions of Alkyl-Substituted Benzene Derivatives by Means of the Pd/C—$H_2$-$D_2O$ System. Chemistry—A European Journal. 13(14):4052-63.

[P] Hale L V, Szymczak N K (2016) Stereoretentive deuteration of α-chiral amines with D2O. Journal of the American Chemical Society. 138(41):13489-92.

[Q1] Derdau V, Atzrodt J (2006) CH/CD exchange reactions of aromatic compounds in $D_2O$ with NaBD4-activated catalysts. Synlett. (12):1918-22.

[Q2] Derdau V, Atzrodt J, Zimmermann J, Kroll C, Bruckner F (2009) Hydrogen-Deuterium Exchange Reactions of Aromatic Compounds and Heterocycles by NaBD4-Activated Rhodium, Platinum and Palladium Catalysts. Chemistry—a European Journal. 15(40):10397-404.

[R1] Ito N, Watahiki T, Maesawa T, Maegawa T, Sajiki H (2008) HD exchange reaction taking advantage of the synergistic effect of heterogeneous palladium and platinum mixed catalyst. Synthesis. 09:1467-78.

[R2] Maegawa T, Ito N, Oono K, Monguchi Y, Sajiki H (2009) Bimetallic Palladium-Platinum-on-Carbon-Catalyzed HD Exchange Reaction: Synergistic Effect on Multiple Deuterium Incorporation. Synthesis. (16):2674-8.

[S] Kar S, Goeppert A, Sen R, Kothandaraman J, Prakash G S (2018) Regioselective deuteration of alcohols in $D_2O$ catalysed by homogeneous manganese and iron pincer complexes. Green Chemistry.

[AI1] Segler M H, Preuss M, Waller M P (2018) Planning chemical syntheses with deep neural networks and symbolic AI. Nature. 555(7698):604.

[AI2] Klucznik T, Mikulak-Klucznik B, McCormack M P, Lima H, Szymkue S, Bhowmick M, Molga K, Zhou Y, Rickershauser L, Gajewska E P, Toutchkine A (2018) Efficient syntheses of diverse, medicinally relevant targets planned by computer and executed in the laboratory. Chem. 4(3):522-32.

[AI3] Segler M H, Preuss M, Waller M P. Learning to Plan Chemical Syntheses (2017) arXiv preprint arXiv: 1708.04202.

[Ex1] Loh Y Y, Nagao K, Hoover A J, Hesk D, Rivera N R, Colletti S L, Davies I W, MacMillan D W (2017) Photoredox-catalyzed deuteration and tritiation of pharmaceutical compounds. Science. eaap9674.

[Ex2] Yu R P, Hesk D, Rivera N, Pelczer I, Chirik P J (2016) Iron-catalysed tritiation of pharmaceuticals. Nature. 529 (7585):195.

[Ex3] Zhan M, Zhang T, Huang H, Xie Y, Chen Y (2014) A simple method for α-position deuterated carbonyl compounds with pyrrolidine as catalyst. Journal of Labelled Compounds and Radiopharmaceuticals. 57(8):533-9.

[Ex4] Fodor-Csorba K, Galli G, Holly S, Gacs-Baitz E (2002) Microwave-assisted deuterium exchange reactions for the preparation of reactive intermediates. Tetrahedron letters. 43(21):3789-92.

[AA1] Takeda R, Abe H, Shibata N, Moriwaki H, Izawa K, Soloshonok V A (2017) Asymmetric synthesis of α-deuterated α-amino acids. Organic & biomolecular chemistry. 15(33):6978-83.

[AA2] O'Reilly E, Balducci D, Paradisi F (2010) A stereoselective synthesis of α-deuterium-labelled (S)-α-amino acids. Amino acids. 39(3):849-58.

[AA3] Johns R B, Whelan D J (1966) Synthesis of α-deuterated amino acids. Australian Journal of Chemistry. 19(11):2143-7.

[AA4] Mosin O, Ignatov I, Skladnev D, Shvets V (2015) The Biosynthesis of Deuterium Labeled Amino Acids Using a Strain of Facultative Methylotrophic Bacterium Brevibacterium Methylicum 5662 With RuMP Cycle of Carbon Assimilation. European Journal of Molecular Biotechnology. (1):37-52.

[AA5] Blomquist A T, Cedergren R J, Hiscock B F, Tripp S L, Harpp D N (1966) Synthesis of highly deuterated amino acids. Proceedings of the National Academy of Sciences. 55(3):453-6.

[AA6] Thanassi J W (1971) General procedure for the preparation of deuterated and tritiated amino acids by incorporation of solvent isotope during synthesis. The Journal of organic chemistry. 36(20):3019-21.

[113] Rigoulet M, Ouhabi R, Leverve X, Putod-Paramelle F, Guérin B (1989) Almitrine, a new kind of energy-trans-

[114] Rigoulet M, Fraisse L, Ouhabi R, Guérin B, Fontaine E, Leverve X (1990) Flux-dependent increase in the stoichiometry of charge translocation by mitochondrial ATPase/ATP synthase induced by almitrine. Biochimica et Biophysica Acta (BBA)—Bioenergetics. 1018(1):91-7.

[115] Leverve X M, Fontaine E, Putod-Paramelle F, Rigoulet M (1994) Decrease in cytosolic ATP/ADP ratio and activation of pyruvate kinase after in vitro addition of almitrine in hepatocytes isolated from fasted rats. The FEBS Journal. 224(3):967-74.

[116] Rigoulet M (1990) Control processes in oxidative phosphorylation: kinetic constraints and stoichiometry. Biochimica et Biophysica Acta (BBA)—Bioenergetics. 1018(2-3):185-9.

[117] Cayman chemical Safety data sheet for carboplatin. www.caymanchem.com/msdss/13112 m.pdf (accessed on Sep. 10, 2017)

[118] Guidechem Safety data sheet for almitrine dimesylate. www.guidechem.com/msds/29608-49-9.html (accessed on Sep. 10, 2017)

[119] Mangin P, Krieger J, Kurtz D. Effect of oral almitrine on the sleep apnea syndrome. Revue francaise des maladies respiratoires. 1983; 11(6):899-906.

[120] European Medicines Agency (23 May 2013) Assessment report for almitrine-containing medicinal products for oral use. www.ema.europa.eu/docs/en_GB/document_library/Referrals_document/Almitrine/Recommendation_provided_by_Pharmacovigilance_Risk_Assessment_Committee/WC500144134.pdf (accessed on Dec. 7, 2017)

[121] Stavchansky S, Doluisio J T, Macleod C M, Szalkowski M B, Bachand R T, Heilman R, Sebree T B, Geary R S (1989) Single oral dose proportionality pharmacokinetics of almitrine bismesylate in humans. Biopharmaceutics & drug disposition. 10(3):229-37.

[122] bionumbers.hms.harvard.edu/bionumber.aspx?id=109718 (accessed on Jun. 18, 2020)

[123] Bury T, Jeannot J P, Ansquer J C, Radermecker M (1989) Dose-response and pharmacokinetic study with almitrine bismesylate after single oral administrations in COPD patients. European Respiratory Journal. 2(1):49-55.

[124] Oral almitrine to be withdrawn by EU Member States (29 May 2013) www.ema.europa.eu/docs/en_GB/document_library/Referrals_document/Almitrine/Position_provided_by_CMDh/WC500143802.pdf (accessed on Jun. 20, 2018)

[125] Cotten J F (2014) The latest pharmacologic ventilator. Anesthesiology: The Journal of the American Society of Anesthesiologists. 121(3):442-4.

[126] Golder F J, Hewitt M M, McLeod J F (2013) Respiratory stimulant drugs in the post-operative setting. Respiratory physiology & neurobiology. 189(2):395-402.

[127] B'chir A, Mebazaa A, Losser M R, Romieu M, Payen D (1998) Intravenous almitrine bismesylate reversibly induces lactic acidosis and hepatic dysfunction in patients with acute lung injury. Anesthesiology: The Journal of the American Society of Anesthesiologists. 89(4):823-30.

[128] Chan S C, Liu C L, Lo C M, Lam B K, Lee E W, Wong Y, Fan S T (2006) Estimating liver weight of adults by body weight and gender. World journal of gastroenterology. 12(14):2217.

[129] Yamanaka Y, Shimada T, Mochizuki R, Suzuki Y, Takenouchi K, Takeda T, Uno H, Izawa Y, Fujiwara K (1997) Neuronal and muscular inclusions in rats with hindlimb dysfunction after treating with difluorobenzhydrylpiperadine. Toxicologic pathology. 25(2):150-7.

[130] Yamanaka Y, Sakamoto E, Sakuma Y, Uno H, Koyama T, Izawa Y, Fujiwara K (1995) Lipidosis of the dorsal root ganglia in rats treated with an almitrine metabolite. Archives of toxicology. 69(6):391.

The invention claimed is:
1. A method of ameliorating Non-Small Cell Lung Cancer (NSCLC) in a subject
wherein the method comprises administering to the subject an effective amount of at least one compound, or a composition(s) containing at least one compound (optionally a pharmaceutical composition also comprising one or more of a pharmaceutically-acceptable carrier[s], additive[s], diluent[s]), of the following formula:

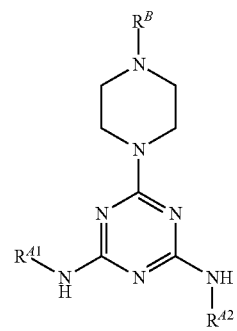

or a pharmaceutically-acceptable salt, solvate, hydrate or prodrug thereof,
wherein
$R^{A1}$ and $R^{A2}$ are each independently selected from the groups

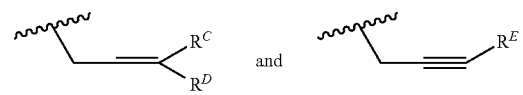

wherein $R^C$ and $R^D$ are each independently selected from hydrogen, deuterium, halogen and alkyl, and wherein $R^E$ is hydrogen, deuterium, or alkyl;
$R^B$ is selected from $R^{B1}$, hydrogen and deuterium;
wherein $R^{B1}$ is selected from phenyl, benzyl, pyridyl, pyrimidyl and pyrazinyl optionally substituted with one or more substituents $R^{B2}$;
wherein each $R^{B2}$ is independently selected from halogen, alkyl, alkoxy, nitro, amino, methoxy and polyhalogen alkyl;
or $R^B$ is a phenylalkyl of the formula:

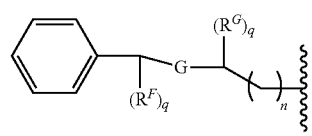

wherein $R^F$ and $R^G$ are hydrogen or alkyl, G is a carbon-carbon double bond or a carbon-carbon single bond, n is 0 or 1 and q is 0 or 1 provided that where q is 0, G is a carbon-carbon double bond and where q is 1, G is a carbon-carbon single bond,
or $R^B$ is a diphenylalkyl of the formula

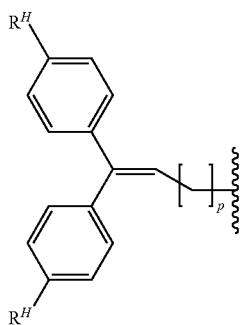

wherein $R^H$ is hydrogen or halogen, and p is 0, 1 or 2; or $R^B$ is the group

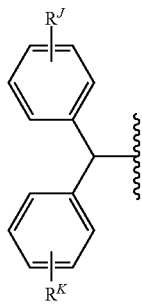

wherein $R^J$ and $R^K$ each independently represent 1-5 optional substituents on each ring, and wherein each $R^J$ and each $R^K$, when present, is independently selected from halogen, alkyl, alkoxy, nitro, amino and polyhalogen alkyl.

2. A method according to claim 1, wherein one or more of the following applies:
$R^B$ is the group:

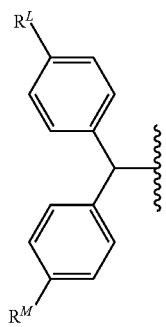

wherein $R^L$ and $R^M$ are each independently selected from halogen, alkyl, alkoxy, nitro, amino and polyhalogen alkyl;
$R^{A1}$ and $R^{A2}$ are each independently selected from the group

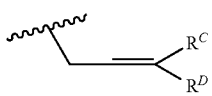

wherein $R^C$ and $R^D$ are each independently selected from hydrogen, deuterium, halogen and alkyl.

3. A method of claim 2 wherein the method comprises administering to the subject an effective amount of the compound of the following formula:

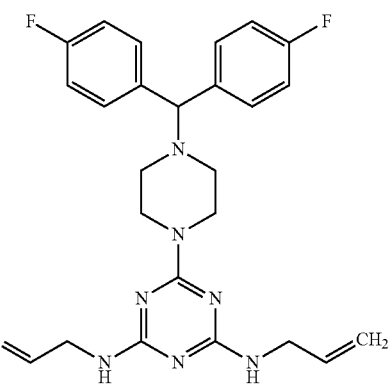

or a pharmaceutically-acceptable salt, solvate, hydrate or prodrug thereof.

4. A method of claim 3 wherein it is almitrine dimesylate that is administered.

5. A method of claim 1 wherein the NSCLC is a carcinoma.

6. A method of claim 5 wherein the carcinoma is an adenocarcinoma.

7. A method of claim 5 wherein the carcinoma is a squamous cell carcinoma.

8. A method of claim 5 wherein the carcinoma is a large-cell lung carcinoma.

\* \* \* \* \*